(12) United States Patent
Boudreault et al.

(10) Patent No.: US 7,645,741 B2
(45) Date of Patent: *Jan. 12, 2010

(54) IAP BIR DOMAIN BINDING COMPOUNDS

(75) Inventors: Alain Boudreault, Dorval (CA); James B. Jaquith, Pincourt (CA); Patrick Bureau, Kirkland (CA); John W. Gillard, Baie D'Urfé (CA); Alain Laurent, Montreal (CA)

(73) Assignee: Aegera Therapeutics, Inc., Verdun, Quebec ( * ) Notice: Subject to any disclaimer, the term of this patent is extended or adjusted under 35 U.S.C. 154(b) by 0 days.

This patent is subject to a terminal disclaimer.

(21) Appl. No.: 11/979,280

(22) Filed: Nov. 1, 2007

(65) Prior Publication Data

US 2008/0207525 A1  Aug. 28, 2008

Related U.S. Application Data

(63) Continuation of application No. 11/723,044, filed on Mar. 16, 2007.

(60) Provisional application No. 60/782,523, filed on Mar. 16, 2006, provisional application No. 60/876,994, filed on Dec. 26, 2006.

(51) Int. Cl.
*A61K 38/08* (2006.01)
*A61K 39/395* (2006.01)
*A61P 35/00* (2006.01)
*C07K 7/06* (2006.01)
*C12Q 1/02* (2006.01)

(52) U.S. Cl. ............................ 514/15; 514/16; 514/17; 514/397; 514/422; 514/423; 424/130.1; 435/29; 530/328; 530/329

(58) Field of Classification Search ........................ None
See application file for complete search history.

(56) References Cited

U.S. PATENT DOCUMENTS

| 6,110,691 | A | 8/2000 | Wang et al. |
|---|---|---|---|
| 6,608,026 | B1 | 8/2003 | Wang et al. |
| 6,992,063 | B2 | 1/2006 | Shi |

(Continued)

FOREIGN PATENT DOCUMENTS

| CA | 2491041 | 1/2004 |
|---|---|---|
| CA | 2 582 734 A1 | 9/2005 |
| CA | 2 560 162 A1 | 10/2005 |
| CA | 2 574 040 A1 | 2/2006 |
| JP | 61183297 | 8/1986 |
| JP | 4208299 | 7/1992 |
| WO | WO 02/30959 | 4/2002 |
| WO | WO 02/096930 | 12/2002 |
| WO | WO 03/086470 A2 | 10/2003 |
| WO | WO 2004/005248 A1 | 1/2004 |
| WO | WO 02/26775 A2 | 4/2004 |
| WO | WO 2005/069888 | 8/2005 |
| WO | WO 2005/074989 A2 | 8/2005 |
| WO | WO 2005/084317 A2 | 9/2005 |
| WO | WO 2005/094818 | 10/2005 |
| WO | WO 2005/097791 A1 | 10/2005 |
| WO | WO 2006/010118 A2 | 1/2006 |
| WO | WO 2006/017295 A2 | 2/2006 |
| WO | WO 2006/069063 A1 | 6/2006 |
| WO | WO 2006/113376 A1 | 10/2006 |

(Continued)

OTHER PUBLICATIONS

Interferon Gamma from GenBank Accession No. NP_776511, pp. 1-3. Accessed Jul. 1, 2008.I.*
IAP from GenBank Accession No. Q13490, pp. 1-6. Accessed Jul. 1, 2008.*
XIAP from GenBank Accession No. CAB95312, pp. 1-3, Accessed Jul. 1, 2008.*

(Continued)

*Primary Examiner*—Cecilia Tsang
*Assistant Examiner*—Julie Ha
(74) *Attorney, Agent, or Firm*—Leydig, Voit & Mayer, Ltd.

(57) ABSTRACT

Disclosed is an isomer, enantiomer, diastereoisomer or tautomer of a compound represented by Formula I or II

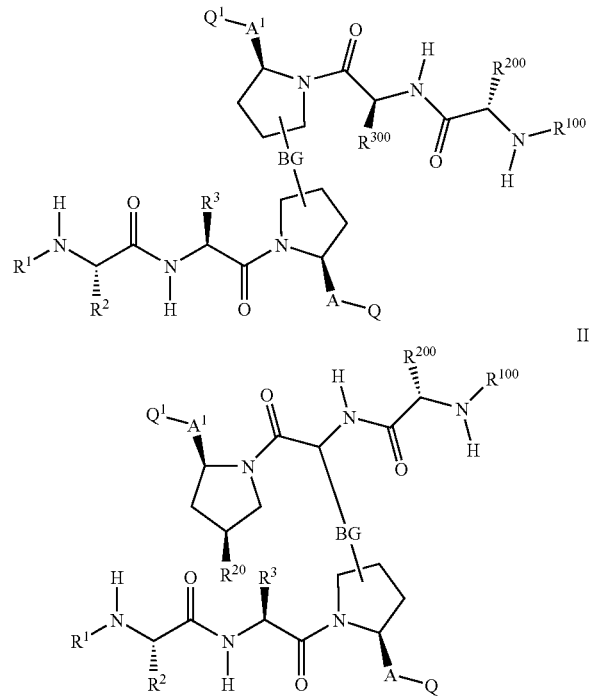

or a salt thereof, in which $R^1$, $R^2$, $R^3$, $R^{100}$, $R^{200}$, $R^{300}$, A, $A^1$, BG, Q and $Q^1$ are substituents described herein. Also disclosed is the use of compounds of Formula I and II to treat proliferative disorders such as cancer.

47 Claims, 2 Drawing Sheets

U.S. PATENT DOCUMENTS

| | | | |
|---|---|---|---|
| 7,041,784 | B2 | 5/2006 | Wang et al. |
| 7,094,758 | B2 | 8/2006 | Wang et al. |
| 7,229,617 | B2 | 6/2007 | Nasoff et al. |
| 2004/0180828 | A1 | 9/2004 | Shi |
| 2005/0197403 | A1 | 9/2005 | Harran et al. |
| 2005/0234042 | A1 | 10/2005 | Palermo et al. |
| 2006/0014700 | A1 | 1/2006 | Cohen et al. |
| 2006/0025347 | A1 | 2/2006 | Condon et al. |
| 2006/0194741 | A1 | 8/2006 | Condon et al. |
| 2006/0211627 | A1 | 9/2006 | Reed et al. |
| 2006/0258581 | A1 | 11/2006 | Reed et al. |
| 2007/0032437 | A1 | 2/2007 | Shi et al. |
| 2007/0042428 | A1 | 2/2007 | Springs et al. |
| 2007/0093428 | A1 | 4/2007 | Laurent |
| 2007/0093429 | A1 | 4/2007 | Laurent et al. |
| 2007/0219140 | A1 | 9/2007 | Laurent et al. |
| 2008/0069812 | A1 | 3/2008 | Boudreault et al. |
| 2008/0089896 | A1 | 4/2008 | Wang et al. |
| 2008/0207525 | A1 | 8/2008 | Boudreault et al. |

FOREIGN PATENT DOCUMENTS

| | | |
|---|---|---|
| WO | WO 2006/122408 A1 | 11/2006 |
| WO | WO 2006/128455 A2 | 12/2006 |
| WO | WO 2006/133147 A2 | 12/2006 |
| WO | WO 2007/048224 A1 | 5/2007 |
| WO | WO 2007/075525 A2 | 7/2007 |
| WO | WO 2007/101347 A1 | 9/2007 |
| WO | WO 2007/104162 A1 | 9/2007 |
| WO | WO 2007/106192 A2 | 9/2007 |
| WO | WO 2007/130626 A2 | 11/2007 |
| WO | WO 2007/131366 A1 | 11/2007 |
| WO | WO 2007/136921 A2 | 11/2007 |
| WO | WO 2008/014229 A2 | 1/2008 |
| WO | WO 2008/014236 A1 | 1/2008 |
| WO | WO 2008/014238 A2 | 1/2008 |
| WO | WO 2008/014240 A2 | 1/2008 |
| WO | WO 2008/014252 A2 | 1/2008 |
| WO | WO 2008/014263 A2 | 1/2008 |
| WO | WO 2008/016893 A1 | 2/2008 |
| WO | WO 2008/045905 A1 | 4/2008 |
| WO | WO 2008/057172 A2 | 5/2008 |
| WO | WO 2008/067280 A2 | 6/2008 |
| WO | WO 2008/073306 A1 | 6/2008 |
| WO | WO 2008/079735 A1 | 7/2008 |
| WO | WO 2008/085610 A1 | 7/2008 |
| WO | WO 2008/128121 A1 | 10/2008 |
| WO | WO 2008/128171 A2 | 10/2008 |
| WO | WO 2008/134679 A1 | 11/2008 |
| WO | WO 2008/144925 A1 | 12/2008 |
| WO | WO 2009/060292 A2 | 5/2009 |

OTHER PUBLICATIONS

Mencel JJ, Regan JR, Barton J, Menard PR, Bruno JG, Calvo RR, Kornberg BE, Schwab A, Neiss ES, Suh JT, "Angiotensin Converting Enzyme Inhibitors. 10. Aryl Sulfonamide Substituted N-[1-Carboxy-3-phenylpropyl]-L-alanyl-L-proline Derivatives as Novel Antihypertensives." J. Med. Chem., 1990, 33: 1606-1615.*

Arnt et al., *J. Biol. Chem.*, "Synthetic Smac/Diablo peptides enhance the effects of chemotherapeutic agents by binding XIAP and cIAP1 in Situ," 277(46): 44236-44243 (2002).

Bertrand et al., *Mol. Cell*, "cIAP1 and cIAP2 facilitate cancer cell survival by functioning as E3 ligases that promote RIP1 ubiquitination," 30: 689-700 (2008).

Bucher et al., *Helv. Chim. Acta.*, 78(4):935-46 (1995).

Chai et al., *Nature*, "Structural and biochemical basis of apoptotic activation by Smac/Diablo," 406: 855-62 (2000).

Chauhan et al., *Blood*, "Targeting mitochondrial factor Smac/Diablo as therapy for multiple myeloma (MM)," 109(3): 1220-7 (2007).

Chen et al., *Bioorg. Med. Chem. Lett.*, "Design, synthesis, and characterization of new embelin derivatives as potent inhibitors of X-linked inhibitor of apoptosis protein," 16(22): 5805-5808 (2006).

Eckelman et al., *Cell Death Differ.*, "The mechanism of peptide-binding specificity of IAP BIR domains," 15(5): 920-8 (2008).

Elmore et al., *Annual Rep. Med. Chem.*, "Inhibitors of Anti-apoptotic Proteins for Cancer Therapy," 40: 245-62 (2006).

Franklin et al., *Biochemistry*, "Structure and function analysis of peptide antagonists of melanoma inhibitor of apoptosis (ML-IAP)," 42: 8223-31 (2003).

Fulda et al., *Nature Medicine*, "Smac agonists sensitize for Apo2L/Trail- or anticancer drug-induced apoptosis and induce regression of malignant glioma in vivo," 8: 808-15 (2002).

Gao et al., *J. Biol. Chem.*, "A dimeric Smac/Diablo peptide directly relieves caspase-3 inhibition by XIAP. Dynamic and cooperative regulation of XIAP by Smac/Diablo," 282(42): 30718-27 (2007).

Haining et al., *Proc. Natl. Acad. Sci. USA*, "The proapoptotic function of Drosophila HID is conserved in mammalian cells," 96(9): 4936-41 (1999).

Liu et al., *Nature*, "Structural basis for binding of Smac/Diablo to the XIAP BIR3 domain," 408: 1004-8 (2000).

Marik et al., *J. Peptide. Res.*, "Synthesis and effect of shortened oostatic decapeptide (TMOF) analogs with isosteric structures on reproduction of *Neobelleria bullata*," 57(5): 401-8 (2001).

McCarthy et al., *J. Biol. Chem.*, "Apoptosis induced by Drosophila reaper and grim in a human system. Attenuation by inhibitor of apoptosis proteins (cIAPS)," 273(37): 24009-15 (1998).

Nikolovska-Coleska et al., *Anal. Biochem.*, "Development and optimization of a binding assay for the XIAP BIR3 domain using fluorescence polarization," 332: 261-273 (2004).

Nikolovska-Coleska et al., *J. Med. Chem.*, "Discovery of embelin as a cell-permeable, small-molecular weight inhibitor of XIAP through structure-based computational screening of a tradition herbal medicine three-dimensional structure database," 47(10): 2430-40 (2004).

Nikolovska-Coleska et al., *Anal. Biochem.*, "Design and characterization of bivalent Smac-based peptides as antagonists of XIAP and development and validation of a fluorescence polarization assay for XIAP containing both BIR2 and BIR3 domains," 374(1): 87-98 (2008).

Park et al., *Bioorg. Med. Chem. Lett.*, "Non-peptidic small molecule inhibitors of XIAP," 15(3): 771-5 (2005).

Petersen et al., *Cancer Cell*, "Autocrine TNFalpha signaling renders human cancer cells susceptible to Smac-mimetic-induced apoptosis," 12(5): 445-56 (2007).

Srinivasula et al., *J. Biol. Chem.*, "Molecular determinants of the caspase-promoting activity of Smac/Diablo and its role in the death receptor pathway," 275(46): 36152-7 (2000).

Sun et al., *J. Am. Chem. Soc.*, "Structure-Based Design of Potent, Conformationally Constrained Smac Mimetics," 126(51): 16686-87 2004.

Sun et al., *J. Med. Chem.*, "Structure-based design, synthesis, and evaluation of conformationally constrained mimetics of the second mitochondria-derived activator of caspase that target the X-linked inhibitor of apoptosis protein/caspase-9 interaction site," 47(17): 4147-50 (2004).

Sun et al., *Tetrahedron Letters*, "Design and synthesis of a potent biotinylated Smac mimetic," 46: 7015-18 (2005).

Sun et al., *J. Med. Chem.*, "Design, synthesis, and evaluation of a potent, cell-permeable, conformationally constrained second mitochondria derived activator of caspase (Smac) mimetic," 49(26): 7916-20 (2006).

Sun et al., *J. Am. Chem. Soc.*, "Design, synthesis, and characterization of a potent, nonpeptide, cell-permeable, bivalent Smac mimetic that concurrently targets both the BIR2 and BIR3 domains in XIAP," 129(49): 15279-94 (2007).

Sweeney et al., *Biochemistry*, "Determination of the sequence specificity of XIAP BIR domains by screening a combinatorial peptide library," 45(49): 14740-8 (2006).

Terui et al., *Cancer Res.*, "NH2-terminal pentapeptide of endothelial interleukin 8 is responsible for the induction of apoptosis in leukemic cells and has an antitumor effect in vivo," *Cancer Res* 59(22): 5651-5 (1999).

Varfolomeev et al., *Cell*, "IAP antagonists induce autoubiquitination of c-IAPs, NF-kappaB activation, and TNFalpha-dependent apoptosis," 131(4): 669-81 (2007).

Vince et al., *Cell*, "IAP antagonists target cIAP1 to induce TNFalpha-dependent apoptosis," 131(4): 682-93 (2007).

Voskoglou-Nomikos et al., *Clin. Cancer Res.*, "Clinical Predictive Value of the in vitro Cell Line, Human Xenograft, and Mouse Allograft Preclinical Cancer Models," 9:4227-4239 (2003).

Vucic et al., *Mol. Cell. Biol.*, "Inhibitor of apoptosis proteins physically interact with and block apoptosis induced by Drosophila proteins HID and Grim," 18(6): 3300-9 (1998).

Wist et al., *Bioorg. Med. Chem.*, "Structure-activity based study of the Smac-binding pocket within the BIR3 domain of XIAP," 15(8): 2935-43 (2007).

Wu et al., *Nature*, "Structural basis of IAP recognition by Smac/Diablo," 408: 1008-12 (2000).

Wu et al., *Chem. Biol.*, "Development and characterization of nonpeptidic small molecule inhibitors of the XIAP/caspase-3 interaction," 10(8): 759-67 (2003).

Zobel et al., *ACS Chem. Biol.*, "Design, Synthesis, and Biological Activity of a Potent Smac Mimetic That Sensitizes Cancer Cells to Apoptosis by Antagonizing IAPs," 1(8): 525-33 (2006).

Glover, Constance J. et al,"A High-Throughput Screen for Identification.."Analytical Biochemistry 320 (2003), pp. 157-169.

Kipp, R.A. et al, Molecular Targeting of Inhibitor of Apoptosis Protein.., Biochemistry, vol. 41, No. 23, pp. 7344-7349 (2002).

Li, Lin et al, "A Small Molecule Smac Mimic Potentiates Trail-and..", Science, vol. 305, pp. (2004).

Oost, Thorsten K. et al, "Discovery of Potent Antagonists of the Antiapoptotic . . . " Journal of Medicinal Chemistry, pp. A-J (2004).

Sun, Yaiying et al "Structure-Based Design, Synthesis and Biochemical Testing of Novel" Bioorganic & Medicinal Chemistry Letters 15 (2005) 793-797.

\* cited by examiner

US 7,645,741 B2

IAP BIR DOMAIN BINDING COMPOUNDS

CROSS-REFERENCE TO RELATED APPLICATIONS

This application is a continuation of U.S. Ser. No. 11/723,044, filed Mar. 16, 2007 (now pending), which claims priority from previously filed U.S. Provisional Application No. 60/782,523 filed on Mar. 16, 2006 and previously filed U.S. Provisional Application No. 60/876,994 filed on Dec. 26, 2006.

FIELD OF THE INVENTION

The present invention concerns bridged compounds that bind to IAP BIR domains, and which are useful for treating proliferative disorders and disorders of dysregulated apoptosis, such as cancer.

BACKGROUND OF THE INVENTION

Apoptosis, or programmed cell death, typically occurs in the normal development and maintenance of healthy tissues in multicellular organisms. It is a complex process which results in the removal of damaged, diseased or developmentally redundant cells, in the absence of signs of inflammation or necrosis.

Intrinsic apoptotic pathways are known to be dysregulated, most particularly in cancer and lymphoproliferative syndromes, as well as autoimmune disorders such as multiple sclerosis, in neurodegenerative diseases and in inflammation. As well, alterations in a host apoptotic response have been described in the development or maintenance of viral and bacterial infections.

The caspases are a family of proteolytic enzymes from the class of cysteine proteases which are known to initiate and execute apoptosis. In normal cells, the caspases are present as inactive zymogens, which are catalytically activated following external signals, for example those resulting from ligand driven Death Receptor activation, such as cytokines or immunological agents, or by release of mitochondrial factors, such as cytochrome C following genotoxic, chemotoxic, or radiation-induced cellular injury. The Inhibitors of Apoptosis Proteins (IAPs) constitute a family of proteins which are capable of binding to and inhibiting the caspases, thereby suppressing cellular apoptosis. Because of their central role in regulating Caspase activity, the IAPs are capable of inhibiting programmed cell death from a wide variety of triggers, which include loss of homeostatic, or endogenous cellular growth control mechanisms, as well as chemotherapeutic drugs and irradiation.

The IAPs contain one to three homologous structural domains known as baculovirus IAP repeat (BIR) domains. They may also contain a RING zinc finger domain at the C-terminus, with a capability of inducing ubiquitinylation of IAP-binding molecules via its E3 ligase function. The human IAPs, XIAP, HIAP1 (also referred to as cIAP2), and HIAP2 (cIAP1) each have three BIR domains, and a carboxy terminal RING zinc finger. Another IAP, NAIP, has three BIR domains (BIR1, BIR2 and BIR3), but no RING domain, whereas Livin, TsIAP and MLIAP have a single BIR domain and a RING domain. The X chromosome-linked inhibitor of apoptosis (XIAP) is an example of an IAP which can inhibit the initiator caspase, known as caspase-9, and the effector caspases, Caspase-3 and Caspase-7, by direct binding. It can also induce the removal of caspases through the ubiquitylation-mediated proteasome pathway via the E3 ligase activity of a RING zinc finger domain. It is via the BIR3 domain that XIAP binds to and inhibits caspase-9. The linker-BIR2 domain of XIAP inhibits the activity of caspases-3 and -7. The BIR domains have also been associated with the interactions of IAPs with tumor necrosis factor-receptor associated factor (TRAFs) -1 and -2, and to TAB1, as adaptor proteins effecting survival signaling through NFkB activation. The IAPs thus function as a direct break on the apoptosis cascade, by preventing the action of, or inhibiting active caspases and by re-directing cellular signaling to a pro-survival mode.

Progress in the cancer field has led to a new paradigm in cancer biology wherein neoplasia may be viewed as a failure of cancer cells to execute normal pathways of apoptosis. Normal cells receive continuous feedback from their environment through various intracellular and extracellular factors, and "commit suicide" if removed from this context. This induction of apoptosis is achieved by activation of the caspase cascade. Cancer cells, however, gain the ability to overcome or bypass this apoptosis regulation and continue with inappropriate proliferation. The majority of treatments for cancer induce at least a partial apoptotic response in the cancer target cell, resulting in remission or initiation of tumor regression. In many cases, however, residual cells which are apoptosis-resistant are capable of escaping therapy and continuing the process of oncogenic/genetic change, resulting in the emergence of highly drug-resistant, metastatic disease which overcomes our ability to effectively treat the disease. Furthermore, most cancer therapies, including radiation therapy and traditional chemotherapy do induce apoptosis in cancer cells, but cause additional cellular injury, due to their lack of specificity in inducing apoptosis solely in cancer cells. The need to improve the specificity/potency of pro-apoptosis agents used to treat cancer, and indeed other proliferative disorders, is important because of the benefits in decreasing the side effects associated with administration of these agents. Therefore, finding novel means of inducing apoptosis in cancer cells is a highly desired medical need and its solution offers the possibility of entirely new treatments for cancer.

A growing body of data indicates that cancer cells may avoid apoptosis by the sustained over-expression of one or more members of the IAP family of proteins, as documented in many primary tumor biopsy samples, as well as most established cancer cell lines. Epidemiological studies have demonstrated that over-expression of the various IAPs is associated with poor clinical prognosis and survival. For XIAP this is shown in cancers as diverse as leukemia and ovarian cancer. Over expression of HIAP1 and HIAP2 resulting from the frequent chromosome amplification of the 11q21-q23 region, which encompasses both, has been observed in a variety of malignancies, including medulloblastomas, renal cell carcinomas, glioblastomas, and gastric carcinomas. (X) IAP negative regulatory molecules such as XAF, appear to be tumor suppressors, which are very frequently lost in clinical cancers. Thus, by their ability to suppress the activation and execution of the intrinsic mediators of apoptosis, the caspases, the IAPs may directly contribute to tumor progression and resistance to pharmaceutical intervention. Induction of apoptosis in cancer cells by the use of potent small molecules which bind to specific IAP domains is the subject of this invention.

We and others have demonstrated the critical importance of the individual BIR domains for affecting the antiapoptotic function of the IAPs. We have proposed that antagonists of the IAPs, which may bind to the individual BIR domains, would disrupt the antiapoptotic function of the IAPs. Indeed, individual BIRs serve as critical binding sites for the N-terminal Ser-Gly-Val-Asp, Ser-Gly-Pro-Ile and Ala-Thre-Pro-Ile residues of the Caspases 3, 7, and 9, respectively, and such binding is imperative for the Caspase-inhibitory function of the IAPs. The binding of N-terminal AxPy tetra-peptide residues to XIAP results in the release of the active caspases 3, 7 and 9. In the case of the other IAPs, the functions of the BIRs, when ligand-bound, appear to direct the activation of the ubiquitin ligase RING function of the IAPs to a bound target, or the IAPs themselves, to cause proteosomal loss. In either case, small molecule antagonists of this target should be excellent pro-apoptotic agents, with potential uses in cancer, various proliferative disorders and inflammation.

A mammalian mitochondrial protein, namely Second Mitochondria-derived Activator of Caspases (SMAC) which antagonizes IAP function, binds mainly to the BIR 3 or 2 sites on respective IAPs via an AxPy amino-terminal tetrapeptide. Four Drosophila death-inducing proteins, Reaper, HID, Grim, and Sickle, which antagonize the ability of the Drosophila IAPs to inhibit caspases, also bind the BIR domains of the analogous Drosophila IAPs via a short AxPy amino-terminal tetrapeptide, a sequence that fits into the BIR binding pocket and disrupts IAP-caspase interactions.

The overall topology of individual BIR domains is highly conserved between the human IAPs and between individual BIR domains of the human IAPs, each BIR being a zinc finger polypeptide domain, locked into a coordinated Zn atom by two cysteines and a histidine residue. The X-ray crystallographic structures of XIAP BIR2 and BIR3 reveal a critical binding pocket for an AXPY motif on the surface of each BIR domain. There are alterations in the intervening amino acid sequences that form the binding pocket and groove in both BIR2 and BIR3. Likewise, we have described homologous domains in the BIRs of other IAPs cIAP1 and cIAP2. This opens the possibility of obtaining various classes of natural and synthetic binding compounds which will have different specificity and binding affinities between each of the BIR domains for each of the IAPs. Discerning the way in which such compounds will affect the biological function of the IAPs in cancer cells vs normal cells is a major new challenge in the discovery of novel mechanism agents to treat cancer and other proliferative disorders where dysregulated IAP function is observed. It is our finding that certain classes of BIR binding compounds may bind to IAP BIRs, with unexpected selectivity and potency, resulting in distinct therapeutic advantages for certain structural classes.

A number of peptidic AxPy-like and heterocyclic modified AxPy peptidic compounds have been described which activate cellular Caspase 3 by reportedly binding to XIAP BIR3. For a recent reviews, see Elmore et al., Annual Reports in Medicinal Chemistry, 40 (2006) 245-262; Sun et al., Bioorg. Med. Chem. Let. 15 (2005) 793-797; Oost et al., J. Med. Chem., 2004, 47(18), 4417-4426; Park et al., Bioorg. Med. Chem. Lett. 15 (2005) 771-775; Franklin et al., Biochemistry, Vol. 42, No. 27, 2003, 8223-8231; Kip et al., Biochemistry 2002, 41, 7344-7349; Wu et al., Chemistry and Biology, Vol. 10, 759-767 (2003); Glover et al., Analytical Biochemistry, 320 (2003) 157-169; United States published patent application number 20020177557; and United States published patent application number 20040180828; United States published patent application number US2006/0025347A1; United States published patent application number US2005/0197403A1; and United States published patent application number US2006/0194741A1.

The aforesaid compounds have been shown to target an isolated BIR3 domain of XIAP via displacement of a fluorescently-labeled probe and they appear to induce an apoptotic event in a select set of cancer cell lines with potency in the low micromolar-nanomolar range. These compounds displayed poor in-vivo activity, likely due to limited bioavailability and may therefore have limited therapeutic application.

Thus, IAP BIR domains represent an attractive target for the discovery and development of novel therapeutic agents, especially for the treatment of proliferative disorders such as cancer.

SUMMARY OF THE INVENTION

The inventors have previously disclosed a series of compounds which bind to the BIR units of the IAPs and induce apoptosis in various cancer cell lines (US published patent application number 20060264379). A characteristic of these compounds is the presence of a central pyrrolidine unit. We now herein disclose that the linkage of two BIR binding units via a substituted pyrrolidine, with preference for the site, orientation and chemical nature of the linkage, provides novel and distinctly advantageous classes of compounds with up to 1000 fold increase in potency, resulting from induction of apoptosis, against various cancer cell lines, over their corresponding non-bridged BIR binding compounds and that these compounds display the requisite potency, stability and pharmaceutical properties for the treatment of human cancers. Advantageously, the chemical nature of the bridging group can be chosen to cause the translation of the high intrinsic (sub-nanomolar) cellular potency to microgram/kg potency in inhibiting IAPs in several in-vivo xenograft models of human cancers. Furthermore, the compounds described have pharmaceutically acceptable stability in a range of mammalian tissues and fluids and have pharmaceutical properties which ensure adequate solubility and bioavailability using parenteral administration, suitable for clinical uses.

In one embodiment of the present invention, there is provided an isomer, enantiomer, diastereoisomer or tautomer of a compound represented by Formula I or II:

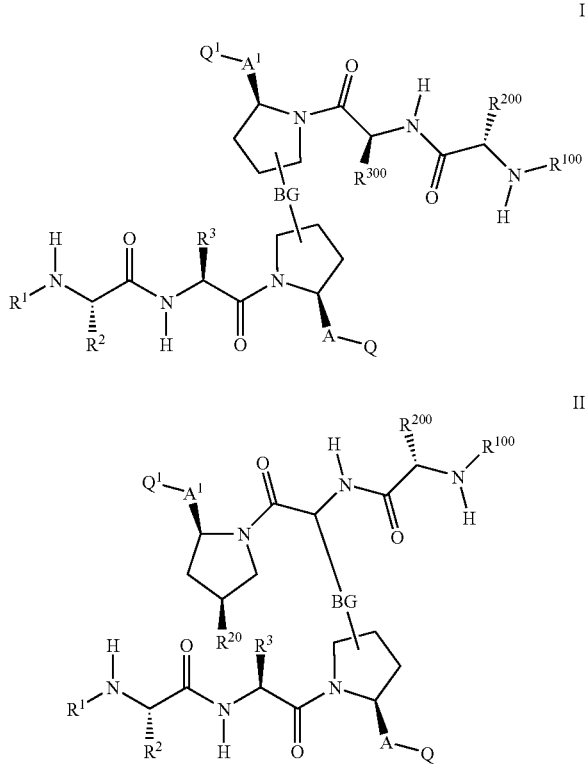

wherein
m is 0, 1 or 2;
Y is NH, O or S;
BG is
1) —X-L-$X^1$—;
X and $X^1$ are independently selected from
1) O,
2) $NR^{13}$,
3) S,
4) —$C_1$-$C_6$ alkyl-,
5) —$C_1$-$C_6$ alkyl-O—,
6) —$C_1$-$C_6$ alkyl-$NR^{13}$—,
7) —$C_1$-$C_6$ alkyl-S—, 8) 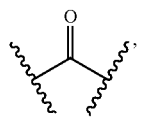

9) 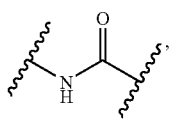

10) 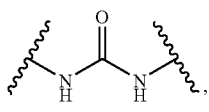

11) 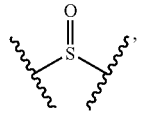

12) 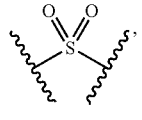

13) 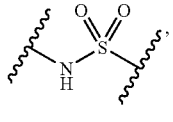

14) 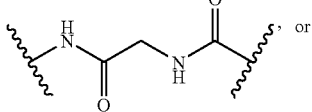, or

15) 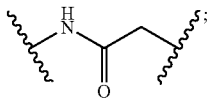;

L is selected from:
1) —$C_1$-$C_{20}$ alkyl-,
2) —$C_2$-$C_6$ alkenyl-,
3) —$C_2$-$C_4$ alkynyl-,
4) —$C_3$-$C_7$ cycloalkyl-,
5) -aryl-,
6) -biphenyl-,
7) -heteroaryl-,
8) -heterocyclyl-,
9) —$C_1$-$C_6$ alkyl-$C_2$-$C_6$ alkenyl) -$C_1$-$C_6$ alkyl-,
10) —$C_1$-$C_6$ alkyl-($C_2$-$C_4$ alkynyl) -$C_1$-$C_6$ alkyl-,
11) —$C_1$-$C_6$ alkyl-$C_3$-$C_7$ cycloalkyl) -$C_1$-$C_6$ alkyl-,
12) —$C_1$-$C_6$ alkyl-aryl-$C_1$-$C_6$ alkyl-,
13) —$C_1$-$C_6$ alkyl-biphenyl-$C_1$-$C_6$ alkyl-,
14) —$C_1$-$C_6$ alkyl-heteroaryl-$C_1$-$C_6$ alkyl-,
15) —$C_1$-$C_6$ alkyl-heterocycyl-$C_1$-$C_6$ alkyl-,
16) —$C_1$-$C_6$ alkyl-Y—$C_1$-$C_6$ alkyl-,
17) -aryl-Y-aryl-,
18) -heteroaryl-Y-heteroaryl-,
19) -heterocyclyl-Y-heterocyclyl-, 20) 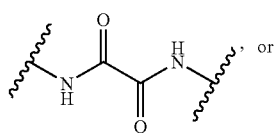, or 21) 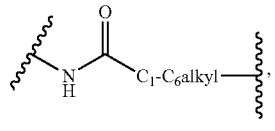;

wherein the alkyl, alkenyl, alkynyl and cycloalkyl are optionally substituted with one or more $R^6$ substituents, and the aryl, biphenyl, heteroaryl, and heterocyclyl are optionally substituted with one or more $R^{10}$ substituents;
Q and $Q^1$ are independently selected from
1) $NR^4R^5$,
2) $OR^{11}$, or
3) $S(O)_mR^{11}$; or
Q and $Q^1$ are independently selected from
1) aryl, or
2) heteroaryl, the aryl and the heteroaryl being optionally substituted with one or more $R^{10}$ substituents;
A and $A^1$ are independently selected from
1) —$CH_2$—,
2) —$CH_2CH_2$—,
3) —CH($C_1$-$C_6$ alkyl),
4) —CH($C_3$-$C_7$ cycloalkyl),
5) —$C_3$-$C_7$ cycloalkyl-,
6) —CH($C_1$-$C_6$ alkyl-$C_3$-$C_7$ cycloalkyl),
7) —C(O)—, or
8) —C(O) $OR^{13}$;
$R^1$ and $R^{100}$ are independently selected from
1) H, or
2) $C_1$-$C_6$ alkyl optionally substituted with one or more $R^6$ substituents;
$R^2$ and $R^{200}$ are independently selected from
1) H, or
2) $C_1$-$C_6$ alkyl optionally substituted with one or more $R^6$ substituents;
$R^3$ and $R^{300}$ are independently $C_1$-$C_6$ alkyl optionally substituted with one or more $R^6$ substituents;
$R^4$ and $R^5$ are each independently selected from
1) H,
2) haloalkyl,
3) $C_1$-$C_6$ alkyl,
4) $C_2$-$C_6$ alkenyl,
5) $C_2$-$C_4$ alkynyl,
6) $C_3$-$C_7$ cycloalkyl, 7) $C_3$-$C_7$ cycloalkenyl,
8) aryl,
9) heteroaryl,
10) heterocyclyl,
11) heterobicyclyl,
12) —C(O)—$R^{11}$,
13) —C(O)O—$R^{11}$,
14) —C(=Y) $NR^8R^9$, or
15) —S(O)$_2$—$R^{11}$, wherein the alkyl, alkenyl, alkynyl, cycloalkyl, and cycloalkenyl are optionally substituted with one or more $R^6$ substituents; and wherein the aryl, heteroaryl, heterocyclyl, and heterobicyclyl are optionally substituted with one or more $R^{10}$ substituents;

$R^6$ is
1) halogen,
2) $NO_2$,
3) CN,
4) haloalkyl,
5) $C_1$-$C_6$ alkyl,
6) $C_2$-$C_6$ alkenyl,
7) $C_2$-$C_4$ alkynyl,
8) $C_3$-$C_7$ cycloalkyl,
9) $C_3$-$C_7$ cycloalkenyl,
10) aryl,
11) heteroaryl,
12) heterocyclyl,
13) heterobicyclyl,
14) $OR^7$,
15) S(O)$_m R^7$,
16) $NR^8R^9$,
17) $NR^8S(O)_2R^{11}$,
18) $COR^7$,
19) C(O)$OR^7$,
20) $CONR^8R^9$,
21) S(O)$_2NR^8R^9$
22) OC(O)$R^7$,
23) OC(O)Y—$R^{11}$,
24) SC(O)$R^7$, or
25) NC(Y)$NR^8R^9$, wherein the aryl, heteroaryl, heterocyclyl, and heterobicyclyl is optionally substituted with one or more $R^{10}$ substituents;

$R^7$ is
1) H,
2) haloalkyl,
3) $C_1$-$C_6$ alkyl,
4) $C_2$-$C_6$ alkenyl,
5) $C_2$-$C_4$ alkynyl,
6) $C_3$-$C_7$ cycloalkyl,
7) $C_3$-$C_7$ cycloalkenyl,
8) aryl,
9) heteroaryl,
10) heterocyclyl,
11) heterobicyclyl,
12) $R^8R^9$N C(=Y), or
13) $C_1$-$C_6$ alkyl-$C_2$-$C_4$ alkenyl, or
14) $C_1$-$C_6$ alkyl-$C_2$-$C_4$ alkynyl, wherein the alkyl, alkenyl, alkynyl, cycloalkyl, cycloalkenyl is optionally substituted with one or more $R^6$ substituents; and wherein the aryl, heteroaryl, heterocyclyl, and heterobicyclyl is optionally substituted with one or more $R^{10}$ substituents;

$R^8$ and $R^9$ are each independently
1) H,
2) haloalkyl,
3) $C_1$-$C_6$ alkyl,
4) $C_2$-$C_6$ alkenyl,
5) $C_2$-$C_4$ alkynyl,
6) $C_3$-$C_7$ cycloalkyl,
7) $C_3$-$C_7$ cycloalkenyl,
8) aryl,
9) heteroaryl,
10) heterocyclyl,
11) heterobicyclyl,
12) C(O)$R^{11}$,
13) C(O)Y—$R^{11}$, or
14) S(O)$_2$—$R^{11}$, wherein the alkyl, alkenyl, alkynyl, cycloalkyl, cycloalkenyl is optionally substituted with one or more $R^6$ substituents; and wherein the aryl, heteroaryl, heterocyclyl, and heterobicyclyl is optionally substituted with one or more $R^{10}$ substituents;

or $R^8$ and $R^9$ together with the nitrogen atom to which they are bonded form a five, six or seven membered heterocyclic ring optionally substituted with one or more $R^6$ substituents;

$R^{10}$ is
1) halogen,
2) $NO_2$,
3) CN,
4) B(O$R^{13}$)(O$R^{14}$),
5) $C_1$-$C_6$ alkyl,
6) $C_2$-$C_6$ alkenyl,
7) $C_2$-$C_4$ alkynyl,
8) $C_3$-$C_7$ cycloalkyl,
9) $C_3$-$C_7$ cycloalkenyl,
10) haloalkyl,
11) $OR^7$,
12) $NR^3R^9$,
13) $SR^7$,
14) $COR^7$,
15) C(O)O $R^7$,
16) S(O)$_m R^7$,
17) $CONR^8R^9$,
18) S(O)$_2NR^8R^9$,
19) aryl,
20) heteroaryl,
21) heterocyclyl, or
22) heterobicyclyl, wherein the alkyl, alkenyl, alkynyl, cycloalkyl, and cycloalkenyl is optionally substituted with one or more $R^6$ substituents;

$R^{11}$ is
1) haloalkyl,
2) $C_1$-$C_6$ alkyl,
3) $C_2$-$C_6$ alkenyl,
4) $C_2$-$C_4$ alkynyl,
5) $C_3$-$C_7$ cycloalkyl,
6) $C_3$-$C_7$ cycloalkenyl,
7) aryl,
8) heteroaryl,
9) heterocyclyl, or
10) heterobicyclyl, wherein the alkyl, alkenyl, alkynyl, cycloalkyl, cycloalkenyl is optionally substituted with one or more $R^6$ substituents; and wherein the aryl, heteroaryl, heterocyclyl, and heterobicyclyl is optionally substituted with one or more $R^{10}$ substituents;

$R^{12}$ is
1) haloalkyl,
2) $C_1$-$C_6$ alkyl,
3) $C_2$-$C_6$ alkenyl,
54) $C_2$-$C_4$ alkynyl,
5) $C_3$-$C_7$ cycloalkyl, 6) $C_3$-$C_7$ cycloalkenyl,
7) aryl,
8) heteroaryl,
9) heterocyclyl,
10) heterobicyclyl,
11) C(O)—$R^{11}$,
12) C(O)O—$R^{11}$,
13) C(O)NR$^8$R$^9$,
14) S(O)$_m$—$R^{11}$, or
15) C(=Y)NR$^8$R$^9$, wherein the alkyl, alkenyl, alkynyl, cycloalkyl, cycloalkenyl is optionally substituted with one or more $R^6$ substituents; and wherein the aryl, heteroaryl, heterocyclyl, and heterobicyclyl is optionally substituted with one or more $R^{10}$ substituents;

$R^{13}$ and $R^{14}$ are each independently
1) H, or
2) $C_1$-$C_6$ alkyl; or $R^{13}$ and $R^{14}$ are combined to form a heterocyclic ring or a heterobicyclyl ring;

$R^{20}$ is
1) H,
2) NH$_2$, or
3) NHFmoc;

or a prodrug; or the compound of Formula I or II is labeled with a detectable label or an affinity tag.

In another aspect of the present invention, there is provided an intermediate compound represented by Formula 1-iv:

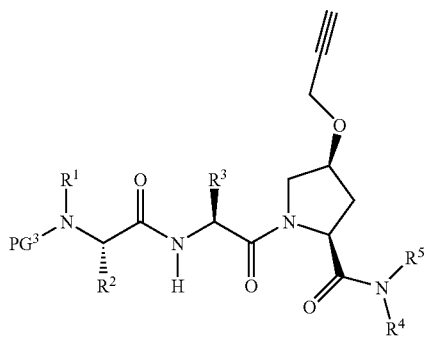

wherein PG$^3$, R$^1$, R$^2$, R$^3$, R$^4$, and R$^5$ are as defined herein.

In another aspect of the present invention, there is provided an intermediate compound represented by Formula 2-iv:

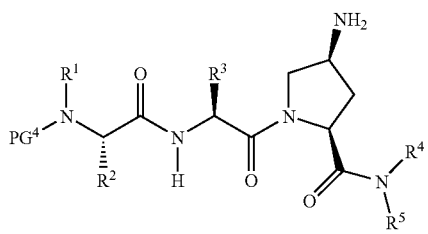

wherein PG$^4$, R$^1$, R$^2$, R$^3$, R$^4$, and R$^5$ are as defined herein.

In another aspect of the present invention, there is provided an intermediate compound represented by Formula 3-ii:

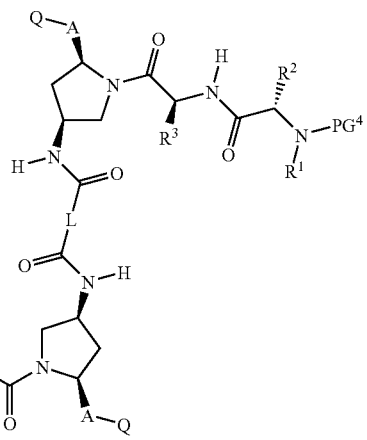

wherein PG$^4$, R$^1$, R$^2$, R$^3$, A, and Q are as defined herein, and L is —(CH$_2$)$_r$—, —(CH$_2$)$_r$—Y—(CH$_2$)$_r$—, -alkyl-aryl-alkyl-, -alkyl-heteroaryl-alkyl-, cycloalkyl, aryl or heteroaryl.

In another aspect of the present invention, there is provided an intermediate compound represented by Formula 4(i):

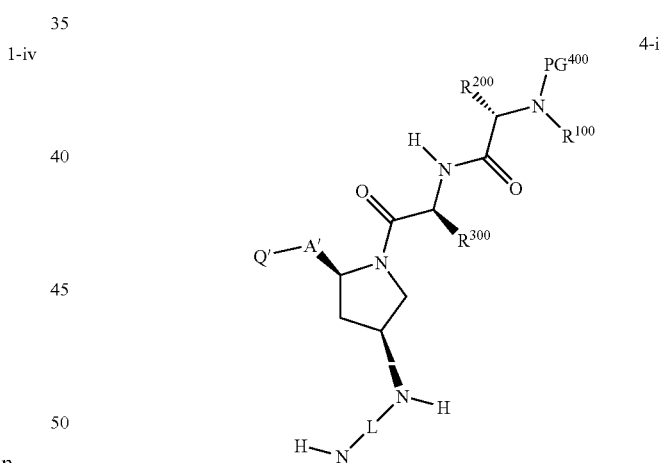

wherein PG$^4$, PG$^{400}$ L, R$^1$, R$^{100}$, R$^2$, R$^{200}$, R$^3$, R$^{300}$, A, A$^1$, Q and Q$^1$ are as defined herein.

In another aspect of the present invention, there is provided an intermediate compound represented by Formula 6-ii:

6-ii

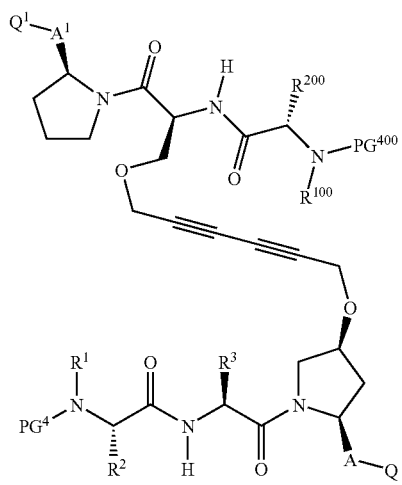

wherein $PG^4$, $PG^{400}$, $R^1$, $R^{100}$, $R^2$, $R^{200}$, $R^3$, $R^{300}$, A $A^1$, Q and $Q^1$ are as defined herein.

In another aspect of the present invention, there is provided an intermediate compound represented by Formula 7-v:

7-v

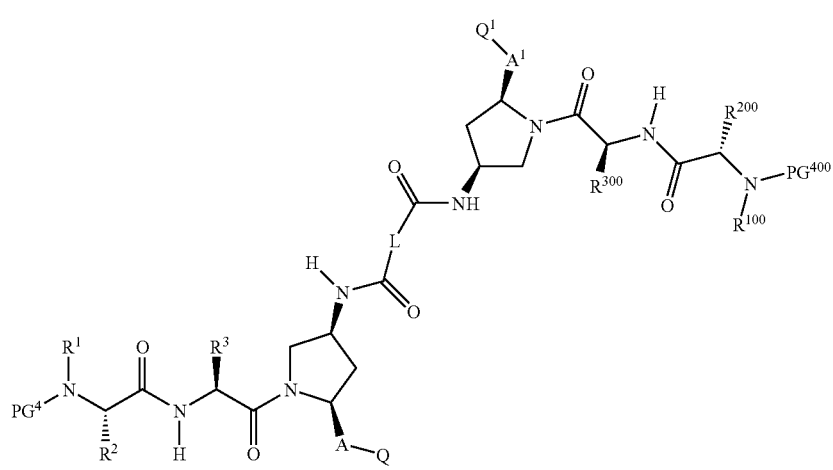

wherein $PG^4$, $PG^{400}$, L, $R^1$, $R^{100}$, $R^2$, $R^{200}$, $R^3$, $R^{300}$, A, $A^1$, Q and $Q^1$ are as defined herein.

In another aspect of the present invention, there is provided an intermediate compound represented by Formula 8-ii:

8-ii

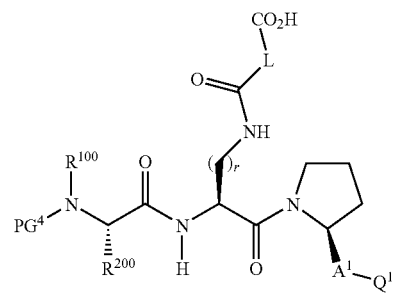

wherein $PG^4$ r, L, $R^{100}$, $R^{200}$, $A^1$, and $Q^1$ are as defined herein.

In another aspect of the present invention, there is provided an intermediate compound represented by Formula 8-iii:

8-iii

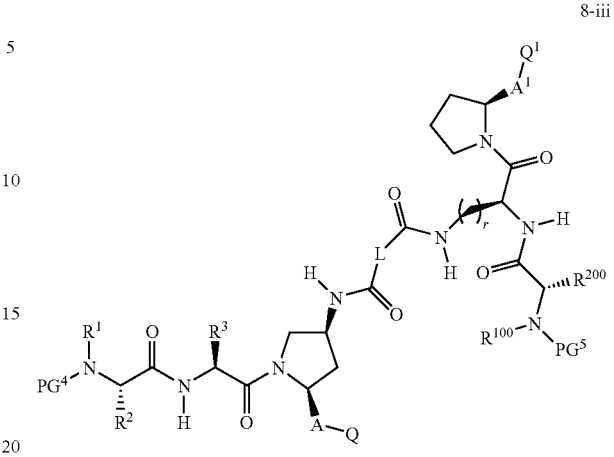

wherein $PG^4$, r, L, $R^1$, $R^{100}$, $R^2$, $R^{200}$, $R^3$, A, $A^1$, Q and $Q^1$ are as defined herein.

In another aspect of the present invention, there is provided an intermediate compound represented by Formula 17-i:

17-i

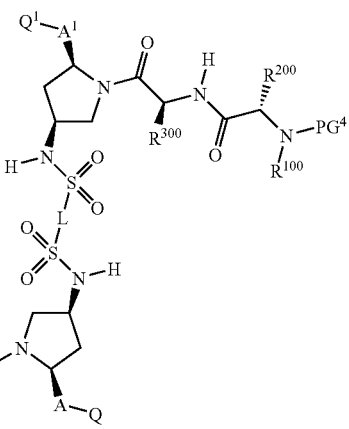

wherein $PG^4$ L, $R^1$, $R^{100}$, $R^2$, $R^{200}$, $R^3$, $R^{300}$, A, $A^1$, Q and $Q^1$ are as defined herein.

In another aspect of the present invention, there is provided an intermediate compound represented by Formula 18-i:

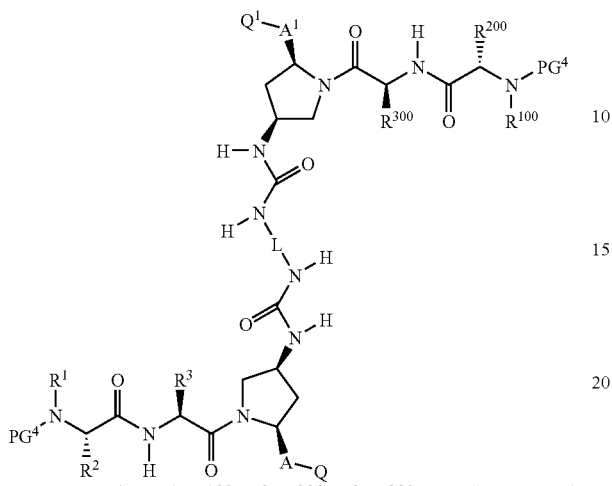

18-i wherein $PG^4$ L, $R^1$, $R^{100}$, $R^2$, $R^{200}$, $R^3$, $R^{300}$, A, $A^1$, Q and $Q^1$ are as defined herein.

In another aspect of the present invention, there is provided an intermediate compound represented by Formula 19-2:

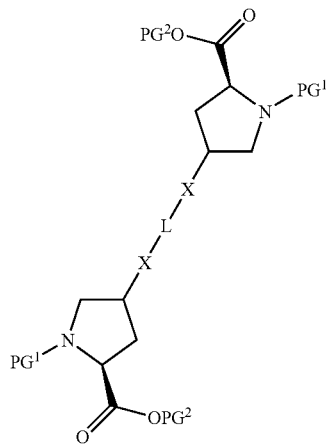

19-2 wherein $PG^1$, $PG^2$, L, X are as defined herein.

In another aspect of the present invention, there is provided an intermediate compound represented by Formula 19-3:

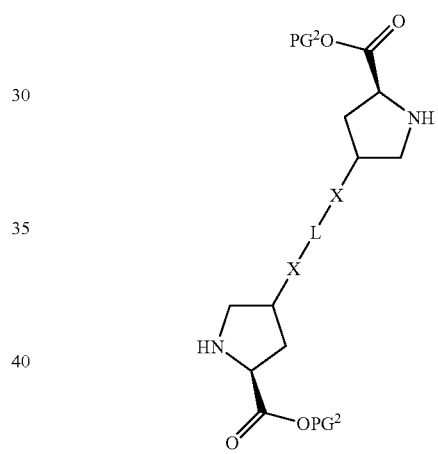

19-3 wherein $PG^2$, L, and X, are as defined herein.

In another aspect of the present invention, there is provided an intermediate compound represented by Formula 19-8:

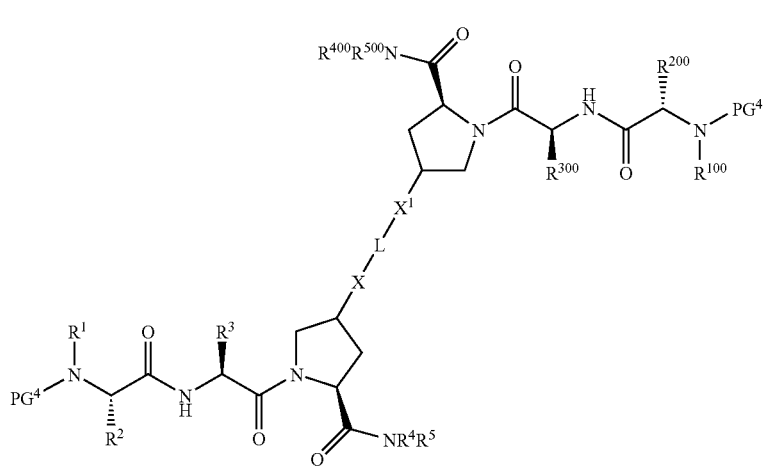

19-8 wherein $PG^4$, L, X, $X^1$, $R^1$, $R^{100}$, $R^2$, $R^{200}$, $R^3$, $R^{300}$, $R^4$, $R^{40}$, $R^5$ and $R^{500}$ are as defined herein.

In another aspect of the present invention, there is provided an intermediate compound represented by Formula 20-1a:

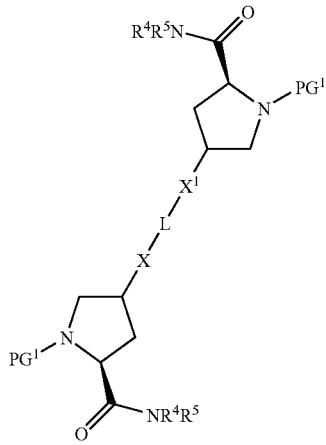

20-1a wherein $PG^1$, L, X, $X^1$, $R^4$ and $R^5$ are as defined herein.

In another aspect of the present invention, there is provided an intermediate compound represented by Formula 20-2:

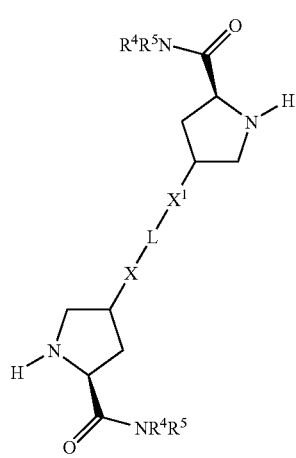

20-2 wherein $PG^4$, L, X, and $X^1$, are as defined herein.

In another aspect of the present invention, there is provided an intermediate compound represented by Formula 20-4:

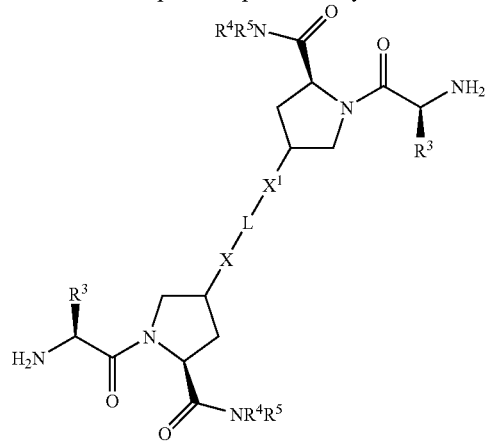

wherein $PG^4$ L, X, $X^1$, $R^1$, $R^{100}$, $R^2$, $R^{200}$, $R^3$, $R^{300}$, $R^4$, $R^{400}$, $R^5$, and $R^{500}$ are as defined herein.

In another aspect of the present invention, there is provided a process for producing compounds represented by Formula I, described hereinabove, the process comprising:

a) coupling two intermediates represented by Formula 1-iv:

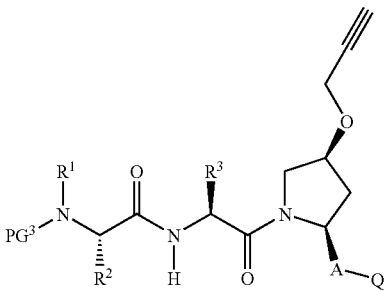

1-iv wherein $PG^3$, $R^1$, $R^2$, $R^3$, A, and Q are as defined herein, in a solvent; and b) removing the protecting groups so as to form compounds of Formula 1.

In another aspect of the present invention, there is provided a process for producing compounds represented by Formula I, described hereinabove, the process comprising:

a) coupling an intermediate represented by Formula 3-i:

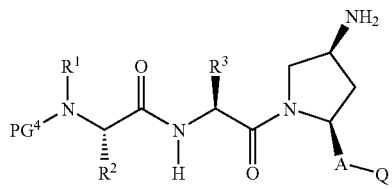

3-i wherein $PG^4$ is a protecting group, and $R^1$, $R^2$, $R^3$, A, and Q are as defined herein, and an activated diacid (0.5 equiv) in a solvent; and b) removing the protecting groups so as to form compounds of Formula I.

In another aspect of the present invention, there is provided a method for the preparation of a pharmaceutically acceptable salt of compound of formula I and II, by the treatment of a compound of formula I or II with 1 to 2 equiv of a pharmaceutically acceptable acid, as defined herein.

In another aspect of the present invention, there is provided a pharmaceutical composition comprising a compound, as described above, mixed with a pharmaceutically acceptable carrier, diluent or excipient.

In another aspect of the present invention, there is provided a pharmaceutical composition adapted for administration as an agent for treating a proliferative disorder in a subject, comprising a therapeutically effective amount of a compound, as described above.

In another aspect of the present invention, there is provided a pharmaceutical composition comprising a compound of Formula I in combination with one or more death receptor agonists, for example, an agonist of TRAIL receptor.

In another aspect of the present invention, there is provided a pharmaceutical composition comprising a compound of formula I in combination with any therapeutic agent that increases the response of one or more death receptor agonists, for example cytotoxic cytokines such as interferons.

In another aspect of the present invention, there is provided a method of preparing a pharmaceutical composition, the method comprising: mixing a compound, as described above, with a pharmaceutically acceptable carrier, diluent or excipient.

In another aspect of the present invention, there is provided a method of treating a disease state characterized by insufficient apoptosis, the method comprising: administering to a subject in need thereof, a therapeutically effective amount of a pharmaceutical composition, as described above, so as to treat the disease state.

In another aspect of the present invention, there is provided a method of modulating IAP function, the method comprising: contacting a cell with a compound of the present invention so as to prevent binding of a BIR binding protein to an IAP BIR domain thereby modulating the IAP function.

In another aspect of the present invention, there is provided a method of treating a proliferative disease, the method comprising: administering to a subject in need thereof, a therapeutically effective amount of the pharmaceutical composition, as described above, so as to treat the proliferative disease.

In another aspect of the present invention, there is provided a method of treating cancer, the method comprising: administering to a subject in need thereof, a therapeutically effective amount of the pharmaceutical composition, as described above, so as to treat the cancer.

In another aspect of the present invention, there is provided a method of treating cancer, the method comprising: administering to the subject in need thereof, a therapeutically effective amount of a pharmaceutical composition, as described above, in combination or sequentially with an agent selected from:
a) an estrogen receptor modulator,
b) an androgen receptor modulator,
c) retinoid receptor modulator,
d) a cytotoxic agent,
e) an antiproliferative agent,
f) a prenyl-protein transferase inhibitor,
g) an HMG-CoA reductase inhibitor,
h) an HIV protease inhibitor,
i) a reverse transcriptase inhibitor,
k) an angiogenesis inhibitor,
l) a PPAR-γ agonist,
m) a PPAR-δ agonist,
n) an inhibitor of inherent multidrug resistance,
o) an anti-emetic agent,
p) an agent useful in the treatment of anemia,
q) agents useful in the treatment of neutropenia,
r) an immunologic-enhancing drug,
s) a proteasome inhibitor,
t) an HDAC inhibitor,
u) an inhibitor of the chymotrypsin-like activity in the proteasome,
v) E3 ligase inhibitors,
w) a modulator of the immune system such as, but not limited to, interferon-alpha, *Bacillus* Calmette-Guerin (BCG), and ionizing radition (UVB) that can induce the release of cytokines, such as the interleukins, TNF, or induce release of death receptor ligands such as TRAIL,
x) a modulator of death receptors TRAIL and TRAIL receptor agonists such as the humanized antibodies HGS-ETR1 and HGS-ETR2, or in combination or sequentially with radiation therapy, so as to treat the cancer.

In another aspect of the present invention, there is provided a method for the treatment or prevention of a proliferative disorder in a subject, the method comprising: administering to the subject a therapeutically effective amount of the composition, described above.

In another aspect of the present invention, the method further comprises administering to the subject a therapeutically effective amount of a chemotherapeutic agent prior to, simultaneously with or after administration of the composition.

In yet another aspect, the method further comprises administering to the subject a therapeutically effective amount of a death receptor agonist prior to, simultaneously with or after administration of the composition. The death receptor agonist is TRAIL or the death receptor agonist is a TRAIL antibody. The death receptor agonist is typically administered in an amount that produces a synergistic effect.

In another aspect of the present invention, there is provided a probe, the probe being a compound of Formula I or II above, the compound being labeled with a detectable label or an affinity tag.

In another aspect of the present invention, there is provided a method of identifying compounds that bind to an IAP BIR domain, the assay comprising:
a) contacting an IAP BIR domain with a probe to form a probe:BIR domain complex, the probe being displaceable by a test compound;
b) measuring a signal from the probe so as to establish a reference level;
c) incubating the probe:BIR domain complex with the test compound;
d) measuring the signal from the probe;
e) comparing the signal from step d) with the reference level, a modulation of the
signal being an indication that the test compound binds to the BIR domain, wherein the probe is a compound of Formula I or II labeled with a detectable label or an affinity label.

BRIEF DESCRIPTION OF THE FIGURES

Further aspects and advantages of the present invention will become better understood with reference to the description in association with the following Figures, wherein.

DETAILED DESCRIPTION OF THE INVENTION

Figure 1:
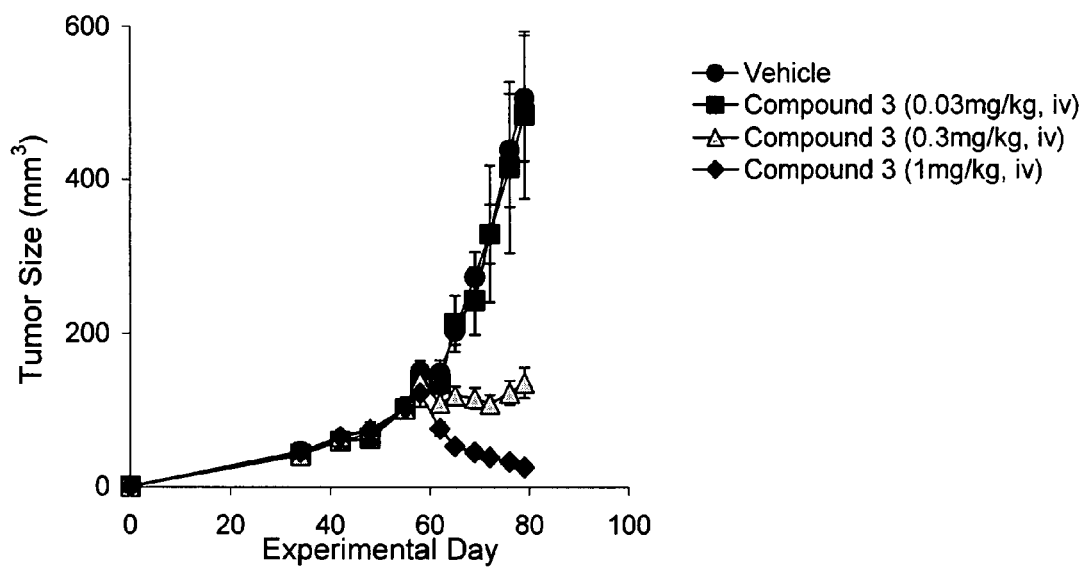
FIG. 1 depicts SKOV-3 Human Ovarian Cancer Cell Line Xenograph Study with compound 3. Female CD-1 nude mice (approximately 20-25 g) were subcutaneously injected $5\times10^6$ SKOV-3 human ovarian tumor cells in 50% matrigel subcutaneously in the right flank. On day 55, when tumors were approximately 100 mm$^3$, treatment was initiated with compound 3 treating with compound for 5 consecutive days followed by 2 days with no drug treatment for the duration of the experiment. Tumor size was measured with digital calipers and calculated as $V=(a\times b^2)/2$, wherein, a is the longest dimension and b is the width. Tumor regression was observed at 1 mg/kg while tumor stasis was observed to 0.3 mg/kg.

In many cancer and other diseases, an up-regulation of IAPs induced by gene defects or by chemotherapeutic agents has been correlated to an increased resistance to apoptosis.

Conversely, our results show that cells decreased in IAP levels are more sensitive to chemotherapeutic agents and to death receptor agonists such as TRAIL. It is believed that a small molecule, which will antagonize IAP function, or a loss of IAPs from diseased cells, will be useful as a therapeutic agent. We report herein that compounds of the instant invention can directly bind to IAPs, cause a down regulation of IAP proteins in cells, and induce apoptosis in cancer cells. Furthermore, compounds of the instant invention have demonstrated synergistic effects in combination with clinically relevant agents used in the treatment of cancer.

We have discovered a novel series of bridged compounds, which bind to the intact cellular IAPs and results in profound, sustained IAP protein down-modulation and enhanced cellular apoptosis of cancer cells through enhanced release of active Caspase 3. This biological response has been observed in various cell lines derived from human breast, pancreatic, colon, lung, ovarian cancers and primary human leukemia and lymphoma cells. The compounds were found to be highly synergistic with Death Receptor Agonist-mediated killing, such as TRAIL, TRAIL Receptor Monoclonal Antibodies and TNF-α, in a large and comprehensive range of cancer cells. Based upon these findings, the compounds will find application in treatment of many cancer types, such as solid tumors and tumors originating from the hematopoietic system. Moreover, the compounds of the present invention may also find application in preventing metastatic cancer cell invasion, inflammation, and in other diseases characterized by cells that are resistant to apoptosis via upregulation of any one of the IAPs.

The 'bridging' of two IAP BIR binding units, M1 and M2, described in more detail below, using an appropriate 'bridging unit', linked to one of the pyrrolidine rings, provides bridged IAP BIR binding compounds, which demonstrate significantly increased anti-cancer activity (10-1000 fold), as compared to their monomeric units. This improved activity results from an improved ability to bind to the BIR domains of the intact IAPs, and results in the induction of apoptosis in various cancer cell lines.

Various factors influence the in vitro proapoptotic character of the compounds of the present invention. Specifically, these include i) the point of attachment of the linker/pyrrolidine bond, ii) the stereochemistry at the linker/pyrrolidine bond, iii) the linker moieties themselves, including stereochemistry, regiochemistry, and the rigidity of the linker system, iv) alkyl substitution at $R^1$ and $R^{100}$, and v) the substitution pattern at $R^4$, $R^{400}$, $R^5$, and $R^{500}$.

For ease of description, throughout the description, the compounds of Formula I and Formula II, may also include the use of the terms P1, P2, P3, P4 and P5. These terms refer to the amino acids or modified amino acids within either of Formula I or II. The following illustrates the use of the terms:

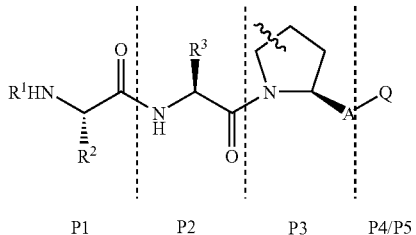

P1  P2  P3  P4/P5 wherein the waved line represents a covalent bond to another BIR binding unit.

The compounds of the present invention may also be represented by Formula 3 or Formula 4 in which M1 and M2 represent independent BIR binding domains.

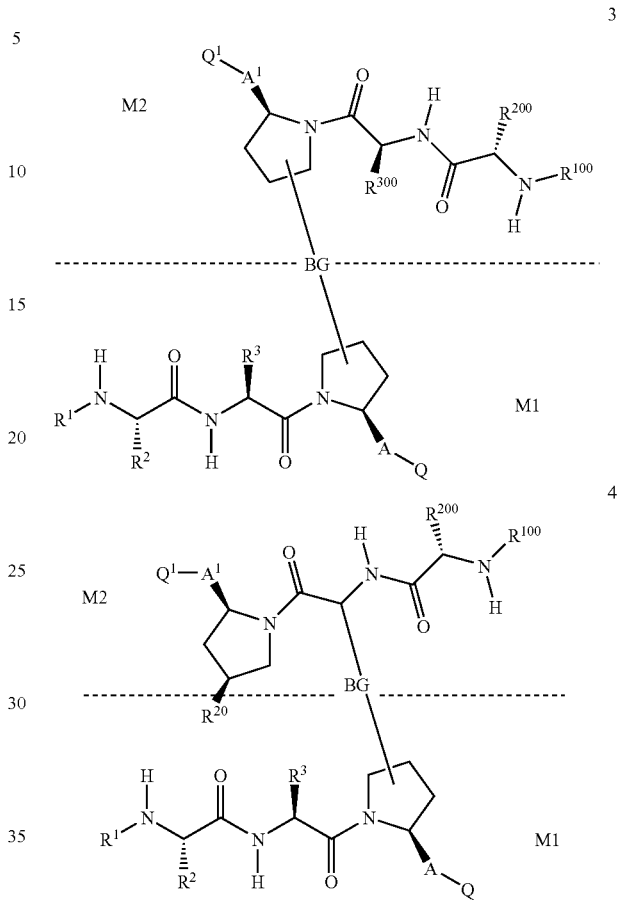

wherein $R^1$, $R^2$, $R^{100}$, $R^{200}$, $R^3$, $R^{300}$, $R^{20}$, A, $A^1$, Q, $Q^1$, and BG as defined herein, and the dotted line represents a hypothetical dividing line for comparing the substituents associated with M1 and M2.

In one subset of Formula 3, $M^1$ is the same as M2 and the dotted line denotes a line of symmetry. In another subset, $M^1$ is different from M2.

In one subset, compounds of Formula 4 are asymmetrical about the dotted line. In another subset the substituents on M1 and M2 are the same. In another subset, the substituents on M1 and M2 are different.

One skilled in the art will recognize that when M1 and M2 are the same, the $R^1$, $R^2$, $R^4$, $R^5$, $R^6$, $R^7$, $R^8$, $R^9$, $R^{10}$, $R^{11}$, $R^{13}$, $R^{14}$, r, m, Y, A, Q, and X substituents in M1 have the same meaning as the $R^{100}$, $R^{200}$, $R^4$, $R^5$, $R^6$, $R^7$, $R^8$, $R^9$, $R^{10}$, $R^{11}$, $R^{13}$, $R^{14}$, r, m, Y, $A^1$, $Q^1$, and $X^1$ substituents respectively in M2. When M1 and M2 are different, at least one $R^1$, $R^2$, $R^{100}$, $R^{200}$, $R^4$, $R^5$, $R^6$, $R^7$, $R^8$, $R^9$, $R^{10}$, $R^{11}$, $R^{13}$, $R^{14}$, r, m, Y, A, $A^1$, Q, $Q^1$, X, and $X^1$ substituent is different in either of M1 or M2.

Alternatively the substituents in $M^1$ can be defined as $R^1$, $R^2$, $R^4$, $R^5$, $R^6$, $R^7$, $R^8$, $R^9$, $R^{10}$, $R^{11}$, $R^{13}$, $R^{14}$, r, m, p, Y, A, Q, and X, and those in M2 can be defined as $R^{100}$, $R^{200}$, $R^{400}$, $R^{500}$, $R^{600}$, $R^{700}$, $R^{800}$, $R^{900}$, $R^{1000}$, $R^{1100}$, $R^{1300}$, $R^{1400}$, $r^1$, $m^1$, $Y^1$, $A^1$, $Q^1$ and $X^1$ respectively. In the case where M1 and M2 are the same, the $R^1$, $R^2$, $R^4$, $R^5$, $R^6$, $R^7$, $R^8$, $R^9$, $R^{10}$, $R^{11}$, $R^{13}$, $R^{14}$, r, m, Y, A, Q, and X substituents in M1 have the same meanings as $R^{100}$, $R^{200}$, $R^{400}$, $R^{500}$, $R^{600}$, $R^{700}$, $R^{800}$, $R^{900}$, $R^{1000}$, $R^{1100}$, $R^{1300}$, $R^{1400}$, $r^1$, $m^1$, $Y^1$, $A^1$, $Q^1$ and $X^1$ respectively in M2. In the case where M1 and M2 are different, at least one of the aforesaid substituents is different.

The compounds of the present invention are useful as BIR domain binding compounds in mammalian IAPs and are represented by either Formula I or Formula II. The following are embodiments, groups and substituents of the compounds according to Formula I and Formula II, which are described hereinafter in detail.

A and $A^1$:

In one subset of compounds of Formula I or II, A and $A^1$ are both $CH_2$.

In an alternative subset of compounds of Formula I or II, A and $A^1$ are both C=O.

In another alternative subset of compounds of Formula I or II, A is $CH_2$ and $A^1$ is C=O.

In another alternative subset of compounds of Formula I or II, A and $A^1$ are both $C(O)OCH_3$.

In another alternative subset of compounds of Formula I or II, A and $A^1$ are both C(O)OH.

Any and each individual definition of A and $A^1$ as set out herein may be combined with any and each individual definition of Core, $R^1$, $R^2$, $R^{100}$, $R^{200}$, $R^3$, $R^{300}$, Q, $Q^1$, and BG as set out herein.

Core:

Therefore, for compounds of Formula I, the present invention comprises compounds of Formula 1A through 1C:

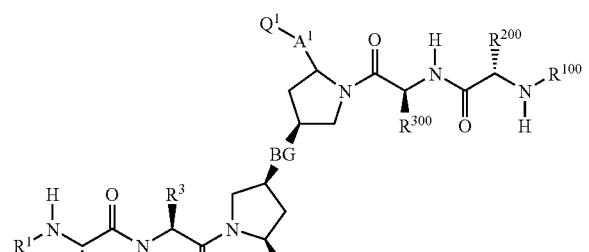

1A

1B

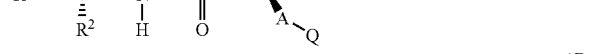

1C

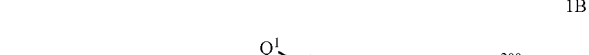

wherein BG, A, $A^1$, Q, $Q^1$, $R^1$, $R^{100}$, $R^2$, $R^{200}$, $R^3$, and $R^{300}$ are as defined hereinabove and hereinafter.

In one example, the present invention comprises compounds of Formula 1A.

In an alternative example, the present invention comprises compounds of Formula 1B.

In another alternative example, the present invention comprises compounds of Formula 1C.

Alternatively, compounds of Formula II comprise compounds of Formula 2A and 2B:

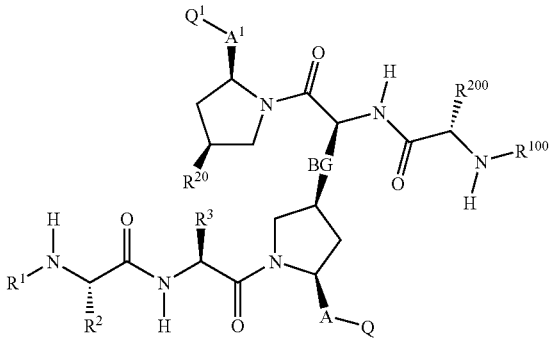

2A

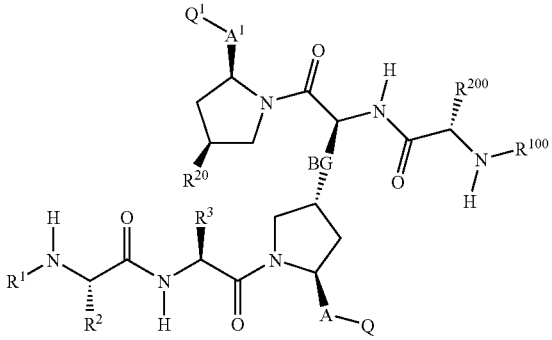

2B wherein BG, A, $A^1$, Q, $Q^1$, $R^1$, $R^{100}$, $R^2$, $R^{200}$ $R^3$, $R^{300}$ and $R^{20}$ are as defined hereinabove and hereinafter.

In one example, the example invention comprises of Formula 2A.

Any and each individual definition of Core as set out herein may be combined with any and each individual definition of A, $A^1$, $R^1$, $R^2$, $R^{100}$, $R^{200}$, $R^3$, $R^{300}$, $R^{20}$, Q, $Q^1$, and BG as set out herein.

BG:

In one subset of the aforesaid compounds, BG is —X-L-$X^1$—.

In one subset, for compounds of Formula I in which BG is —X-L-$X^1$—, the invention comprises compounds of Formula 1a through 1c:

One further subset of the aforesaid compounds comprises compounds of Formula 1.1a through 1.1c:

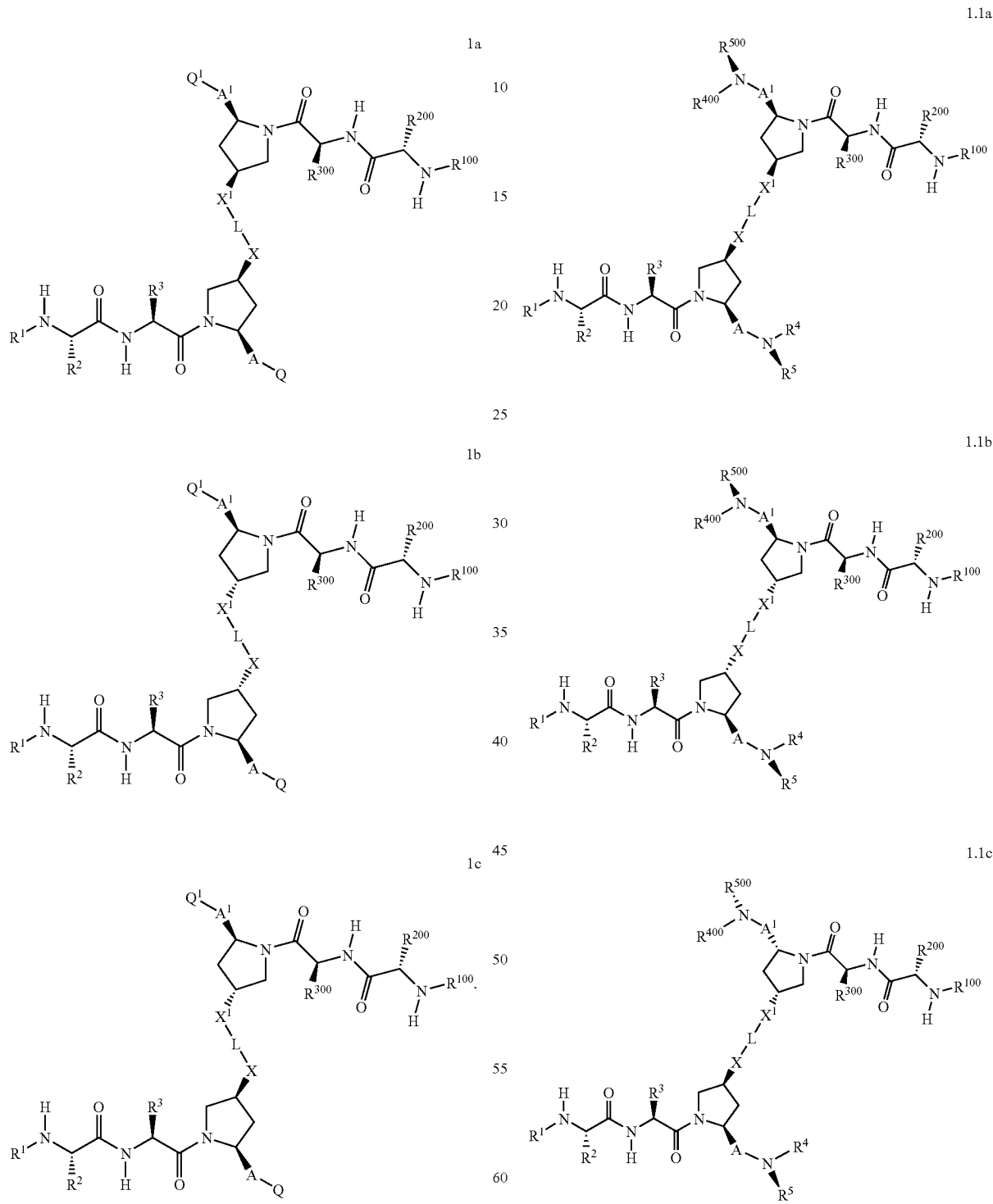

wherein L, X, $X^1$, A, $A^1$, Q, $Q^1$, $R^1$, $R^{100}$, $R^2$, $R^{200}$, $R^3$, and $R^{300}$ are as defined hereinabove and hereinafter.

wherein L, X, $X^1$, A, $A^1$, $R^1$, $R^{100}$, $R^2$, $R^{200}$, $R^3$, $R^{300}$, $R^4$, $R^{400}$, $R^5$ and $R^{500}$ are as defined hereinabove and hereinafter.

In one subset, for compounds of Formula II in which BG is —X-L-X$^1$—, the invention comprises compounds of Formula 2a:

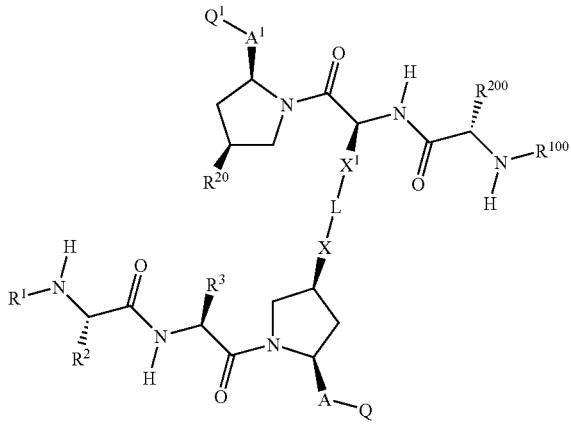

2a wherein L, X, X$^1$, A, A$^1$, Q, Q$^1$, R$^1$, R$^{100}$, R$^2$, R$^{200}$, R$^3$ and R$^{20}$ are as defined hereinabove and hereinafter.

Any and each individual definition of BG as set out herein may be combined with any and each individual definition of Core, R$^1$, R$^2$, R$^{100}$, R$^{200}$, R$^3$, R$^{300}$, A, A$^1$, Q, and Q$^1$ as set out herein.

X and X$^1$:

In one subset of the aforesaid compounds, X and X$^1$ are independently selected from
1) O,
2) NR$^{13}$,
3) S,
4) C$_1$-C$_6$ alkyl-O—,
5) C$_1$-C$_6$ alkyl,
6) 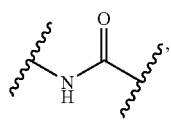
7) 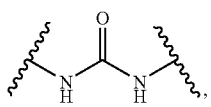
8) 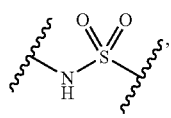
9) 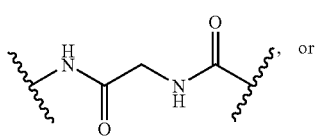, or 10) 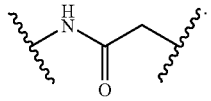

In one example X and X$^1$ are independently selected from:
1) O,
2) 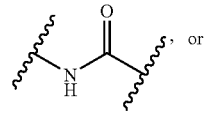, or
3) 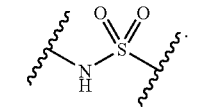

Any and each individual definition of X and X$^1$ as set out herein may be combined with any and each individual definition of Core, L, A, A$^1$, R$^1$, R$^2$, R$^{100}$, R$^{200}$, R$^3$, R$^{300}$, R$^{20}$, Q, Q$^1$, and BG as set out herein.

L:

In one subset of the aforesaid compounds, L is selected from:
1) —C$_1$-C$_{20}$ alkyl-,
2) —C$_3$-C$_7$ cycloalkyl-,
3) -aryl-,
4) -biphenyl-,
5) -heteroaryl-,
6) —C$_1$-C$_6$ alkyl-(C$_2$-C$_4$ alkynyl)-C$_1$-C$_6$ alkyl-,
7) —C$_1$-C$_6$ alkyl-aryl-C$_1$-C$_6$ alkyl-,
8) -aryl-Y-aryl-,
9) 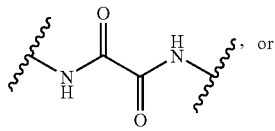, or 10) 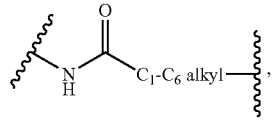, wherein the alkyl and cycloalkyl are optionally substituted with one or more R$^6$ substituents, and the aryl, biphenyl and heteroaryl are optionally substituted with one or more R$^{10}$ substituents.

Typical examples of L include

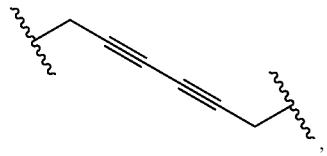,

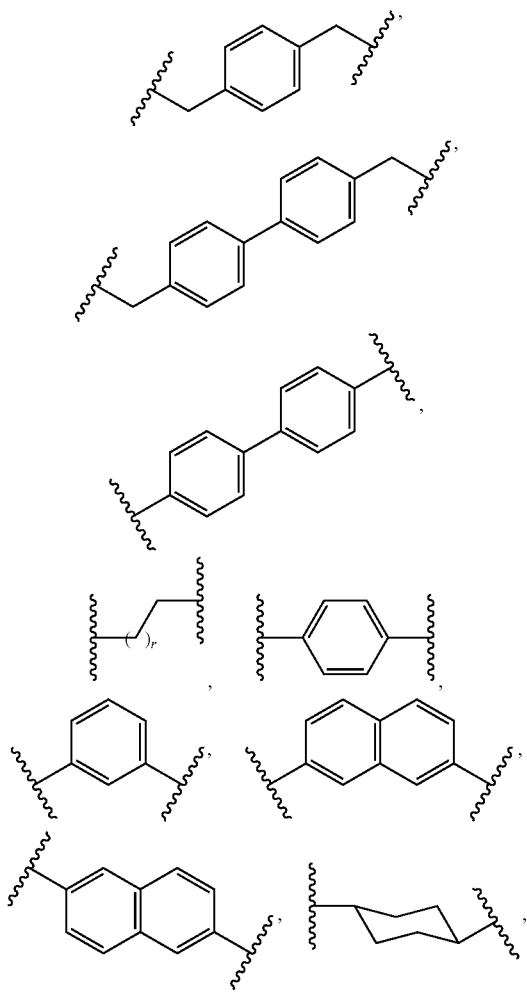

Any and each individual definition of L as set out herein may be combined with any and each individual definition of Core, A, A$^1$, r, R$^1$, R$^2$, Ro, R$^{200}$, R$^3$, R$^{300}$, R$^{20}$, X, X$^1$, Q, or Q$^1$, as set out herein.

r:

In the aforesaid aspect, r is an integer of 1, 2, 3, 4, 5, 6, 7, 8, 9 or 10.

Any and each individual definition of r as set out herein may be combined with any and each individual definition of Core, A, L, A$^1$, R$^1$, R$^2$, R$^{100}$, R$^{200}$, R$^3$, R$^{300}$, R$^{20}$, Q, Q$^1$, X and X$^1$ as set out herein.

More explicitly, the invention comprises compounds of Formula 1.1 through 1.18:

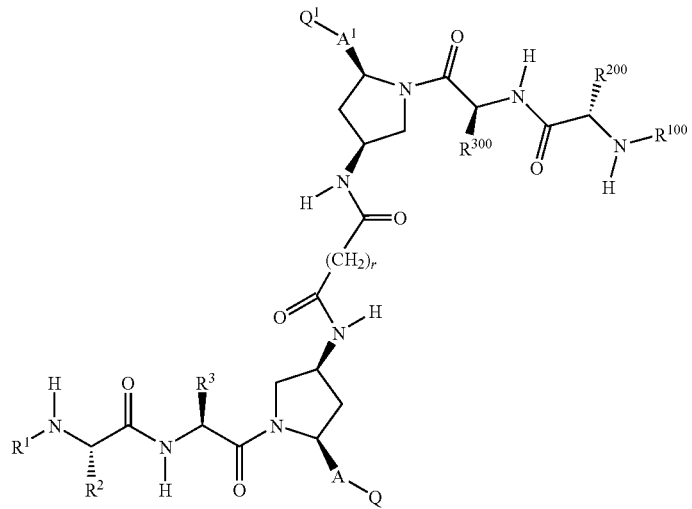
1.2
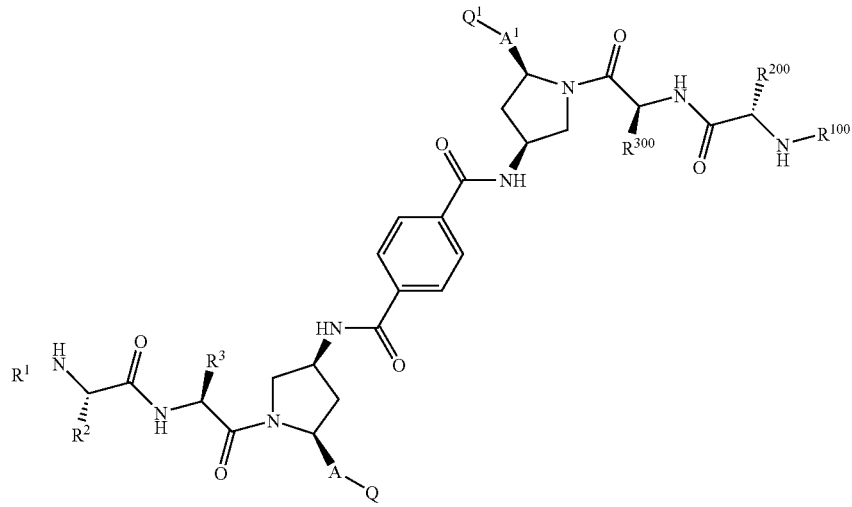
1.3
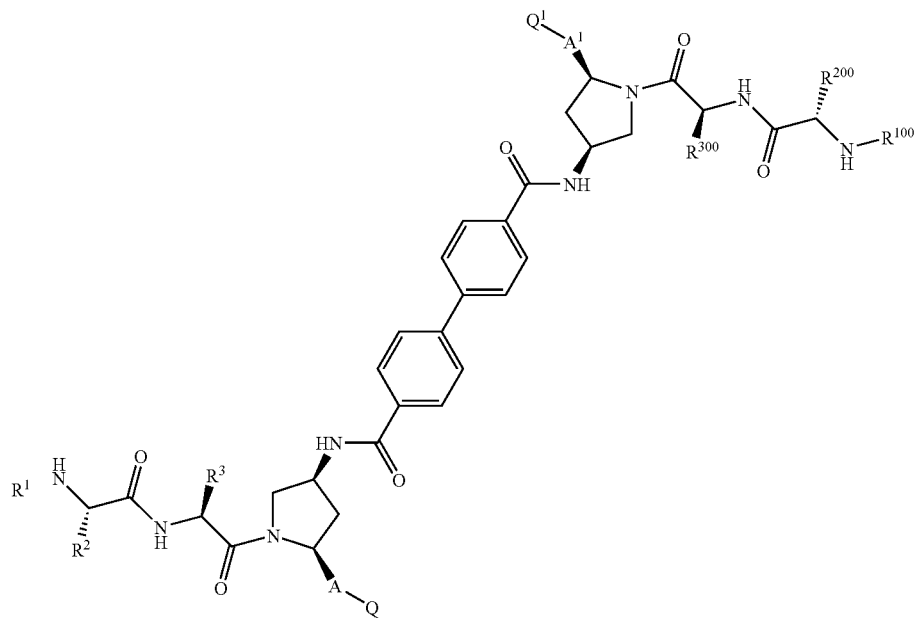
1.4

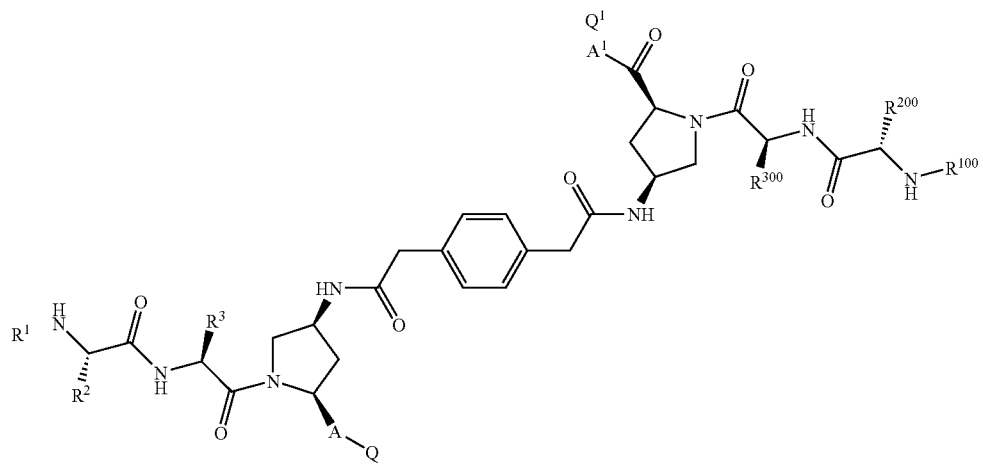
1.5
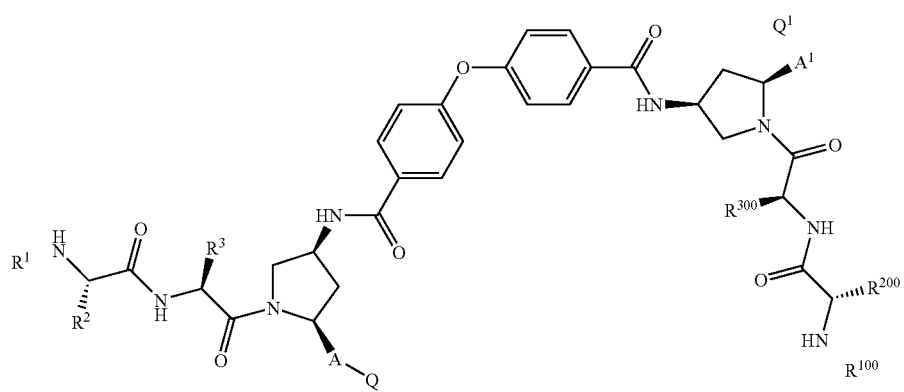
1.6
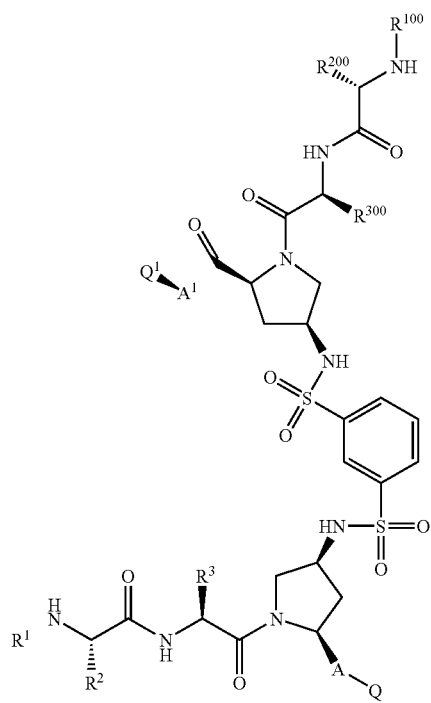
1.7

-continued
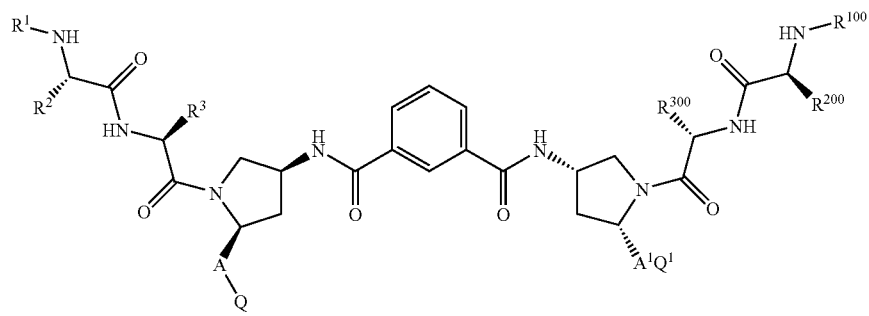
1.8
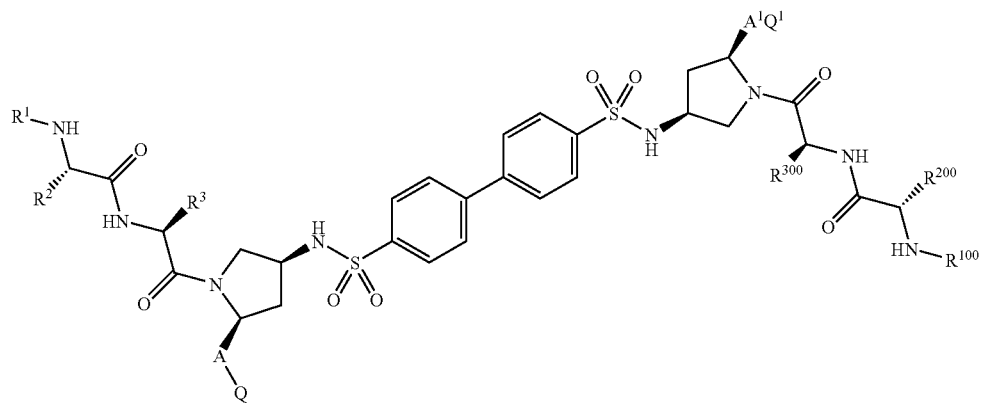
1.9
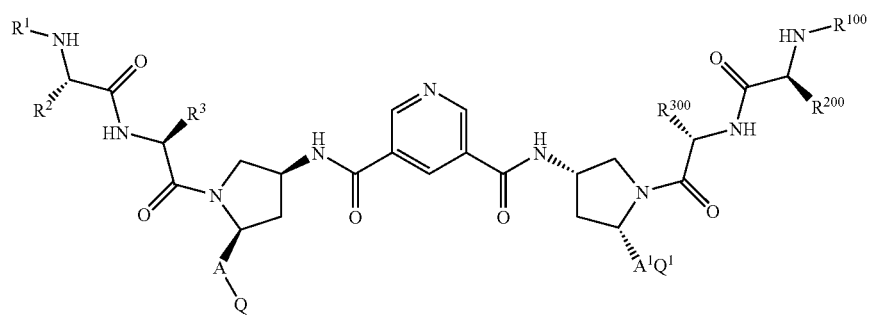
1.10
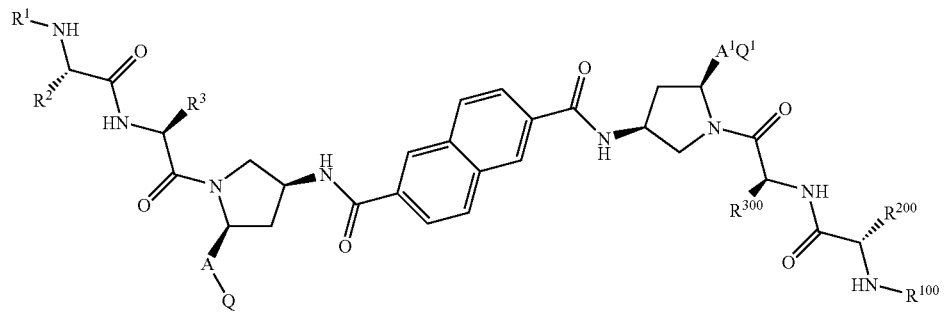
1.11
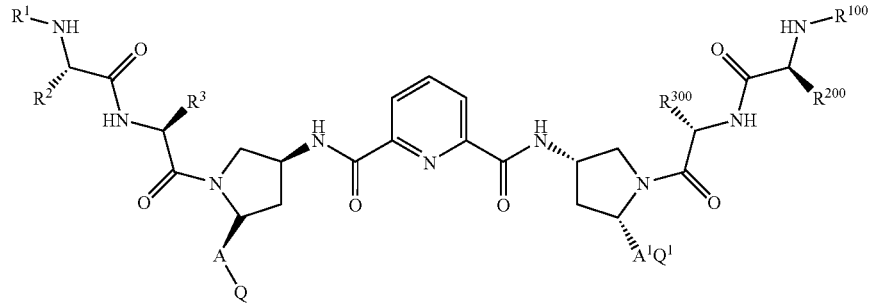
1.12

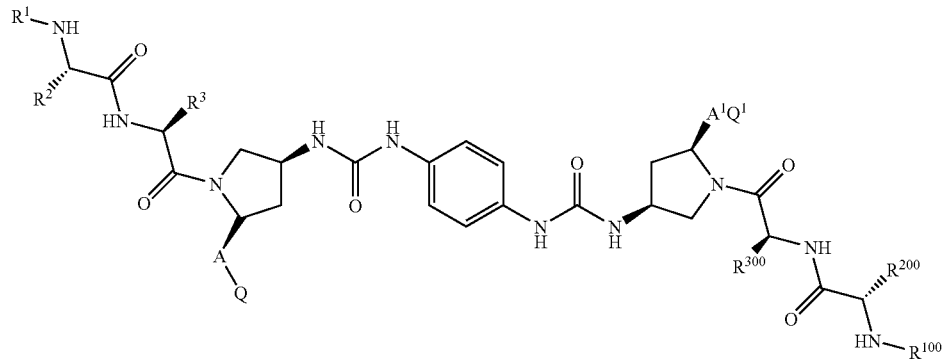
1.13
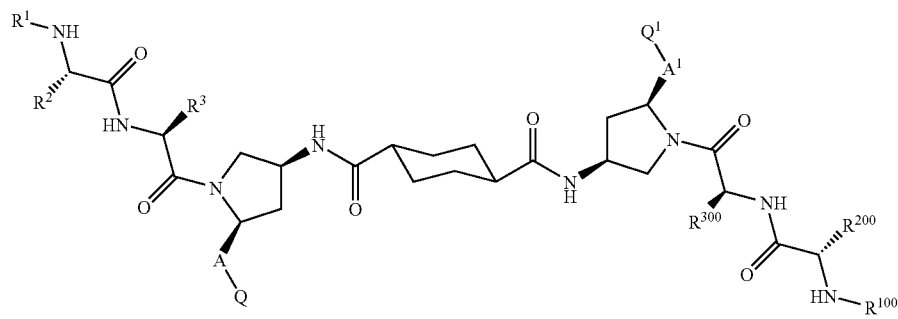
1.14
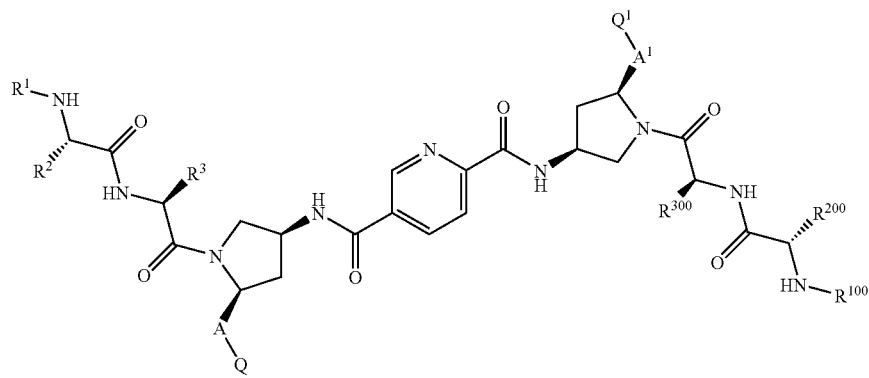
1.15
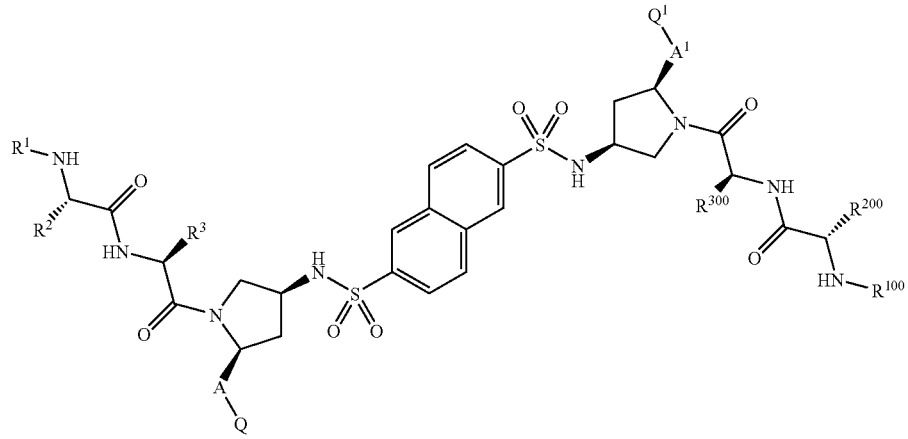
1.16

-continued
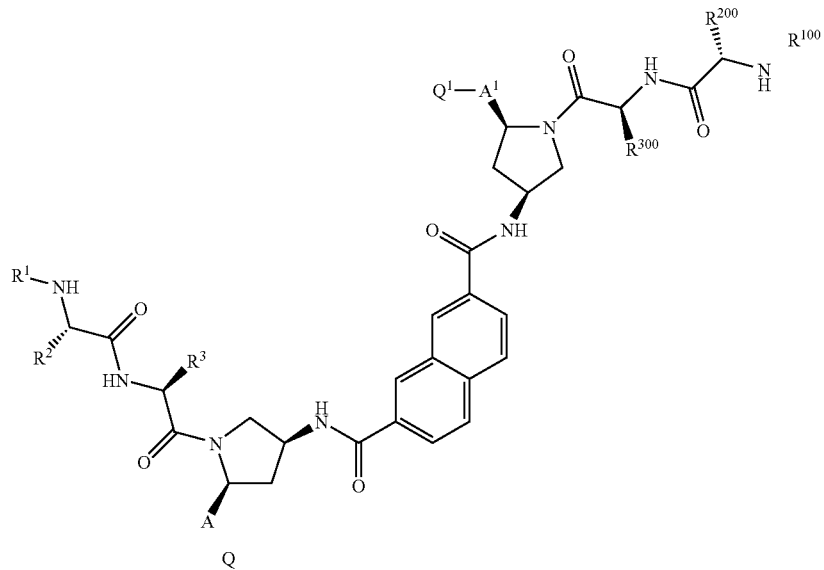
1.17
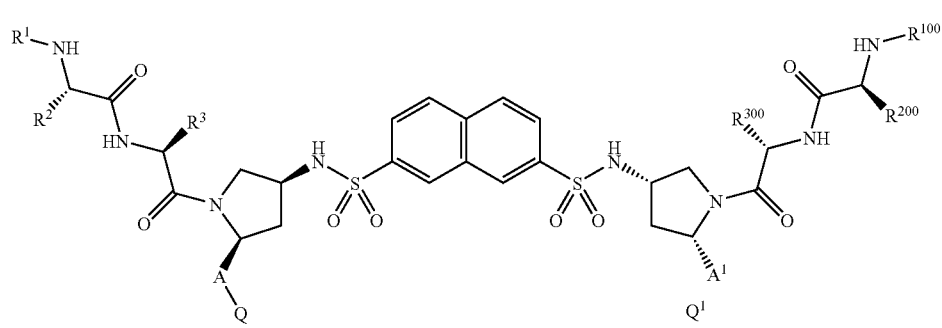
1.18
wherein r, A, A$^1$, Q, Q$^1$, R$^1$, R$^{100}$, R$^2$, R$^{200}$, R$^3$ and R$^{300}$ are as defined hereinabove.
Alternatively more explicitly, the invention comprises compounds of Formula 2.1 and 2.2:
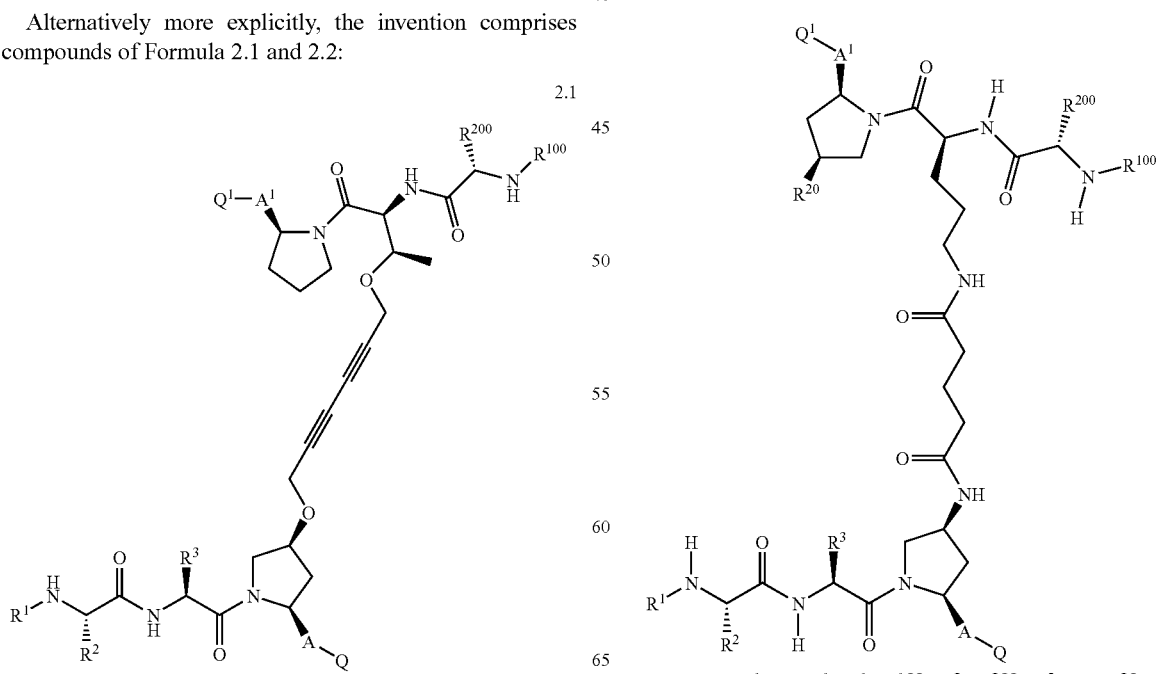
2.1
2.2
wherein A, A$^1$, Q, Q$^1$, R$^1$, R$^{100}$, R$^2$, R$^{200}$, R$^3$ and R$^{20}$ are as defined hereinabove.

$R^1$ and $R^{100}$:

In one subset of the aforesaid compounds $R^1$ and $R^{100}$ are both H.

In one subset of the aforesaid compounds $R^1$ and $R^{100}$ are both $C_1$-$C_6$ alkyl.

In one example, $R^1$ and $R^{100}$ are both $CH_3$.

Any and each individual definition of $R^1$ and $R^{100}$ as set out herein may be combined with any and each individual definition of Core, A, $A^1$, $R^2$, $R^{200}$, $R^3$, $R^{300}$, Q, $Q^1$, B, $B^1$, and BG as set out herein.

$R^2$ and $R^{200}$:

In one subset of the aforesaid compounds $R^2$ and $R^{200}$ are both $C_1$-$C_6$ alkyl optionally substituted with OH.

In one example, $R^2$ and $R^{200}$ are both $CH_3$.
In another example, $R^2$ is $CH_2OH$ and $R^{300}$ is $CH_3$.
In another example, $R^2$ and $R^{200}$ are both $CH_2OH$.
In another example, $R^2$ and $R^{200}$ are both $CH_2CH_3$.

Any and each individual definition of $R^2$ and $R^{200}$ as set out herein may be combined with any and each individual definition of Core, A, $A^1$, $R^1$, $R^{100}$, $R^3$, $R^{300}$, Q, $Q^1$, and BG as set out herein.

$R^3$ and $R^{300}$:

In one subset of compounds of Formula II, $R^3$ and $R^{300}$ are both $C_1$-$C_6$ alkyl.

In one example, $R^3$ and $R^{300}$ are both $C(CH_3)_3$.

In subset of compounds of Formula I, $R^3$ is $C_1$-$C_6$ alkyl. In one example, $R^3$ is $C(CH_3)_3$.

Any and each individual definition of $R^3$ and $R^{300}$ as set out herein may be combined with any and each individual definition of Core, A, $A^1$, $R^1$, $R^{100}$, $R^2$, $R^{200}$, Q, $Q^1$, and BG as set out herein.

Q and $Q^1$:

In one subset of the aforesaid compounds, Q and $Q^1$ are both $NR^4R^5$, wherein $R^4$ and $R^5$ are as defined herein.

Any and each individual definition of Q and Q' as set out herein may be combined with any and each individual definition of Core, A, $A^1$, $R^1$, $R^{100}$, $R^2$, $R^{200}$, $R^3$, $R^{300}$ and BG as set out herein.

$R^4$ and $R^5$:

In one subset of the aforesaid compounds in which A and $A^1$ are both C=O, $R^4$ is H and $R^5$ is selected from
1) $C_1$-$C_6$ alkyl
2) $C_2$-$C_6$ alkenyl,
3) $C_2$-$C_4$ alkynyl,
4) $C_3$-$C_7$ cycloalkyl,
5) $C_3$-$C_7$ cycloalkenyl,
6) aryl,
7) heteroaryl,
8) heterocyclyl, or
9) heterobicyclyl, wherein the alkyl, alkenyl, alkynyl, cycloalkyl, and cycloalkenyl are optionally substituted with one or more R6 substituents; and wherein the aryl, heteroaryl, heterocyclyl, and heterobicyclyl are optionally substituted with one or more $R^{10}$ substituents;

wherein $R^6$ and $R^{10}$ are as defined herein.

In another subset of the above compounds, $R^4$ is H and $R^5$ is selected from:
1) $C_1$-$C_6$ alkyl, or
2) aryl, wherein the alkyl is optionally substituted with one or two $R^6$ substituents; and wherein the aryl is optionally substituted with one $R^{10}$ substituent;

wherein $R^6$ and $R^{10}$ are as defined herein.

Examples of the aforesaid subset include, $R^4$ is H and $R^5$ is selected from the group consisting of:

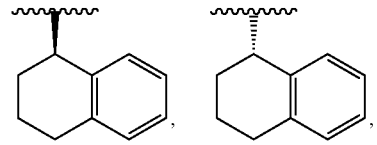

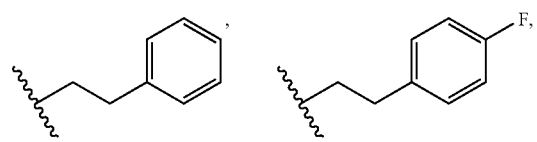

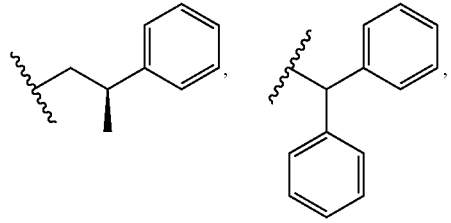

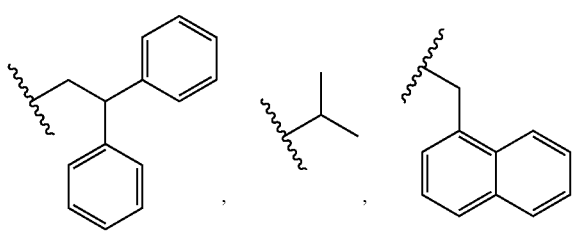

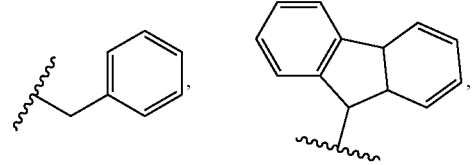

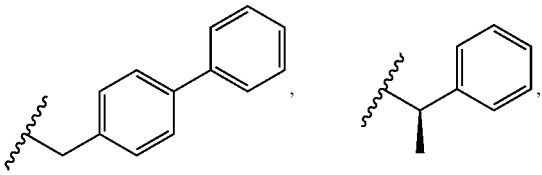

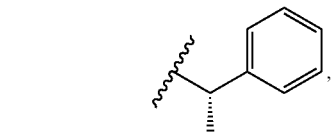

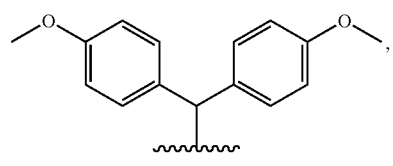

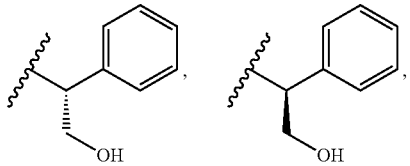

-continued
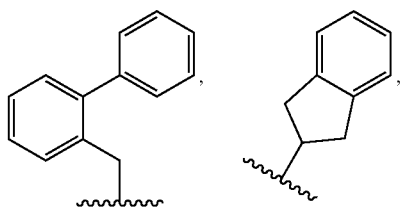,
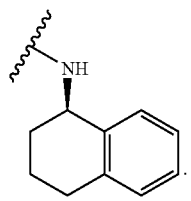,
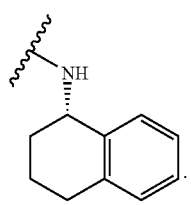, and
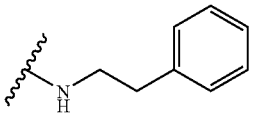.
Therefore, when A and A¹ are both C=O, then Q and Q¹ are both
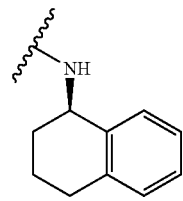.
In another example, Q and Q¹ are both
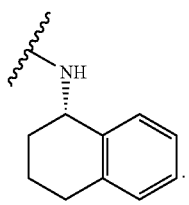.
In another example, Q is
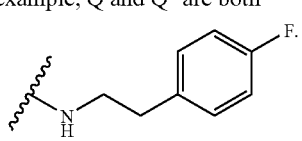
and Q¹ is
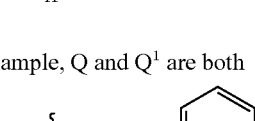.
In another example, Q and Q¹ are both
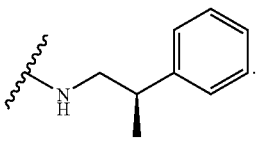.
In another example, Q and Q¹ are both
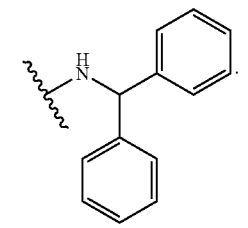.
In another example, Q and Q¹ are both
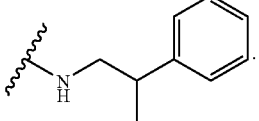.
In another example, Q and Q¹ are both
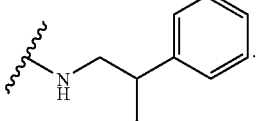.
In another example, Q and Q¹ are both
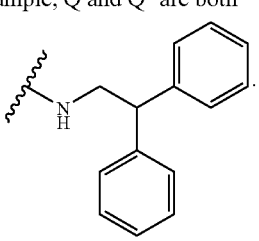.

In another example, Q and Q¹ are both

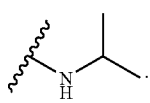

In another example, Q and Q¹ are both

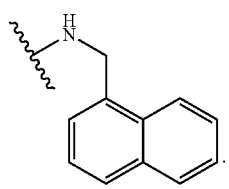

In another example, Q and Q¹ are both

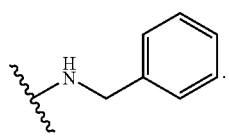

In another example, Q and Q¹ are both

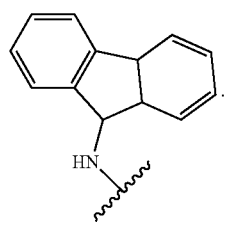

In another example, Q and Q¹ are both

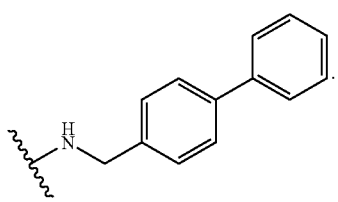

In another example, Q and Q¹ are both

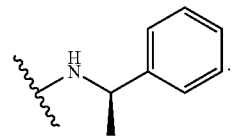

In another example, Q and Q¹ are both

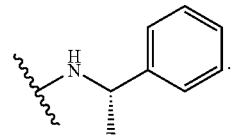

In another example, Q and Q¹ are both

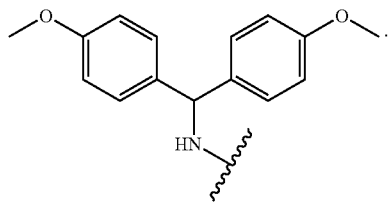

In another example, Q and Q¹ are both

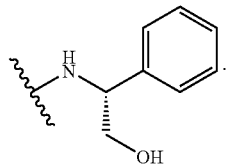

In another example, Q and Q¹ are both

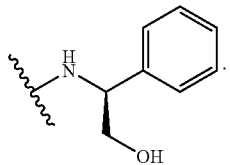

In another example, Q and Q¹ are both

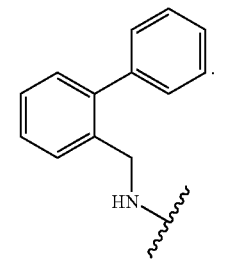

In another example, Q and Q¹ are both

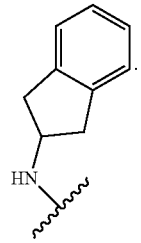

In another example, Q and Q¹ are both

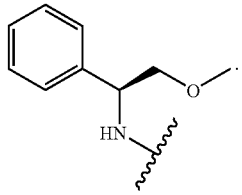

In another example, Q and Q¹ are both

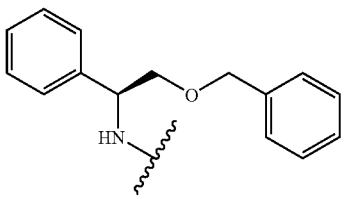

In another example, Q and Q are both

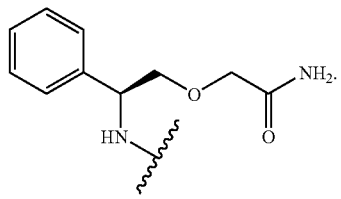

In another example, Q and Q¹ are both

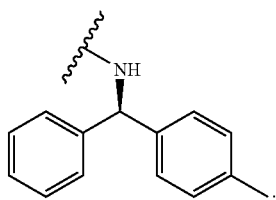

In another example, Q and Q¹ are both

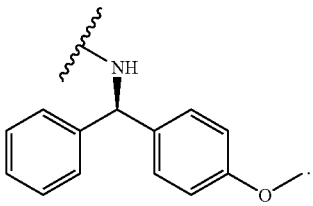

In an alternative subset of the aforesaid compounds in which A and A¹ are both $CH_2$, then $R^4$ and $R^5$ are each independently
1) haloalkyl,
2) $C_1$-$C_6$ alkyl,
3) $C_2$-$C_6$ alkenyl,
4) $C_2$-$C_4$ alkynyl,
5) $C_3$-$C_7$ cycloalkyl,
6) $C_3$-$C_7$ cycloalkenyl,
7) aryl,
8) heteroaryl,
9) heterocyclyl,
10) heterobicyclyl,
11) —C(O)—$R^{11}$,
12) —C(O)O—$R^{11}$,
13) —C(=Y)$NR^8R^9$, or
14) —S(O)$_2$—$R^{11}$, wherein the alkyl, alkenyl, alkynyl, cycloalkyl, and cycloalkenyl are optionally substituted with one or more $R^6$ substituents; and wherein the aryl, heteroaryl, heterocyclyl, and heterobicyclyl are optionally substituted with one or more $R^{10}$ substituents;

wherein Y, $R^6$, $R^8$, $R^9$, $R^{10}$ and $R^{11}$ are as defined herein.

In another subset of the above compounds, $R^4$ and $R^5$ are independently selected from
1) $C_1$-$C_6$ alkyl,
2) —C(O)—$R^{11}$,
3) —C(O)O—$R^{11}$, or
4) —S(O)$_2$—$R^{11}$, wherein the alkyl is substituted with an $R^6$ substituent;

wherein $R^6$ and $R^{11}$ are as defined herein.

In one subset of the aforesaid compounds, $R^4$ is $S(O)_2CH_3$ and $R^5$ is

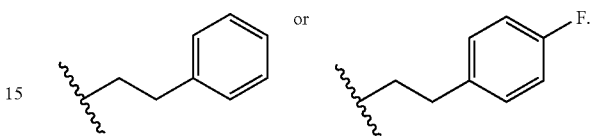

In another subset of the aforesaid compounds, $R^4$ is $C(O)CH_3$ and $R^5$ is

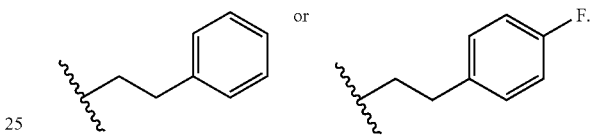

In another subset of the aforesaid compounds, $R^4$ is

and $R^5$ is

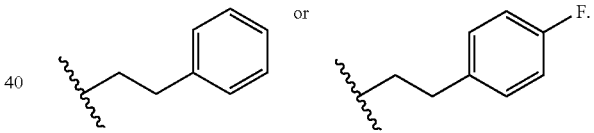

Any and each individual definition of $R^4$ and $R^5$ as set out herein may be combined with any and each individual definition of Core, A, A¹, R¹, $R^{100}$, R², $R^{200}$, R³, $R^{300}$, and BG as set out herein.

$R^{11}$:

In one subset of the aforesaid compounds,
$R^{11}$ is
1) $C_1$-$C_6$ alkyl, or
2) aryl, wherein the alkyl is optionally substituted with one or more $R^6$ substituents; and wherein the aryl is optionally substituted with one or more $R^{10}$ substituents;

wherein $R^6$ and $R^{10}$ are as defined herein.

In one subset of the aforesaid compounds, $R^{11}$ is
1) $C_1$-$C_6$ alkyl optionally substituted with one or two $R^6$ substituents, or
2) phenyl optionally substituted with one $R^{10}$ substituent;

wherein the $R^6$ and the $R^{10}$ substituents are as defined herein.

Any and each individual definition of $R^{11}$ as set out herein may be combined with any and each individual definition of Core, A, A¹, R¹, $R^{100}$, R², $R^{200}$, R⁴, R⁵, R³, $R^{300}$ and BG as set out herein.

$R^6$:

In one subset of the aforesaid compounds, $R^6$ is
1) halogen,
2) $NO_2$,
3) CN,
4) aryl,
5) heteroaryl,
6) heterocyclyl,
7) heterobicyclyl,
8) $OR^7$,
9) $SR^7$, or
10) $NR^8R^9$, wherein the aryl, heteroaryl, heterocyclyl, and heterobicyclyl is optionally substituted with one or more $R^{10}$ substituents;

wherein $R^7$, $R^8$, $R^9$ and $R^{10}$ are as defined herein.

In another subset of the aforesaid compounds, $R^6$ is
1) halogen,
2) aryl, or
3) $NR^8R^9$, wherein the aryl is optionally substituted with one $R^{10}$ substituent;

wherein $R^8$, $R^9$ and $R^{10}$ are as defined herein.

In one subset of the aforesaid compounds, $R^6$ is
1) halogen,
2) phenyl, or
3) $NR^8R^9$, wherein the phenyl is optionally substituted with one $R^{10}$ substituent;

wherein $R^8$ and $R^9$ are as defined herein.

Any and each individual definition of $R^6$ as set out herein may be combined with any and each individual definition of Core, A, $A^1$, $R^1$, $R^{100}$, $R^2$, $R^{200}$, $R^4$, $R^5$, $R^3$, $R^{300}$ and BG as set out herein.

$R^8$ and $R^9$:

In one subset of the aforesaid compounds, $R^8$ and $R^9$ are each independently
1) H,
2) haloalkyl,
3) $C_1$-$C_6$ alkyl,
4) $C_2$-$C_6$ alkenyl,
5) $C_2$-$C_4$ alkynyl,
6) $C_3$-$C_7$ cycloalkyl, or
7) $C_3$-$C_7$ cycloalkenyl, wherein the alkyl, alkenyl, alkynyl, cycloalkyl, cycloalkenyl is optionally substituted with one or more $R^6$ substituents;

wherein the $R^6$ substituents are as defined herein.

In another subset of the aforesaid compounds, $R^8$ and $R^9$ are each independently
1) H, or
2) $C_1$-$C_6$ alkyl, wherein the alkyl is optionally substituted with an aryl.

Any and each individual definition of $R^8$ and $R^9$ as set out herein may be combined with any and each individual definition of Core, A, $A^1$, $R^1$, $R^{100}$, $R^2$, $R^{200}$, $R^4$, $R^5$, $R^3$, $R^{300}$ and BG as set out herein.

$R^{10}$:

In one aspect of the aforesaid compounds, $R^{10}$ is
1) halogen,
2) $NO_2$,
3) CN,
4) haloalkyl,
5) $OR^7$,
6) $NR^8R^9$, or
7) $SR^7$;

wherein $R^7$, $R^8$, and $R^9$ are as defined herein.

In another aspect of the aforesaid compounds, $R^{10}$ is
1) halogen, or
2) $OC_1$-$C_6$ alkyl.

Any and each individual definition of $R^{10}$ as set out herein may be combined with any and each individual definition of Core, A, $A^1$, $R^1$, $R^{100}$, $R^2$, $R^{200}$, $R^4$, $R^5$, $R^3$, $R^{300}$ and BG as set out herein.

Alternatively, the invention provides an isomer, enantiomer, diastereoisomer or tautomer of a compound represented by Formula I or Formula 2:

wherein n is 0 or 1;

m is 0, 1 or 2;

p is 1 or 2;

Y is NH, O or S;

LG is

2) —X-L-$X^1$—;

X and $X^1$ are independently selected from
1) O,
2) $NR^{13}$
3) S,
4) $C_1$-$C_6$ alkyl-O—,
5) $C_1$-$C_6$ alkyl-$NR^{13}$—,
6) $C_1$-$C_6$ alkyl-S—,
7) $C_1$-$C_6$ alkyl-aryl-O—

8) 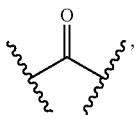

9) 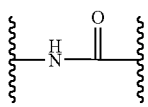

10) 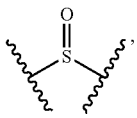

11) 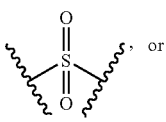, or

12) 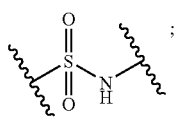;

L is selected from:
1) —$C_1$-$C_{20}$ alkyl-,
2) —$C_2$-$C_6$ alkenyl-,
3) —$C_2$-$C_4$ alkynyl-,
4) —$C_3$-$C_7$ cycloalkyl-,
5) -phenyl-,
6) -biphenyl-,
7) -heteroaryl-,
8) -heterocycyl-,
9) —$C_1$-$C_6$ alkyl-($C_2$-$C_6$ alkenyl) $C_1$-$C_6$ alkyl-,
10) —$C_1$-$C_6$ alkyl-$C_2$-$C_4$ alkynyl)$C_1$-$C_6$ alkyl,
11) —$C_1$-$C_6$ alkyl-$C_3$-$C_7$ cycloalkyl)$C_1$-$C_6$ alkyl,
12) —$C_1$-$C_6$ alkyl-phenyl-$C_1$-$C_6$ alkyl,
13) —$C_1$-$C_6$ alkyl-biphenyl-$C_1$-$C_6$ alkyl,
14) —$C_1$-$C_6$ alkyl-heteroaryl-$C_1$-$C_6$ alkyl,
15) —$C_1$-$C_6$ alkyl heterocycyl-$C_1$-$C_6$ alkyl,
16) —$C_1$-$C_6$ alkyl-O—$C_1$-$C_6$ alkyl,
17) —C(O)-aryl-C(O)—,
18) —C(O)-heteroaryl-C(O)—,
19) —C(O)—($C_1$-$C_6$ alkyl)-aryl-($C_1$-$C_6$ alkyl)-C(O)—,
20) —C(O)— ($C_1$-$C_6$ alkyl)-heteroaryl-($C_1$-$C_6$ alkyl)-C(O)—, or
21) —C(O)— ($C_1$-$C_6$ alkyl)-($C_3$-$C_7$ cycloalkyl) ($C_1$-$C_6$ alkyl)-C(O)—;

Q and $Q^1$ are independently selected from
1) $NR^4R^5$,
2) $OR^{11}$, or
3) $S(O)_mR^{11}$; or Q and $Q^1$ are independently selected from aryl or heteroaryl, being optionally substituted with $R^{12}$ substituents; or Q and $Q^1$ are independently

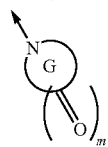

wherein G is a 5, 6 or 7 membered ring which optionally incorporates one or more heteroatoms selected from S, N or O, and which is optionally substituted with one or more $R^{12}$ substituents, the ring being optionally fused with an aryl or a heteroaryl, the aryl and the heteroaryl being optionally substituted with one or more $R^{12}$ substituents;

A and $A^1$ are independently selected from
1) —$CH_2$—,
2) —$CH_2CH_2$—,
3) —CH($C_1$-$C_6$ alkyl),
4) —CH($C_3$-$C_7$ cycloalkyl)-,
5) —$C_3$-$C_7$ cycloalkyl-,
6) —CH($C_1$-$C_6$ alkyl-$C_3$-$C_7$ cycloalkyl)-, or
7) —C(O)—;

$R^1$ and $R^{100}$ are independently selected from
3) H, or
4) $C_1$-$C_6$ alkyl optionally substituted with one or more $R^6$ substituents;

$R^2$ and $R^{200}$ are independently H or $C_1$-$C_6$ alkyl optionally substituted with one or more $R^6$ substituents;

$R^4$ and $R^5$ are independently selected from:
1) H,
2) $C_1$-$C_6$ alkyl,
3) $C_3$-$C_7$ cycloalkyl,
4) haloalkyl,
5) aryl,
6) biphenyl,
7) heteroaryl-aryl,
8) aryl-heteroaryl,
9) aryl-heterocyclyl,
10) heterocyclyl,
11) heteroaryl,
12) heterocyclyl,
13) $C_1$-$C_6$ alkyl-$O_nC(O)$—,
14) haloalkyl-$O_nC(O)$—,
15) $C_3$-$C_7$ cycloalkyl-$O_nC(O)$—,
16) aryl-$O_nC(O)$—,
17) heteroaryl-$O_nC(O)$—,
18) heterocyclyl-$O_nC(O)$—,
19) $R^8R^9NC(=Y)$—,
20) $C_1$-$C_6$ alkyl-$S(O)_2$—,
21) $C_3$-$C_7$ cycloalkyl-$S(O)_2$—,
22) aryl-$S(O)_2$—,
23) heteroaryl-$S(O)_2$—,
24) heterocyclyl-$S(O)_2$—,
25) fused aryl-$C_3$-$C_7$ cycloalkyl—,
26) fused heteroaryl-$C_3$-$C_7$ cycloalkyl—,
27) fused aryl-heterocyclyl—,
28) fused heteroraryl-heterocyclyl—,
29) fused aryl-$C_3$-$C_7$ cycloalkyl-$O_nC(O)$—,
30) fused heteroaryl-$C_3$-$C_7$ cycloalkyl-$O_nC(O)$—,
31) fused aryl-heterocyclyl-$O_nC(O)$—, or
32) fused heteroaryl-heterocyclyl-$O_nC(O)$—, wherein the alkyl and the cycloalkyl are optionally substituted with one or more $R^6$ substituents, and the aryl, the heteroaryl and the heterocyclyl are optionally substituted with one or more $R^{10}$ substituents;

$R^6$ is independently selected from:
1) halogen,
2) $C_1$-$C_6$ alkyl,
3) $C_3$-$C_7$ cycloalkyl,
4) haloalkyl,
5) aryl,
6) heteroaryl,
7) heterocyclyl,
8) $OR^7$,
9) $S(O)_m R^7$,
10) $NR^8 R^9$,
11) $COR^7$,
12) $C(O)OR^7$,
13) $OC(O)R^7$,
14) $SC(O)R^7$,
15) $CONR^8 R^9$,
16) $S(O)_2 NR^8 R^9$, or
17) $N(=Y)NR^8 R^9$, wherein the aryl, the heteroaryl and the heterocylyl are optionally substituted with one or more $R^{10}$ substituents;
$R^7$ is independently selected from:
1) H,
2) $C_1$-$C_6$ alkyl,
3) $C_3$-$C_7$ cycloalkyl,
4) haloalkyl,
5) aryl,
6) heteroaryl,
7) heterocyclyl,
8) $C(=Y)NR^8 R^9$, or
9) $C_1$-$C_6$ alkyl-$C_2$-$C_4$ alkynyl, wherein the aryl, heteroaryl, and heterocyclyl are optionally substituted with one or more $R^{10}$;
$R^8$ and $R^9$ are independently selected from:
1) H,
2) $C_1$-$C_6$ alkyl,
3) $C_3$-$C_7$ cycloalkyl,
4) haloalkyl,
5) aryl,
6) heteroaryl,
7) heterocyclyl,
8) $COC_1$-$C_6$ alkyl,
9) $COC_3$-$C_3$ cycloalkyl
10) CO-aryl,
11) CO-heteroaryl,
12) CO-heterocyclyl,
13) $C(O)Y$—$C_1$-$C_6$ alkyl,
14) $C(O)Y$—$C_3$-$C_3$ cycloalkyl
15) $C(O)Y$-aryl,
16) $C(O)Y$-heteroaryl, or
17) $C(O)Y$ heterocyclyl, wherein the aryl, the heteroaryl and the heterocyclyl are optionally substituted with one or more $R^{10}$ substituents;

or $R^8$ and $R^9$ together with the nitrogen atom to which they are bonded form a five, six or seven membered heterocyclic ring optionally substituted with one or more $R^6$ substituents;
$R^{10}$ is independently selected from:
1) halogen,
2) $NO_2$,
3) CN,
4) $C_1$-$C_6$ alkyl,
5) haloalkyl,
6) $C_3$-$C_7$ cycloalkyl,
7) $OR^7$,
8) $NR^8 R^9$,
9) $SR^7$,
10) $COR^7$,
11) $CO_2 R^7$,
12) $S(O)_m R^7$,
13) $CONR^8 R^9$, or
14) $S(O)_2 NR^8 R^9$, wherein the alkyl is optionally substituted with one or more $R^6$ substituents;
$R^{11}$ is independently selected from
1) $C_1$-$C_6$ alkyl,
2) $C_3$-$C_7$ cycloalkyl,
3) aryl,
4) heteroaryl, or
5) heterocyclyl, wherein the alkyl and the cycloalkyl are optionally substituted with one or more $R^6$ substituents, and the aryl, the heteroaryl and the heterocyclyl are optionally substituted with one or more $R^{10}$ substituents;
$R^{12}$ is independently selected from
1) $C_1$-$C_6$ alkyl,
2) $C_3$-$C_7$ cycloalkyl,
3) haloalkyl,
4) aryl,
5) heteroaryl,
6) heterocyclyl,
7) $C_1$-$C_6$ alkyl-$O_n C(O)$—,
8) haloalkyl-$O_n C(O)$—,
9) $C_3$-$C_7$ cycloalkyl-$O_n C(O)$—,
10) aryl-$O_n C(O)$—,
11) heteroaryl-$O_n C(O)$—,
12) heterocyclyl-$O_n C(O)$—,
13) $R^8 R^9 NC(O)$—,
14) $C_1$-$C_6$ alkyl-$S(O)_m$—,
15) $C_3$-$C_7$ cycloalkyl-$S(O)_m$—,
16) aryl-$S(O)_m$—,
17) heteroaryl-$S(O)_m$—,
18) heterocyclyl-$S(O)_m$—,
19) fused aryl-$C_3$-$C_7$ cycloalkyl,
20) fused heteroaryl-$C_3$-$C_7$ cycloalkyl, or
21) $C(=Y)$—$NR^8 R^9$, wherein the alkyl and the cycloalkyl are optionally substituted with one or more $R^6$ substituents, and the aryl, the heteroaryl and the heterocyclyl are optionally substituted with one or more $R^{10}$ substituents;
$R^{13}$ is
1) H,
2) $C_1$-$C_6$ alkyl,
3) $C_3$-$C_7$ cycloalkyl,
4) haloalkyl,
5) aryl,
6) heteroaryl,
7) heterocyclyl,
8) $C_1$-$C_6$ alkyl-$O_n C(O)$—,
9) haloalkyl-$O_n C(O)$—,
10) $C_3$-$C_7$ cycloalkyl-$O_n C(O)$',
11) aryl-$O_n C(O)$—,
12) heteroaryl-$O_n C(O)$—, or
13) heterocyclyl-$O_n C(O)$—;

or a prodrug, or a pharmaceutically acceptable salt, or labeled with a detectable label or an affinity tag thereof.

If any variable, such as $R^6$, $R^{600}$, $R^{10}$, $R^{1000}$ and the like, occurs more than one time in any constituent structure, the definition of the variable at each occurrence is independent at every other occurrence. If a substituent is itself substituted with one or more substituents, it is to be understood that that the one or more substituents may be attached to the same carbon atom or different carbon atoms. Combinations of substituents and variables defined herein are allowed only if they produce chemically stable compounds.

One skilled in the art will understand that substitution patterns and substituents on compounds of the present invention may be selected to provide compounds that are chemically stable and can be readily synthesized using the chemistry set forth in the examples and chemistry techniques well known in the art using readily available starting materials.

It is to be understood that many substituents or groups described herein have functional group equivalents, which means that the group or substituent may be replaced by another group or substituent that has similar electronic, hybridization or bonding properties.

Definitions

Unless otherwise specified, the following definitions apply:

The singular forms "a", "an" and "the" include corresponding plural references unless the context clearly dictates otherwise.

As used herein, the term "comprising" is intended to mean that the list of elements following the word "comprising" are required or mandatory but that other elements are optional and may or may not be present.

As used herein, the term "consisting of" is intended to mean including and limited to whatever follows the phrase "consisting of". Thus the phrase "consisting of" indicates that the listed elements are required or mandatory and that no other elements may be present.

As used herein, the term "alkyl" is intended to include both branched and straight chain saturated aliphatic hydrocarbon groups having the specified number of carbon atoms, for example, $C_1$-$C_6$ as in $C_1$-$C_6$— alkyl is defined as including groups having 1, 2, 3, 4, 5 or 6 carbons in a linear or branched arrangement, and $C_1$-$C_4$ as in $C_1$-$C_4$ alkyl is defined as including groups having 1, 2, 3, or 4 carbons in a linear or branched arrangement, and for example, $C_1$-$C_{20}$ as in $C_1$-$C_{20}$— alkyl is defined as including groups having 1, 2, 3, 4, 5, 6, 7, 8, 9, 10, 11, 12, 13, 14, 15, 16, 17, 18, 19 or 20 carbons in a linear or branched arrangement, Examples of $C_1$-$C_6$-alkyl and $C_1$-$C_4$ alkyl as defined above include, but are not limited to, methyl, ethyl, n-propyl, i-propyl, n-butyl, t-butyl, i-butyl, pentyl and hexyl.

As used herein, the term, "alkenyl" is intended to mean unsaturated straight or branched chain hydrocarbon groups having the specified number of carbon atoms therein, and in which at least two of the carbon atoms are bonded to each other by a double bond, and having either E or Z regeochemistry and combinations thereof. For example, $C_2$-$C_6$ as in $C_2$-$C_6$ alkenyl is defined as including groups having 2, 3, 4, 5, or 6 carbons in a linear or branched arrangement, at least two of the carbon atoms being bonded together by a double bond. Examples of $C_2$-$C_6$ alkenyl include ethenyl (vinyl), 1-propenyl, 2-propenyl, 1-butenyl and the like.

As used herein, the term "alkynyl" is intended to mean unsaturated, straight chain hydrocarbon groups having the specified number of carbon atoms therein and in which at least two carbon atoms are bonded together by a triple bond. For example $C_2$-$C_4$ as in $C_2$-$C_4$ alkynyl is defined as including groups having 2, 3, or 4 carbon atoms in a chain, at least two of the carbon atoms being bonded together by a triple bond. Examples of such alkynyls include ethynyl, 1-propynyl, 2-propynyl and the like.

As used herein, the term "cycloalkyl" is intended to mean a monocyclic saturated aliphatic hydrocarbon group having the specified number of carbon atoms therein, for example, $C_3$-$C_7$ as in $C_3$-$C_7$ cycloalkyl is defined as including groups having 3, 4, 5, 6, or 7 carbons in a monocyclic arrangement. Examples of $C_3$-$C_7$ cycloalkyl as defined above include, but are not limited to, cyclopropyl, cyclobutyl, cyclopentyl, cyclohexyl and cycloheptyl.

As used herein, the term "cycloalkenyl" is intended to mean a monocyclic saturated aliphatic hydrocarbon group having the specified number of carbon atoms therein, for example, $C_3$-$C_7$ as in $C_3$-$C_7$ cycloalkenyl is defined as including groups having 3, 4, 5, 6, or 7 carbons in a monocyclic arrangement. Examples of $C_3$-$C_7$ cycloalkenyl as defined above include, but are not limited to, cyclopentenyl, and cyclohexenyl.

As used herein, the term "halo" or "halogen" is intended to mean fluorine, chlorine, bromine and iodine.

As used herein, the term "haloalkyl" is intended to mean an alkyl as defined above, in which each hydrogen atom may be successively replaced by a halogen atom. Examples of haloalkyls include, but are not limited to, $CH_2F$, $CHF_2$ and $CF_3$.

As used herein, the term "aryl", either alone or in combination with another radical, means a carbocyclic aromatic monocyclic group containing 6 carbon atoms which may be further fused to a second 5- or 6-membered carbocyclic group which may be aromatic, saturated or unsaturated. Aryl includes, but is not limited to, phenyl, indanyl, 1-naphthyl, 2-naphthyl and tetrahydronaphthyl. The aryls may be connected to another group either at a suitable position on the cycloalkyl ring or the aromatic ring. For example:

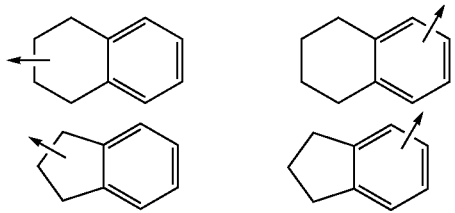

Arrowed lines drawn from the ring system indicate that the bond may be attached to any of the suitable ring atoms.

As used herein, the term "biphenyl" is intended to mean two phenyl groups bonded together at any one of the available sites on the phenyl ring. For example:

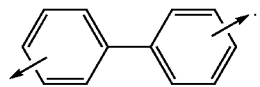

As used herein, the term "heteroaryl" is intended to mean a monocyclic or bicyclic ring system of up to ten atoms, wherein at least one ring is aromatic, and contains from 1 to 4 hetero atoms selected from the group consisting of O, N, and S. The heteroaryl substituent may be attached either via a ring carbon atom or one of the heteroatoms. Examples of heteroaryl groups include, but are not limited to thienyl, benzimidazolyl, benzo[b]thienyl, furyl, benzofuranyl, pyranyl, isobenzofuranyl, chromenyl, xanthenyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalazinyl, napthyridinyl, quinoxalinyl, quinazolinyl, cinnolinyl, pteridinyl, isothiazolyl, isochromanyl, chromanyl, isoxazolyl, furazanyl, indolinyl, isoindolinyl, thiazolo[4,5-b]-pyridine, and fluoroscein derivatives such as:

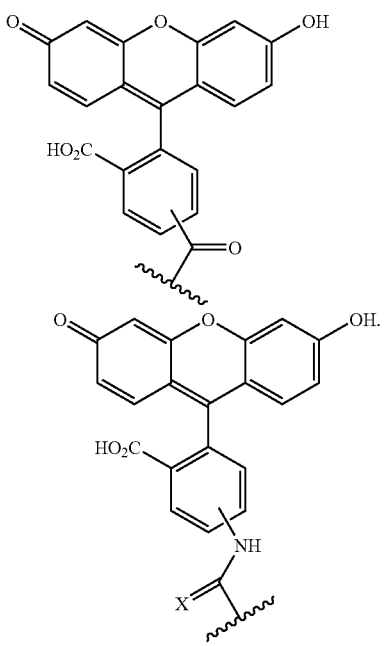

or

As used herein, the term "heterocycle", "heterocyclic" or "heterocyclyl" is intended to mean a 5, 6, or 7 membered non-aromatic ring system containing from 1 to 4 heteroatoms selected from the group consisting of O, N and S. Examples of heterocycles include, but are not limited to pyrrolidinyl, tetrahydrofuranyl, piperidyl, pyrrolinyl, piperazinyl, imidazolidinyl, morpholinyl, imidazolinyl, pyrazolidinyl, pyrazolinyl, and

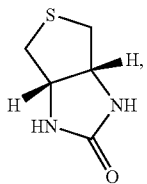

As used herein, the term "heterobicycle" either alone or in combination with another radical, is intended to mean a heterocycle as defined above fused to another cycle, be it a heterocycle, an aryl or any other cycle defined herein. Examples of such heterobicycles include, but are not limited to, coumarin, benzo[d][1,3]dioxole, 2,3-dihydrobenzo[b][1,4]dioxine and 3,4-dihydro-2H-benzo[b][1,4]dioxepine.

As used herein, the term "heteroaryl" is intended to mean a monocyclic or bicyclic ring system of up to ten atoms, wherein at least one ring is aromatic, and contains from 1 to 4 hetero atoms selected from the group consisting of O, N, and S. The heteroaryl substituent may be attached either via a ring carbon atom or one of the heteroatoms. Examples of heteroaryl groups include, but are not limited to thienyl, benzimidazolyl, benzo[b]thienyl, furyl, benzofuranyl, pyranyl, isobenzofuranyl, chromenyl, xanthenyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalazinyl, napthyridinyl, quinoxalinyl, quinazolinyl, cinnolinyl, pteridinyl, isothiazolyl, isochromanyl, chromanyl, isoxazolyl, furazanyl, indolinyl, and isoindolinyl, As used herein, the term "heterocycle", "heterocyclic" or "heterocyclyl" is intended to mean a 5, 6, or 7 membered non-aromatic ring system containing from 1 to 4 heteroatoms selected from the group consisting of O, N and S. Examples of heterocycles include, but are not limited to pyrrolidinyl, tetrahydrofuranyl, piperidyl, pyrrolinyl, piperazinyl, imidazolidinyl, morpholinyl, imidazolinyl, pyrazolidinyl, and pyrazolinyl, As used herein, the term "heteroatom" is intended to mean O, S or N.

As used herein, the term "actived diacid" is intended to mean a diacid wherein the carboxylic acid moieties have been transformed to, for example, but not limited to, acid halides, a succinate esters, or HOBt esters, either in situ or in a separate synthetic step. For example, succinyl chloride and terephthaloyl chloride are examples of "diacid chlorides". HOBt esters can be formed in situ by the treatment of a diacid with a dehydrating agent such as DCC, EDC, HBTU, or others, a base such as DIPEA, and HOBt in an appropriate solvent. The reaction of an activated diacid with an amine will result in the conversion of the acid functionality to an amide functionality.

As used herein, the term "detectable label" is intended to mean a group that may be linked to a compound of the present invention to produce a probe or to an IAP BIR domain, such that when the probe is associated with the BIR domain, the label allows either direct or indirect recognition of the probe so that it may be detected, measured and quantified.

As used herein, the term "affinity tag" is intended to mean a ligand or group, which is linked to either a compound of the present invention or to an IAP BIR domain to allow another compound to be extracted from a solution to which the ligand or group is attached.

As used herein, the term "probe" is intended to mean a compound of Formula I which is labeled with either a detectable label or an affinity tag, and which is capable of binding, either covalently or non-covalently, to an IAP BIR domain. When, for example, the probe is non-covalently bound, it may be displaced by a test compound. When, for example, the probe is bound covalently, it may be used to form cross-linked adducts, which may be quantified and inhibited by a test compound.

As used herein, the term "optionally substituted with one or more substituents" or its equivalent term "optionally substituted with at least one substituent" is intended to mean that the subsequently described event of circumstances may or may not occur, and that the description includes instances where the event or circumstance occurs and instances in which it does not. The definition is intended to mean from zero to five substituents.

If the substituents themselves are incompatible with the synthetic methods of the present invention, the substituent may be protected with a suitable protecting group (PG) that is stable to the reaction conditions used in these methods. The protecting group may be removed at a suitable point in the reaction sequence of the method to provide a desired intermediate or target compound. Suitable protecting groups and the methods for protecting and de-protecting different substituents using such suitable protecting groups are well known to those skilled in the art; examples of which may be found in T. Greene and P. Wuts, Protecting Groups in Chemical Synthesis (3$^{rd}$ ed.), John Wiley & Sons, NY (1999), which is incorporated herein by reference in its entirety. Examples of protecting groups used throughout include, but are not limited to Fmoc, Bn, Boc, CBz and COCF$_3$. In some instances, a substituent may be specifically selected to be reactive under the reaction conditions used in the methods of this invention. Under these circumstances, the reaction conditions convert the selected substituent into another substituent that is either useful in an intermediate compound in the methods of this invention or is a desired substituent in a target compound.

Abbreviations for α-amino acids used throughout are as follows:

| Amino acid | Abbreviation |
|---|---|
| α-Amino butyric acid | Abu |
| Alanine | Ala |
| Arginine | Arg |
| Aspartic acid | Asp |
| Asparagine | Asn |
| Cysteine | Cys |
| Glutamic acid | Glu |
| Gutamine | Gln |
| Glycine | Gly |
| Isoleucine | Ile |
| Histidine | His |
| Leucine | Leu |
| Lysine | Lys |
| Methionine | Met |
| Phenylalanine | Phe |
| Proline | Pro |
| Serine | Ser |
| Threonine | Thr |
| Tryptophan | Trp |
| Tyrosine | Tyr |
| Valine | Val |

As used herein, the term "residue" when referring to α-amino acids is intended to mean a radical derived from the corresponding α-amino acid by eliminating the hydroxyl of the carboxy group and one hydrogen of the α-amino group. For example, the terms Gln, Ala, Gly, Ile, Arg, Asp, Phe, Ser, Leu, Cys, Asn, and Tyr represent the residues of L-glutamine, L-alanine, glycine, L-isoleucine, L-arginine, L-aspartic acid, L-phenylalanine, L-serine, L-leucine, L-cysteine, L-asparagine, and L-tyrosine, respectively.

As used herein, the term "subject" is intended to mean humans and non-human mammals such as primates, cats, dogs, swine, cattle, sheep, goats, horses, rabbits, rats, mice and the like.

As used herein, the term "prodrug" is intended to mean a compound that may be converted under physiological conditions or by solvolysis to a biologically active compound of the present invention. Thus, the term "prodrug" refers to a precursor of a compound of the invention that is pharmaceutically acceptable. A prodrug may be inactive or display limited activity when administered to a subject in need thereof, but is converted in vivo to an active compound of the present invention. Typically, prodrugs are transformed in vivo to yield the compound of the invention, for example, by hydrolysis in blood or other organs by enzymatic processing. The prodrug compound often offers advantages of solubility, tissue compatibility or delayed release in the subject (see, Bundgard, H., Design of Prodrugs (1985), pp. 7-9, 21-24 (Elsevier, Amsterdam). The definition of prodrug includes any covalently bonded carriers which release the active compound of the invention in vivo when such prodrug is administered to a subject. Prodrugs of a compound of the present invention may be prepared by modifying functional groups present in the compound of the invention in such a way that the modifications are cleaved, either in routine manipulation or in vivo, to a parent compound of the invention.

As used herein, the term "pharmaceutically acceptable carrier, diluent or excipient" is intended to mean, without limitation, any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, emulsifier, or encapsulating agent, such as a liposome, cyclodextrins, encapsulating polymeric delivery systems or polyethyleneglycol matrix, which is acceptable for use in the subject, preferably humans.

As used herein, the term "pharmaceutically acceptable salt" is intended to mean both acid and base addition salts.

As used herein, the term "pharmaceutically acceptable acid addition salt" is intended to mean those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid and the like, and organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

As used herein, the term "pharmaceutically acceptable base addition salt" is intended to mean those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like.

As used herein, the term "BIR domain binding" is intended to mean the action of a compound of the present invention upon an IAP BIR domain, which blocks or diminishes the binding of IAPs to BIR binding proteins or is involved in displacing BIR binding proteins from an IAP. Examples of BIR binding proteins include, but are not limited to, caspases and mitochondrially derived BIR binding proteins such as Smac, Omi/WTR2A and the like.

As used herein, the term "insufficient apoptosis" is intended to mean a state wherein a disease is caused or continues because cells deleterious to the subject have not apoptosed. This includes, but is not limited to, cancer cells that survive in a subject without treatment, cancer cells that survive in a subject during or following anti-cancer treatment, or immune cells whose action is deleterious to the subject, and includes, neutrophils, monocytes and auto-reactive T-cells.

As used herein, the term "therapeutically effective amount" is intended to mean an amount of a compound of Formula I or II which, when administered to a subject is sufficient to effect treatment for a disease-state associated with insufficient apoptosis. The amount of the compound of Formula I will vary depending on the compound, the condition and its severity, and the age of the subject to be treated, but can be determined routinely by one of ordinary skill in the art having regard to his own knowledge and to this disclosure.

As used herein, the term "treating" or "treatment" is intended to mean treatment of a disease-state associated with insufficient apoptosis, as disclosed herein, in a subject, and includes: (i) preventing a disease or condition associated with insufficient apoptosis from occurring in a subject, in particular, when such mammal is predisposed to the disease or condition but has not yet been diagnosed as having it; (ii) inhibiting a disease or condition associated with insufficient apoptosis, i.e., arresting its development; or (iii) relieving a disease or condition associated with insufficient apoptosis, i.e., causing regression of the condition.

As used herein, the term "treating cancer" is intended to mean the administration of a pharmaceutical composition of the present invention to a subject, preferably a human, which is afflicted with cancer to cause an alleviation of the cancer by killing, inhibiting the growth, or inhibiting the metastasis of the cancer cells.

As used herein, the term "preventing disease" is intended to mean, in the case of cancer, the post-surgical, post-chemotherapy or post-radiotherapy administration of a pharmaceutical composition of the present invention to a subject, preferably a human, which was afflicted with cancer to prevent the regrowth of the cancer by killing, inhibiting the growth, or inhibiting the metastasis of any remaining cancer cells. Also included in this definition is the prevention of prosurvival conditions that lead to diseases such as asthma, MS and the like.

As used herein, the term "synergistic effect" is intended to mean that the effect achieved with the combination of the compounds of the present invention and either the chemotherapeutic agents or death receptor agonists of the invention is greater than the effect which is obtained with only one of the compounds, agents or agonists, or advantageously the effect which is obtained with the combination of the above compounds, agents or agonists is greater than the addition of the effects obtained with each of the compounds, agents or agonists used separately. Such synergy enables smaller doses to be given.

As used herein, the term "apoptosis" or "programmed cell death" is intended to mean the regulated process of cell death wherein a dying cell displays a set of well-characterized biochemical hallmarks that include cell membrane blebbing, cell soma shrinkage, chromatin condensation, and DNA laddering, as well as any caspase-mediated cell death.

As used herein, the term "BIR domain" or "BIR" are used interchangeably throughout and are intended to mean a domain which is characterized by a number of invariant amino acid residue including conserved cysteines and one conserved hisitidine residue within the sequence Cys-(Xaa1)$_2$ Cys-(Xaa1)$_{16}$His-(Xaa1)$_{6-8}$Cys. Typically, the amino acid sequence of the consensus sequence is: Xaa1-Xaa1-Xaa1-Arg-Leu-Xaa1-Thr-Phe-Xaa1-Xaa1-Trp-Pro-Xaa2-Xaa1-Xaa1-Xaa2-Xaa2-Xaa1-Xaa1-Xaa1-Xaa1-Leu-Ala-Xaa1-Ala-Gly-Phe-Tyr-Tyr-Xaa1-Gly-Xaa1-Xaa1-Asp-Xaa1-Val-Xaa1-Cys-Phe-Xaa1-Cys-Xaa1-Xaa1-Xaa1-Xaa1-Xaa1-Xaa1-Trp-Xaa1-Xaa1-Xaa1-Asp-Xaa1-Xaa1-Xaa1-Xaa1-Xaa1-His-Xaa1-Xaa1-Xaa1-Xaa1-Pro-Xaa1-Cys-Xaa1-Phe-Val, wherein Xaa1 is any amino acid and Xaa2 is any amino acid or is absent. Preferably the sequence is substantially identical to one of the BIR domain sequences provided for XIAP, HIAP1, or HIAP2 herein.

The BIR domain residues are listed below (see Genome Biology (2001) 1-10):

| | XIAP | HIAP-1 | HIAP-2 |
|---|---|---|---|
| BIR1 | 21-93 | 41-113 | 24-96 |
| BIR2 | 159-230 | 179-250 | 164-235 |
| BIR3 | 258-330 | 264-336 | 250-322 |
| Seq. # | P98170 | XP-006266 | XP-006267 |

As used herein, the term "ring zinc finger" or "RZF" is intended to mean a domain having the amino acid sequence of the consensus sequence: Glu-Xaa1-Xaa1-Xaa1-Xaa1-Xaa1-Xaa1-Xaa2-Xaa1-Xaa1-Xaa1-Cys-Lys-Xaa3-Cys-Met-Xaa1-Xaa1-Xaa1-Xaa1-Xaa1-Xaa3-Xaa1-Phe-Xaa1-Pro-Cys-Gly-His-Xaa1-Xaa1-Xaa1-Cys-Xaa1-Xaa1-Cys-Ala-Xaa1-Xaa1-Xaa1-Xaa1-Xaa1-Cys-Pro-Xaa1-Cys, wherein Xaa1 is any amino acid, Xaa2 is Glu or Asp, and Xaa3 is Val or Ile.

As used herein, the term "IAP" is intended to mean a polypeptide or protein, or fragment thereof, encoded by an IAP gene. Examples of IAPs include, but are not limited to human or mouse NAIP (Birc 1), HIAP-1 (cIAP2, Birc 3), HIAP-2 (cIAP1, Birc 2), XIAP (Birc 4), survivin (Birc 5), livin (ML-IAP, Birc 7), ILP-2 (Birc 8) and Apollon/BRUCE (Birc 6) (see for example U.S. Pat. Nos. 6,107,041; 6,133,437; 6,156,535; 6,541,457; 6,656,704; 6,689,562; Deveraux and Reed, Genes Dev. 13, 239-252, 1999; Kasof and Gomes, J. Biol. Chem., 276, 3238-3246, 2001; Vucic et al., Curr. Biol. 10, 1359-1366, 2000; Ashab et al. FEBS Lett., 495, 56-60, 2001, the contents of which are hereby incorporated by reference).

As used herein, the term "IAP gene" is intended to mean a gene encoding a polypeptide having at least one BIR domain and which is capable of modulating (inhibiting or enhancing) apoptosis in a cell or tissue. The IAP gene is a gene having about 50% or greater nucleotide sequence identity to at least one of human or mouse NAIP (Birc 1), HIAP-1 (cIAP2, Birc 3), HIAP-2 (cIAP1, Birc 2), XIAP (Birc 4), survivin (Birc 5), livin (ML-IAP, Birc 7), ILP-2 (Birc 8) and Apollon/BRUCE (Birc 6). The region of sequence over which identity is measured is a region encoding at least one BIR domain and a ring zinc finger domain. Mammalian IAP genes include nucleotide sequences isolated from any mammalian source.

As used herein, the term "IC$_{50}$" is intended to mean an amount, concentration or dosage of a particular compound of the present invention that achieves a 50% inhibition of a maximal response, such as displacement of maximal fluorescent probe binding in an assay that measures such response.

As used herein, the term "EC$_{50}$" is intended to mean an amount, concentration or dosage of a particular compound of the present invention that achieves a 50% inhibition of cell survival.

As used herein, the term "modulate" or "modulating" is intended to mean the treatment, prevention, suppression, enhancement or induction of a function or condition using the compounds of the present invention. For example, the compounds of the present invention can modulate IAP function in a subject, thereby enhancing apoptosis by significantly reducing, or essentially eliminating the interaction of activated apoptotic proteins, such as caspase-3, 7 and 9, with the BIR domains of mammalian IAPs or by inducing the loss of XIAP protein in a cell.

As used herein, the term "enhancing apoptosis" is intended to mean increasing the number of cells that apoptose in a given cell population either in vitro or in vivo. Examples of cell populations include, but are not limited to, ovarian cancer cells, colon cancer cells, breast cancer cells, lung cancer cells, pancreatic cancer cells, or T cells and the like. It will be appreciated that the degree of apoptosis enhancement provided by an apoptosis-enhancing compound of the present invention in a given assay will vary, but that one skilled in the art can determine the statistically significant change in the level of apoptosis that identifies a compound that enhances apoptosis otherwise limited by an IAP. Preferably "enhancing apoptosis" means that the increase in the number of cells undergoing apoptosis is at least 25%, more preferably the increase is 50%, and most preferably the increase is at least one-fold. Preferably the sample monitored is a sample of cells that normally undergo insufficient apoptosis (i.e., cancer cells). Methods for detecting the changes in the level of apoptosis (i.e., enhancement or reduction) are described in the Examples and include methods that quantitate the fragmentation of DNA, methods that quantitate the translocation phosphatoylserine from the cytoplasmic to the extracellular side of the membrane, determination of activation of the caspases and methods quantitate the release of cytochrome C and the apoptosis inhibitory factor into the cytoplasm by mitochondria.

As used herein, the term "proliferative disease" or "proliferative disorder" is intended to mean a disease that is caused by or results in inappropriately high levels of cell division, inappropriately low levels of apoptosis, or both. For example, cancers such as lymphoma, leukemia, melanoma, ovarian cancer, breast cancer, pancreatic cancer, and lung cancer, and autoimmune disorders are all examples of proliferative diseases.

As used herein, the term "death receptor agonist" is intended to mean an agent capable of stimulating by direct or indirect contact the pro apoptotic response mediated by the death-receptors. For example, an agonist TRAIL receptor Antibody would bind to TRAIL receptor (S) and trigger an apoptotic response. On the other hand, other agent such as interferon-a could trigger the release of endogeneous TRAIL and/or up regulate the TRAIL receptors in such a way that the cell pro-apoptotic response is amplified.

The compounds of the present invention, or their pharmaceutically acceptable salts may contain one or more asymmetric centers, chiral axes and chiral planes and may thus give rise to enantiomers, diastereomers, and other stereoisomeric forms and may be defined in terms of absolute stereochemistry, such as (R)- or (S)- or, as (D)- or (L)- for amino acids. The present invention is intended to include all such possible isomers, as well as, their racemic and optically pure forms. Optically active (+) and (−), (R)- and (S)-, or (D)- and (L)-isomers may be prepared using chiral synthons or chiral reagents, or resolved using conventional techniques, such as reverse phase HPLC. The racemic mixtures may be prepared and thereafter separated into individual optical isomers or these optical isomers may be prepared by chiral synthesis. The enantiomers may be resolved by methods known to those skilled in the art, for example by formation of diastereoisomeric salts which may then be separated by crystallization, gas-liquid or liquid chromatography, selective reaction of one enantiomer with an enantiomer specific reagent. It will also be appreciated by those skilled in the art that where the desired enantiomer is converted into another chemical entity by a separation technique, an additional step is then required to form the desired enantiomeric form. Alternatively specific enantiomers may be synthesized by asymmetric synthesis using optically active reagents, substrates, catalysts, or solvents or by converting one enantiomer to another by asymmetric transformation.

Certain compounds of the present invention may exist in Zwitterionic form and the present invention includes Zwitterionic forms of these compounds and mixtures thereof.

Utilities

The compounds of the present invention are useful as IAP BIR domain binding compounds and as such the compounds, compositions and method of the present invention include application to the cells or subjects afflicted with or having a predisposition towards developing a particular disease state, which is characterized by insufficient apoptosis. Thus, the compounds, compositions and methods of the present invention are used to treat cellular proliferative diseases/disorders, which include, but are not limited to, i) cancer, ii) autoimmune disease, iii) inflammatory disorders, iv) proliferation induced post medical procedures, including, but not limited to, surgery, angioplasty, and the like.

The compounds of the present invention may also be useful in the treatment of diseases in which there is a defect in the programmed cell-death or the apoptotic machinery (TRAIL, FAS, apoptosome), such as multiple sclerosis, artherosclerosis, inflammation, autoimmunity and the like.

The treatment involves administration to a subject in need thereof a compound of the present invention or a pharmaceutically acceptable salt thereof, or a pharmaceutical composition comprising a pharmaceutical carrier and a therapeutically effective amount of a compound of the present invention, or a pharmaceutically acceptable salt thereof. In particular, the compounds, compositions and methods of the present invention are useful for the treatment of cancer including solid tumors such as skin, breast, brain, lung, testicular carcinomas, and the like. Cancers that may be treated by the compounds, compositions and methods of the invention include, but are not limited to the following:

| Tissue | Example |
| --- | --- |
| Adrenal gland | neuroblastoma |
| Bone | osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors |
| Cardiac | sarcoma (angiosarcoma, fibrosarcoma, rhabdomyosarcoma, liposarcoma), myxoma, rhabdomyoma, fibroma, lipoma and teratoma |
| Gastrointestinal | esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma) |
| Genitourinary tract | kidney (adenocarcinoma, Wilm's tumor [nephroblastoma], lymphoma, leukemia), bladder and urethra (squamous cell |

| Tissue | Example |
|---|---|
| | carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma) |
| Gynecological | uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma) |
| Hematologic | blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma] |
| Liver | hepatoma (hepatocellular carcinoma), cholangiocarcinoma, hepatoblastoma, angiosarcoma, hepatocellular adenoma, hemangioma |
| Lung | bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma |
| Nervous system | skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma) |
| Skin | malignant melanoma, basal cell carcinoma, squamous cell carcinoma, Karposi's sarcoma, moles dysplastic nevi, lipoma, angioma, dermatofibroma, keloids |

The compounds of the present invention, or their pharmaceutically acceptable salts or their prodrugs, may be administered in pure form or in an appropriate pharmaceutical composition, and can be carried out via any of the accepted modes of Galenic pharmaceutical practice.

The pharmaceutical compositions of the present invention can be prepared by mixing a compound of the present invention with an appropriate pharmaceutically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. Typical routes of administering such pharmaceutical compositions include, without limitation, oral, topical, transdermal, inhalation, parenteral (subcutaneous injections, intravenous, intramuscular, intrasternal injection or infusion techniques), sublingual, ocular, rectal, vaginal, and intranasal. Pharmaceutical compositions of the present invention are formulated so as to allow the active ingredients contained therein to be bioavailable upon administration of the composition to a subject. Compositions that will be administered to a subject or patient take the form of one or more dosage units, where for example, a tablet may be a single dosage unit, and a container of a compound of the present invention in aerosol form may hold a plurality of dosage units. Actual methods of preparing such dosage forms are known, or will be apparent, to those skilled in this art; for example, see Remington's Pharmaceutical Sciences, 18th Ed., (Mack Publishing Company, Easton, Pa., 1990). The composition to be administered will, in any event, contain a therapeutically effective amount of a compound of the present invention, or a pharmaceutically acceptable salt thereof, for treatment of a disease-state as described above.

A pharmaceutical composition of the present invention may be in the form of a solid or liquid. In one aspect, the carrier(s) are particulate, so that the compositions are, for example, in tablet or powder form. The carrier(s) may be liquid, with the compositions being, for example, an oral syrup, injectable liquid or an aerosol, which is useful in, for example inhalatory administration.

For oral administration, the pharmaceutical composition is preferably in either solid or liquid form, where semi-solid, semi-liquid, suspension and gel forms are included within the forms considered herein as either solid or liquid.

As a solid composition for oral administration, the pharmaceutical composition may be formulated into a powder, granule, compressed tablet, pill, capsule, chewing gum, wafer or the like form. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent.

When the pharmaceutical composition is in the form of a capsule, e.g., a gelatin capsule, it may contain, in addition to materials of the above type, a liquid carrier such as polyethylene glycol or oil such as soybean or vegetable oil.

The pharmaceutical composition may be in the form of a liquid, e.g., an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions of the present invention, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; encapsulating agents such as cyclodextrins or functionalized cyclodextrins, including, but not limited to, $\alpha$, $\beta$, or $\delta$-hydroxypropylcyclodextins or Captisol; antioxidants such as ascorbic acid or sodium bisulfite; chelating agents such as ethylenediamine tetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. An injectable pharmaceutical composition is preferably sterile.

A liquid pharmaceutical composition of the present invention used for either parenteral or oral administration should contain an amount of a compound of the present invention such that a suitable dosage will be obtained. Typically, this amount is at least 0.01% of a compound of the present invention in the composition. When intended for oral administration, this amount may be varied to be between 0.1 and about 70% of the weight of the composition. For parenteral usage, compositions and preparations according to the present invention are prepared so that a parenteral dosage unit contains between 0.01 to 10% by weight of the compound of the present invention. Pharmaceutical compositions may be further diluted at the time of administration; for example a parenteral formulation may be further diluted with a sterile, isotonic solution for injection such as 0.9% saline, 5 wt % dextrose (D5W), Ringer's solution, or others.

The pharmaceutical composition of the present invention may be used for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. Topical formulations may contain a concentration of the compound of the present invention from about 0.1 to about 10% w/v (weight per unit volume).

The pharmaceutical composition of the present invention may be used for rectal administration to treat for example, colon cancer, in the form, e.g., of a suppository, which will melt in the rectum and release the drug. The composition for rectal administration may contain an oleaginous base as a suitable nonirritating excipient. Such bases include, without limitation, lanolin, cocoa butter and polyethylene glycol.

The pharmaceutical composition of the present invention may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule.

The pharmaceutical composition of the present invention in solid or liquid form may include an agent that binds to the compound of the present invention and thereby assists in the delivery of the compound. Suitable agents that may act in this capacity include, but are not limited to, a monoclonal or polyclonal antibody, a protein or a liposome.

The pharmaceutical composition of the present invention may consist of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols of compounds of the present invention may be delivered in single phase, bi-phasic, or tri-phasic systems in order to deliver the active ingredient(s). Delivery of the aerosol includes the necessary container, activators, valves, subcontainers, and the like, which together may form a kit. One skilled in the art, without undue experimentation may determine preferred aerosols.

The pharmaceutical compositions of the present invention may be prepared by methodology well known in the pharmaceutical art. For example, a pharmaceutical composition intended to be administered by injection can be prepared by admixing a compound of the present invention with sterile, distilled water so as to form a solution. A surfactant may be added to facilitate the formation of a homogeneous solution or suspension. Surfactants are compounds that non-covalently interact with the compound of the present invention so as to facilitate dissolution or homogeneous suspension of the compound in the aqueous delivery system.

The compounds of the present invention, or their pharmaceutically acceptable salts, are administered in a therapeutically effective amount, which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disorder or condition; and the subject undergoing therapy. Generally, a therapeutically effective daily dose may be from about 0.1 mg to about 40 mg/kg of body weight per day or twice per day of a compound of the present invention, or a pharmaceutically acceptable salt thereof.

Combination Therapy

The compounds of the present invention, or pharmaceutically acceptable salts thereof, may also be administered simultaneously with, prior to, or after administration of one or more of the therapeutic agents described below. Such combination therapy may include administration of a single pharmaceutical dosage formulation which contains a compound of the present invention and one or more additional agents given below, as well as administration of the compound of the present invention and each of additional agent in its own separate pharmaceutical dosage formulation. For example, a compound of the present invention and a chemotherapeutic agent, such as taxol (paclitaxel), taxotere, etoposide, cisplatin, vincristine, vinblastine, and the like, can be administered to the patient either together in a single oral dosage composition such as a tablet or capsule, or each agent administered in separate oral dosage formulations or via intravenous injection. Where separate dosage formulations are used, the compounds of the present invention and one or more additional agents can be administered at essentially the same time, i.e., concurrently, or at separately staggered times, i.e., sequentially; combination therapy is understood to include all these regimens. In addition, these compounds may synergize with molecules that may stimulate the death receptor apoptotic pathway through a direct or indirect manner, as for example, the compounds of the present invention may be used in combination with soluble TRAIL any agent or procedures that can cause an increase in circulating level of TRAIL, such as interferon-alpha or radiation.

Thus, the present invention also encompasses the use of the compounds of the present invention in combination with radiation therapy or one or more additional agents such as those described in WO 03/099211 (PCT/US03/15861), which is hereby incorporated by reference.

Examples of such additional agents include, but are not limited to the following:
a) an estrogen receptor modulator,
b) an androgen receptor modulator,
c) retinoid receptor modulator,
d) a cytotoxic agent,
e) an antiproliferative agent,
f) a prenyl-protein transferase inhibitor,
g) an HMG-CoA reductase inhibitor,
h) an HIV protease inhibitor,
i) a reverse transcriptase inhibitor,
k) an angiogenesis inhibitor,
l) a PPAR-γ agonist,
m) a PPAR-δ agonist,
n) an inhibitor of inherent multidrug resistance,
o) an anti-emetic agent,
p) an agent useful in the treatment of anemia,
q) agents useful in the treatment of neutropenia,
r) an immunologic-enhancing drug,
s) a proteasome inhibitor such as Velcade and MG132 (7-Leu-Leu-aldehyde) (see He at al. in Oncogene (2004) 23, 2554-2558),
t) an HDAC inhibitor, such as sodium butyrate, phenyl butyrate, hydroamic acids, cyclin tetrapeptide and the like (see Rosato et al,. Molecular Cancer Therapeutics 2003, 1273-1284),
u) an inhibitor of the chymotrypsin-like activity in the proteasome,
v) E3 ligase inhibitors,
w) a modulator of the immune system such as interferon-alpha and ionizing radition (UVB) that can induce the release of cytokines, such as the interleukins, TNF, or induce release of Death receptor Ligands such as TRAIL,
x) a modulator of death receptors TRAIL and TRAIL receptor agonists such as the Humanized antibodies HGS-ETR1 and HGS-ETR2, or in combination or sequentially with radiation therapy, so as to treat the cancer.

Additional combinations may also include agents which reduce the toxicity of the aforesaid agents, such as hepatic toxicity, neuronal toxicity, nephrotoxicity and the like.

In one example, co-administration of one of the compounds of Formula I of the present invention with a death receptor agonist such as TRAIL, such as a small molecule or an antibody that mimics TRAIL may cause an advantageous synergistic effect. Moreover, the compounds of the present invention may be used in combination with any compounds that cause an increase in circulating levels of TRAIL.

Vinca Alkaloids and Related Compounds

Vinca alkaloids that can be used in combination with the nucleobase oligomers of the invention to treat cancer and other neoplasms include vincristine, vinblastine, vindesine, vinflunine, vinorelbine, and anhydrovinblastine.

Dolastatins are oligopeptides that primarily interfere with tubulin at the vinca alkaloid binding domain. These compounds can also be used in combination with the compounds of the invention to treat cancer and other neoplasms. Dolastatins include dolastatin-10 (NCS 376128), dolastatin-15, ILX651, TZT-1027, symplostatin 1, symplostatin 3, and LU103793 (cemadotin).

Cryptophycins (e.g., cryptophycin 1 and cryptophycin 52 (LY355703)) bind tubulin within the vinca alkaloid-binding domain and induce G2/M arrest and apoptosis. Any of these compounds can be used in combination with the compounds of the invention to treat cancer and other neoplasms.

Other microtubule disrupting compounds that can be used in conjunction with the compounds of the invention to treat cancer and other neoplasms are described in U.S. Pat. Nos. 6,458,765; 6,433,187; 6,323,315; 6,258,841; 6,143,721; 6,127,377; 6,103,698; 6,023,626; 5,985,837; 5,965,537; 5,955,423; 5,952,298; 5,939,527; 5,886,025; 5,831,002; 5,741,892; 5,665,860; 5,654,399; 5,635,483; 5,599,902; 5,530,097; 5,521,284; 5,504,191; 4,879,278; and 4,816,444, and U.S. patent application Publication Nos. 2003/0153505 A1; 2003/0083263 A1; and 2003/0055002 A1, each of which is hereby incorporated by reference.

Taxanes and Other Micortubule Stabilizing Compounds

Taxanes such as paclitaxel, doxetaxel, RPR 109881A, SB-T-1213, SB-T-1250, SB-T-101187, BMS-275183, BR T 216, DJ-927, MAC-321, IDN5109, and IDN5390 can be used in combination with the compounds of the invention to treat cancer and other neoplasms. Taxane analogs (e.g., BMS-184476, BMS-188797) and functionally related non-taxanes (e.g., epothilones (e.g., epothilone A, epothilone B (EP0906), deoxyepothilone B, and epothilone B lactam (BMS-247550)), eleutherobin, discodermolide, 2-epi-discodermolide, 2-des-methyldiscodermolide, 5-hydroxymethyldiscoder-molide, 19-des-aminocarbonyldiscodermolide, 9(13)-cyclodiscodermolide, and laulimalide) can also be used in the methods and compositions of the invention.

Other microtubule stabilizing compounds that can be used in combination with the compounds of the invention to treat cancer and other neoplasms are described in U.S. Pat. Nos. 6,624,317; 6,610,736; 6,605,599; 6,589,968; 6,583,290; 6,576,658; 6,515,017; 6,531,497; 6,500,858; 6,498,257; 6,495,594; 6,489,314; 6,458,976; 6,441,186; 6,441,025; 6,414,015; 6,387,927; 6,380,395; 6,380,394; 6,362,217; 6,359,140; 6,306,893; 6,302,838; 6,300,355; 6,291,690; 6,291,684; 6,268,381; 6,262,107; 6,262,094; 6,147,234; 6,136,808; 6,127,406; 6,100,411; 6,096,909; 6,025,385; 6,011,056; 5,965,718; 5,955,489; 5,919,815; 5,912,263; 5,840,750; 5,821,263; 5,767,297; 5,728,725; 5,721,268; 5,719,177; 5,714,513; 5,587,489; 5,473,057; 5,407,674; 5,250,722; 5,010,099; and 4,939,168; and U.S. patent application Publication Nos. 2003/0186965 A1; 2003/0176710 A1; 2003/0176473 A1; 2003/0144523 A1; 2003/0134883 A1; 2003/0087888 A1; 2003/0060623 A1; 2003/0045711 A1; 2003/0023082 A1; 2002/0198256 A1; 2002/0193361 A1; 2002/0188014 A1; 2002/0165257 A1; 2002/0156110 A1; 2002/0128471 A1; 2002/0045609 A1; 2002/0022651 A1; 2002/0016356 A1; 2002/0002292 A1, each of which is hereby incorporated by reference.

Other chemotherapeutic agents that may be administered with a compound of the present invention are listed in the following Table:

| | | |
|---|---|---|
| Alkylating agents | cyclophosphamide<br>lomustine<br>busulfan<br>procarbazine<br>ifosfamide<br>altretamine<br>melphalan<br>estramustine phosphate<br>hexamethylmelamine | mechlorethamine<br>thiotepa<br>streptozocin<br>chlorambucil<br>temozolomide<br>dacarbazine<br>semustine<br>carmustine |
| Platinum agents | cisplatin<br>carboplatinum<br>oxaliplatin<br>ZD-0473 (AnorMED)<br>spiroplatinum<br>lobaplatin (Aeterna)<br>carboxyphthalatoplatinum<br>satraplatin (Johnson Matthey) | tetraplatin<br>BBR-3464 (Hoffmann-La Roche)<br>Ormiplatin<br>SM-11355 (Sumitomo)<br>iproplatin<br>AP-5280 (Access) |
| Antimetabolites | azacytidine<br>tomudex<br>gemcitabine<br>trimetrexate<br>capecitabine<br>deoxycoformycin<br>5-fluorouracil<br>fludarabine<br>floxuridine<br>pentostatin<br>2-chlorodeoxyadenosine<br>raltitrexed | 6-mercaptopurine<br>hydroxyurea<br>6-thioguanine<br>decitabine (SuperGen)<br>cytarabin<br>clofarabine (Bioenvision)<br>2-fluorodeoxy cytidine<br>irofulven (MGI Pharma) methotrexate<br>DMDC (Hoffmann-La Roche)<br>idatrexate<br>ethynylcytidine (Taiho) |
| Topoisomerase inhibitors | amsacrine<br>rubitecan (SuperGen)<br>epirubicin<br>exatecan mesylate (Daiichi)<br>etoposide<br>quinamed (ChemGenex)<br>teniposide or mitoxantrone<br>gimatecan (Sigma-Tau)<br>irinotecan (CPT-11)<br>diflomotecan (Beaufour-Ipsen)<br>7-ethyl-10-hydroxy-camptothecin | TAS-103 (Taiho)<br>Topotecan<br>elsamitrucin (Spectrum) dexrazoxanet (TopoTarget)<br>J-107088 (Merck & Co)<br>pixantrone (Novuspharma)<br>BNP-1350 (BioNumerik)<br>rebeccamycin analogue (Exelixis)<br>CKD-602 (Chong Kun Dang)<br>BBR-3576 (Novuspharma)<br>KW-2170 (Kyowa Hakko) |
| Antitumor antibiotics | dactinomycin (actinomycin D)<br>amonafide<br>doxorubicin (adriamycin)<br>azonafide<br>deoxyrubicin<br>anthrapyrazole<br>valrubicin<br>oxantrazole<br>daunorubicin (daunomycin)<br>losoxantrone<br>epirubicin<br>bleomycin sulfate (blenoxane)<br>therarubicin | bleomycinic acid<br>idarubicin<br>bleomycin A<br>rubidazone<br>bleomycin B<br>plicamycinp<br>mitomycin C<br>porfiromycin<br>MEN-10755 (Menarini)<br>cyanomorpholinodoxorubicin<br>GPX-100 (Gem Pharmaceuticals)<br>mitoxantrone (novantrone) |
| Antimitotic agents | paclitaxel<br>SB 408075 (GlaxoSmithKline)<br>docetaxel<br>E7010 (Abbott)<br>Colchicines<br>PG-TXL (Cell Therapeutics)<br>vinblastine<br>IDN 5109 (Bayer)<br>Vincristine<br>A 105972 (Abbott)<br>Vinorelbine<br>A 204197 (Abbott)<br>Vindesine<br>LU 223651 (BASF)<br>dolastatin 10 (NCI)<br>D 24851 (ASTAMedica)<br>rhizoxin (Fujisawa)<br>ER-86526 (Eisai)<br>mivobulin (Warner-Lambert)<br>combretastatin A4 (BMS)<br>cemadotin (BASF)<br>isohomohalichondrin-B (PharmaMar) | RPR 109881A (Aventis)<br>ZD 6126 (AstraZeneca)<br>TXD 258 (Aventis)<br>PEG-paclitaxel (Enzon)<br>epothilone B (Novartis)<br>AZ10992 (Asahi)<br>T 900607 (Tularik)<br>IDN-5109 (Indena)<br>T 138067 (Tularik)<br>AVLB (Prescient NeuroPharma)<br>cryptophycin 52 (Eli Lilly)<br>azaepothilone B (BMS)<br>vinflunine (Fabre)<br>BNP-7787 (BioNumerik)<br>auristatin PE (Teikoku Hormone)<br>CA-4 prodrug (OXiGENE)<br>BMS 247550 (BMS)<br>dolastatin-10 (NIH)<br>BMS 184476(BMS)<br>CA-4 (OXiGENE)<br>BMS 188797 (BMS)<br>taxoprexin (Protarga) |
| Aromatase inhibitors | Aminoglutethimide<br>Exemestane<br>Letrozole<br>atamestane (BioMedicines) | anastrazole<br>YM-511 (Yamanouchi)<br>formestane |

-continued

| | | |
|---|---|---|
| Thymidylate synthase inhibitors | pemetrexed (Eli Lilly) nolatrexed (Eximias) | ZD-9331 (BTG) CoFactor ™ (BioKeys) |
| DNA antagonists | trabectedin (PharmaMar) mafosfamide (Baxter International) glufosfamide (Baxter International) apaziquone (Spectrum Pharmaceuticals) | albumin + 32P (Isotope Solutions) O6 benzyl guanine (Paligent) thymectacin (NewBiotics) edotreotide (Novartis) |
| Farnesyltransferase inhibitors | arglabin (NuOncology Labs) tipifarnib (Johnson & Johnson) lonafarnib (Schering-Plough) | perillyl alcohol (DOR BioPharma) BAY-43-9006 (Bayer) |
| Pump inhibitors | CBT-1 (CBA Pharma) zosuquidar trihydrochloride (Eli Lilly) | tariquidar (Xenova) biricodar dicitrate (Vertex) MS-209 (Schering AG) |
| Histone acetyltransferase inhibitors | tacedinaline (Pfizer) pivaloyloxymethyl butyrate (Titan) SAHA (Aton Pharma) | depsipeptide (Fujisawa) MS-275 (Schering AG) |
| Metalloproteinase inhibitors | Neovastat (Aeterna Laboratories) CMT-3 (CollaGenex) | marimastat (British Biotech) BMS-275291 (Celltech) |
| Ribonucleoside reductase inhibitors | gallium maltolate (Titan) tezacitabine (Aventis) | triapine (Vion) didox (Molecules for Health) |
| TNF alpha agonists/antagonists | virulizin (Lorus Therapeutics) revimid (Celgene) | CDC-394 (Celgene) |
| Endothelin A receptor antagonist | atrasentan (Abbott) YM-598 (Yamanouchi) | ZD-4054 (AstraZeneca) |
| Retinoic acid receptor agonists | fenretinide (Johnson & Johnson) alitretinoin (Ligand) | LGD-1550 (Ligand) |
| Immuno-modulators | Interferon dexosome therapy (Anosys) oncophage (Antigenics) pentrix (Australian Cancer Technology) GMK (Progenics) ISF-154 (Tragen) adenocarcinoma vaccine (Biomira) cancer vaccine (Intercell) CTP-37 (A VI BioPharma) | norelin (Biostar) IRX-2 (Immuno-Rx) BLP-25 (Biomira) PEP-005 (Peplin Biotech) MGV (Progenics) synchrovax vaccines (CTL Immuno) beta.-alethine (Dovetail) melanoma vaccine (CTL Immuno) CLL therapy (Vasogen) p21 RAS vaccine (GemVax) |
| Hormonal and antihormonal agents | estrogens Prednisone conjugated estrogens methylprednisolone ethinyl estradiol prednisolone chlortrianisen aminoglutethimide idenestrol leuprolide hydroxyprogesterone caproate goserelin medroxyprogesterone leuporelin testosterone | bicalutamide testosterone propionate; fluoxymesterone flutamide methyltestosterone octreotide diethylstilbestrol nilutamide megestrol mitotane tamoxifen P-04 (Novogen) Toremofine 2-methoxyestradiol (EntreMed) dexamethasone arzoxifene (Eli Lilly) |
| Photodynamic agents | talaporfin (Light Sciences) Pd-bacteriopheophorbide (Yeda) Theralux (Theratechnologies) lutetium texaphyrin (Pharmacyclics) | motexafin gadolinium (Pharmacyclics) hypericin |
| Tyrosine Kinase Inhibitors | imatinib (Novartis) kahalide F (PharmaMar) leflunomide (Sugen/Pharmacia) CEP-701 (Cephalon) ZD1839 (AstraZeneca) CEP-751 (Cephalon) erlotinib (Oncogene Science) MLN518 (Millenium) canertinib (Pfizer) PKC412 (Novartis) squalamine (Genaera) phenoxodiol ( ) SU5416 (Pharmacia) trastuzumab (Genentech) SU6668 (Pharmacia) | C225 (ImClone) ZD4190 (AstraZeneca) rhu-Mab (Genentech) ZD6474 (AstraZeneca) MDX-H210 (Medarex) vatalanib (Novartis) 2C4 (Genentech) PKI166 (Novartis) MDX-447 (Medarex) GW2016 (GlaxoSmithKline) ABX-EGF (Abgenix) EKB-509 (Wyeth) IMC-1C11 (ImClone) EKB-569 (Wyeth) |

Miscellaneous agents

SR-27897 (CCK A inhibitor, Sanofi-Synthelabo)
BCX-1777 (PNP inhibitor, BioCryst)

gemtuzumab (CD33 antibody, Wyeth Ayerst)
CCI-779 (mTOR kinase inhibitor, Wyeth)
PG2 (hematopoiesis enhancer, Pharmagenesis)

-continued

| | |
|---|---|
| tocladesine (cyclic AMP agonist, Ribapharm) | exisulind (PDE V inhibitor, Cell Pathways) |
| ranpirnase (ribonuclease stimulant, Alfacell) | Immunol ™ (triclosan oral rinse, Endo) |
| alvocidib (CDK inhibitor, Aventis) | CP-461 (PDE V inhibitor, Cell Pathways) |
| galarubicin (RNA synthesis inhibitor, Dong-A) | triacetyluridine (uridine prodrug, Wellstat) |
| CV-247 (COX-2 inhibitor, Ivy Medical) | AG-2037 (GART inhibitor, Pfizer) |
| tirapazamine (reducing agent, SRI International) | SN-4071 (sarcoma agent, Signature BioScience) |
| P54 (COX-2 inhibitor, Phytopharm) | WX-UK1 (plasminogen activator inhibitor, Wilex) |
| N-acetylcysteine (reducing agent, Zambon) | |
| CapCell ™ (CYP450 stimulant, Bavarian Nordic) | TransMID-107 .TM. (immunotoxin, KS Biomedix) |
| R-flurbiprofen (NF-kappaB inhibitor, Encore) | PBI-1402 (PMN stimulant, ProMetic LifeSciences) |
| GCS-100 (gal3 antagonist, GlycoGenesys) | |
| 3CPA (NF-kappaB inhibitor, Active Biotech) | PCK-3145 (apoptosis promotor, Procyon) |
| G17DT immunogen (gastrin inhibitor, Aphton) | bortezomib (proteasome inhibitor, Millennium) |
| seocalcitol (vitamin D receptor agonist, Leo) | doranidazole (apoptosis promotor, Pola) |
| efaproxiral (oxygenator, Allos Therapeutics) | SRL-172 (T cell stimulant, SR Pharma) CHS-828 (cytotoxic agent, Leo) |
| 131-I-TM-601 (DNA antagonist, TransMolecular) | |
| | TLK-286 (glutathione S transferase inhibitor, Telik) |
| PI-88 (heparanase inhibitor, Progen) | |
| eflornithine (ODC inhibitor, ILEX Oncology) | trans-retinoic acid (differentiator, NIH) |
| tesmilifene (histamine antagonist, YM BioSciences) | PT-100 (growth factor agonist, Point Therapeutics) |
| minodronic acid (osteoclast inhibitor, Yamanouchi) | MX6 (apoptosis promotor, MAXIA) |
| | midostaurin (PKC inhibitor, Novartis) |
| histamine (histamine H2 receptor agonist, Maxim) | apomine (apoptosis promotor, ILEX Oncology) |
| | bryostatin-1 (PKC stimulant, GPC Biotech) |
| indisulam (p53 stimulant, Eisai) | urocidin (apoptosis promotor, Bioniche) |
| tiazofurin (IMPDH inhibitor, Ribapharm) | CDA-II (apoptosis promotor, Everlife) |
| aplidine (PPT inhibitor, PharmaMar) | Ro-31-7453 (apoptosis promotor, La Roche) |
| cilengitide (integrin antagonist, Merck KGaA) | SDX-101 (apoptosis promotor, Salmedix) |
| rituximab (CD20 antibody, Genentech) | brostallicin (apoptosis promotor, Pharmacia) |
| SR-31747 (IL-1 antagonist, Sanofi-Synthelabo) | ceflatonin (apoptosis promotor, ChemGenex) |

Additional combinations may also include agents which reduce the toxicity of the aforesaid agents, such as hepatic toxicity, neuronal toxicity, nephrotoxicity and the like.

Screening Assays

The compounds of the present invention may also be used in a method to screen for other compounds that bind to an IAP BIR domain. Generally speaking, to use the compounds of the invention in a method of identifying compounds that bind to an IAP BIR domain, the IAP is bound to a support, and a compound of the invention is added to the assay. Alternatively, the compound of the invention may be bound to the support and the IAP is added.

There are a number of ways in which to determine the binding of a compound of the present invention to the BIR domain. In one way, the compound of the invention, for example, may be fluorescently or radioactively labeled and binding determined directly. For example, this may be done by attaching the IAP to a solid support, adding a detectably labeled compound of the invention, washing off excess reagent, and determining whether the amount of the detectable label is that present on the solid support. Numerous blocking and washing steps may be used, which are known to those skilled in the art.

In some cases, only one of the components is labeled. For example, specific residues in the BIR domain may be labeled. Alternatively, more than one component may be labeled with different labels; for example, using $I^{125}$ for the BIR domain, and a fluorescent label for the probe.

The compounds of the invention may also be used as competitors to screen for additional drug candidates or test compounds. As used herein, the terms "drug candidate" or "test compounds" are used interchangeably and describe any molecule, for example, protein, oligopeptide, small organic molecule, polysaccharide, polynucleotide, and the like, to be tested for bioactivity. The compounds may be capable of directly or indirectly altering the IAP biological activity.

Drug candidates can include various chemical classes, although typically they are small organic molecules having a molecular weight of more than 100 and less than about 2,500 Daltons. Candidate agents typically include functional groups necessary for structural interaction with proteins, for example, hydrogen bonding and lipophilic binding, and typically include at least an amine, carbonyl, hydroxyl, ether, or carboxyl group. The drug candidates often include cyclical carbon or heterocyclic structures and/or aromatic or polyaromatic structures substituted with one or more functional groups.

Drug candidates can be obtained from any number of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means.

Competitive screening assays may be done by combining an IAP BIR domain and a probe to form a probe:BIR domain complex in a first sample followed by adding a test compound from a second sample. The binding of the test is determined, and a change or difference in binding between the two samples indicates the presence of a test compound capable of binding to the BIR domain and potentially modulating the IAP's activity.

In one case, the binding of the test compound is determined through the use of competitive binding assays. In this embodiment, the probe is labeled with a fluorescent label. Under certain circumstances, there may be competitive binding between the test compound and the probe. Test compounds which display the probe, resulting in a change in fluorescence as compared to control, are considered to bind to the BIR region.

In one case, the test compound may be labeled. Either the test compound, or a compound of the present invention, or both, is added first to the IAP BIR domain for a time sufficient to allow binding to form a complex.

Formation of the probe:BIR domain complex typically require Incubations of between 4° C. and 40° C. for between 10 minutes to about 1 hour to allow for high-throughput screening. Any excess of reagents are generally removed or washed away. The test compound is then added, and the presence or absence of the labeled component is followed, to indicate binding to the BIR domain.

In one case, the probe is added first, followed by the test compound. Displacement of the probe is an indication the test compound is binding to the BIR domain and thus is capable of binding to, and potentially modulating, the activity of IAP. Either component can be labeled. For example, the presence of probe in the wash solution indicates displacement by the test compound. Alternatively, if the test compound is labeled, the presence of the probe on the support indicates displacement.

In one case, the test compound may be added first, with incubation and washing, followed by the probe. The absence of binding by the probe may indicate the test compound is bound to the BIR domain with a higher affinity. Thus, if the probe is detected on the support, coupled with a lack of test compound binding, may indicate the test compound is capable of binding to the BIR domain.

Modulation is tested by screening for a test compound's ability to modulate the activity of IAP and includes combining a test compound with an IAP BIR domain, as described above, and determining an alteration in the biological activity of the IAP. Therefore in this case, the test compound should both bind to the BIR domain (although this may not be necessary), and alter its biological activity as defined herein.

Positive controls and negative controls may be used in the assays. All control and test samples are performed multiple times to obtain statistically significant results. Following incubation, all samples are washed free of non-specifically bound material and the amount of bound probe determined. For example, where a radiolabel is employed, the samples may be counted in a scintillation counter to determine the amount of bound compound.

Typically, the signals that are detected in the assay may include fluorescence, resonance energy transfer, time resolved fluorescence, radioactivity, fluorescence polarization, plasma resonance, or chemiluminescence and the like, depending on the nature of the label. Detectable labels useful in performing screening assays in this invention include a fluorescent label such as Fluorescein, Oregon green, dansyl, rhodamine, tetramethyl rhodamine, texas red, $Eu^{3+}$; a chemiluminescent label such as luciferase; calorimetric labels; enzymatic markers; or radioisotopes such as tritium, $I^{125}$ and the like Affinity tags, which may be useful in performing the screening assays of the present invention include be biotin, polyhistidine and the like.

Synthesis and Methodology

General methods for the synthesis of the compounds of the present invention are shown below and are disclosed merely for the purpose of illustration and are not meant to be interpreted as limiting the processes to make the compounds by any other methods. Those skilled in the art will readily appreciate that a number of methods are available for the preparation of the compounds of the present invention.

General Procedures

Several methods for preparing symmetrically or non-symmetrically bridged compounds represented by formula I and formula II may be envisioned. General methods are illustrated in Schemes 1 to 8 and Schemes 17 to 20, while specific examples are illustrated in schemes 9 to 16 and Schemes 21 to 26.

Scheme 1 illustrates a general procedure for the preparation of bis-alkynyl bridged compounds of formula 1. $N$-$PG^1$-2-hydroxyproline is deprotonated with NaH and treated with propargyl bromide to provide the proline intermediate 1-i. Activation of the carboxylic acid of 1-i with peptide coupling agents and treatment with a primary or secondary amine, and deprotection of $PG^1$ provides the amide intermediate 1-ii. Peptide coupling of $PG^2(H)N(R^3)CHCO_2H$ with 1-ii is effected by activation of the carboxylic acid of $PG^2(H)N(R^3)CHCO_2H$ with peptide coupling agents, followed by the addition of 1-ii to provide the fully protected amide, which may be further deprotected at $PG^2$ to provide amide 1-iii. Activation of the carboxylic acid of $PG^3(R^1)N(R^2)CHCO_2H$ with peptide coupling agents, followed by the addition of 1-iii to provide the amide intermediate 1-iv. The bis-alkynyl bridging moiety is prepared by homo-coupling of the alkyne moieties of 1-iv using an appropriate catalyst system, and subsequent deprotection of $PG^3$, to provide compound 1-v.

Scheme 1

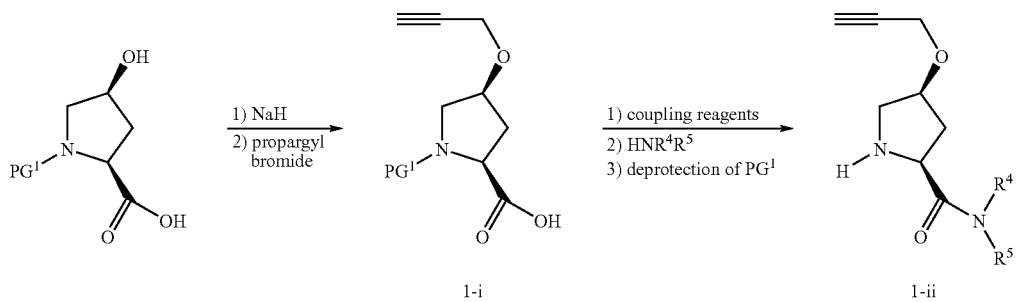

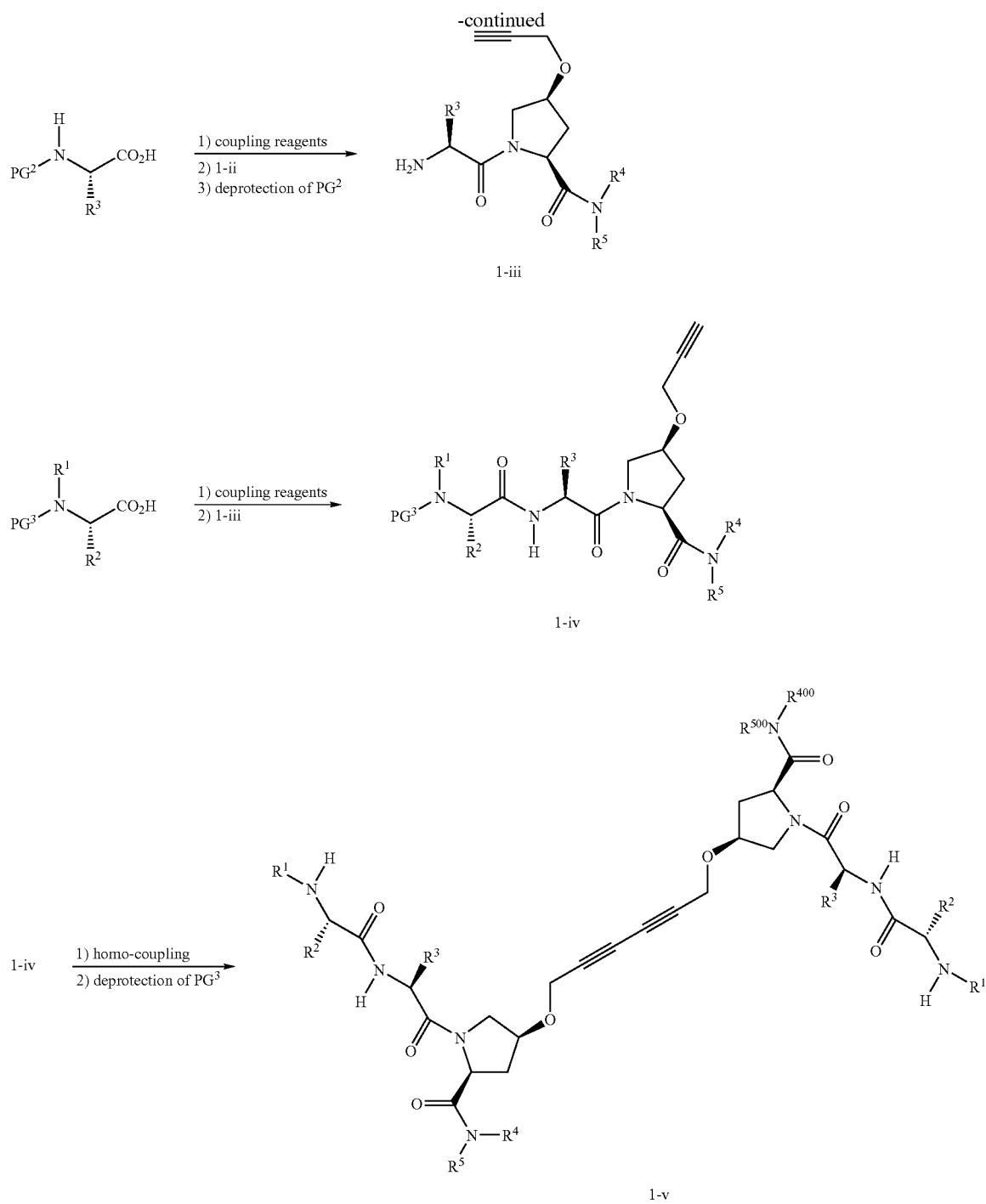

1-v

As illustrated in Scheme 2, intermediate 2-i is prepared via a typical amide coupling/deprotection scheme. As such, the carboxylic acid moiety of PG$^1$-cis-2-amino-Pro(PG$^2$)-OH is activated with amino acid coupling reagents, treated with an amine to provide the corresponding amide, followed by the removal of PG$^1$, under appropriate reaction conditions, to provide intermediate 2-i. In a similar manner, PG$^3$(H)N(R$^3$)HCCO$_2$H is coupled with 2-i, followed by deprotection of PG$^3$, to provide 2-ii. PG$^4$(R$^1$)N(R$^2$)HCCO$_2$H is coupled to 2-ii to provide 2-iii. Deprotection of PG$^2$ provides 2-iv.

Scheme 2

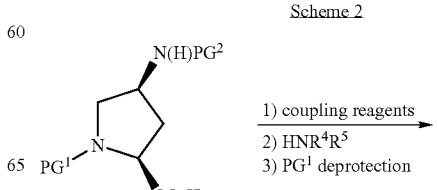

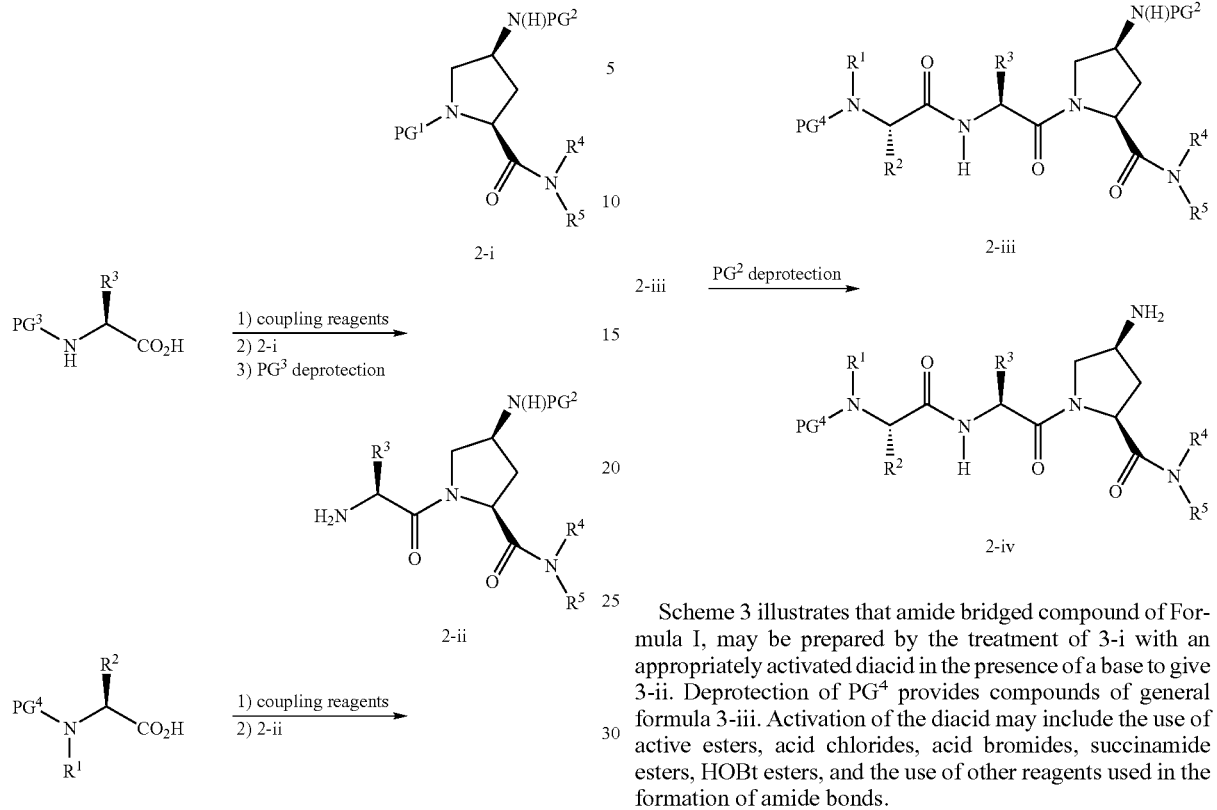

Scheme 3 illustrates that amide bridged compound of Formula I, may be prepared by the treatment of 3-i with an appropriately activated diacid in the presence of a base to give 3-ii. Deprotection of PG⁴ provides compounds of general formula 3-iii. Activation of the diacid may include the use of active esters, acid chlorides, acid bromides, succinamide esters, HOBt esters, and the use of other reagents used in the formation of amide bonds.

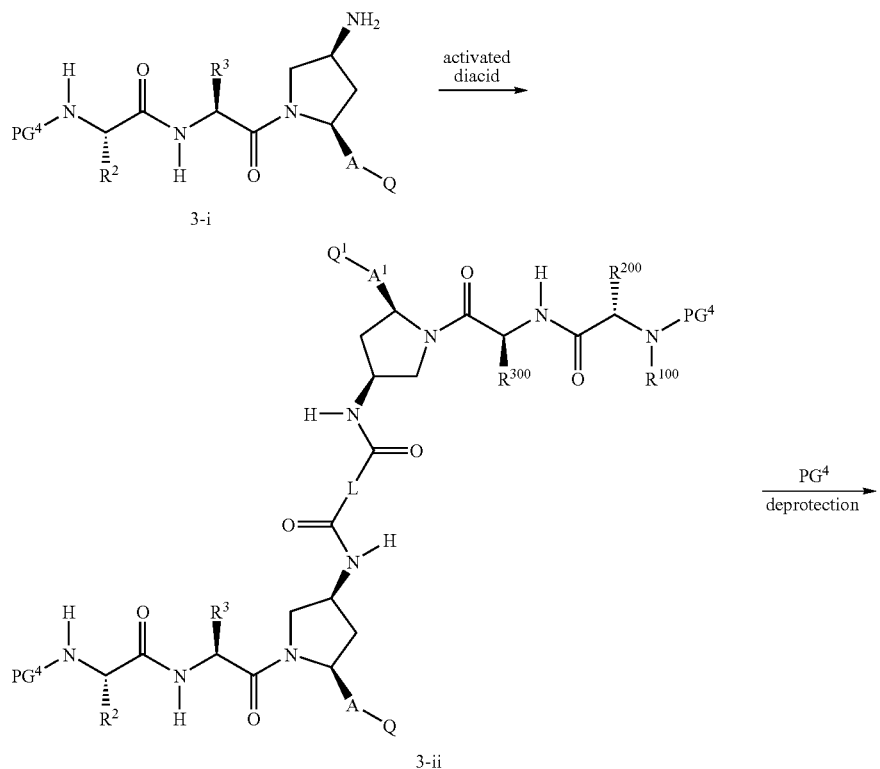

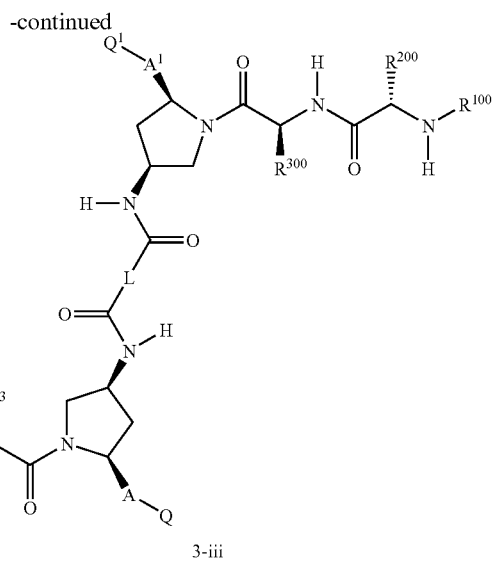

L = —(CH$_2$)$_r$—, —(CH$_2$)$_r$—Y—(CH$_2$)$_r$—, -alkyl-aryl-alkyl-,
-alkyl-heteroaryl-alkyl-, cycloalkyl, aryl or heteroaryl, wherin r is 1-10

3-iii

Scheme 4 illustrates alkyl bridged compounds, which may be prepared using the methods described herein. Treatment of 3-i with 0.5 equiv of an alkyl chain containing two leaving groups, such as 1,5-dibromopentane, 1,10-dibromodecane, and the like, provides intermediate 4-i. Alternatively, reductive amination of 3-i with a dialdehyde may yield intermediate 4-i. Deprotection of PG$^4$ yields compounds of formula 4-ii.

Scheme 4

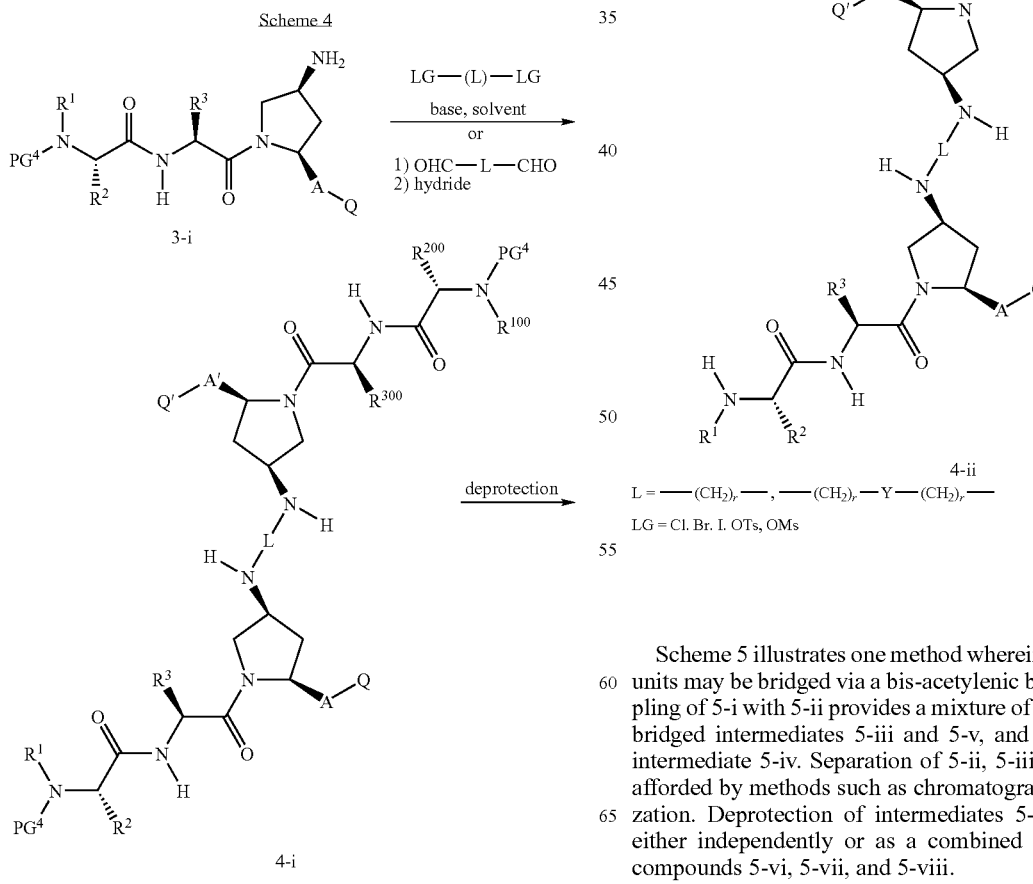

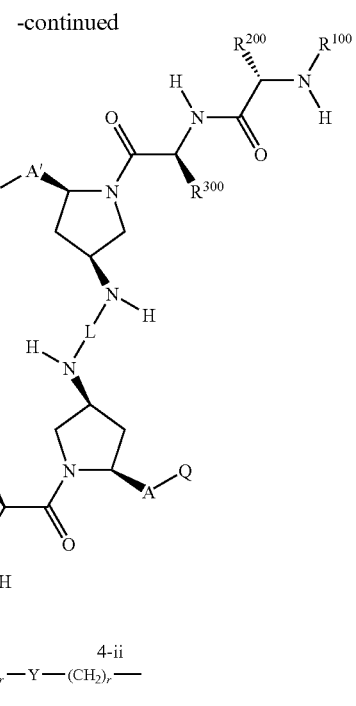

4-ii

L = —(CH$_2$)$_r$—, —(CH$_2$)$_r$—Y—(CH$_2$)$_r$—

LG = Cl. Br. I. OTs, OMs

Scheme 5 illustrates one method wherein two BIR binding units may be bridged via a bis-acetylenic bridging unit. Coupling of 5-i with 5-ii provides a mixture of the symmetrically bridged intermediates 5-iii and 5-v, and the asymmetrical intermediate 5-iv. Separation of 5-ii, 5-iii, and 5-v, may be afforded by methods such as chromatography or recrystallization. Deprotection of intermediates 5-iii, 5-iv, and 5-v, either independently or as a combined mixture, provides compounds 5-vi, 5-vii, and 5-viii.

Scheme 5: Coupling of intermediates 5-i and 5-ii.
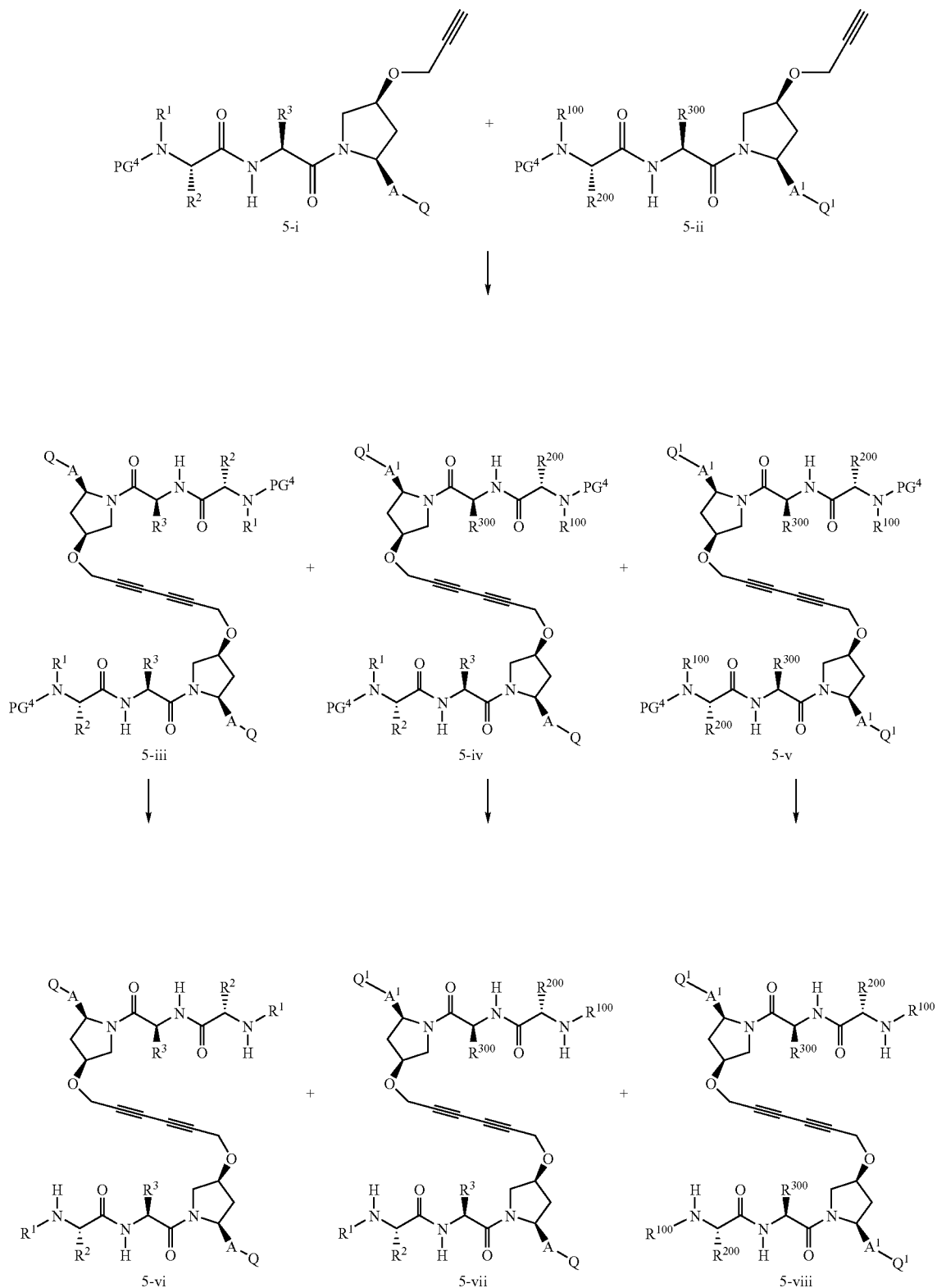

An additional method for the preparation of asymmetrically bridged compounds is illustrated in Scheme 6. Coupling of 5-i with 6-i will provide a mixture of intermediates 6-ii, 5-iii and 6-iii. Separation of 6-ii, 5-iii, and 6-iii, may be afforded by methods such as chromatography or recrystallization. Deprotection of $PG^4$ of intermediates 6-iii provides compound 6-iv.

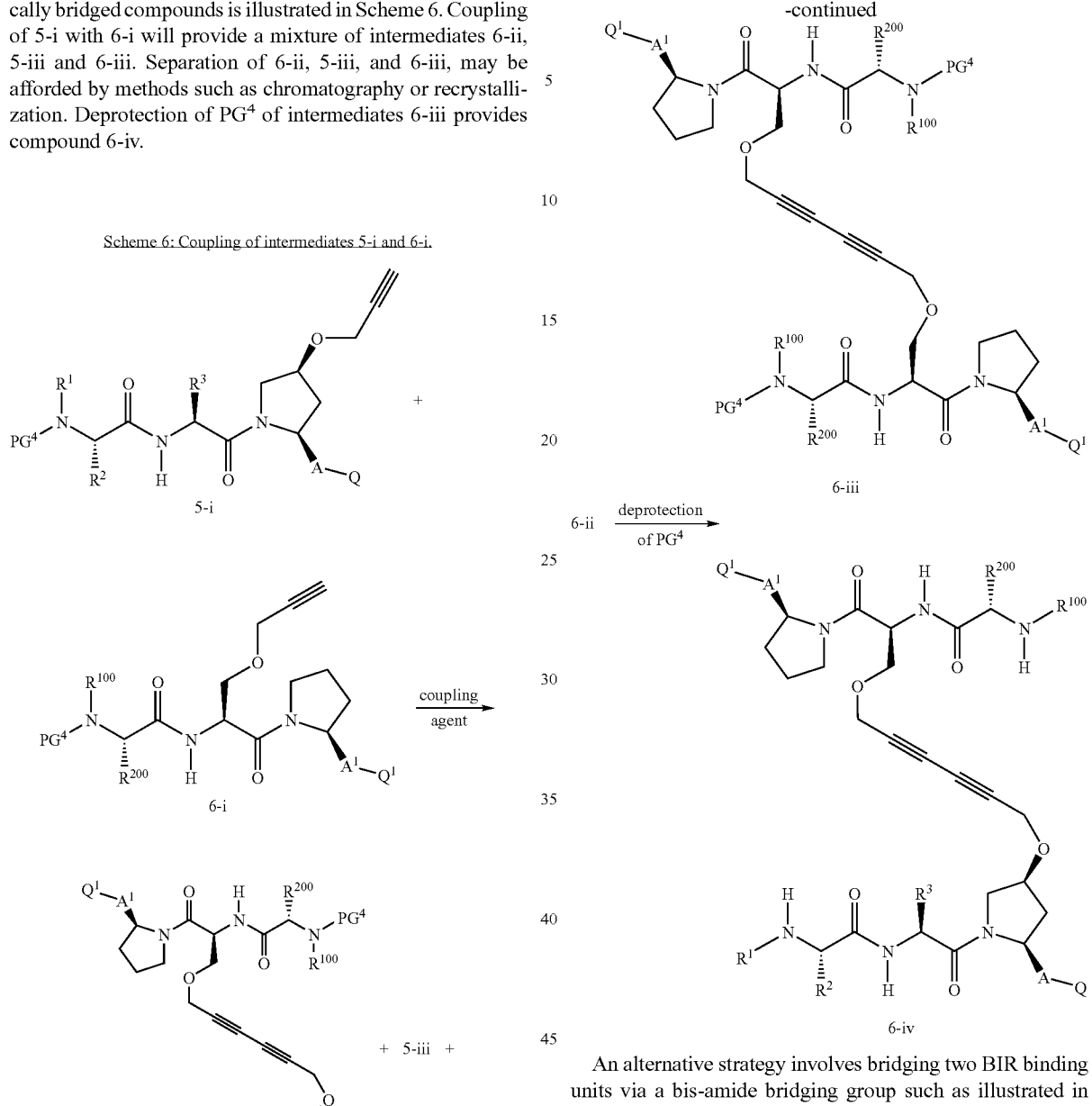

An alternative strategy involves bridging two BIR binding units via a bis-amide bridging group such as illustrated in Schemes 7 and 8.

The mono-protected bridging group $HO_2C$-L-$CO_2PG^5$ is activated with peptide coupling agents and subsequently treated with intermediate 3-i to provide intermediate 7-ii. Deprotection of $PG^5$ provides intermediate 7-iii. Treatment of 7-iii with peptide coupling agents, followed by 7-iv, provides 7-v. Deprotection of $PG^4$ and $PG^{400}$ provides compound 7-vi.

Scheme 7: P3-P3 bis-amide bridged compounds

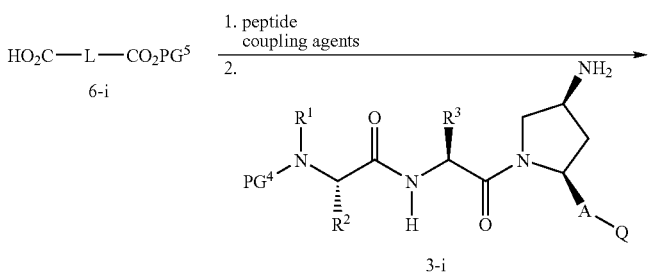

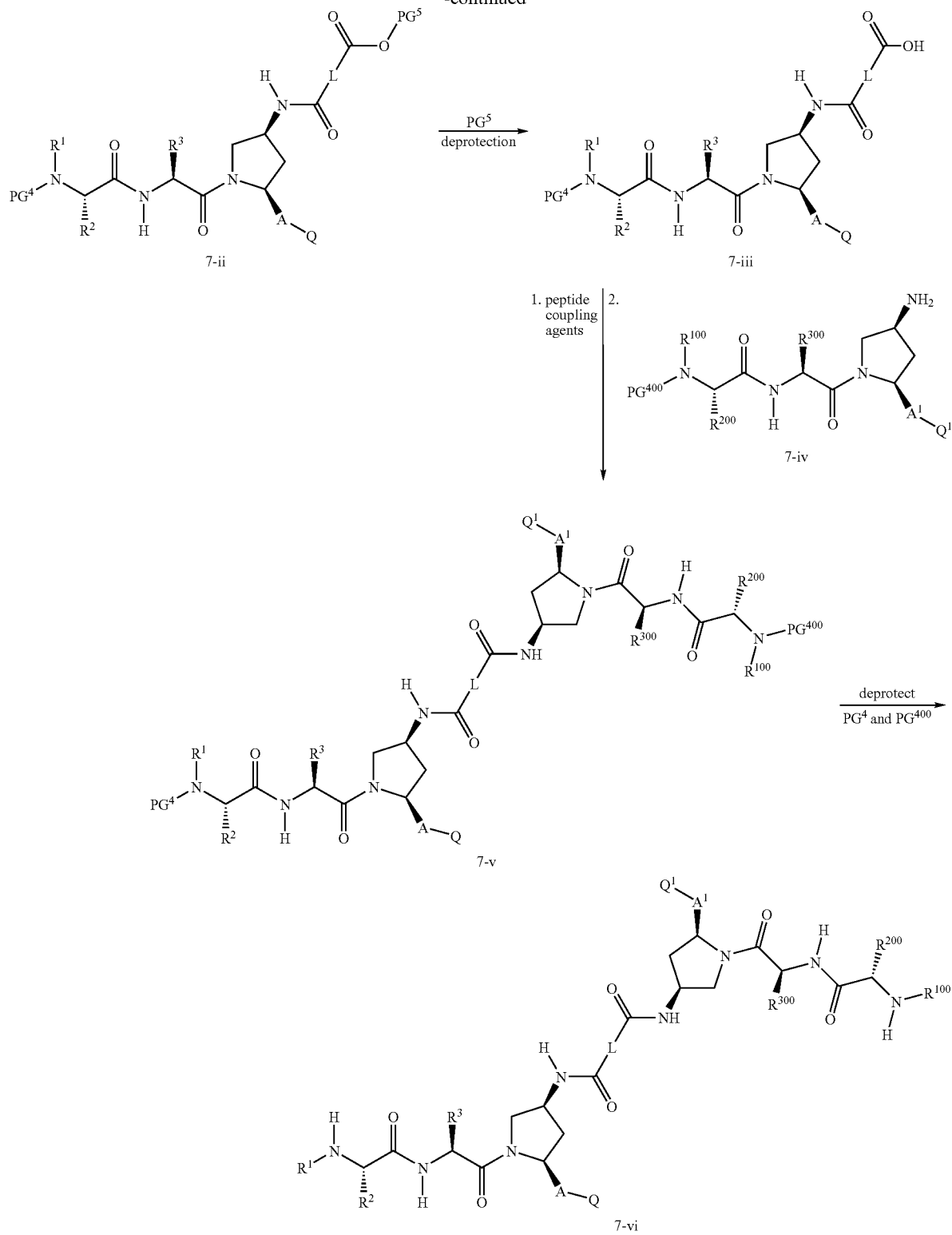

L = ——(CH₂)ᵣ——, ——(CH₂)ᵣ——Y——(CH₂)ᵣ——, aryl, heteroaryl

A similar process may be applied to the preparation of asymmetrically bridged BIR binding units, which have been bridged between P2 and P3, as illustrated in scheme 8. Treatment of 8-i with a cyclic anhydride, such as succinic or glutaric anhydride, provides intermediate 8-ii. Treatment of 8-ii with amide coupling agents followed by 3-i provides intermediate 8-iii. Deprotection of PG⁴ provides compound 8-iv.

Scheme 8: P2-P3 bis-amide bridged compounds

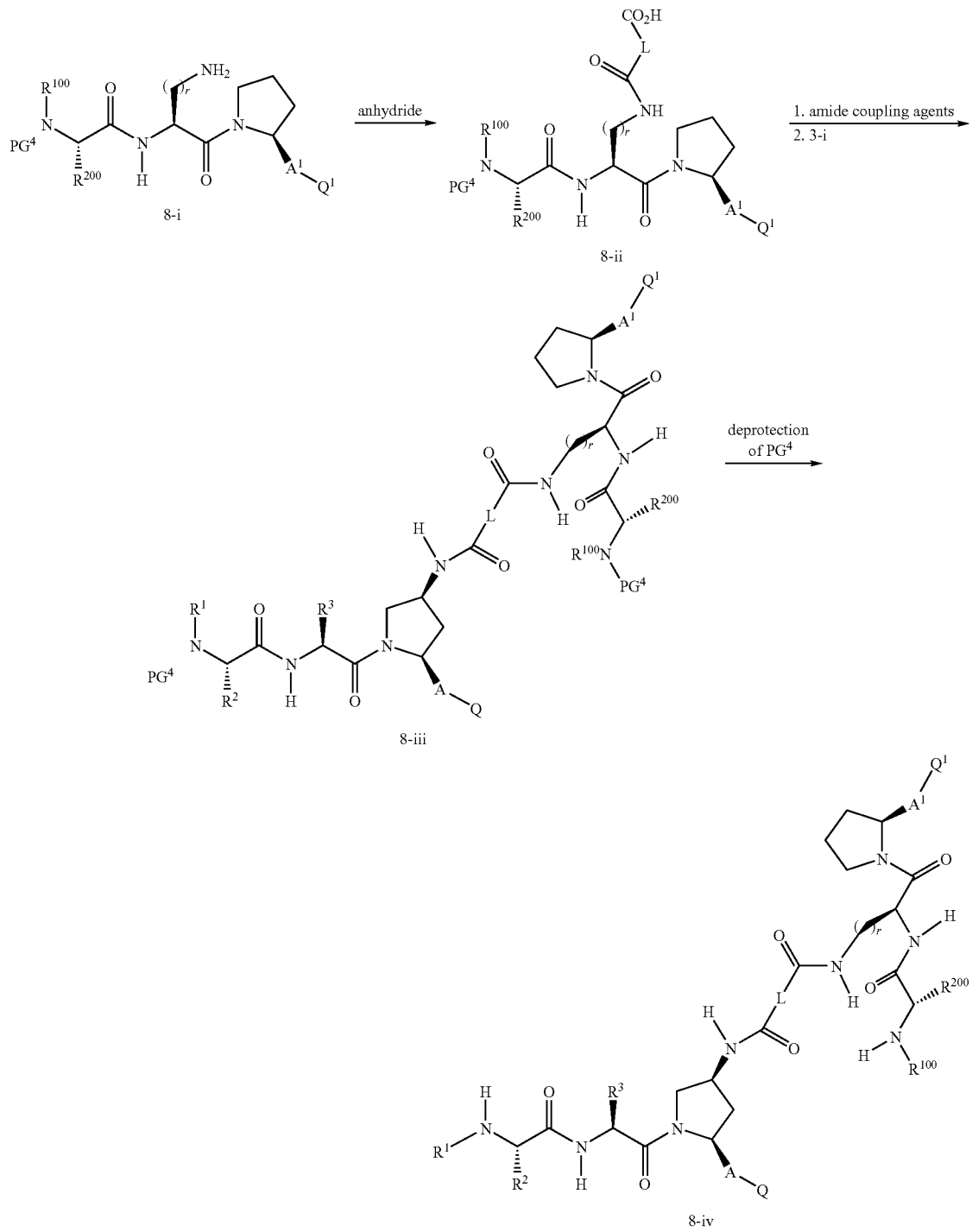

L = —(CH$_2$)$_r$—, —(CH$_2$)$_r$—Y—(CH$_2$)$_r$—, aryl, heteroaryl

Scheme 9 illustrates the synthesis of compound 1. Boc-cis-2-hydroxy-L-proline was treated with NaH in DMF, followed by propargyl bromide to provide intermediate 9-1. Amide coupling with (R)-1,2,3,4-tetrahydro-1-naphthlamine, and Boc deprotection with TFA provided intermediate 9-2. Amide coupling of Boc-tert-BuGly-OH with 9-2, followed by Boc deprotection with TFA provided intermediate 9-3. Amide coupling of Boc-MeAla-OH with intermediate 9-3 provided intermediate 9-4. Homo-coupling of the acetylene groups of 9-4 using a CuI/TMEDA catalyst under O$_2$, yielded intermediate 9-5, which was deprotected using 4N HCl in 1-4, dioxane, to provide compound 1-2HCl.

Scheme 9
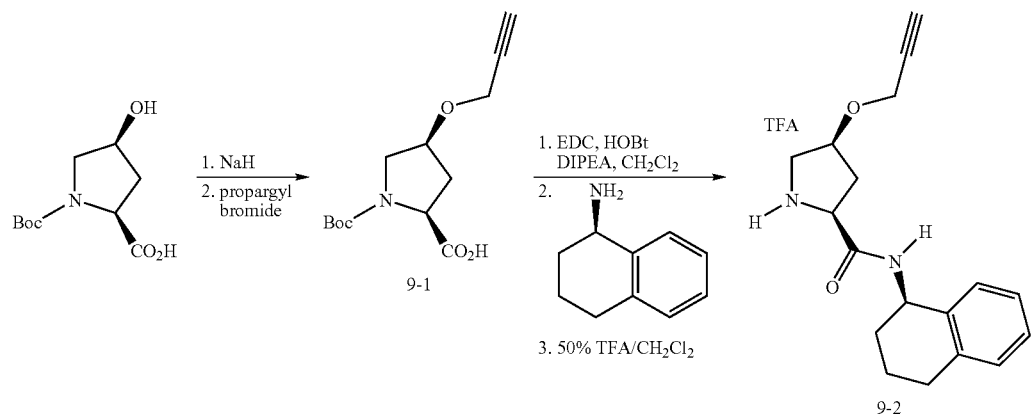
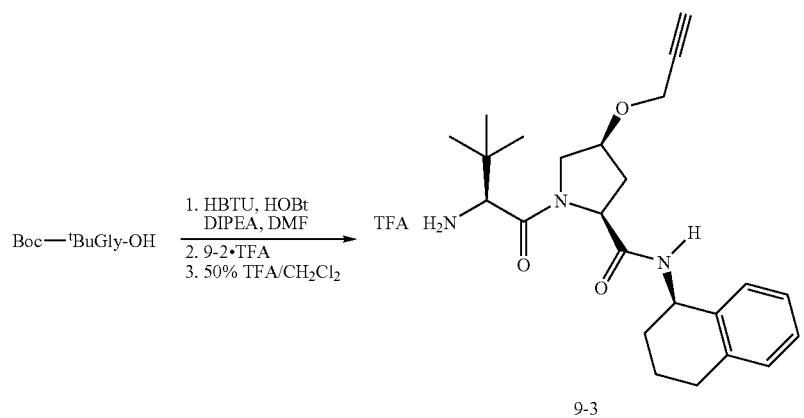
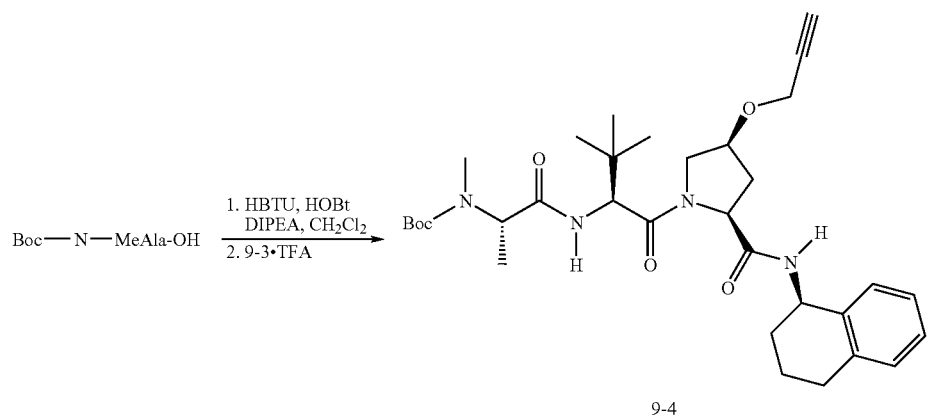

-continued
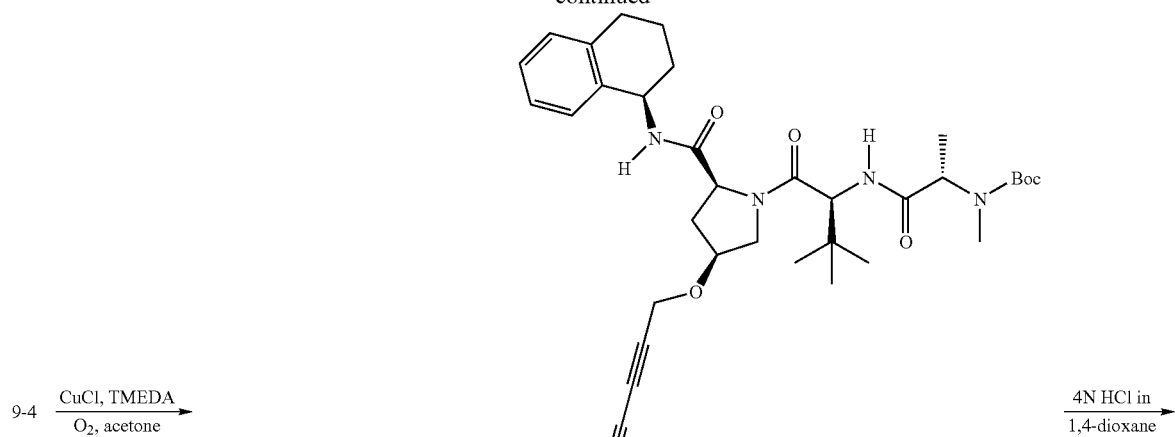
9-4 →(CuCl, TMEDA, O₂, acetone)
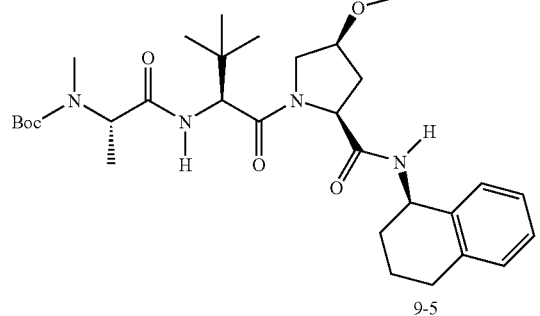
9-5
→(4N HCl in 1,4-dioxane)
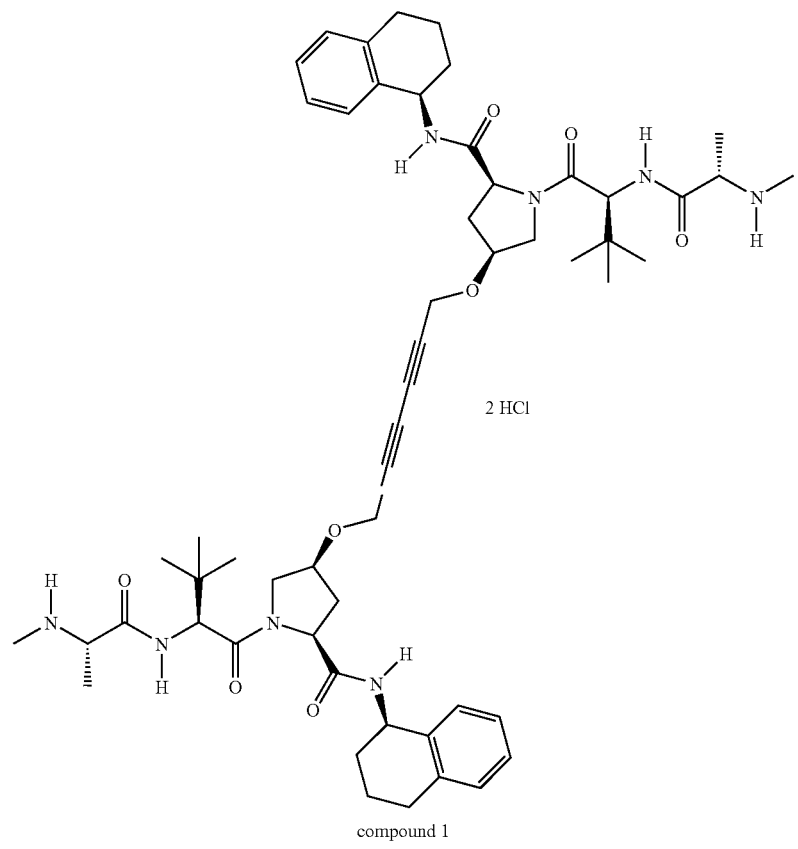
2 HCl
compound 1

Intermediate 10-6 was used in the preparation of compound 2 and 3 (see Schemes 10 to 12). Intermediate 10-5, was prepared using a similar procedure as described for intermediate 9-4, using Fmoc-AMPC(2S, 4S)-OH in the first step. Removal of the Fmoc protection group using a base such as 20% morpholine, in a solvent such as THF, provided intermediate 10-6.

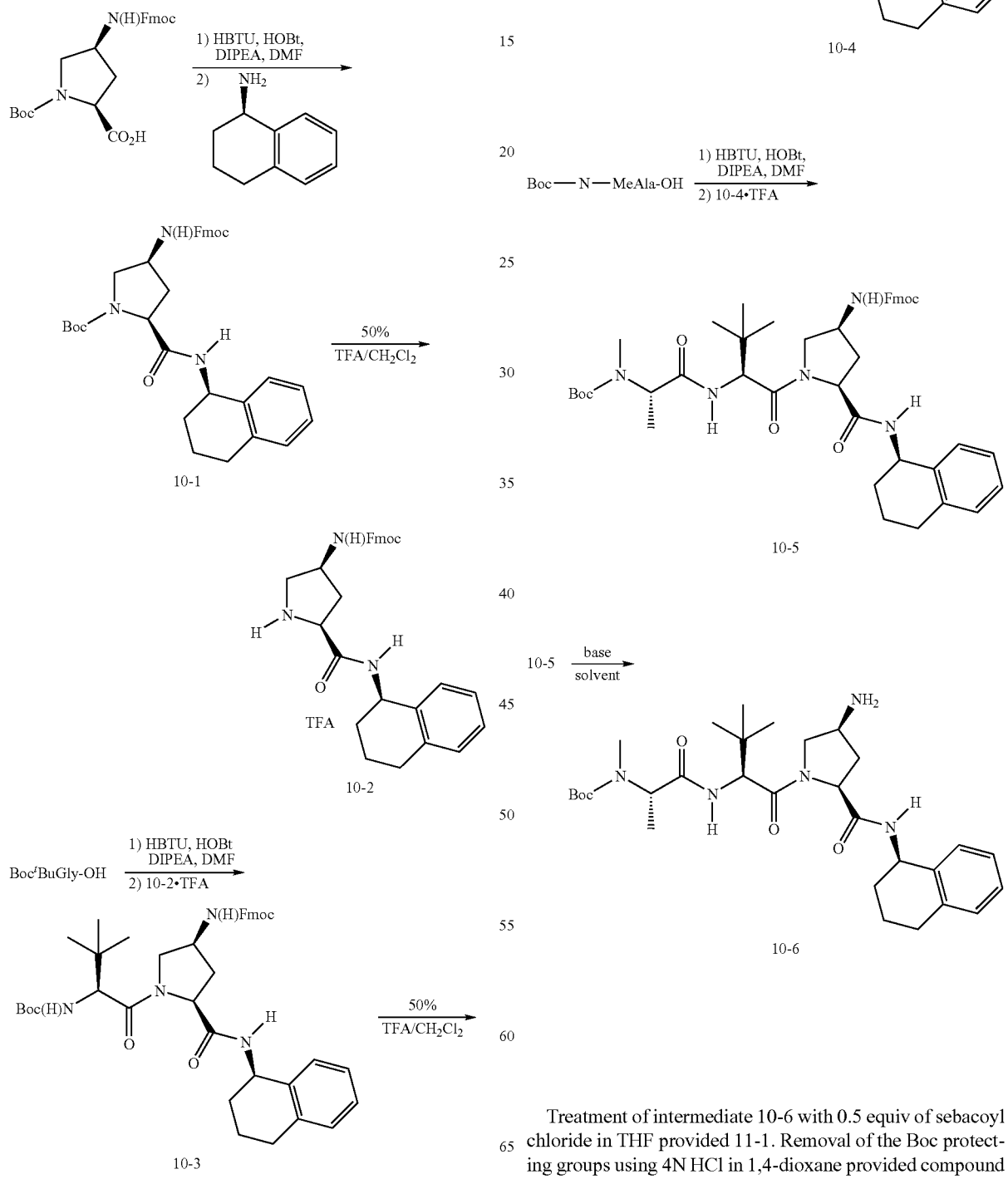

Treatment of intermediate 10-6 with 0.5 equiv of sebacoyl chloride in THF provided 11-1. Removal of the Boc protecting groups using 4N HCl in 1,4-dioxane provided compound 2.2HCl (Scheme 11).

Scheme 11
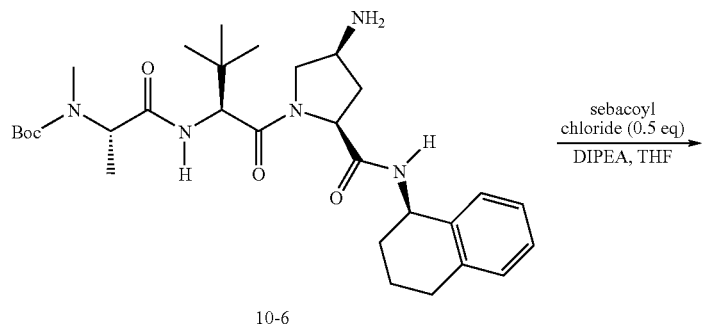
10-6
sebacoyl chloride (0.5 eq)
DIPEA, THF
→
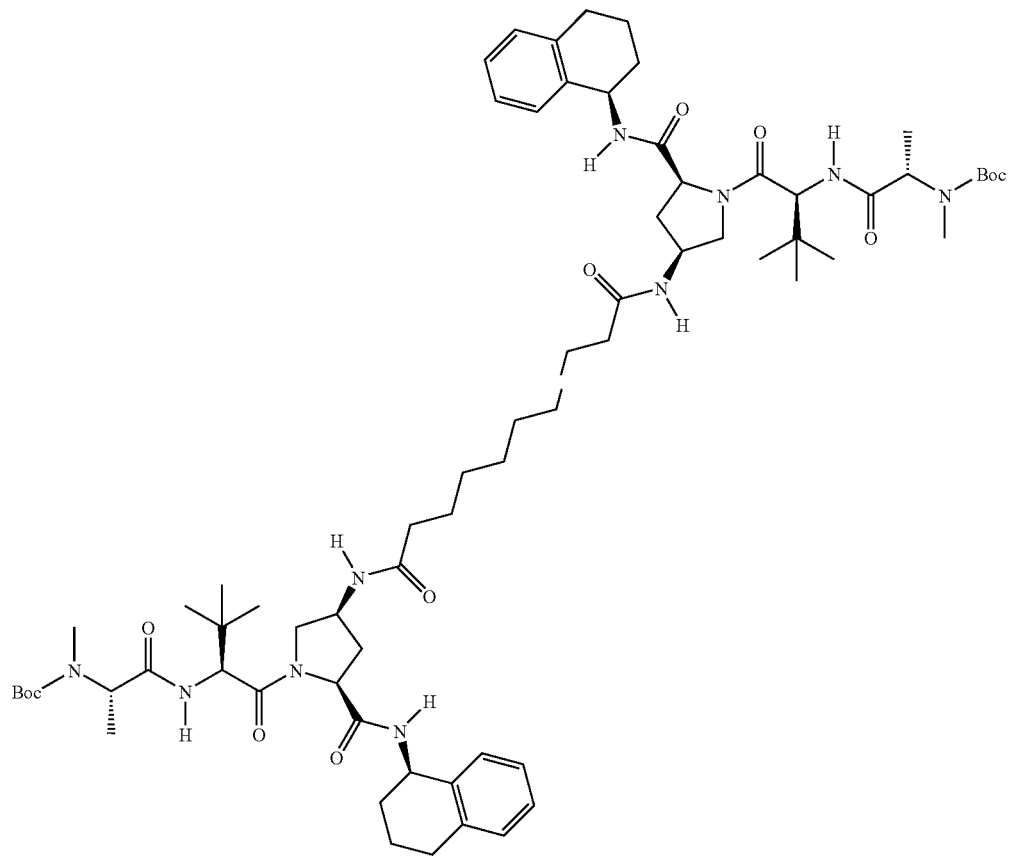
11-1

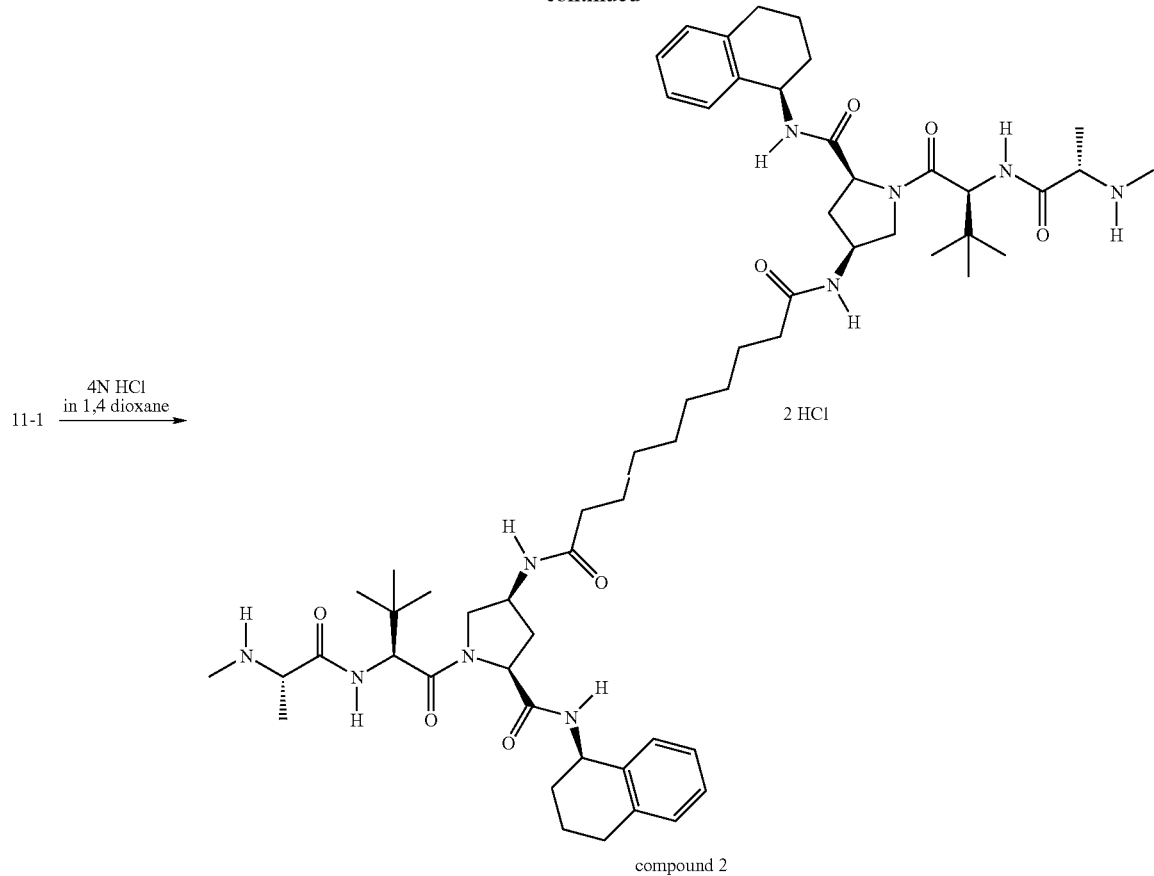
compound 2
Similarly, treatment of intermediate 10-6 with 0.5 equiv of terephthaloyl chloride in THF provided 12-1. Removal of the Boc protecting groups using 1N HCl in 1,4-dioxane provided compound 3.2HCl (Scheme 12).
Scheme 12
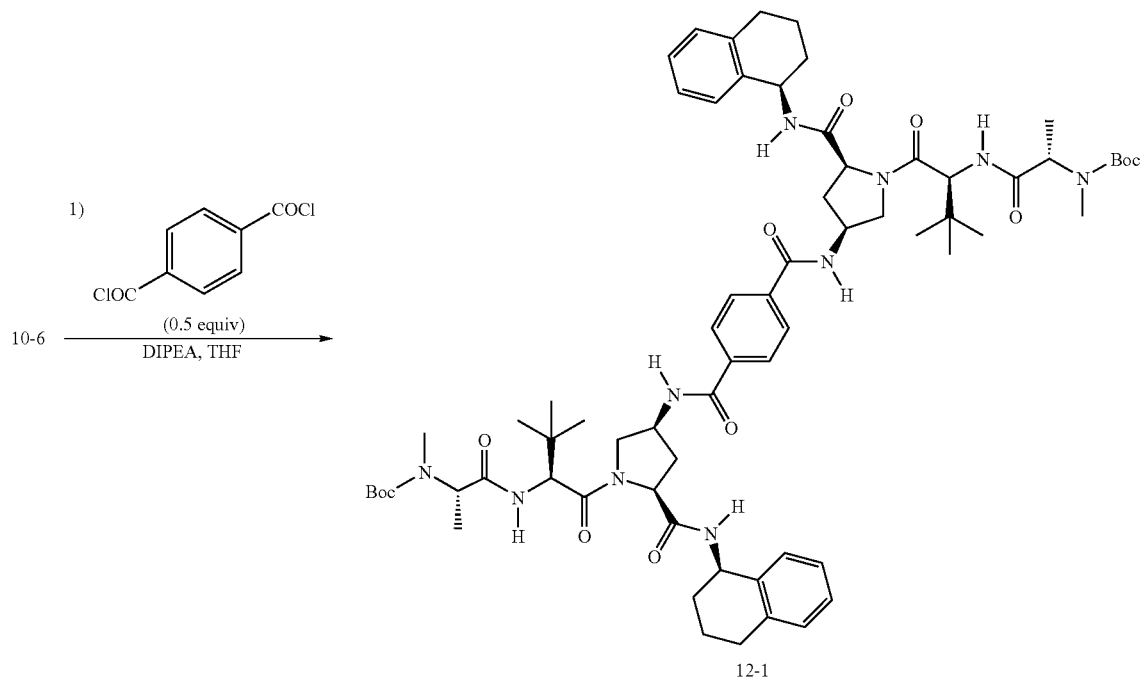
12-1

12-1 →(4N HCl, 1,4-dioxane)

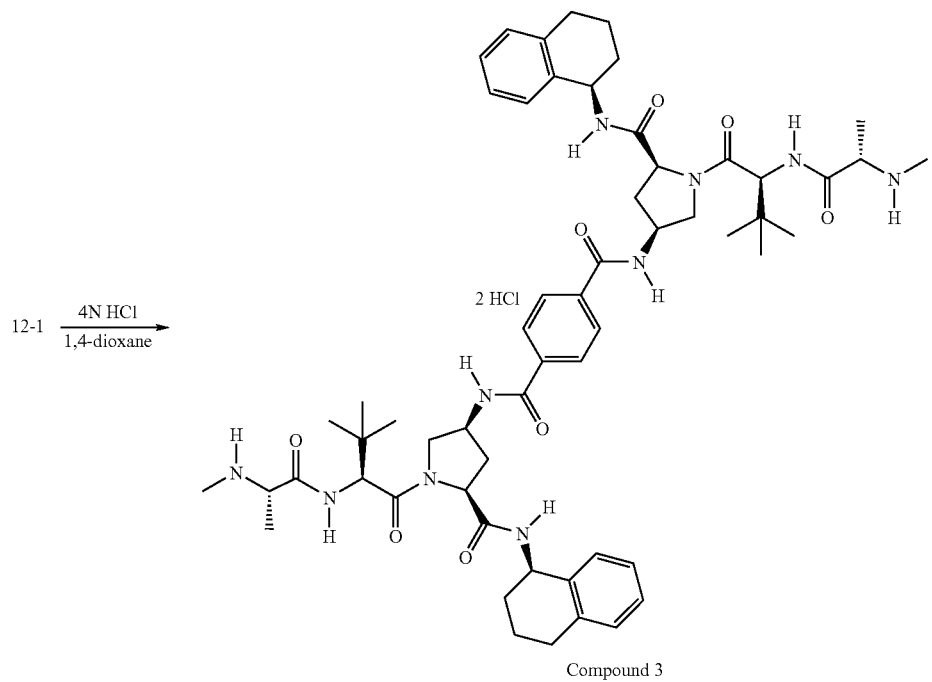

Compound 3

Scheme 13 illustrates the preparation of compounds 4 and 5 Intermediates 9-4 and 13-1 were coupled using a CuCl and TMEDA catalysts system, in acetone, under an oxygen atmosphere, to provide a mixture of intermediates 9-5, 13-2, and 13-3. Separation by silica gel chromatography provided the individual intermediates. Intermediates 13-2 and 13-3 were separately deprotected by treatment with 4N HCl in 1,4-dioxane, to provide compounds 4.2HCl and 5.2HCl, respectively.

Scheme 13: Synthesis of compounds 4 and 5.

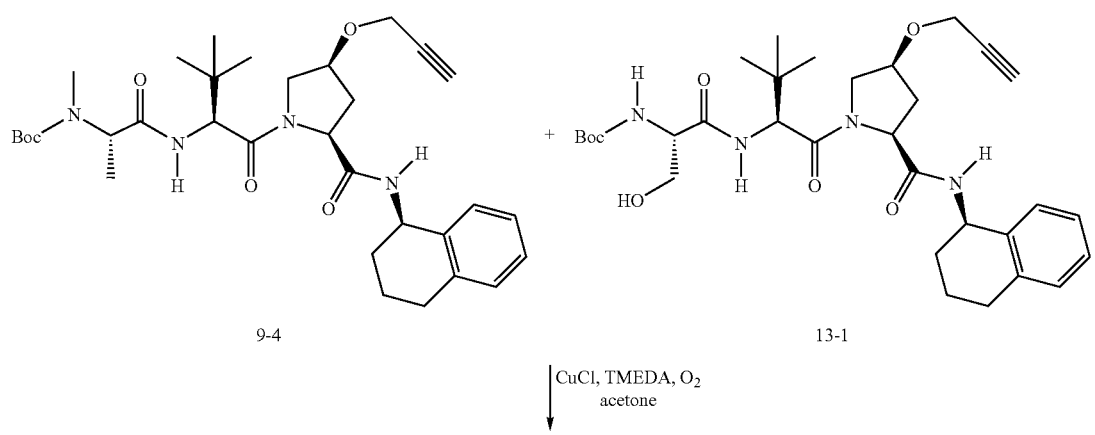

CuCl, TMEDA, O₂
acetone 9-5 + 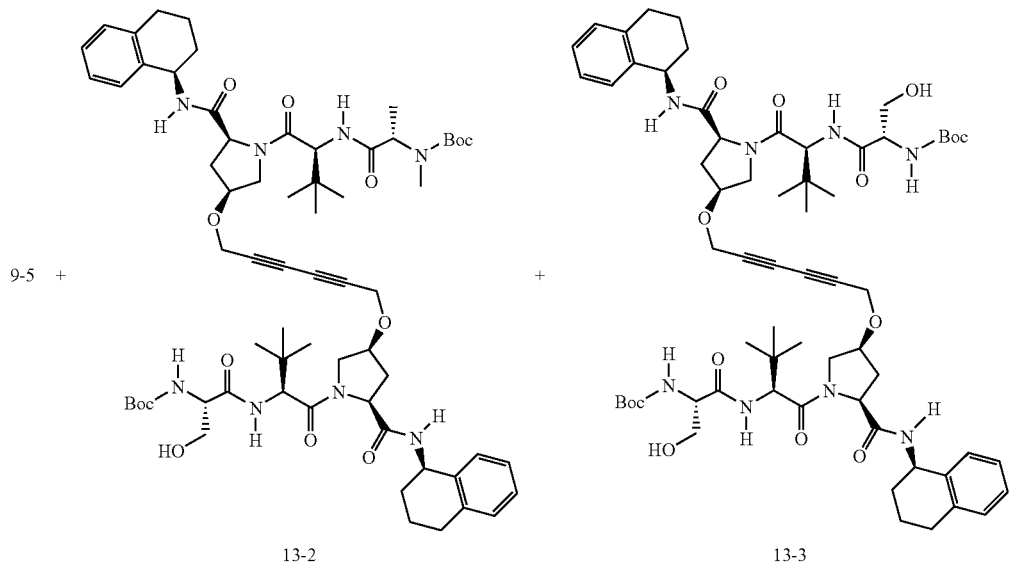 +
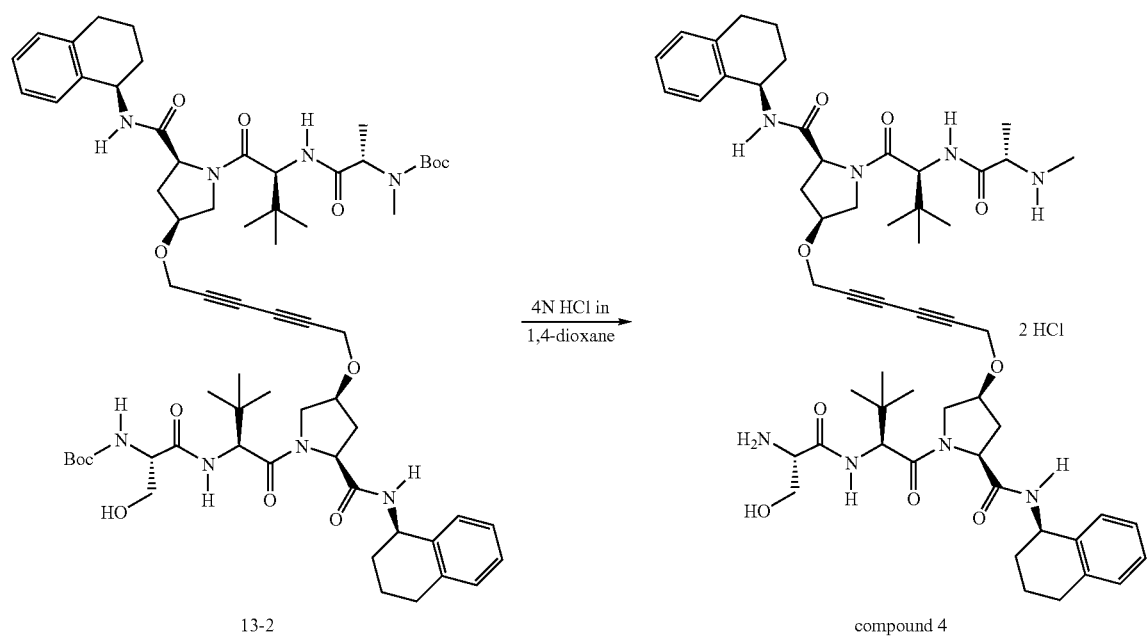

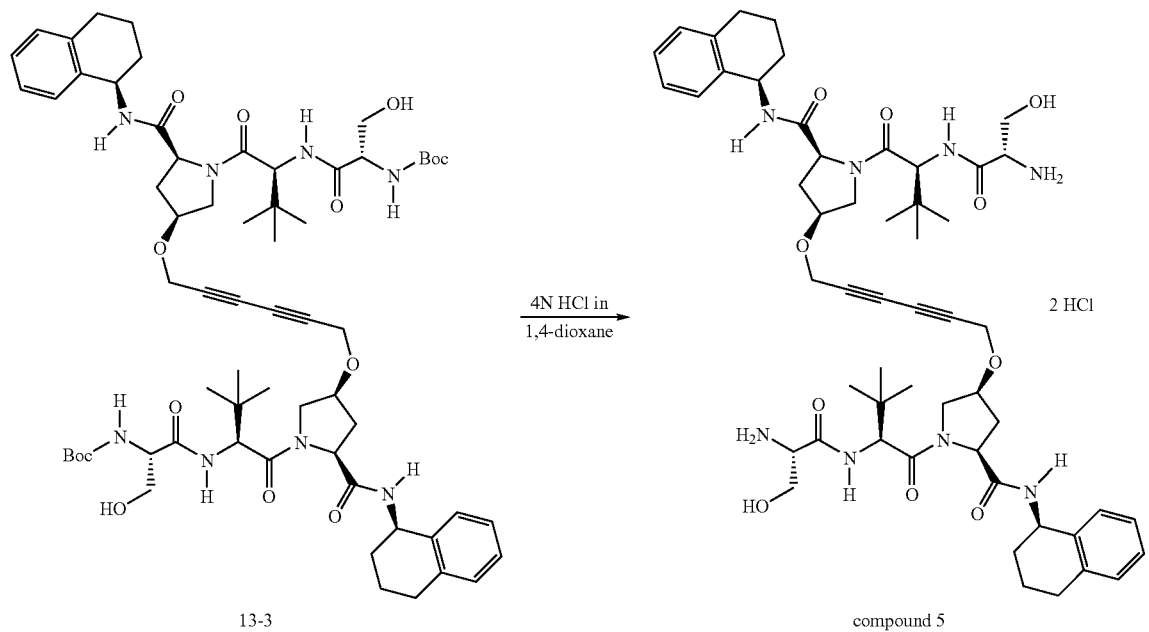
Scheme 14 illustrates the preparation of compound 6. Intermediates 9-4 and 14-1 were coupled using a CuCl and TMEDA catalyst system, in acetone, under an oxygen atmosphere. Intermediate 14-2 was isolated from the resulting mixture by silica gel chromatography. Intermediates 14-2 was Sdeprotected by treatment with 4N HCl in 1,4-dioxane, to provide compound 6.2HCl.
Scheme 14:
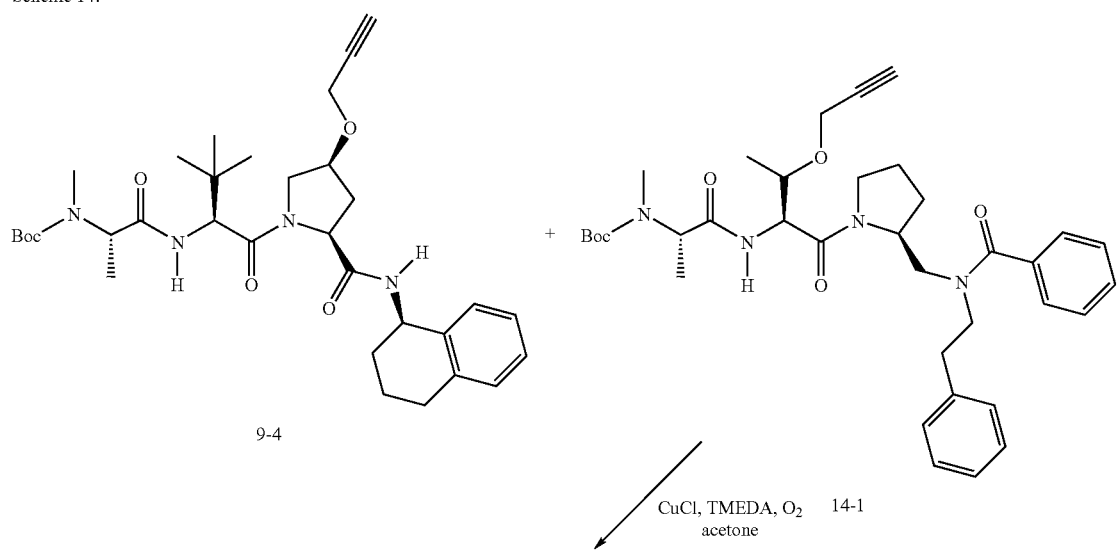

-continued

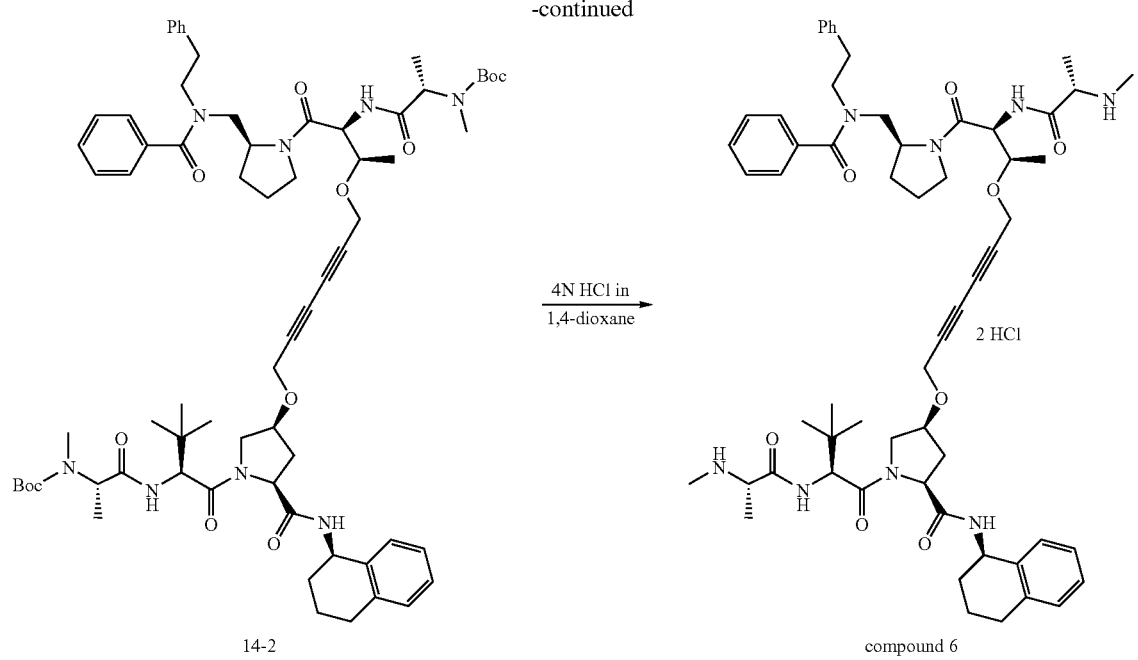

14-2

4N HCl in 1,4-dioxane → compound 6 · 2 HCl

Scheme 15 illustrates the preparation of P2-P3 bridged compounds 7 and 8. Intermediate 15-1 was treated with glutaric anhydride to provide intermediate 15-2. Treatment of 15-2 with HBTU, HOBt, and DIPEA, followed by the addition of 10-6 in DMF, provided intermediate 15-3. Removal of the Cbz protection group using $H_2$ over Pd/C yielded intermediate 15-4. Acylation of 15-4 with Boc-N-MeAla-OH provided intermediate 15-5, which was Boc deprotected using 4N HCl in 1,4-dioxane, provided compound 7.2HCl.

Scheme 15

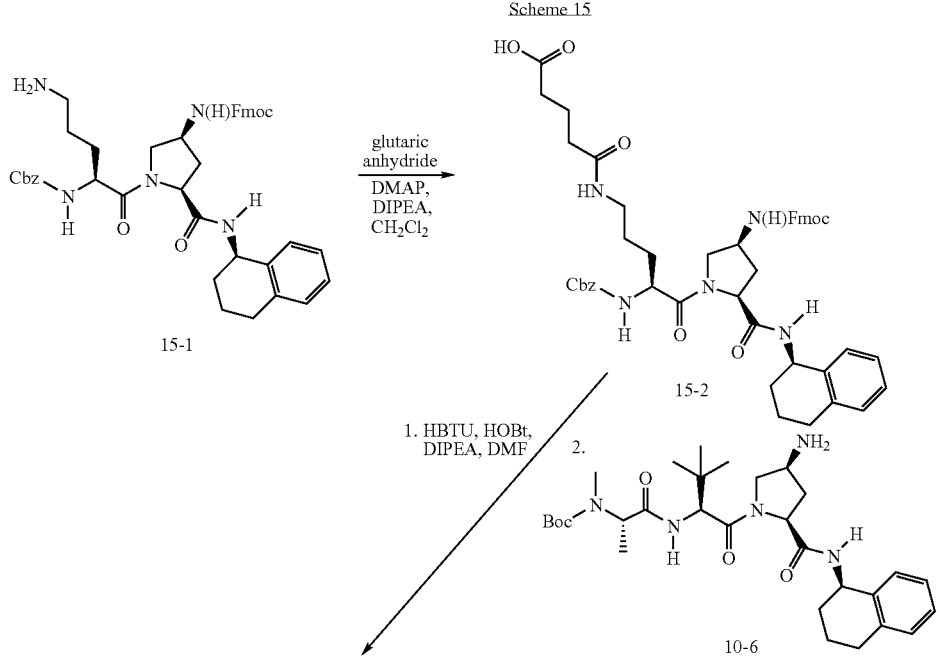

-continued
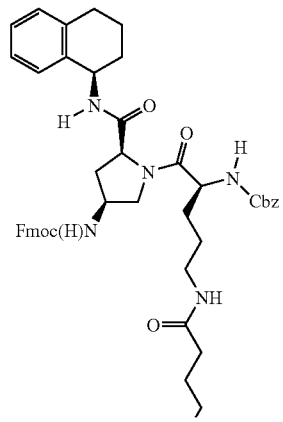
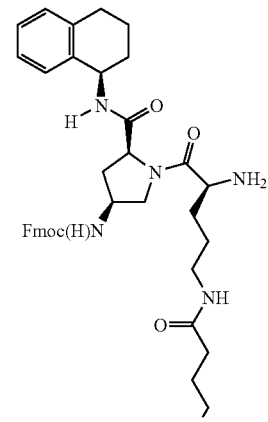
15-3
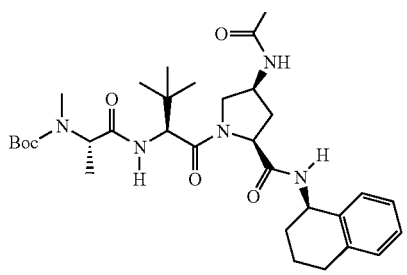
15-4
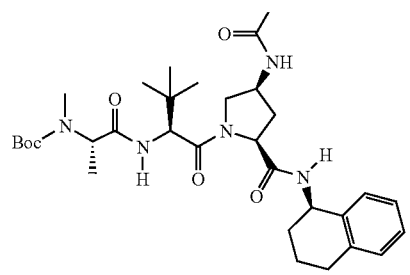
Boc—MeAla-OH  1. HBTU, HOBt DIPEA, DMF
2. 15-4
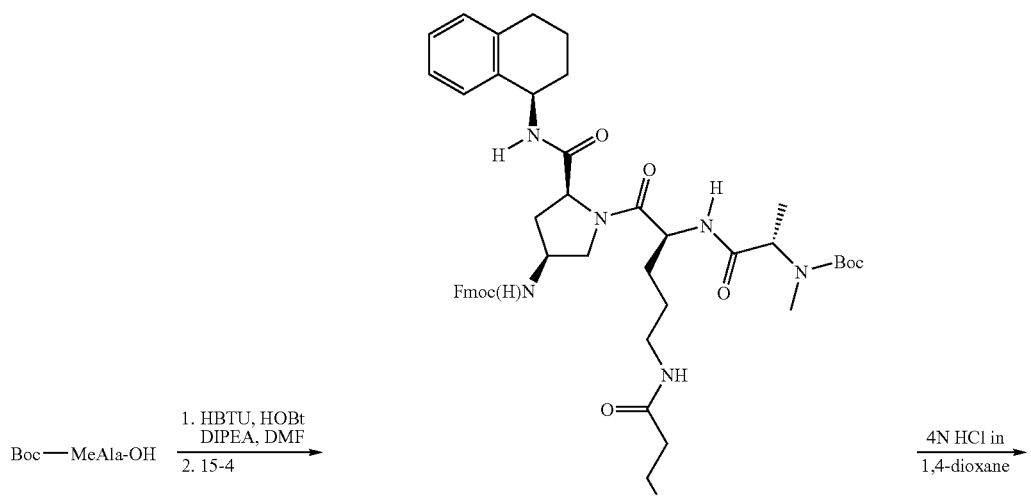
4N HCl in
1,4-dioxane
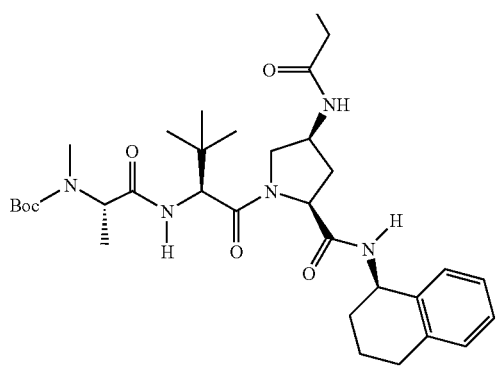
15-5

-continued
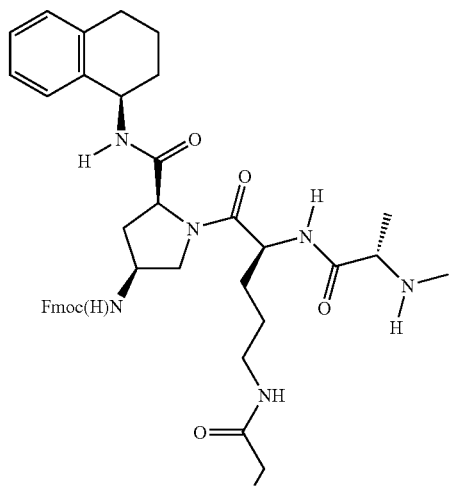
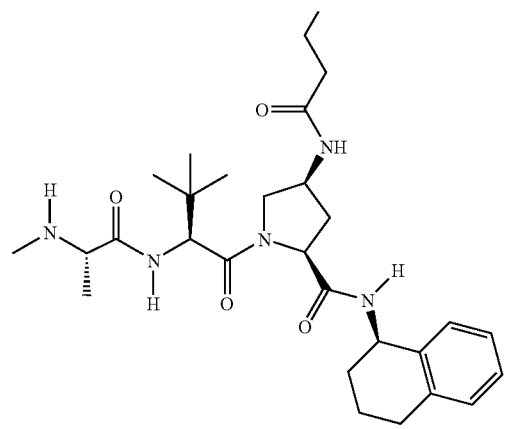
7
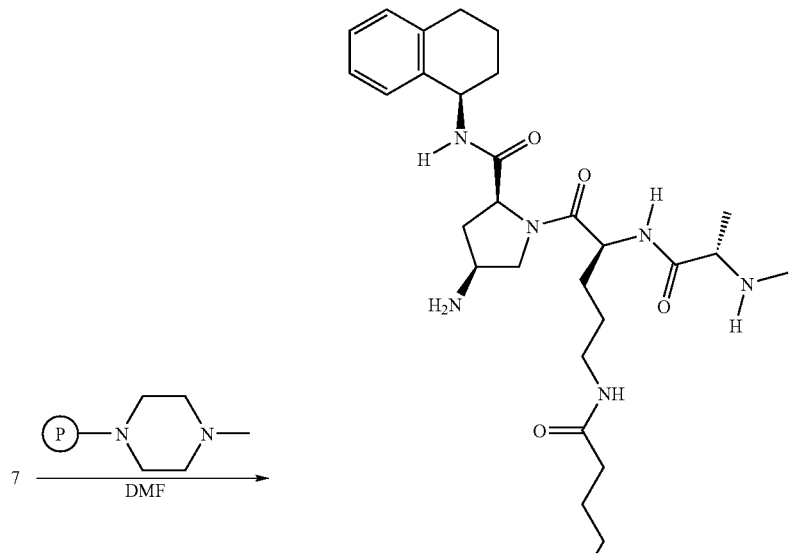

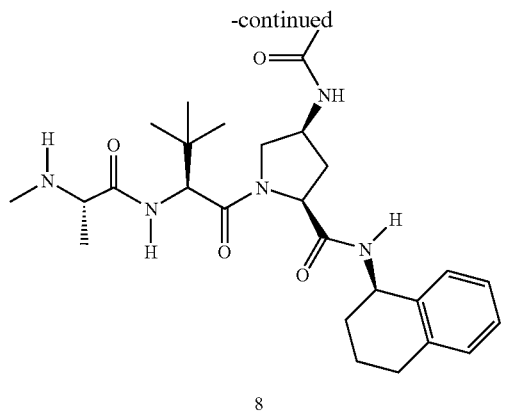

8

Removal of the Fmoc protection group from compound 7.2HCl, using polystyrene supported N-methylpiperazine in DMF provided compound 8. Removal of the Boc protection group from intermediate 15-3, using 4N HCl in 1,4-dioxane, provided compound 9.HCl (see Scheme 16).

Scheme 16

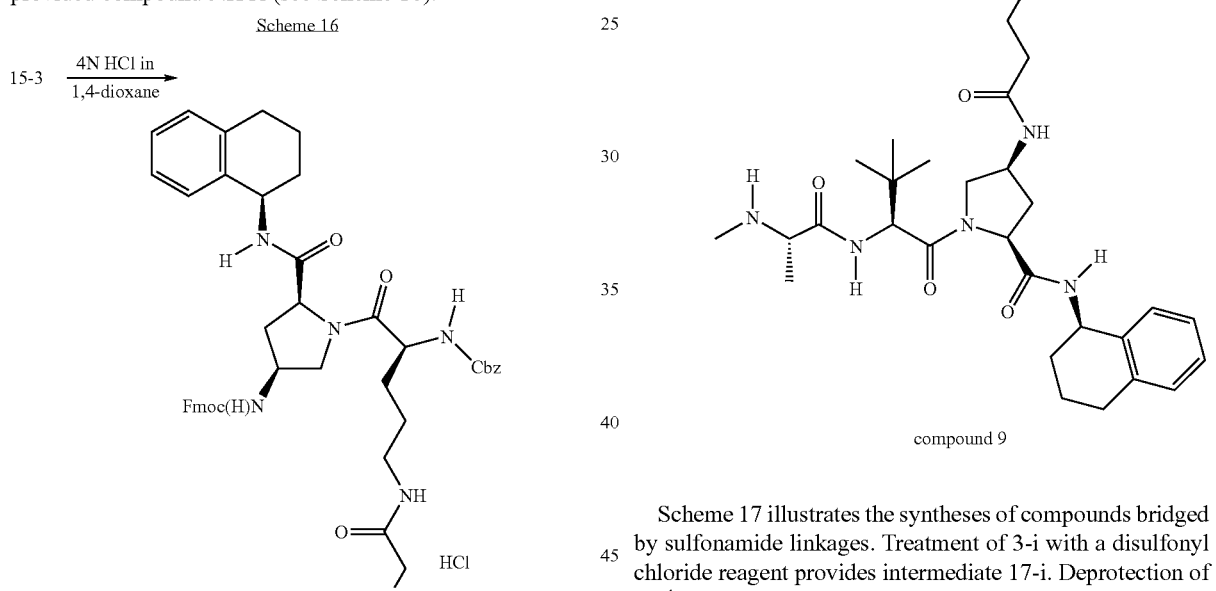

compound 9

Scheme 17 illustrates the syntheses of compounds bridged by sulfonamide linkages. Treatment of 3-i with a disulfonyl chloride reagent provides intermediate 17-i. Deprotection of $PG^4$ provides compound 17-ii.

Scheme 17

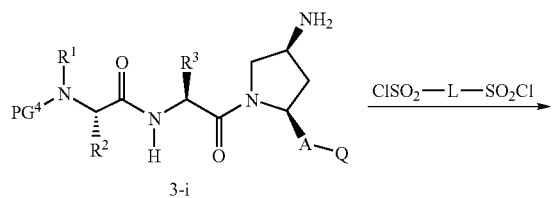

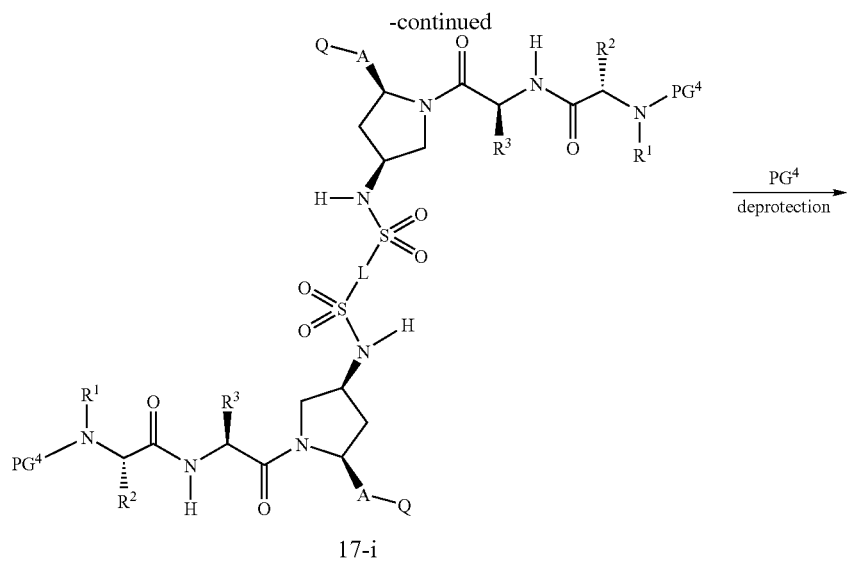
17-i
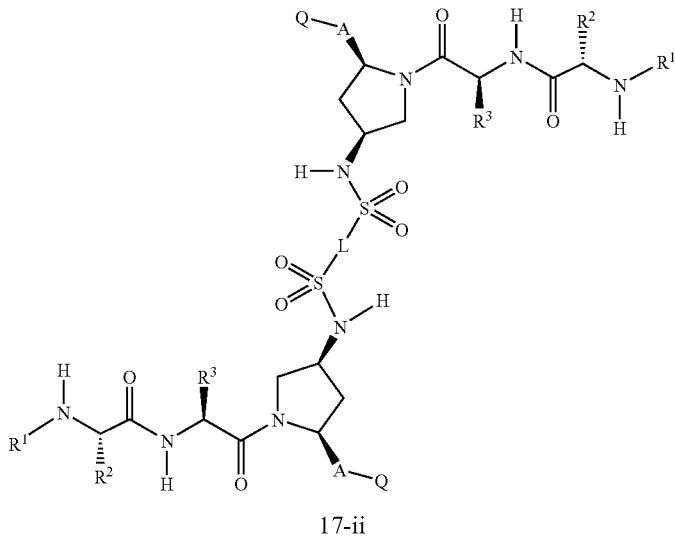
17-ii
Similarly, treatment of 3-i with a bis-isocyanate provides intermediate 18-i, which after deprotection of PG⁴ yields compound 18-ii.
Scheme 18
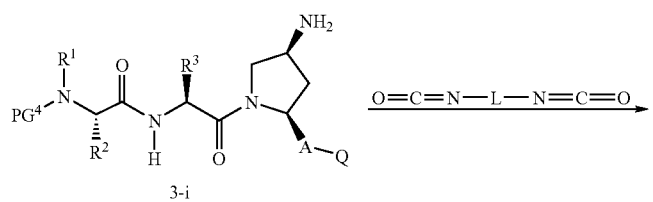
3-i

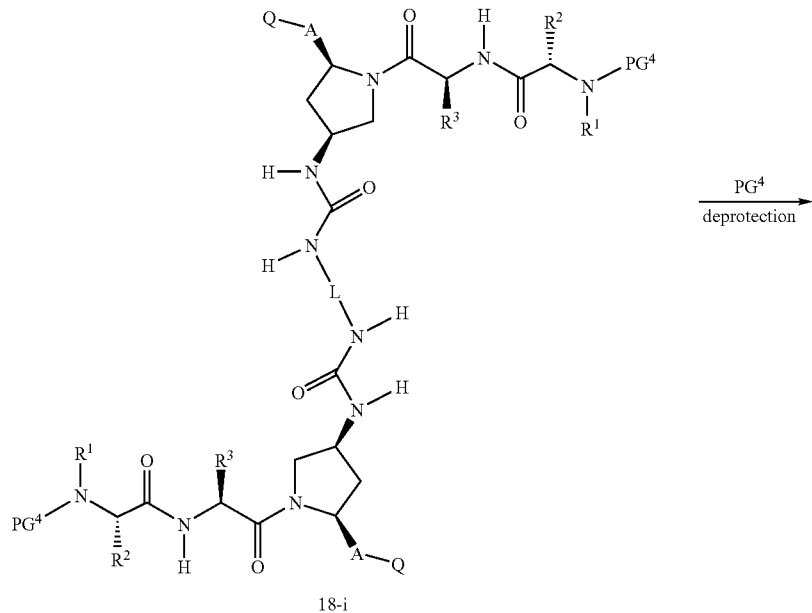

18-i

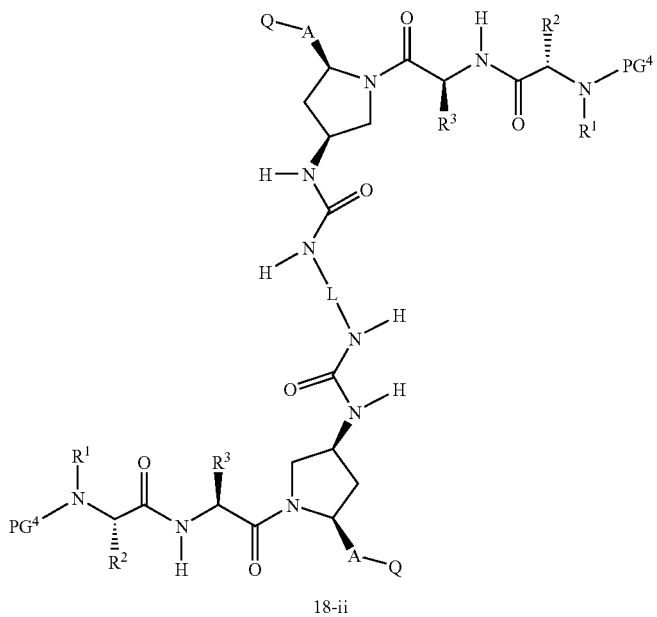

18-ii

Schemes 19a and 19b describe an alternate route to compounds 3-iii, 17-ii or 18-ii, where A=CO and Q=NR⁴R⁵. Protected amino-proline derivative 19-1 is treated with LG-L-LG to provide intermediate 19-2 which is then deprotected at $PG^1$ to yield intermediate 19-3. Intermediate 19-3 is converted intermediate 19-5 by an amino acid coupling/deprotection sequences as described earlier. A third amino acid coupling step converts intermediate 19-5 to intermediate 19-6. Deprotection of 19-6 at $PG^2$ yields the diacid intermediate 19-7. Treatment of 19-7 with amino acid coupling reagents, followed $R^4R^5NH$, yields intermediate 19-8, which upon deprotection of $PG^4$ provided compound 19-9.

Scheme 19a

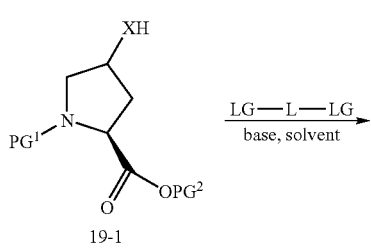

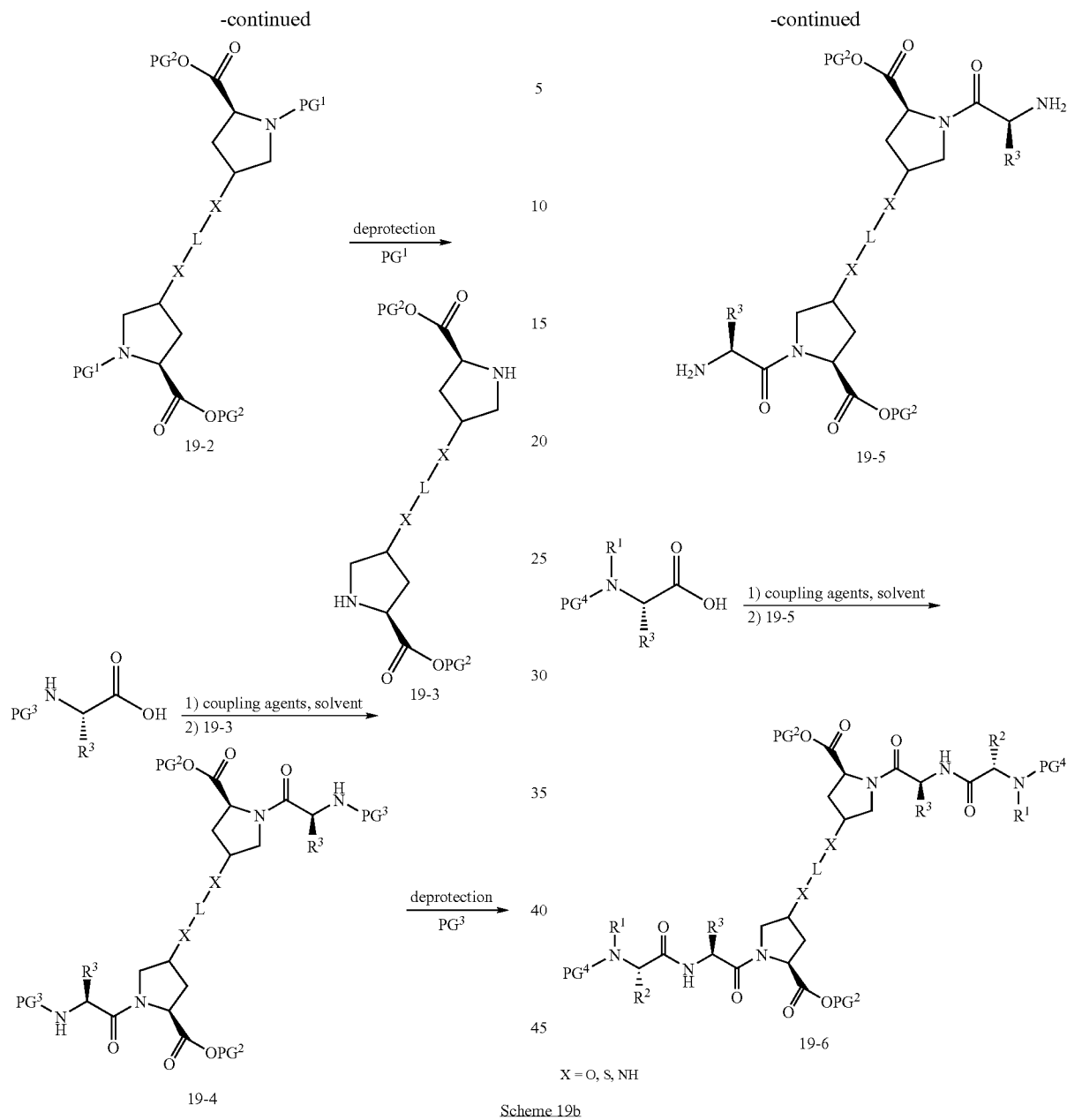
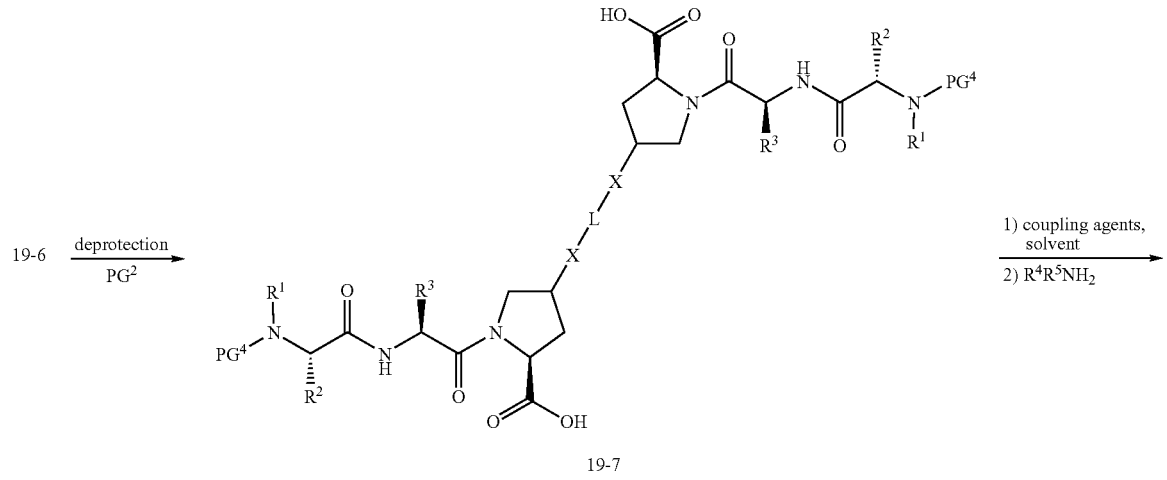

-continued

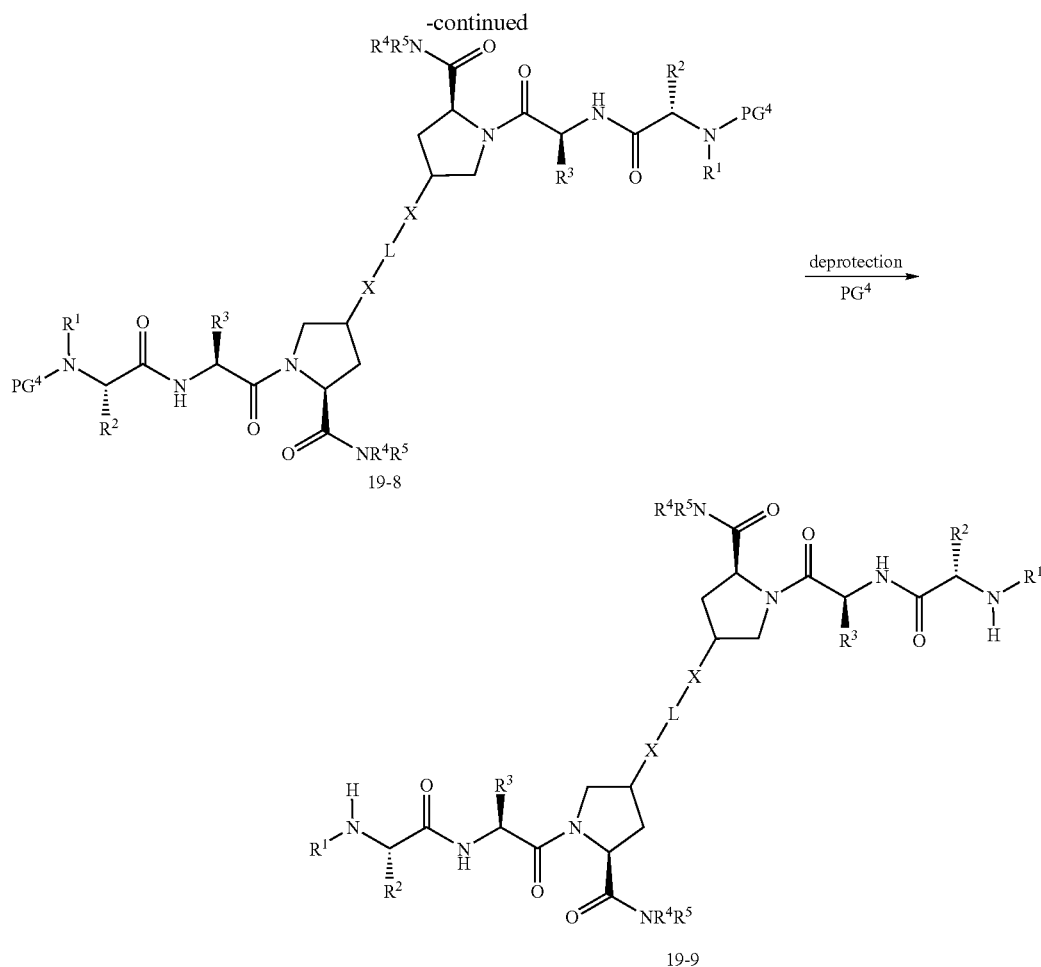

This method can be applied to the synthesis of bridged bis-proline amides, sulfonamids and ureas. For example, in the case where the bridging group includes an Ar moiety, X-L-X=—NHS(O)$_2$—Ar—S(O)$_2$NH—, NHC(O)—Ar—C(O)NH—, or —NHC(O)NH—Ar—NHC(O)NH—, —O—CH$_2$ArCH$_2$—O—.

Alternatively, the proline derivative 19-2 may be deprotected at PG$^2$ and converted to the amide intermediate 20-3. Following a similar procedure as described above, 20-3 can be converted to compound 19-9.

Scheme 20

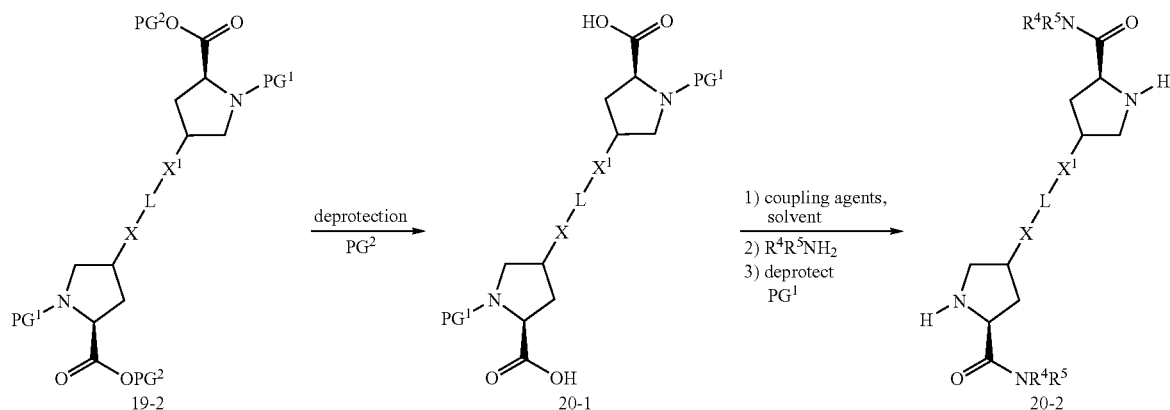

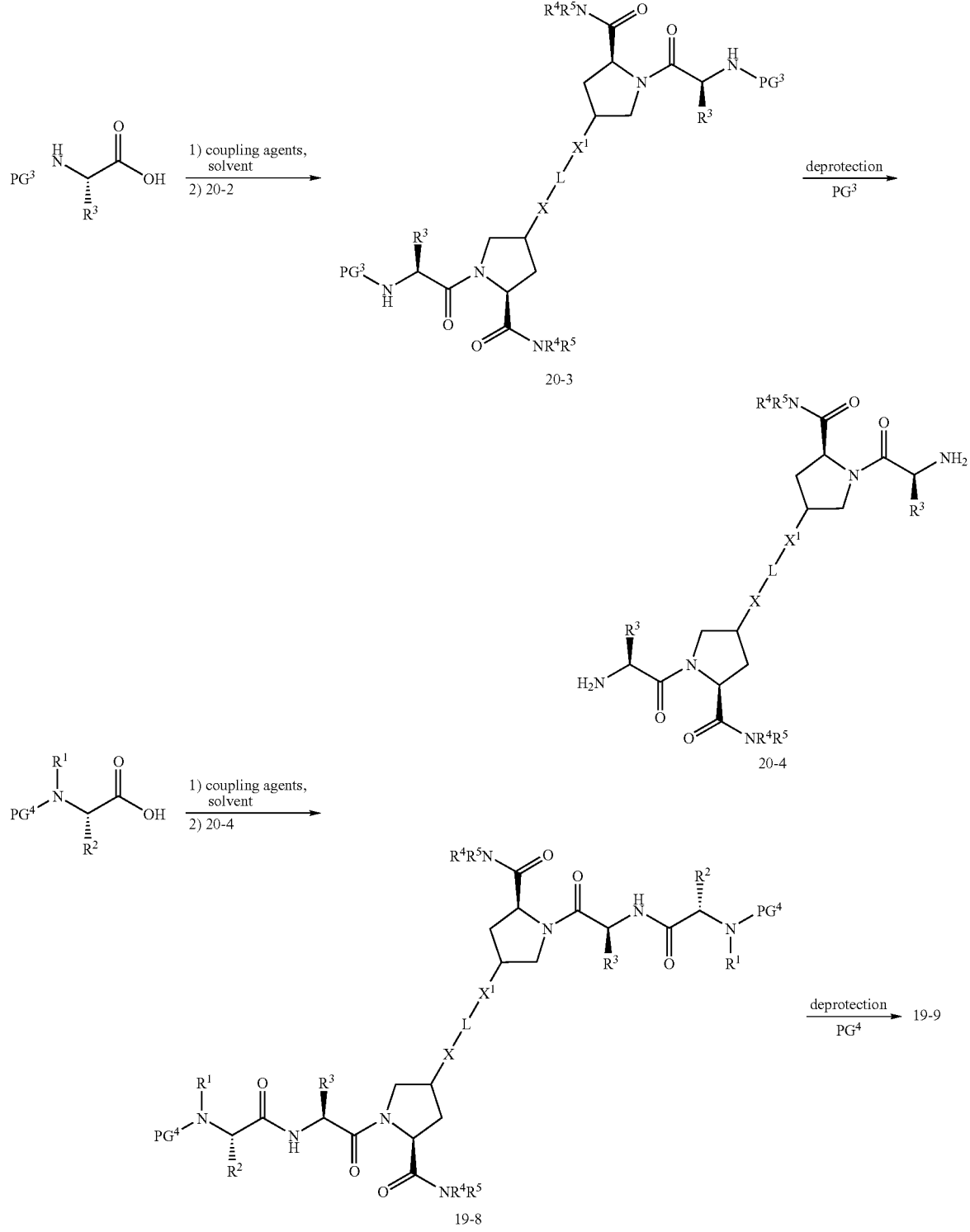

The synthesis of compound 20 is illustrated in Scheme 21. N-Boc-cis-4-amino-L-proline methyl ester, 21-1, was treated with terephthaloyl chloride to provide intermediate 21-2, which was further deprotected with TFA to yield intermediate 21-3. Intermediate 21-3 was coupled to Boc-tert-BuGyl-OH, 21-4, using HBTU and HOBt, followed by TFA deprotection, to provide intermediate 21-6. Intermediate 21-6 was coupled to Boc-N-MeAla-OH, 21-7, using HBTU and HOBt to provide intermediate 21-8. Saponification of the methyl ester using LiOH provided intermediate 21-9. Coupling of intermediate 21-9 with phenethylamine using HBTU and HOBt provided intermediate 21-10 which was deprotected using HCl in 1,4-dioxane to provide compound 20.2HCl.

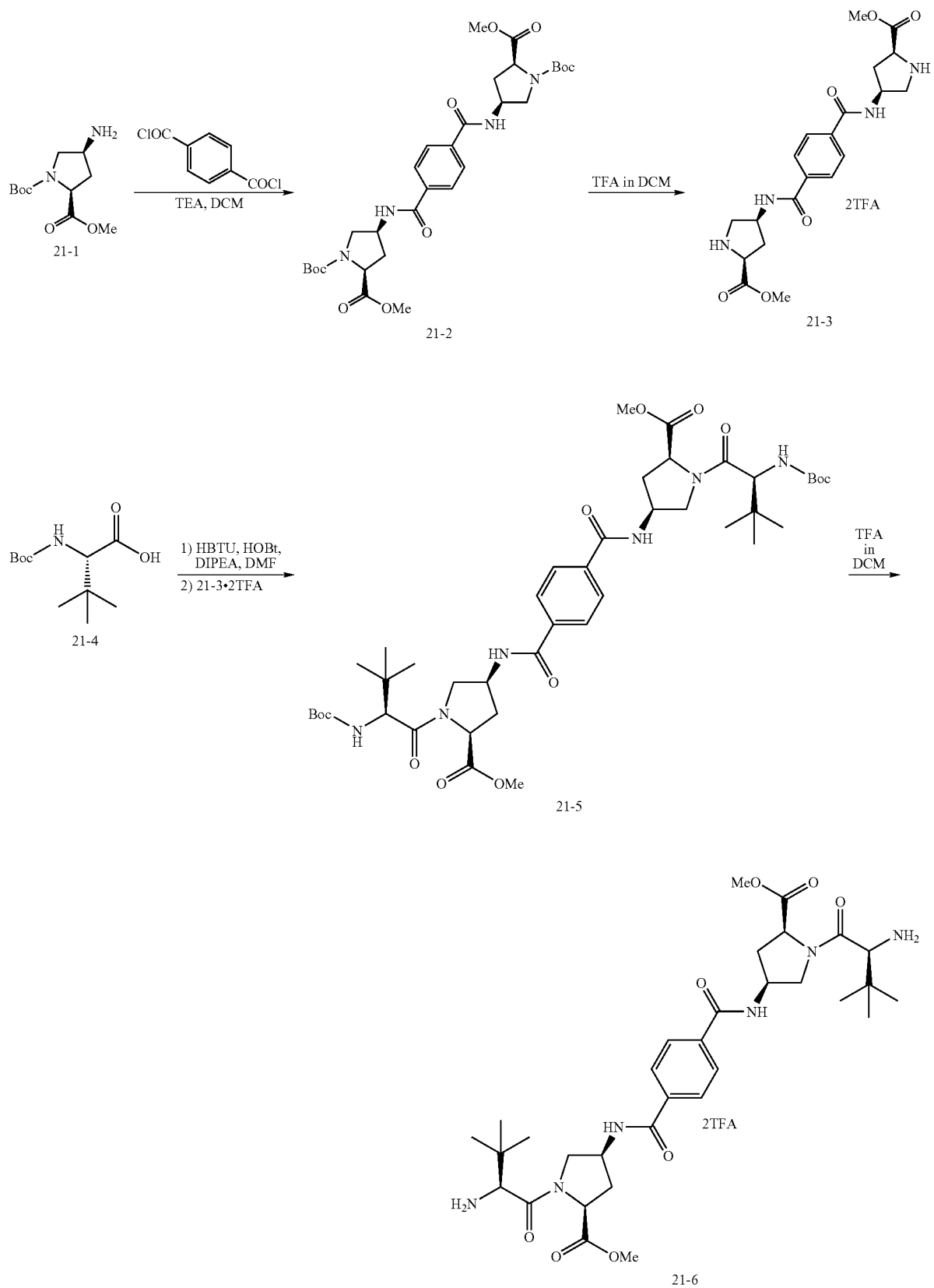
Scheme 21

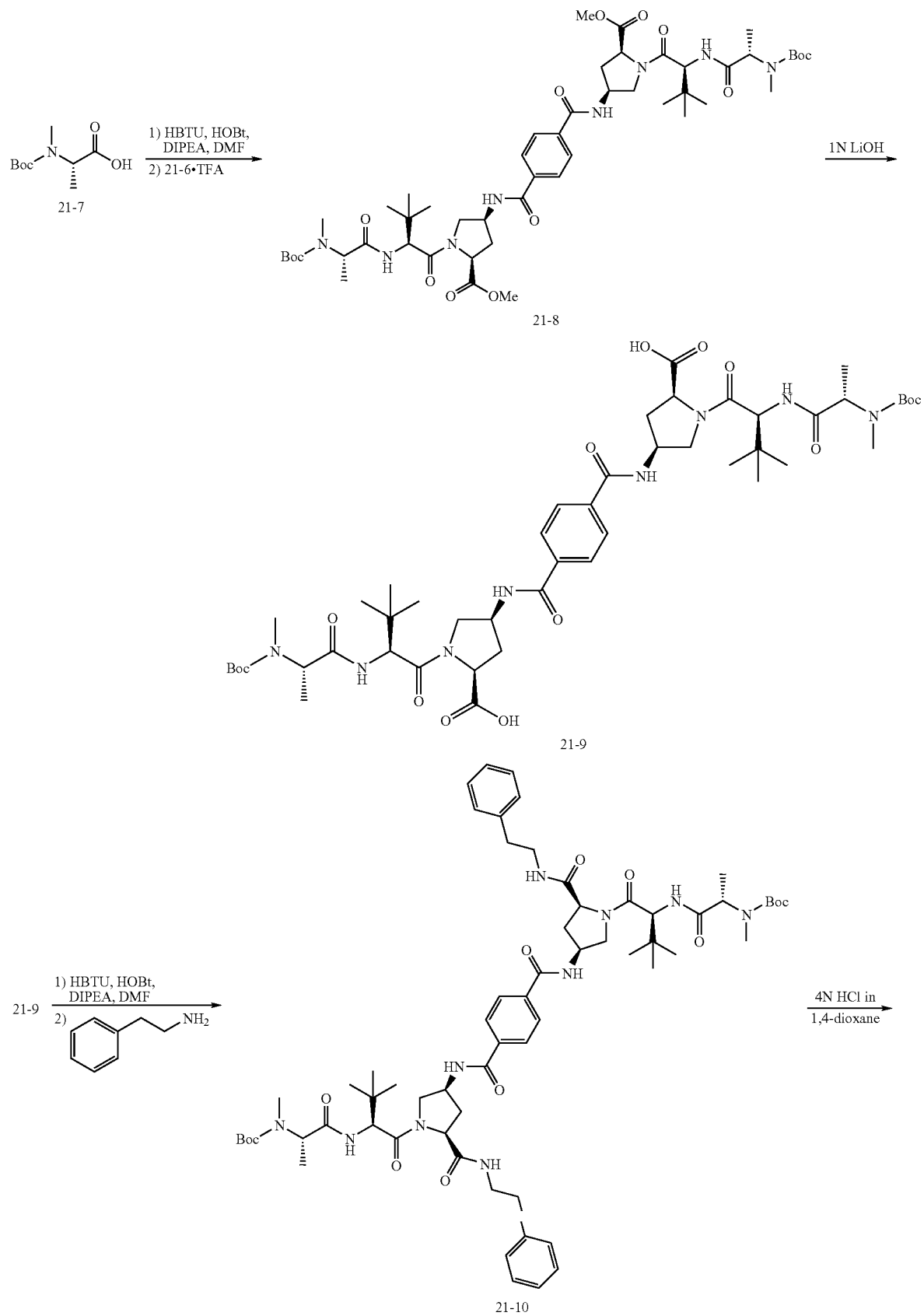

-continued

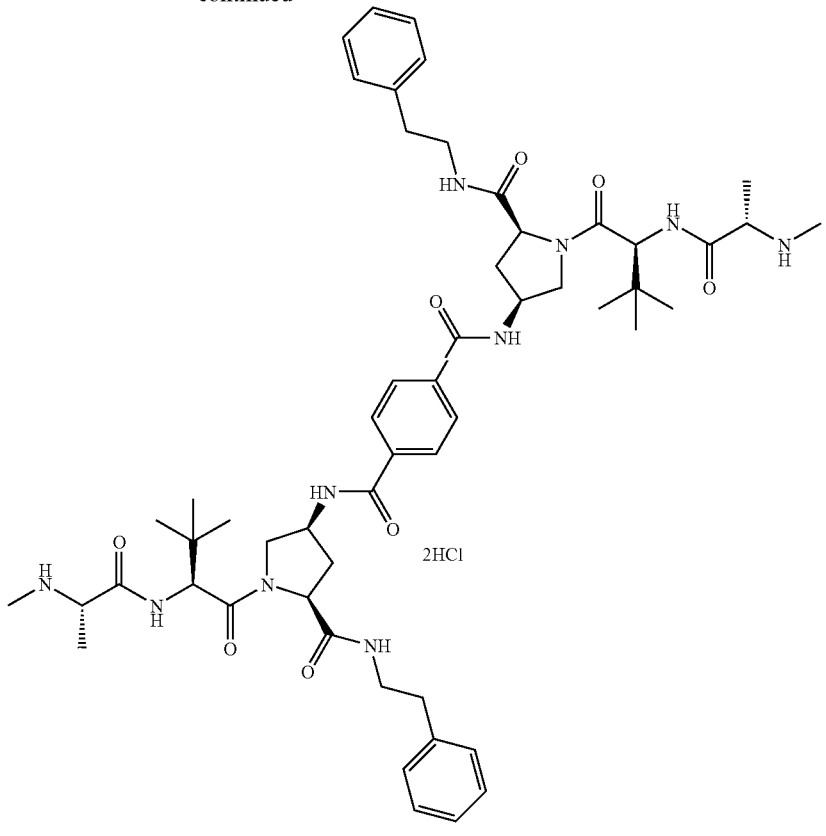

Compound 20

This method was used for the preparation of a number of proline amide derivatives such as compounds 19 to 24 and 46 to 51. This is shown in Scheme 22 wherein, intermediate 21-9 was coupled to 2-propylamide, followed by HCl deprotection to yield compound 22.2HCl, while coupling of intermediate 21-9 to 1,1-diphenylmethylamine followed by deprotection with HCl provided compound 24.2HCl.

Scheme 22

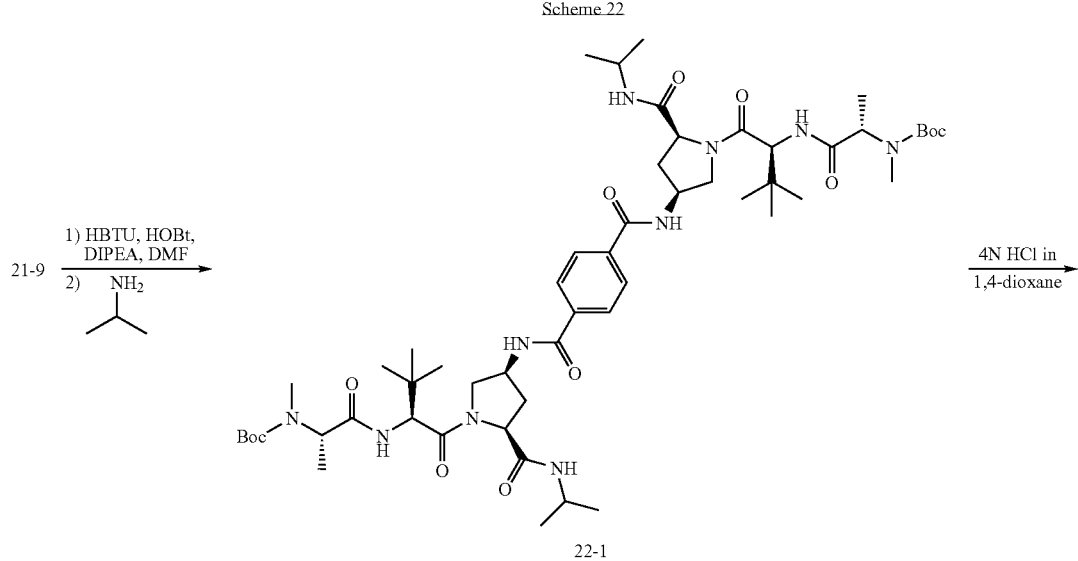

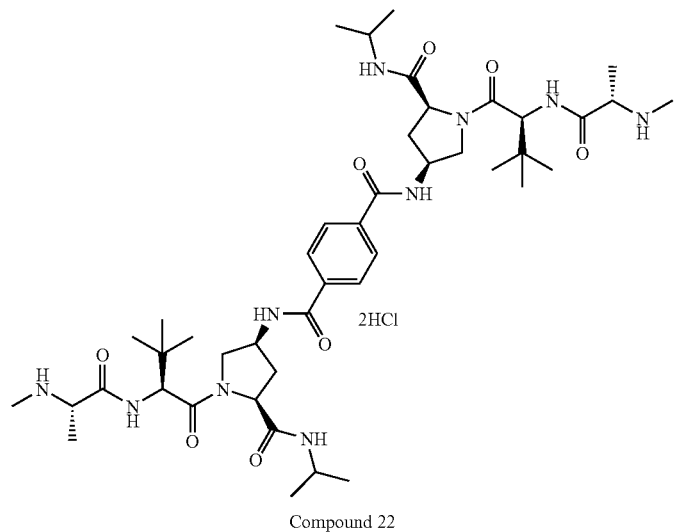
Compound 22
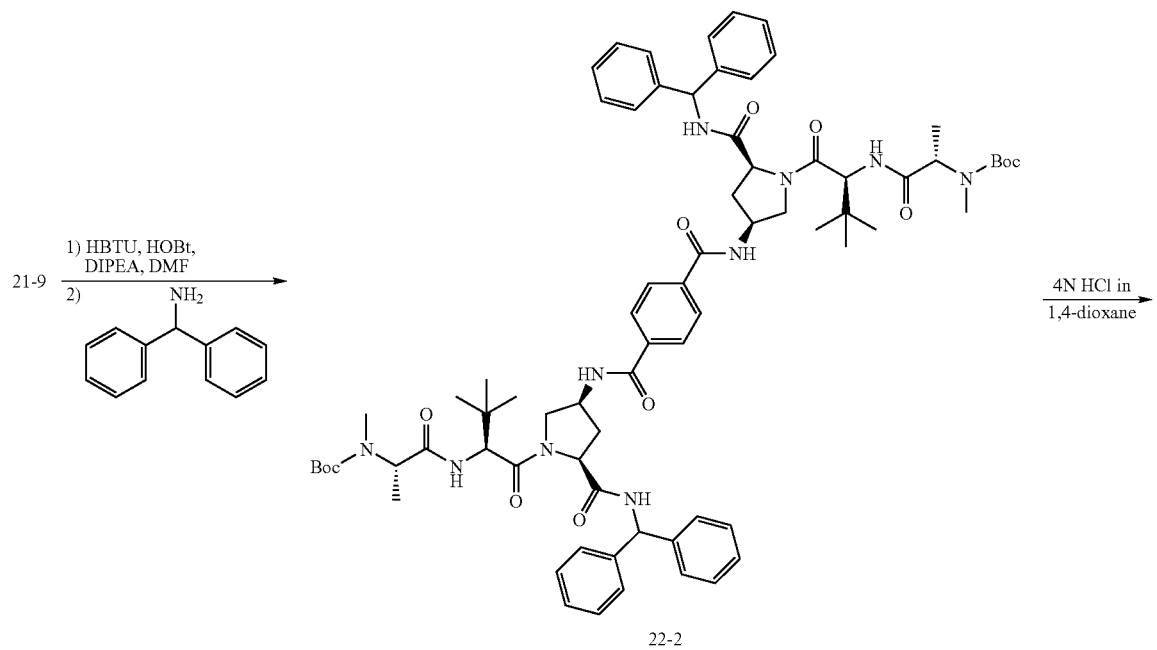

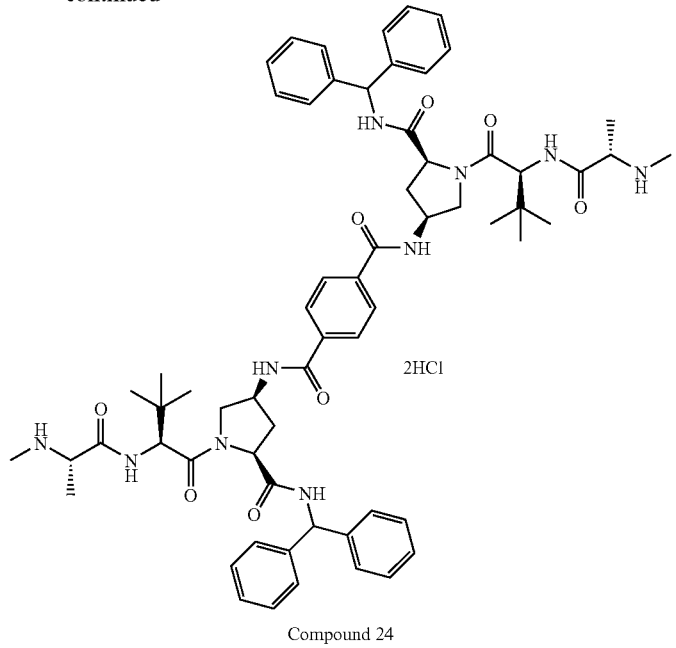

Compound 24

The preparation of pyrrolidine derivatives are described in Scheme 23. The ester moiety of intermediate 21-8 was reduced to alcohol 23-1 which was subsequently oxidized to aldehyde 23-2. Reductive amination using phenethylamine provided intermediate 23-4. Acylation of 23-4 with either acetyl chloride or benzoyl chloride provided 23-5 and 23-6, respectively. Deprotection with 1N HCl in 1,4-dioxane provided compounds 25.2HCl and 27.2HCl.

Scheme 23a

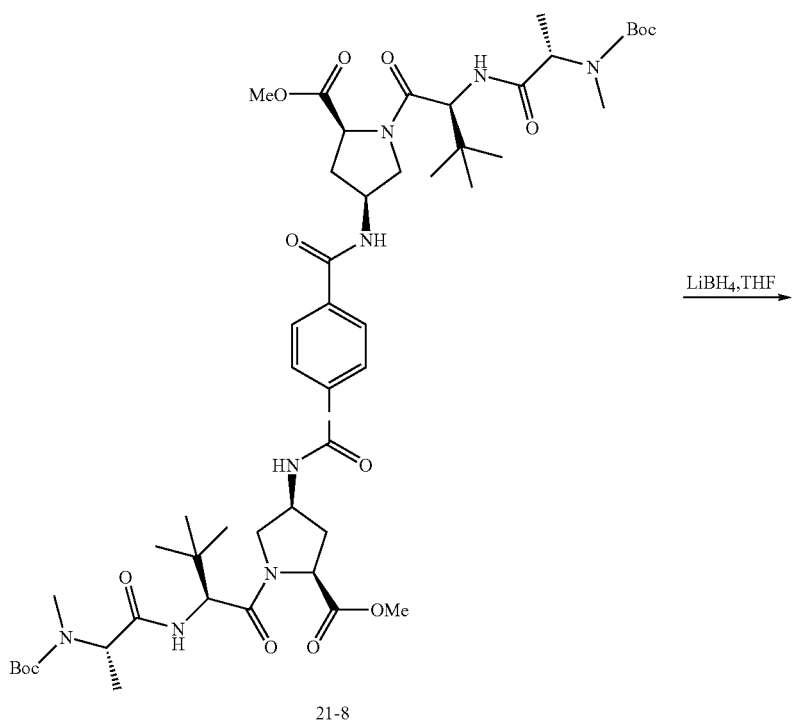

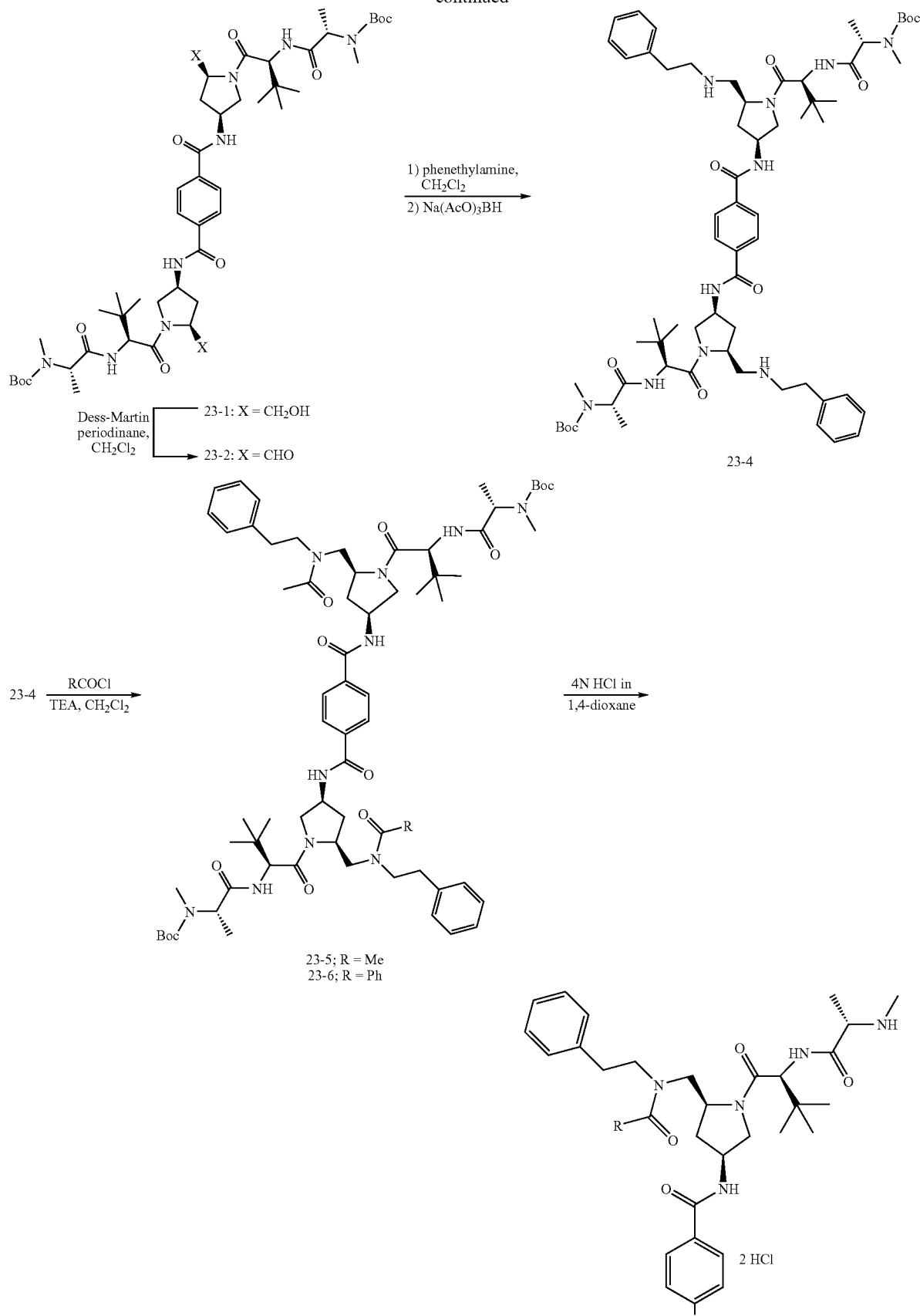

-continued
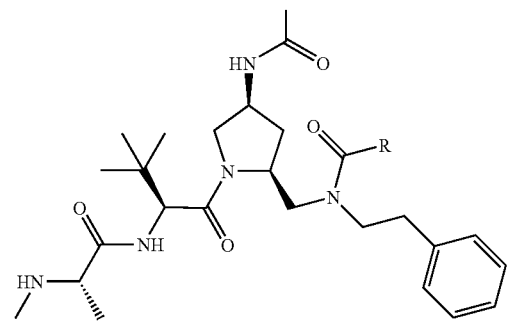
Compound 25; R = Me
Compound 27; R = Ph
Scheme 23h
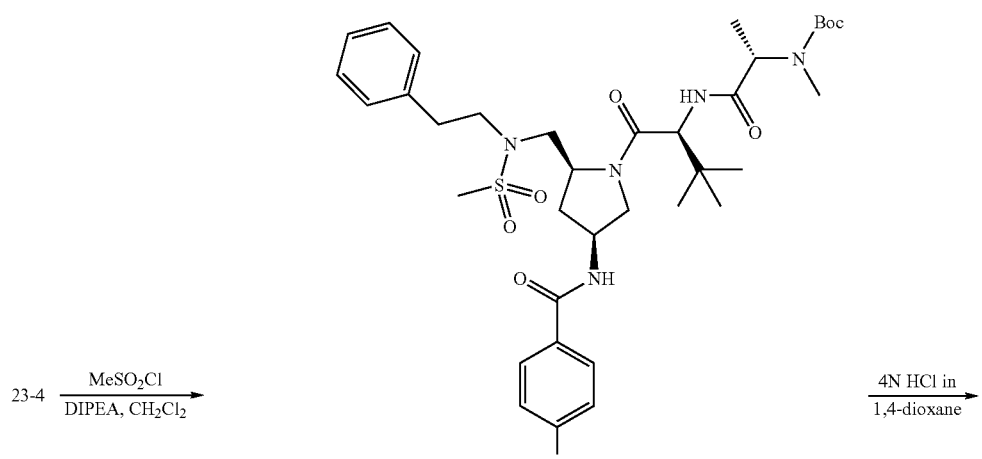
23-4 →(MeSO₂Cl / DIPEA, CH₂Cl₂)→ ... →(4N HCl in 1,4-dioxane)→
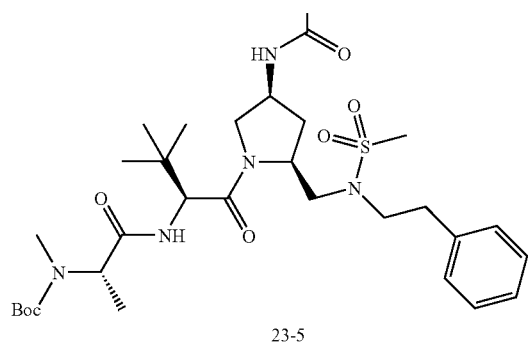
23-5

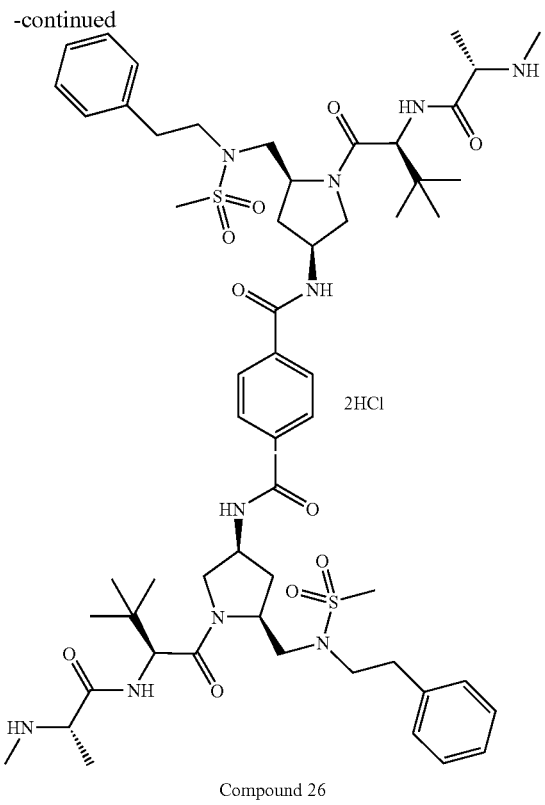

Compound 26

Sulfonylation of 23-4 with methanesulfonyl chloride, followed by deprotection with 1N HCl in 1,4-dioxane provided compound 26.2HCl.

Intermediate 24-1 provided an useful template for the preparation of ether bridged compounds. Intermediate 24-1 was prepared from N-Boc-cis-4-hydroxy-L-proline and α,α'-dibromo-p-xylene as described below. Amide coupling and deprotection of the Boc protecting groups using TFA provided intermediate 24-3. Two sequential amino acid coupling and deprotection steps, as described above, provided compound 29.2HCl.

Scheme 24

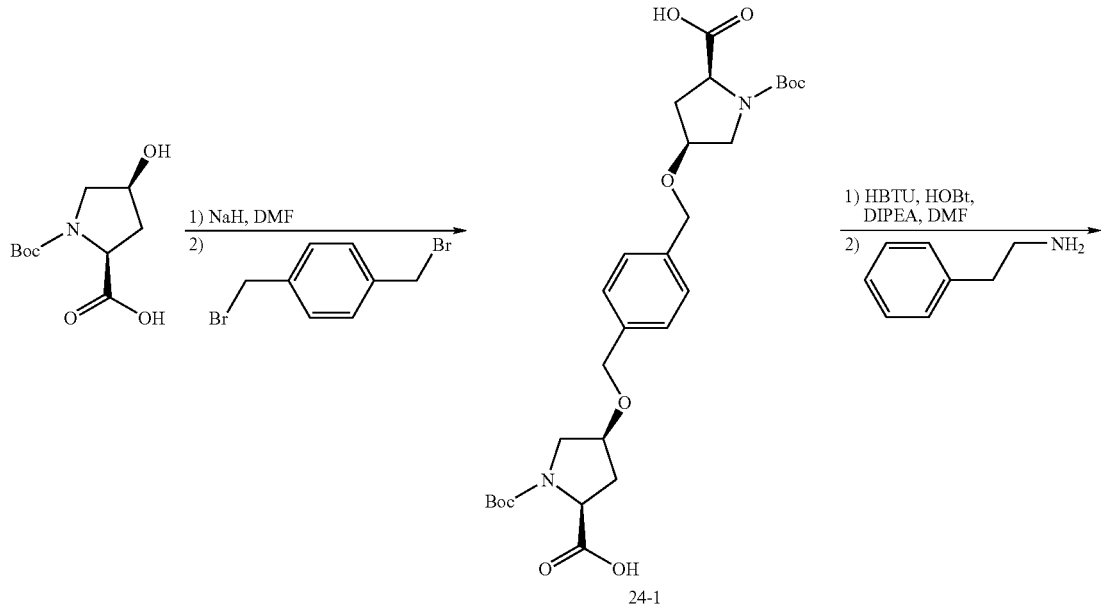

24-1

-continued
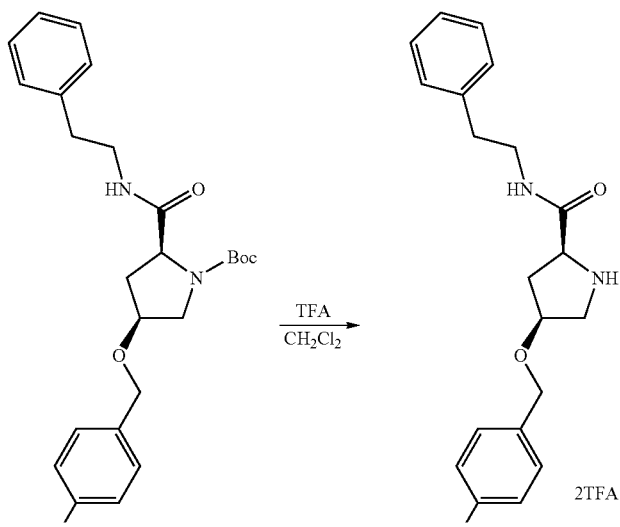
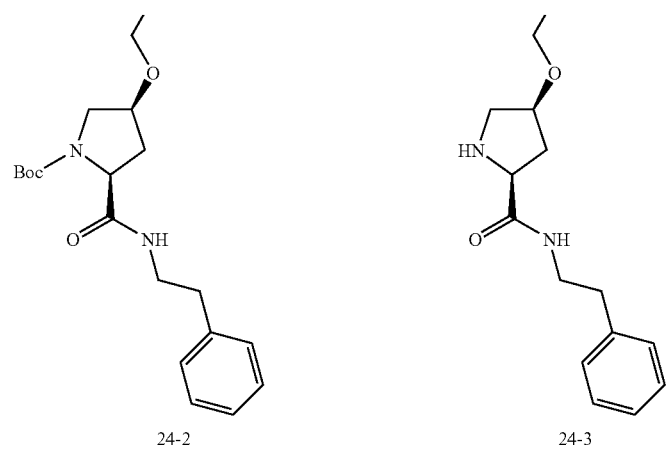
24-2
24-3
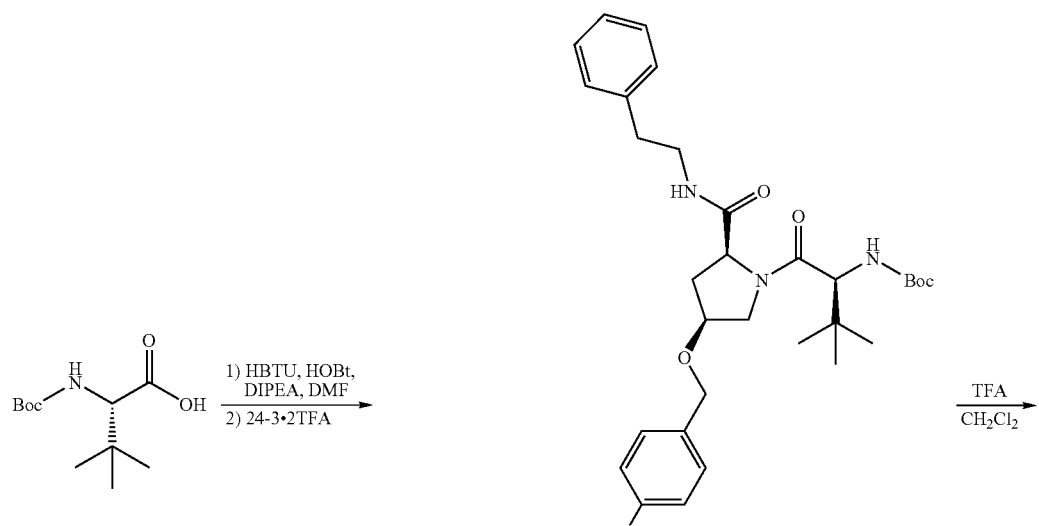

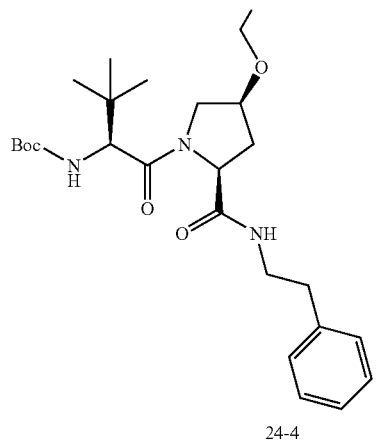
24-4
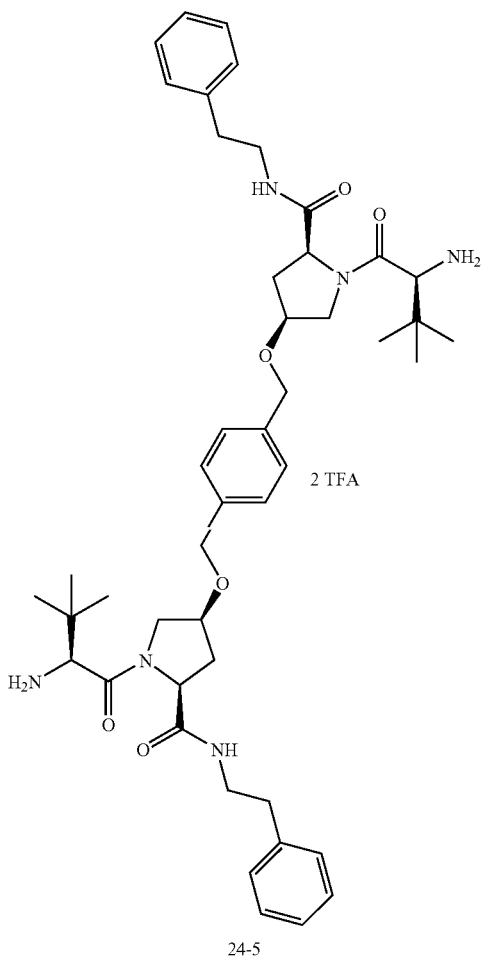
24-5

-continued
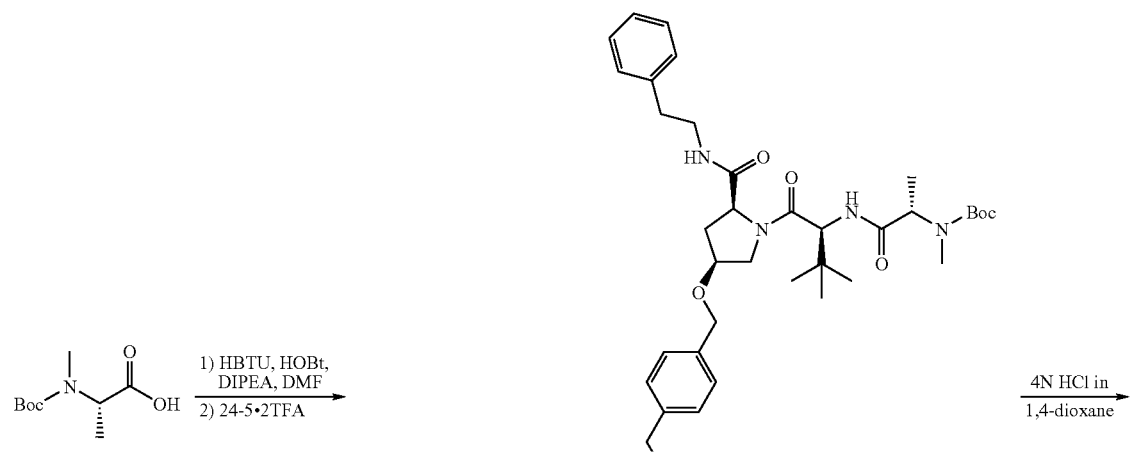
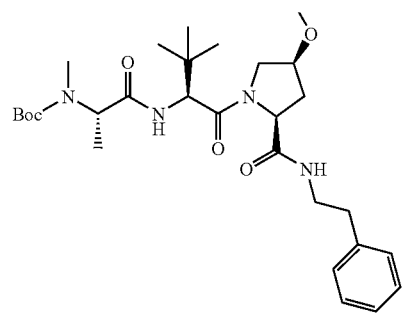
24-6
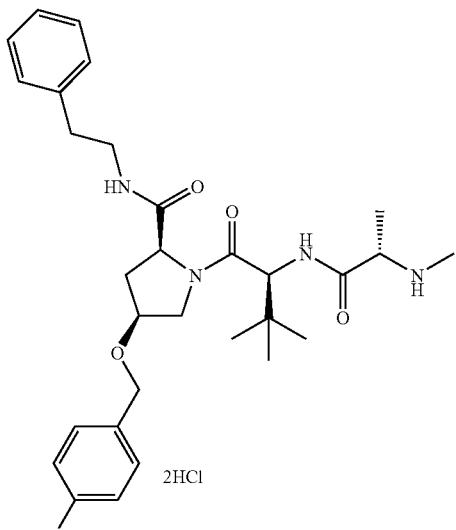
2HCl

-continued

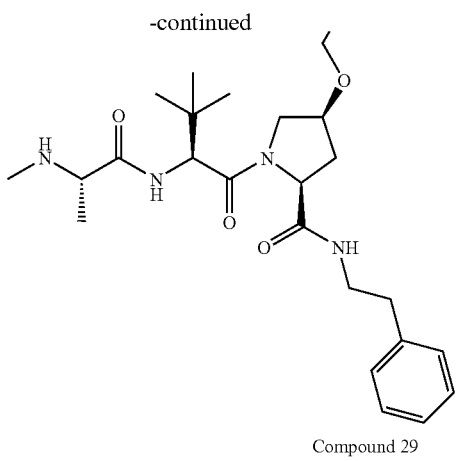

Compound 29

Intermediate 10-6 was bridged using 1,3-benzenedisulfonyl chloride to provide intermediate 25-1. Deprotection with 4N HCl in 1,4-dioxane provided compound 33 as its bis-HCl salt.

Scheme 25

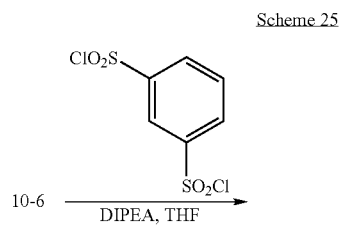

-continued

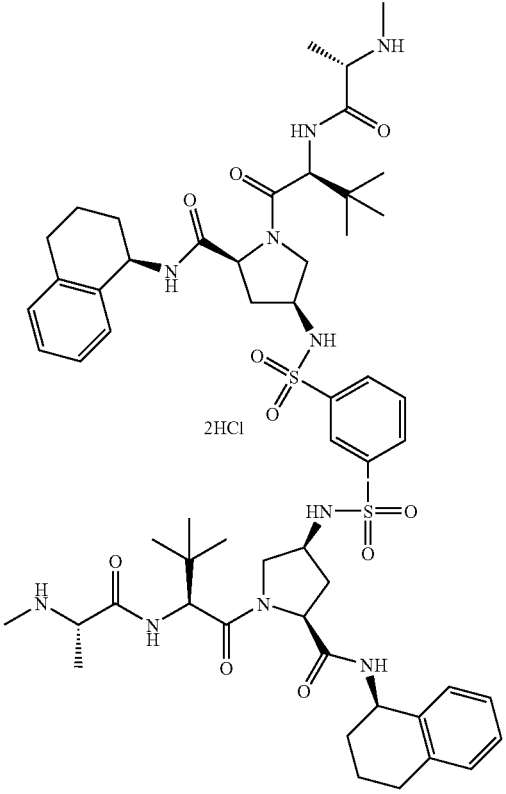

Compound 33

Similarly, intermediate 10-6 was bridged using 1,4-phenylene diisocyanate to provide intermediate 26-1, which upon deprotection with TFA provided compound 44 as is bis-TFA salt.

Scheme 26

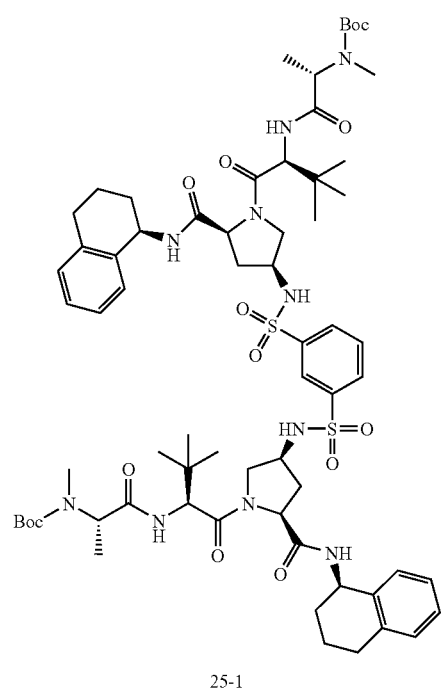

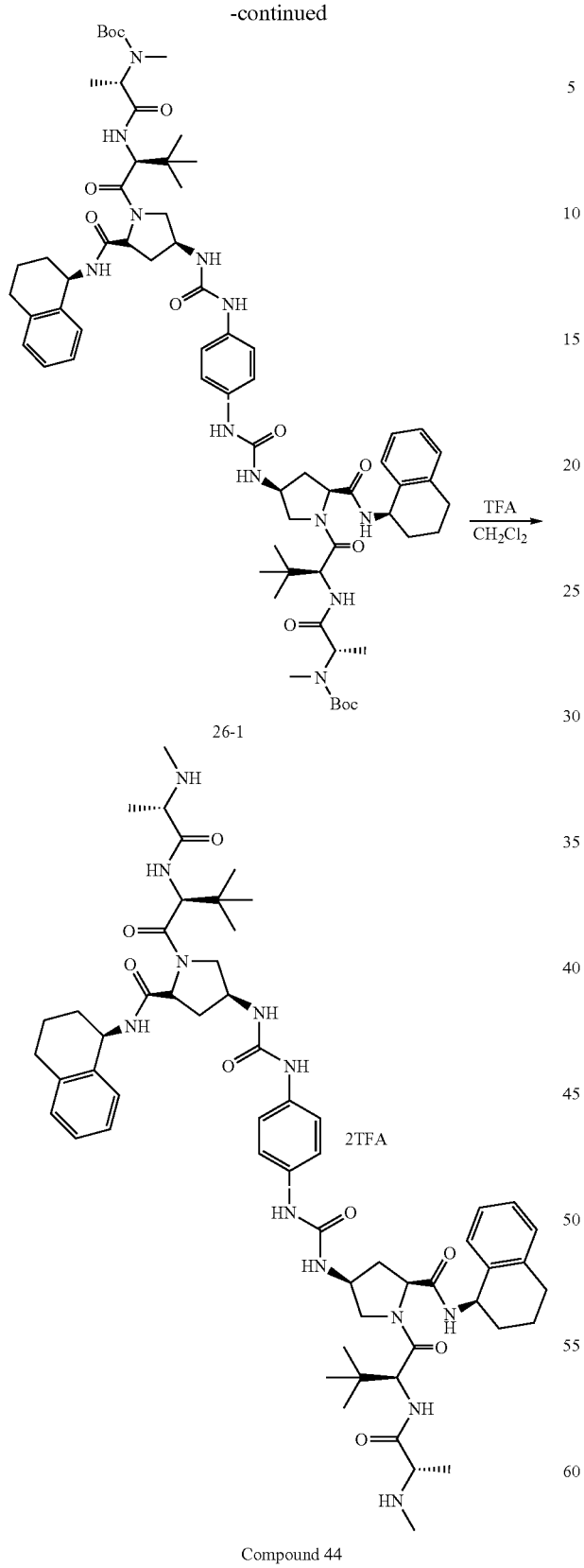

Compound 44

The preparation of compound 35 is illustrated in Scheme 27. Intermediate 10-1 was deprotected by the treatment with piperide in THF to provide intermediate 27-1. Coupling of 27-1 with Cbz-Gly-OH followed by Boc deprotection provided intermediate 27-3 TFA. Coupling of 27-3 with Boc-t-BuGly-OH followed by Boc deprotection provided intermediate 27-5.TFA. Coupling of 27-5.2TFA with Boc-NMeAla-OH provided intermediate 27-6. Removal of the Cbz group using $H_2$ and Pd/C yielded 27-7 which was bridged using terephthaloyl chloride to provide intermediate 27-8. Deprotection of intermediate 27-8 using 4N HCl in 1,4-dioxane provided compounds 35.2HCl.

Scheme 27a

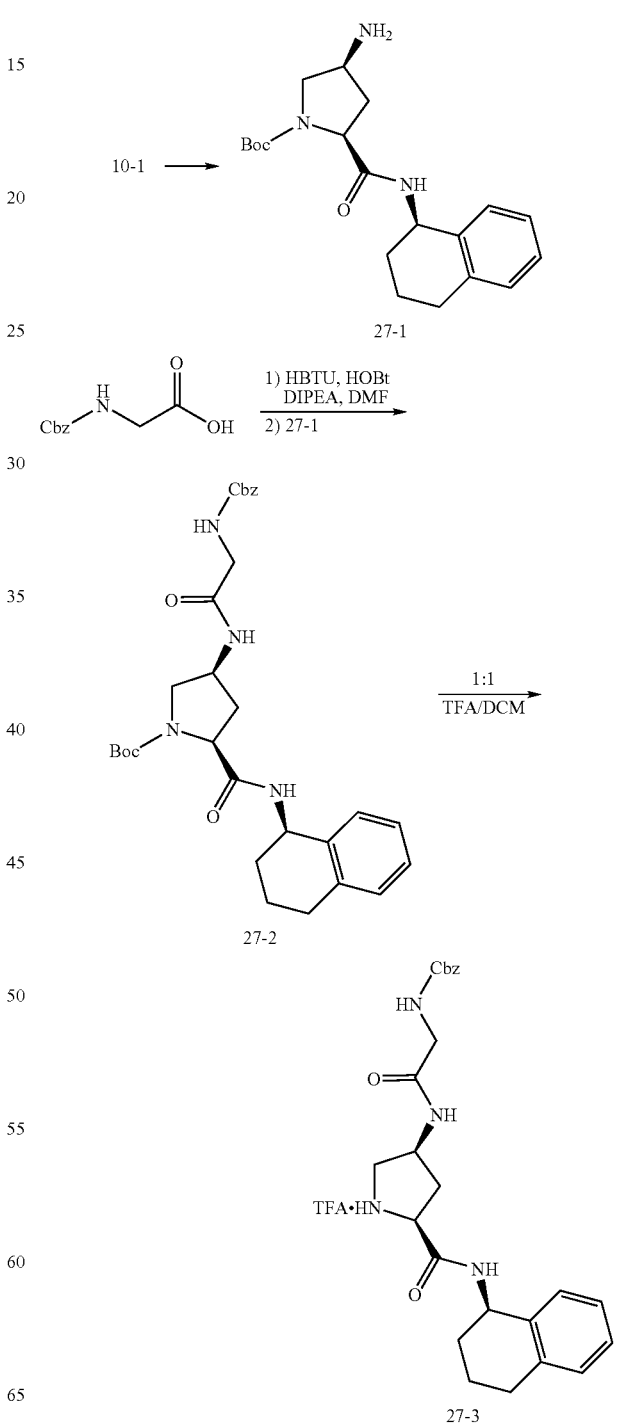

151
-continued
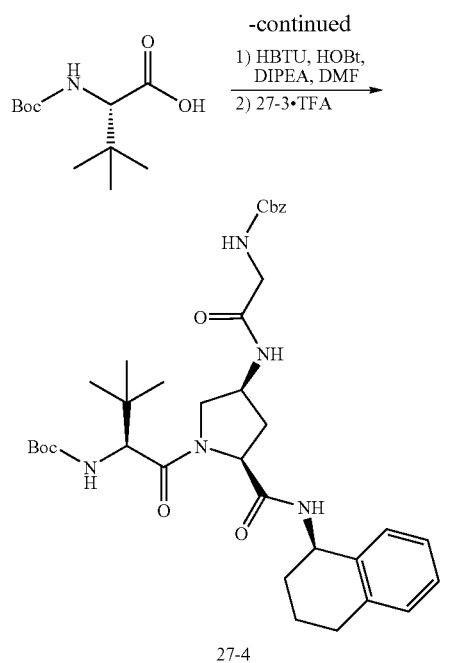
27-4
152
-continued
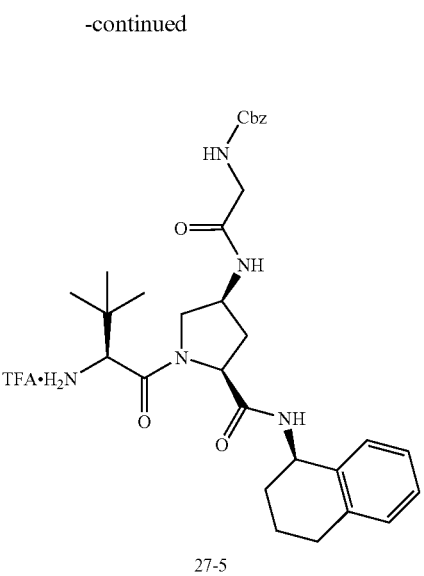
27-5
Scheme 27b
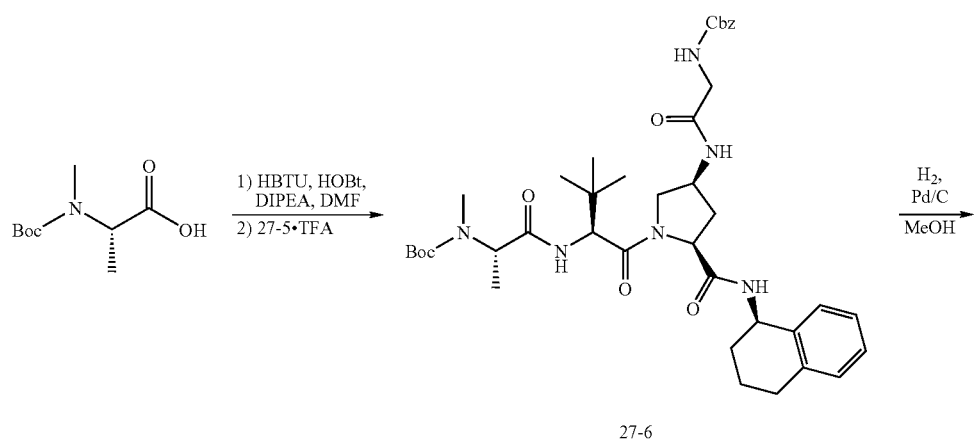
27-6
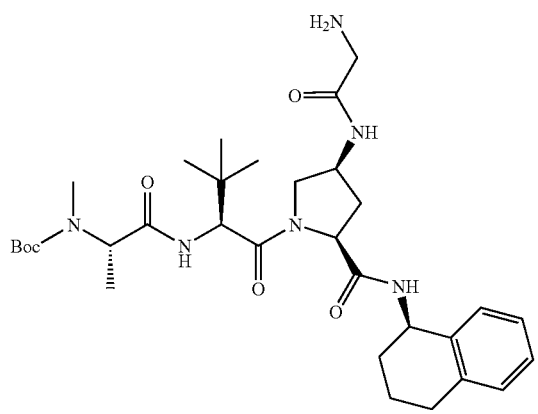
27-7

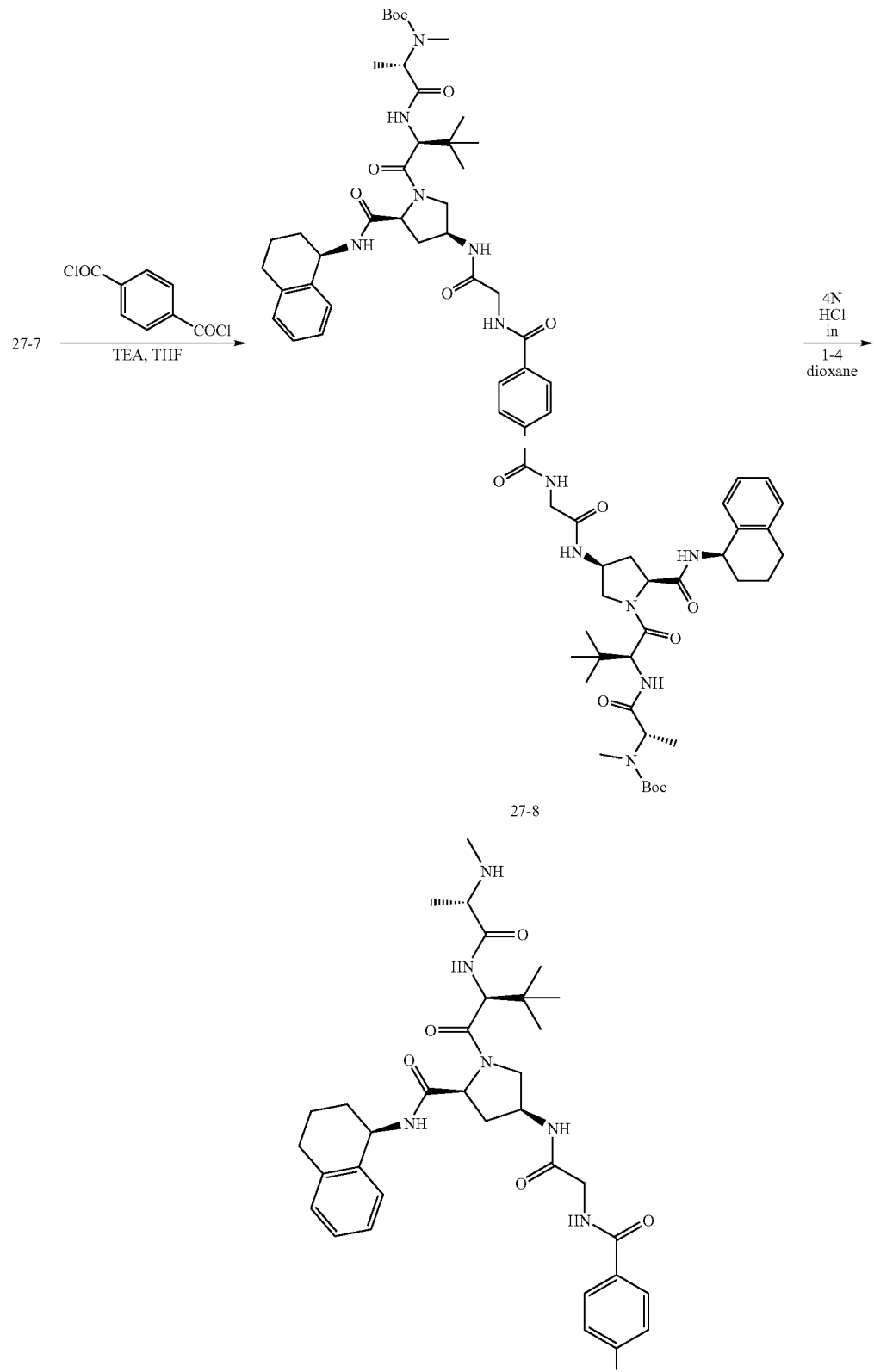

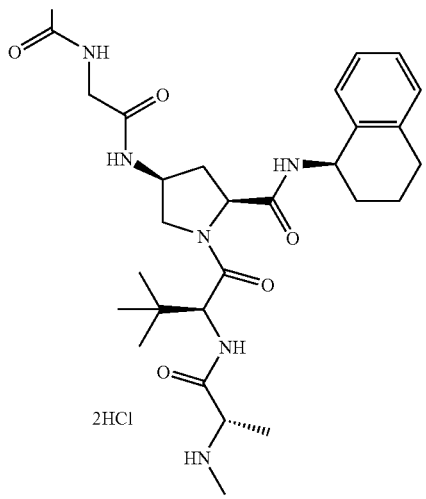

Compound 35

Various chiral amines were prepared from optically active (R)-2-hydroxy-1-phenylethylamine, 28-1. Intermediate 28-1 was Boc protected to provide 28-2. The alcohol moiety of 28-2 was alkylated with various alkyl halides to provide intermediates 28-3, 28-4, and 28-5. Deprotection of intermediates 28-3, 28-4 and 28-5 with HCl yielded the chiral amines 28-6, 28-7, and 28-8.

Scheme 28

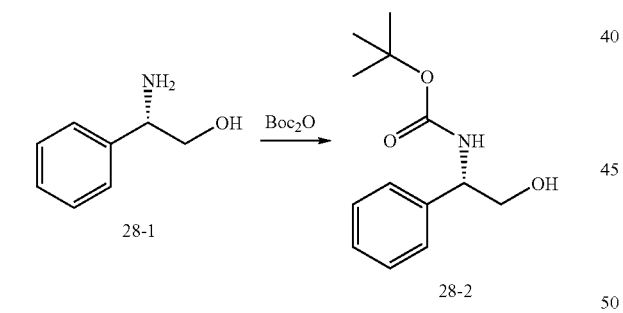

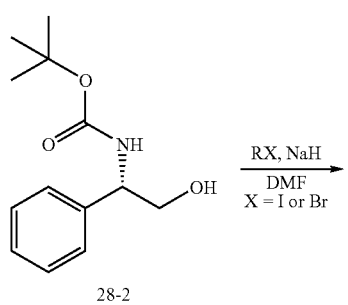

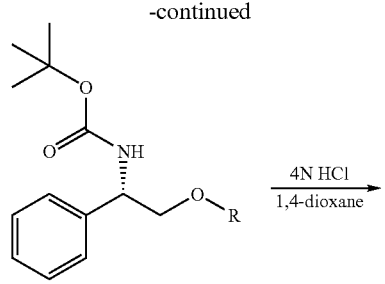

28-3; R = CH$_3$
28-4; R = CH$_2$Ph
28-5; R = CH$_2$CONH$_2$

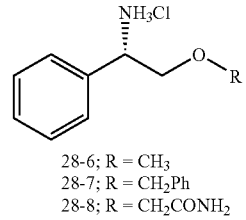

28-6; R = CH$_3$
28-7; R = CH$_2$Ph
28-8; R = CH$_2$CONH$_2$

Intermediates 28-6, 28-7, and 28-8 were coupled with intermediate 21-9 in a manner similar to that illustrated for compounds 22 and 24 (see Scheme 22) to provide compounds 63, 64 and 65, respectively.

Other chiral amines may be obtained commercially or prepared via a number of methods including the conversion or interconversion of ketones, alcohols or azides to amines, using chiral or achiral chemistries, and the chiral resolution of isomers via methods known in the art, such as chromatography or crystallization.

For example, Scheme 29 illustrates the enantioselective synthesis of optically enriched, asymmetric, 1,1-diphenylmethanamines prepared by the addition of aryl boronic acids to chiral sulfinimines, followed by hydrolysis of the sulfinamines with acid to provide the optically enriched amine intermediates characterized by intermediates 29-4 and 29-5 (Bolshan, Y.; Batey, R. A., Org. Letters 2005, 7, 1481-1484).

Scheme 29

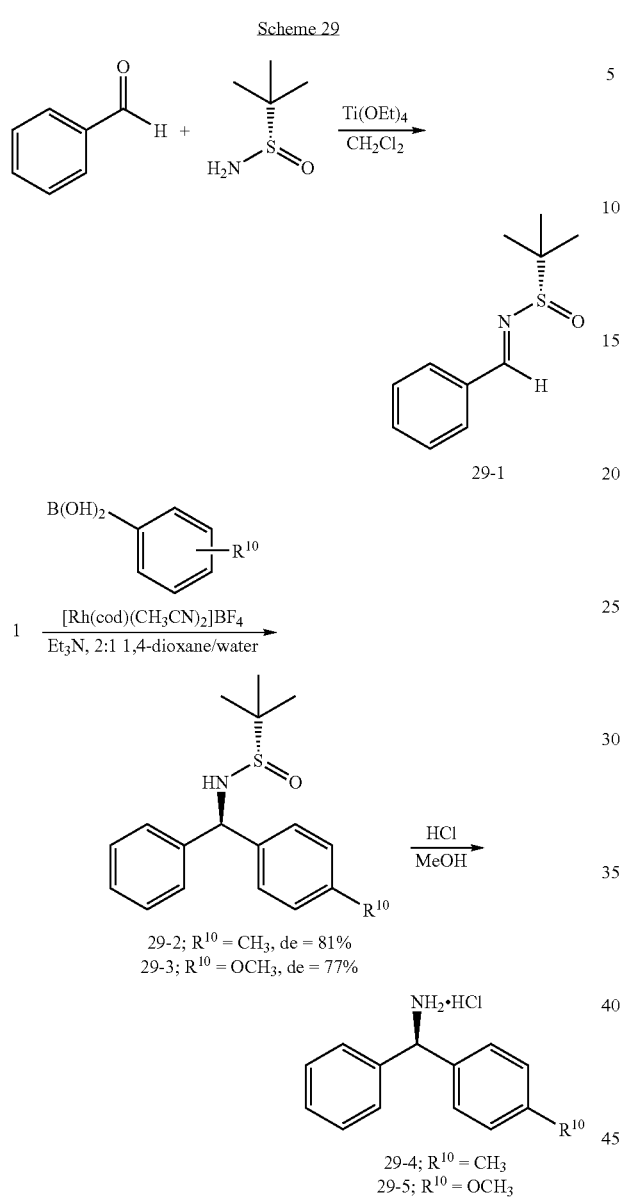

29-2; R¹⁰ = CH₃, de = 81%
29-3; R¹⁰ = OCH₃, de = 77%

29-4; R¹⁰ = CH₃
29-5; R¹⁰ = OCH₃

Intermediates 29-4 and 29-5 were coupled with intermediate 21-9 in a manner similar to that illustrated for compounds 22 and 24 (see Scheme 22) to provide compounds 66 and 67, respectively.

Several methods exist for the conversion of tetralones to chiral 1,2,3,4-tetrahydronaphthyl-1-amines, for example, the method report by R. A. Stalker, et al., Tetrahedron 2002, 58, 4837, as summarized below:

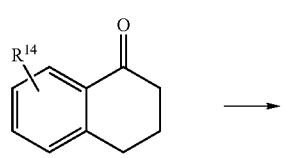

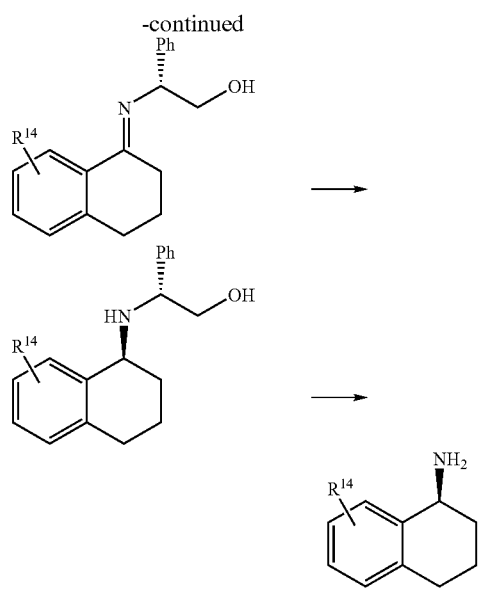

These chiral amines can be incorporated into compounds of the instant invention using similar methods as illustrated in Schemes 21 and 22.

The above Schemes are applicable to both symmetrical compounds and unsymmetrical compounds of the present invention. The substituents $A^1$, $A$, $Q$, $Q^1$, $R^1$, $R^{100}$, $R^2$, $R^{200}$, $R^3$, $R^{300}$, and the like are as defined herein. LG is a leaving group such as, for example, Cl, Br, I, OTs, OSu or OMs.

EXAMPLES

The following abbreviations are used throughout:
Boc: t-butoxycarbonyl;
CBz: benzyloxycarbonyl;
DCM: dichloromethane, $CH_2Cl_2$;
DIPEA: diisopropylethylamine;
DMAP: 4-(dimethylamino)pyridine;
DMF: N,N-dimethylformamide;
DTT: dithiothreitol;
EDC: 3-dimethylaminopropyl-3-ethylcarbodiimide hydrochloride;
EDTA: ethylenediaminetetracetic acid;
Fmoc: N-(9-fluorenylmethoxycarbonyl);
HBTU: O-(benzotriazol-1-yl)-N,N,N',N'-tetramethyluronium hexafluorophosphate;
HCl: hydrochloric acid;
HOAc: acetic acid;
HOBt: 1-hydroxybenzotriazole; HPLC: high performance liquid chromatography;
LCMS: liquid chromatography-mass spectrometer;
MeOH: methanol;
$MgSO_4$: magnesium sulfate;
MS: mass spectrum;
$NaHCO_3$: sodium hydrogen carbonate;
Pd/C: palladium on carbon;
TEA: triethylamine;
THF: tetrahydrofuran; and
TMEDA: N,N,N,N-tetramethylethylenediamine.

Synthetic Methods

Synthesis of compound 1

Step 1: Intermediate 9-1

NaH (440 mg, 11.0 mmol) was suspended in dry DMF (5 mL) under $N_2$ at 0° C. Boc-cis-2-hydroxyl-L-proline (1.00 g, 4.0 mmol) was dissolved in dry DMF (15 mL) and added dropwise to the suspension of NaH. The mixture was left to stir at 0° C. for 10 min. Propargyl bromide (560 μL, 5.0 mmol) was added dropwise to the solution. The mixture was stirred at 0° C. for 1 h then quenched with $H_2O$. The contents were added to a separatory funnel along with EtOAc and 10% citric acid (until pH~2). The organic layer was collected, dried and concentrated under reduced pressure. Flash chromatography (silica, hexanes/THF) yielded intermediate 9-1 as clear oil. MS (m/z) M+Na=292.

Step 2: Intermediate 9-2

Intermediate 9-1 (560 mg, 2.1 mmol), HOBt (444 mg, 2.9 mmol), EDC (563 mg, 2.9 mmol) and DIPEA (1.46 mL, 8.4 mmol) were dissolved in dry dichloromethane (10 mL) under $N_2$ and stirred for 10 min at room temperature. 1,2,3,4-(R)-Tetrahydronaphtyl-1-amine (368 μL, 2.5 mmol) was then added and the solution was left to stir for 24 h at RT. The contents were then added to a separatory funnel along with EtOAc and washed with 10% citric acid (2×), saturated $NaHCO_3$ (2×) and brine. The organic layer was collected, dried and concentrated under reduced pressure. The product was treated with 5 ml of 50% $CH_2Cl_2$/TFA for 1 hr at room temperature. Volatiles were removed in vacuo and the residue triturated with diethyl ether to provide intermediate 9-2-TFA. MS (m/z) M+1=299.

Step Three: Intermediate 9-3

Boc-t-Bu-Gly-OH (484 mg, 2.1 mmol), HOBt (375 mg, 2.4 mmol), HBTU (910 mg, 2.4 mmol) and DIPEA (1.20 mL, 7 mmol) were dissolved in dry DMF (10 mL) under $N_2$ and stirred for 10 min at room temperature. Intermediate 9-2 (720 mg, 1.75 mmol) was then added and the solution was left to stir for 24 h at room temperature. The contents were then added to a separatory funnel along with EtOAc and washed with 10% citric acid (2×), saturated $NaHCO_3$ (2×) and brine. The organic layer was collected, dried and concentrated under reduced pressure. The resulting product was treated with 10 mL of 50% $CH_2Cl_2$/TFA for 1 hr at room temperature. Volatiles were removed in vacuo and the residue triturated with diethyl ether to provide intermediate 9-3.TFA. MS (m/z) M+1=412.

Step 4: Intermediate 9-4

Boc-N-Me-Ala-OH (278 mg, 1.37 mmol), HOBt (227 mg, 1.49 mmol), EDC (293 mg, 1.49 mmol) and DIPEA (796 μL, 4.6 mmol) were dissolved in dry dichloromethane (10 mL) under $N_2$ and stirred for 10 min at RT. Intermediate 9-3-TFA (600 mg, 1.14 mmol) was then added and the solution was left to stir for 24 h at RT. EtOAc was added and the organic layer was washed with 10% citric acid (2×), saturated $NaHCO_3$ (2×) and brine, dried over anhydrous $MgSO_4$, filtered and volatiles removed under reduced pressure. The product was purified by silica gel chromatography, eluting with 10-100% hexanes/THF, to provide intermediate 9-4. MS (m/z) M+Na=619.

Step 5: Compound 1

Intermediate 9-4 (100 mg, 0.17 mmol), CuCl (25 mg, 0.25 mmol) and N,N,N,N-tetramethylethylenediamine (38 μL, 0.25 mmol) were suspended in dry acetone (5 ml) and stirred at room temperature under an $O_2$ atmosphere for 72 h. EtOAc was added and the organic layer was washed with 10% citric acid (2×), saturated $NaHCO_3$ (2×) and brine, dried over anhydrous $MgSO_4$, filtered and volatiles removed under reduced pressure. The product was purified by silica gel chromatography, eluting with 10-100% hexanes/THF, to provide intermediate 9-5. Treatment of 9-5 with 4N HCl in 1,4-dioxane at 0° C., for 2 hrs, and removal of volatiles under reduced pressure provided compound 1 as its bis-HCl salt. MS (m/z) M+1=991.7.

Synthesis of intermediate 10-6

Step 1: Intermediate 10-1

Fmoc-AMPC(2S,4S)-OH (900 mg, 2.0 mmol), HBTU (1.14 g, 3.0 mmol), and HOBt (415 mg, 3.0 mmol) were dissolved in dry DMF (10 mL) and treated with DIPEA (1050 uL, 6.0 mmol). The mixture was stirred for 10 minutes before the addition of (R)-1,2,3,4-tetrahydronaphthyl-1-amine (330 uL, 2.2 mmol). The reaction was stirred overnight before being diluted with ethyl acetate (100 mL) and 10% citric acid (50 mL). The organic layer was separated and washed with 10% citric acid (2×50 mL), saturated sodium bicarbonate (3×25 mL) and brine (1×20 mL), before being dried over anhydrouns magnesium sulphate, filtered, and concentrated under reduced pressure to provide crude 10-1a white solid. This material was 95% pure by LCMS and was advanced to the next step without further purification.

Step 2: Intermediate 10-2

Intermediate 10-1 was dissolved in methylene chloride (10 mL) and treated with TFA (10 mL). The solution was stirred at room temperature for 2 hrs before the volatiles were removed under reduced pressure. The resulting oil was stirred with diethyl ether (25 mL) to provide a light brown solid which was filtered and washed with diethyl ether (2×5 mL), to provide compound 10-2.TFA as a light brown solid (1.17 g).

Step 3: Intermediate 10-3

Boc-t-BuGly-OH (460 mg, 2.0 mmol), HBTU (760 mg, 2.0 mmol), and HOBt (270 mg, 2.0 mmol) and DIPEA (765 uL, 7.5 mmol) were dissolved in dry DMF (10 mL) and the reaction was stirred at room temperature for 10 minutes before intermediate 10-2 (867 mg, 1.5 mmol) was added. The mixture was stirred overnight before being diluted with ethyl acetate (200 mL) and 10% citric acid (50 mL). The organic layer was separated and washed with 10% citric acid (2×50 mL), saturated sodium bicarbonate (3×25 mL) and brine (1×20 mL), before being dried over anhydrous magnesium sulphate, filtered, and concentrated under reduced pressure to provide crude 10-3a white solid (920 mg, >95% pure by LCMS) and was advanced to the next step without further purification.

Step 4: Intermediate 10-4

Intermediate 10-3 was dissolved in methylene chloride (10 mL) and treated with TFA (10 mL). The solution was stirred at room temperature for 2 hrs before the volatiles were removed under reduced pressure. The resulting oil was stirred with diethyl ether (20 mL) to provide a light brown solid which was filtered, wash with diethyl ether (2×5 mL), to provide compound 10-4.TFA a white solid.

Step 5: Intermediate 10-5

Boc-MeAla-OH (308 mg, 1.52 mmol), HBTU (450 mg, 1.91 mmol), and HOBt (260 mg, 1.91 mmol) were dissolved in dry DMF (10 mL). DIPEA (886 uL, 5.0 mmol) was added and the reaction was stirred at room temperature for 10 minutes before intermediate 10-4 (900 mg, 1.27 mmol) was added. The mixture was stirred overnight before being diluted with ethyl acetate (200 mL) and 10% citric acid (50 mL). The organic layer was separated and washed with 10% citric acid (2×50 mL), saturated sodium bicarbonate (3×25 mL) and brine (1×20 mL), before being dried over anhydrous magnesium sulphate, filtered, and concentrated under reduced pressure to provide crude 10-5a white solid (0.87 mg, 95.5% pure by LCMS) and was advanced to the next step without further purification.

Step 6: Intermediate 10-6

Intermediate 10-5 was dissolved in 20% morpholine/THF (10 mL) and the solution was stirred at room temperature for 16 hrs. Volatiles were removed under reduced pressure to provide compound 10-6a white solid. Further purification by silica gel chromatography provide 10-6 which was 95% pure LCMS (MS (m/z) M+1=617.4.

Synthesis of Compound 2

Step 1: Intermediate 11-1

Crude 10-6 (200 mg, 0.251 mmol) was dissolved in THF (5 mL) and cooled to in an ice bath. DIPEA (50 uL, 0.275 mmol) and sebacoyl chloride (26 uL, 0.125 mmol) were added and the reaction was stirred for 4 hours at room temperature before being diluted with ethyl acetate (20 mL) and saturated sodium bicarbonate. The organic layer was separated, washed with brine, dried over anhydrous magnesium sulphate, filtered and the solvent removed under reduced pressure. The resulting crude solid was purified by silica gel chromatography, eluting with a 10-100% hexane/THF gradient, to provide 11-1 as a white solid (55 mg).

Step 2: Compound 2

Intermediate 11-1 (50 mg) was treated with 4N HCl in 1,4-dioxane (3 mL) and stirred for 3 hrs. Volatiles were removed under reduced pressure and the resulting solid was triturated with diethyl ether (3×5 mL). The resulting solid was dried under reduced pressure to provide compound 2.2HCl as an off white solid (30 mg). MS (m/z) (M+2)/2=541.4.

Compound 3

Step 1: Intermediate 12-1

Crude 10-6 (200 mg, 0.251 mmol) was dissolved in THF (5 mL) and cooled to 4° C. on an ice bath. DIPEA (50 uL, 0.275 mmol) was added. Terephthaloyl chloride (26 uL, 0.125 mmol) was added and the reaction was stirred for 16 hours before being diluted with ethyl acetate (20 mL) and saturated sodium bicarbonate. The organic layer was separated, washed with brine, dried over anhydrous magnesium sulphate, filtered and the solvent removed under reduced pressure. The resulting crude solid was purified by silica gel chromatography, eluting with a 25-100% hexanes/THF gradient, to provide 12-1 as a white solid (90 mg).

Step 2: Compound 3

Intermediate 12-1 (90 mg) was treated with 4N HCl in 1,4-dioxane (3 mL) and stirred for 3 hrs. Volatiles were removed under reduced pressure and the resulting solid was triturated with diethyl ether, filtered and washed with diethyl ether (3×5 mL). The resulting solid was dried under reduced pressure to provide compound 3.2HCl as an off white solid (40 mg). MS (m/z) (M+2)/2=523.4.

Compounds 4 and 5

Intermediate 9-4 (130 mg, 0.21 mmol) and intermediate 13-1 (130 mg, 0.22 mmol), CuCl (60 mg, 0.6 mmol) and tetramethylethylenediamine (90 μL, 0.6 mmol) were suspended in dry acetone (15 mL) and stirred at room temperature under an $O_2$ atmosphere for 120 h. EtOAc was added and the organic layer was washed with 10% citric acid (2×), saturated $NaHCO_3$ (2×) and brine, dried over anhydrous $Mg_2SO_4$, filtered, and concentrated under reduced pressure. The product was purified by silica gel chromatography, eluting with 10-100% hexanes/THF, to provide intermediates 9-5, 13-2 and 13-3. Intermediates 13-2 and 13-3 were independently treated with 4N HCl in 1,4-dioxane. Volatiles were removed and the resulting solids triturated with diethyl ether, filtered and washed with diethyl ether, to provide compounds 4 and 5, respectively, as their bis-HCl salts.

Compound 4.2HCl: MS (m/s) M+1=993.5.
Compound 5.2HCl: MS (m/z) M+1=995.6.

Compound 6

Intermediate 9-4 (250 mg, 0.400 mmol), intermediate 14-1 (560 mg, 0.900 mmol), CuCl (267 mg, 2.7 mmol) and tetramethylethylenediamine (405 μL, 2.7 mmol) were suspended in dry acetone (10 mL) and stirred at room temperature under an $O_2$ atmosphere for 72 h. Celite was added and the mixture filtered trough a pad of celite. EtOAc was added to the filtrate and the resulting organic layer was washed with 10% citric acid (2×), saturated $NaHCO_3$ (2×) and brine, dried over anhydrous $Mg_2SO_4$, filtered, and concentrated under reduced pressure. The product was purified by silica gel chromatography, eluting with 10-100% hexanes/THF, to provide intermediate 14-2. Intermediate 14-2 was treated with 4N HCl in 1,4-dioxane. Volatiles were removed and the resulting solids triturated with diethyl ether, filtered and washed with diethyl ether, to provide compound 6 as its bis-HCl salts. MS (m/s) (M+2)/2=514.4.

Compound 7

Step 1:

Intermediate 15-1 (1.0 g, 1.2 mmol), glutaric anhydride (190 mg, 1.7 mmol) and DIPEA (836 μL, 4.8 mmol) were dissolved in dichloromethane (20 mL) under $N_2$ at 0° C. A catalytic amount of DMAP was added and the solution was stirred for 30 min on ice and 24 hrs at room temperature. EtOAc was added to the filtrate and the resulting organic layer was washed with 10% citric acid (2×), saturated $NaHCO_3$ (2×) and brine, dried over anhydrous $Mg_2SO_4$, filtered, and concentrated under reduced pressure to provide intermediate 15-2 as a white solid.

Step 2:

Intermediate 15-2 (420 mg, 0.5 mmol), HOBt (85 mg, 0.63 mmol), HBTU (222 mg, 0.60 mmol) and DIPEA (313 μL, 1.8 mmol) were dissolved in dry DMF (5 ml) under $N_2$ and stirred for 10 min at RT. Intermediate 10-6 (250 mg, 0.45 mmol) was added and the solution was left to stir for 24 hrs at room temperate. EtOAc was added and the resulting organic layer was washed with 10% citric acid (2×), saturated $NaHCO_3$ (2×) and brine, dried over anhydrous $Mg_2SO_4$, filtered, and concentrated under reduced pressure. The product was purified by silica gel chromatography, eluting with 10-100% hexanes/THF, to provide intermediate 15-3.

Step 3:

Intermediate 15-3 (240 mg, 0.17 mmol), 10 wt % Pd/C (50 mg, 50% $H_2O$), were suspended in MeOH (10 mL) and stirred for 24 h at room temperature under a $H_2$ atmosphere (1 atm). The contents were then filtered on celite and washed with MeOH. The filtrate was concentrated under reduced pressure to provide the intermediate 15-4 as a white solid.

Step 4:

BocNMe-Ala-OH (57 mg, 0.28 mmol), HOBt (44 mg, 0.33 mmol), HBTU (116 mg, 0.31 mmol) and DIPEA (90 μL, 0.52 mmol) were dissolved in dry DMF (5 mL) under $N_2$ and treated with intermediate 15-4 (160 mg, 0.13 mmol). After stirring for 24 h at room temperature EtOAc was added and the resulting organic layer was washed with 10% citric acid (2×), saturated NaHCO$_3$ (2×) and brine, dried over anhydrous Mg$_2$SO$_4$, filtered, and concentrated under reduced pressure. The product was purified by silica gel chromatography, eluting with 10-100% hexanes/THF, to provide intermediate 15-5. Intermediate 15-5 was stirred with 4N HCl in 1,4-dioxane for 1 hr at room temperature. Volatiles were removed under reduced pressure to provide compound 7 as its HCl salt. MS (M+2)/2=618.0.

Compound 8:

Compound 7-HCl (100 mg, 0.08 mmol) is dissolved in DMF (1 mL) and added to a CH$_2$Cl$_2$ (5 mL) suspension of piperazinomethyl polystyrene resin (0.86 mmol/g, 356 mg, 0.3 mmol). After shaking at room temperature for 48 hrs an additional 200 mg of resin was added. The mixture was shaken for 20 days at room temperature before being, filtered, washing with MeOH. Volatiles were removed under reduced pressure to provide compound 8 a white solid. MS (m/z) M+1=1012.

Compound 9:

Intermediate 15-3 (10 mg) was treated with 4N HCl in 1,4-dioxane for 1 hr. Volatiles were removed under reduced pressure to provide compounds 9 as its HCl salt. MS (m/s) (M+2)/2=642.

Compounds 10, 11, 12, 13, 14, 15, 16, 39, 40, 41, 42, 43, 52, 55, 56, 57, and 58 and were prepared in a similar manner to that described for compound 2, wherein the corresponding sulfonyl chloride or activated diacid was substituted for sebacoyl chloride in Step 1. MS characterization of these compounds is summarized in Table 1.

Compound 17 was prepared in a similar manner to that described for compound 29 using 1,2,3,4-(R)-tetrahydronaphthyl-1-amine in place of phenethylamide. MS (m/s) (M+2)/2=510.4.

Compound 18:

Intermediate 21-8 was stirred in 4N HCl in 1,4-dioxane for 2 hrs. Volatiles were removed in vacuo and the residue was triturated with diethyl ether to provide compound 18.2HCl as a white solid. MS (m/z) M+1=815.4.

Compounds 19, 21, 22, 23, 24, 31, 32, 46, 47, 48, 49, 50, 51, 54, 59, 60, 61, 63, 64, 65, and 67 were prepared in a similar manner to that described for compound 20, wherein phenethylamine was substituted by the corresponding amine in Step 6. MS characterization of these compounds is summarized in Table 1.

Compound 20

Step 1: Intermediate 21-2

To a solution of N-Boc-cis-4-amino-L-proline methyl ester, 21-1, (10.0 g, 35.61 mmol) in CH$_2$Cl$_2$ cooled to 0° C. were sequentially added TEA (14.88 mL, 106.80 mmol), DMAP (10 mg) and terephthaloyl chloride (3.61 g, 17.80 mmol) and the reaction was stirred overnight at room temperature. Water and ethyl acetate were added, the organic layer was separated, washed with 10% citric acid, aqueous NaHCO$_3$ and brine, dried over anhydrous MgSO$_4$, filtered and concentrated in vacuo. Purification by silica gel chromatography provided intermediate 21-2 as a white solid.

Step 2: Intermediate 21-3.2TFA

Intermediate 21-2 (4.80 g, 7.76 mmol) was dissolved in a mixture of CH$_2$Cl$_2$ (40 mL) and TFA (40 mL) at 0° C. The solution was stirred for 4 hrs at room temperature. Volatiles were removed under reduced pressure and the residue was triturated with diethyl ether to provide intermediate 21-3.2TFA as a white solid. MS (m/z) M+1=419.2

Step 3: Intermediate 21-5

To a solution of Boc-α-tBuGly-OH, 21-4, (3.95 g, 17.07 mmol) in DMF cooled to 0° C. were sequentially added DIPEA (13.5 mL, 77.6 mmol), HOBt (2.62 g, 19.4 mmol) and HBTU (7.36 g, 19.4 mmol). After stirring for 10 minutes intermediate 21-3.2TFA (5.02 g, 7.76 mmol) was added and the reaction mixture was stirred overnight at room temperature. Water and ethyl acetate were added, the organic layer was separated, washed with 10% citric acid, aqueous NaHCO$_3$ and brine, dried over anhydrous MgSO$_4$, filtered and concentrated in vacuo. Purification by silica gel chromatography provided intermediate 21-5 as a white solid.

Step 4: Intermediate 21-6.2TFA

Intermediate 21-5 (6.55 g, 7.76 mmol) was dissolved in a mixture of CH$_2$Cl$_2$ (40 mL) and TFA (40 mL) at 0° C. The solution was stirred for 3 hrs at room temperature. Volatiles were removed under reduced pressure and the residue was triturated with diethyl ether to provide intermediate 21-6.2TFA as a white solid. MS (m/z) M+1=645.4

Step 4: Intermediate 21-8

To a solution of Boc-NMe-Ala-OH, 21-7, (3.15 g, 15.51 mmol) in DMF cooled to 0° C. were sequentially added DIPEA (12.3 mL, 70.5 mmol), HOBt (2.38 g, 17.63 mmol) and HBTU (6.69 g, 17.63 mmol). After stirring for 10 minutes intermediate 21-62TFA (6.15 g, 7.05 mmol) was added and the reaction mixture was stirred overnight at room temperature. Water and ethyl acetate were added, the organic layer was separated, washed with 10% citric acid, aqueous NaHCO$_3$ and brine, dried over anhydrous MgSO$_4$, filtered and concentrated in vacuo. Purification by silica gel chromatography provided intermediate 21-8 as a white solid.

Step 5: Intermediate 21-9

To a solution of intermediate 21-8 (6.20 g, 6.11 mmol) in THF (80 mL) and MeOH (8 mL) cooled to 0° C. was added 1N aqueous LiOH (30.5 mL) and the reaction was stirred overnight at room temperature. PH was adjusted to 6 with 10% citric acid and ethyl acetate was added, the organic layer was separated, washed with brine, dried over anhydrous MgSO$_4$, filtered and concentrated in vacuo to provide intermediate 21-9 as a white solid.

Step 6: Intermediate 21-10

To a solution of intermediate 21-9 (150 mg, 0.15 mmol) in DMF cooled to 0° C. were sequentially added DIPEA (265 uL, 1.52 mmol), HOBt (51 mg, 0.38 mmol) and HBTU (144 mg, 0.38 mmol). After stirring for 10 minutes phenethylamine (42 uL, 0.33 mmol) was added and the reaction mixture was stirred overnight at room temperature. Water and ethyl acetate were added, the organic layer was separated, washed with 10% citric acid, aqueous NaHCO$_3$ and brine, dried over anhydrous MgSO$_4$, filtered and concentrated in vacuo. Purification by silica gel chromatography provided intermediate 21-10 as a white solid.

Step 7: Compound 20.2HCl

4N HCl in 1,4-dioxane (3.0 mL) was added to intermediate 21-10 (145 mg, 0.12 mmol) and the solution was stirred for 1 hr at 0° C. Volatiles were removed under reduced pressure and the residue was triturated with diethyl ether to provide compound 20.2HCl as a white solid. MS (m/z) (M+2)/2=497.6.

Compound 22.2HCl

Step 1: Intermediate 22-1

To a solution of intermediate 21-9 (75 mg, 0.08 mmol) in DMF cooled to 0° C. were sequentially added DIPEA (135 uL, 0.76 mmol), HOBt (26 mg, 0.19 mmol) and HBTU (72 mg, 0.19 mmol). After stirring for 10 minutes isopropylamine (14 uL, 0.17 mmol) was added and the reaction mixture was stirred overnight at room temperature. Water and ethyl acetate were added, the organic layer was separated, washed with 10% citric acid, aqueous NaHCO$_3$ and brine, dried over anhydrous MgSO$_4$, filtered and concentrated in vacuo. Purification by silica gel chromatography provided intermediate 22-1 as a white solid.

Step 2: Compound 22.2HCl

4N HCl in 1,4 dioxane (2.0 mL) was added to intermediate 22-1 (58 mg, 0.05 mmol) and the solution was stirred for 2 hrs at 0° C. Volatiles were removed under reduced pressure and the residue was triturated with diethyl ether to provide compound 22.2HCl as a white solid. MS (m/z) (M+2)/2=435.4.

Compound 24.2HCl

Step 1: Intermediate 22-2

To a solution of intermediate 21-9 (600 mg, 0.61 mmol) in DMF cooled to 0° C. were sequentially added DIPEA (1.0 mL, 6.08 mmol), HOBt (205 mg, 1.52 mmol) and HBTU (576 mg, 1.52 mmol). After stirring for 10 minutes aminodiphenylmethane (230 uL, 1.34 mmol) was added and the reaction mixture was stirred overnight at room temperature. Water and ethyl acetate were added, the organic layer was separated, washed with 10% citric acid, aqueous NaHCO$_3$ and brine, dried over anhydrous MgSO$_4$, filtered and concentrated in vacuo. Purification by silica gel chromatography provided intermediate 22-2 as a white solid.

Step 2: Compound 24.2HCl

4N HCl in 1,4 dioxane (1.9 mL) was added to intermediate 22-2 (660 mg, 0.50 mmol) and the solution was stirred for 1 hr at 0° C. Volatiles were removed under reduced pressure and the residue was triturated with diethyl ether to provide compound 24.2HCl as a white solid. MS (m/z) (M+2)/2=435.4.

Compound 25

Step 1: Intermediate 23-1

To a solution of intermediate 21-8 (1.10 g, 1.08 mmol) in THF cooled to 0° C. was added lithium borohydride (118 mg, 4.86 mmol) and the reaction mixture was stirred for 3 hrs at room temperature. Ethyl acetate and 10% citric acid were added. The organic layer was separated, washed with aqueous NaHCO$_3$ and brine, dried over anhydrous MgSO$_4$, filtered and concentrated in vacuo. Purification by silica gel chromatography provided intermediate 23-1 as a white solid. MS (m/z) M+1=959.6

Step 2: Intermediate 23-2

To a solution of intermediate 23-1 (284 mg, 0.29 mmol) in CH$_2$Cl$_2$ was added Dess Martin periodinane (314 mg, 0.74 mmol) and the reaction was stirred for 5 hrs at room temperature. Aqueous NaHCO$_3$ was added, the organic layer was separated, washed with brine, dried over anhydrous MgSO$_4$, filtered and concentrated in vacuo. Purification by silica gel chromatography provided intermediate 23-2 as a white solid.

Step 3: Intermediate 23-4

To a solution of intermediate 23-2 (282 mg, 0.29 mmol) in CH$_2$Cl$_2$ was added phenethylamine (82 uL, 0.65 mmol). After stirring for 30 min at room temperature sodium triacetoxyborohydride (280 mg, 1.32 mmol) was added and the reaction mixture was stirred for 2 hrs. Saturated aqueous NaHCO$_3$ was added, the organic layer was separated, washed with brine, dried over anhydrous MgSO$_4$, filtered and concentrated in vacuo. Purification by silica gel chromatography provided intermediate 23-4 as a white solid. MS (m/z) M+1=1165.8

Step 4: Intermediate 23-5

To a solution of intermediate 23-4 (100 mg, 0.08 mmol) in CH$_2$Cl$_2$ cooled to 0° C. were sequentially added triethylamine (60 uL, 0.43 mmol) and acetyl chloride (14 uL, 0.19 mmol). The reaction was stirred for 2 hrs at room temperature before water and ethyl acetate were added. The organic layer was separated, washed with 10% citric acid, aqueous NaHCO$_3$ and brine, dried over anhydrous MgSO$_4$, filtered and concentrated in vacuo. Purification by silica gel chromatography provided intermediate 23-5 as a white solid.

Step 5: Compound 25.2HCl

4N HCl in 1,4-dioxane (3 mL) was added to intermediate 23-5 (80 mg, 0.06 mmol) and the solution was stirred for 1 hr at room temperature. Volatiles were removed under reduced pressure and the residue was triturated with diethyl ether to provide compound 25.2HCl as a white solid. MS (m/z) (M+2)/2=525.6.

Compound 26.2HCl

Step 1: Intermediate 23-5

To a solution of intermediate 23-4 (100 mg, 0.08 mmol) in CH$_2$Cl$_2$ cooled to 0° C. were sequentially added TEA (60 uL, 0.43 mmol) and methanesulfonyl chloride (15 uL, 0.19 mmol) and the reaction was stirred for 2 hrs at room temperature. Water and ethyl acetate were added, the organic layer was separated, washed with 10% citric acid, aqueous NaHCO$_3$ and brine, dried over anhydrous MgSO$_4$, filtered and concentrated in vacuo. Purification by silica gel chromatography provided intermediate 23-5 as a white solid.

Step 2: Compound 26.2HCl

4N HCl in 1,4-dioxane (3 mL) was added to intermediate 23-5 (79 mg, 0.06 mmol) and the solution was stirred for 1 hr at room temperature. Volatiles were removed under reduced pressure and the residue was triturated with diethyl ether to provide compound 26.2HCl as a white solid. MS (m/z) (M+2)/2=561.6. Compounds 27, 28 and 30 were prepared in a similar manner to that described for compound 26, wherein for compound 27 and 28 acetyl chloride and benzoyl chloride, respectively, were used in place of methanesulfonyl chloride.

Compound 27-MS (m/z) (M+2)/2=587.6.
Compound 28-MS (m/z) (M+2)/2=543.6.
Compound 30-MS (m/z) (M+2)/2=579.6.

Compound 29

Step 1: Intermediate 24-1

To a 1.0 M solution of NaHMDS in THF (21.6 mL, 21.6 mmol) cooled to 0° C. was slowly added a solution of N-Boc-cis-4-hydroxy-L-proline (2.50 g, 10.8 mmol) in DMF. After stirring for 20 minutes at 0° C. α,α'-dibromo-p-xylene (1.37 g, 5.0 mmol) was added and the reaction mixture was stirred overnight at room temperature. Water and ethyl acetate were added, the organic layer was separated, dried over MgSO$_4$, filtered and concentrated in vacuo. Purification by silica gel chromatography provided intermediate 24-1 as a white solid.

Step 2: Intermediate 24-2

To a solution of intermediate 24-1 (200 mg, 0.35 mmol) in DMF cooled to 0° C. were sequentially added DIPEA (365 uL, 2.1 mmol), HOBt (132 mg, 0.98 mmol) and HBTU (345 mg, 0.91 mmol). After stirring for 10 minutes phenethylamine (107 uL, 0.85 mmol) was added and the reaction mixture was stirred overnight at room temperature. Water and ethyl acetate were added, the organic layer was separated, washed with 10% citric acid, aqueous NaHCO$_3$ and brine, dried over anhydrous MgSO$_4$, filtered and concentrated in vacuo. Purification by silica gel chromatography provided intermediate 24-2 as a white solid.

Step 3: Intermediate 24-3.2TFA

Intermediate 24-2 (260 mg, 0.35 mmol) was dissolved in a mixture of $CH_2Cl_2$ (3 mL) and TFA (3 mL). The solution was stirred for 1 hr at room temperature. Volatiles were removed under reduced pressure and the residue was triturated with diethyl ether to provide intermediate 24-3.2TFA as a white solid. MS (m/z) M+1=571.4

Step 4: Intermediate 24-4

To a solution of Boc-α-$^t$BuGly-OH (256 mg, 1.10 mmol) in DMF cooled to 0° C. were sequentially added DIPEA (361 uL, 2.10 mmol), HOBt (175 mg, 1.3 mmol) and HBTU (455 mg, 1.2 mmol). After stirring for 10 minutes intermediate 24-32TFA (230 mg, 0.46 mmol) was added and the reaction mixture was stirred overnight at room temperature. Water and ethyl acetate were added, the organic layer was separated, washed with 10% citric acid, aqueous $NaHCO_3$ and brine, dried over anhydrous $MgSO_4$, filtered and concentrated in vacuo. Purification by silica gel chromatography provided intermediate 24-4 as a white solid.

Step 5: Intermediate 24-5.2TFA

Intermediate 24-4 (458 mg, 0.46 mmol) was dissolved in a mixture of $CH_2Cl_2$ (3 mL) and TFA (3 mL). The solution was stirred for 30 minutes at room temperature. Volatiles were removed under reduced pressure and the residue was triturated with diethyl ether to provide intermediate 24-5.2TFA as a white solid. MS (m/z) M+1=797.6

Step 6: Intermediate 24-6

To a solution of Boc-NMe-Ala-OH (119 mg, 0.58 mmol) in DMF cooled to 0° C. were sequentially added DIPEA (209 uL, 1.2 mmol), HOBt (91 mg, 0.67 mmol) and HBTU (236 mg, 0.62 mmol). After stirring for 10 minutes intermediate 24-5.2TFA (250 mg, 0.24 mmol) was added and the reaction mixture was stirred overnight at room temperature. Water and ethyl acetate were added, the organic layer was separated, washed with 10% citric acid, aqueous $NaHCO_3$ and brine, dried over anhydrous $MgSO_4$, filtered and concentrated in vacuo. Purification by silica gel chromatography provided intermediate 24-6 as a white solid.

Step 7: Compound 29.2HCl

4N HCl in 1,4-dioxane (1.0 mL) was added to intermediate 24-6 (280 mg, 0.24 mmol) and the solution was stirred for 1 hr at 0° C. Volatiles were removed under reduced pressure and the residue was triturated with diethyl ether to provide compound 29.2HCl as a white solid. MS (m/z) M+1=967.6.

Compound 33

Step 1: Intermediate 25-1

To a solution of intermediate 10-6 (258 mg, 0.50 mmol) in DMF were sequentially added DIPEA (217 uL, 1.25 mmol) and 1,3-benzenedisulfonyl chloride (69 mg, 0.25 mmol) and the reaction was stirred overnight at room temperature. Water and ethyl acetate were added, the organic layer was separated, washed with 10% citric acid, aqueous $NaHCO_3$ and brine, dried over anhydrous $MgSO_4$, filtered and concentrated in vacuo. Purification by silica gel chromatography provided intermediate 25-1 as a white solid.

Step 2: Compound 33.2HCl

4N HCl in 1,4-dioxane (2 mL) was added to intermediate 25-1 (143 mg, 0.11 mmol) and the solution was stirred for 1 hr at 0° C. Volatiles were removed under reduced pressure and the residue was triturated with diethyl ether to provide compound 33.2HCl as a white solid. MS (m/z) (M+2)/2=559.5.

Compound 34:

Compound 34 was prepared in a similar manner to compound 20, wherein N-Boc-cis-4-amino-L-proline methyl ester was substituted with N-Boc-trans-4-amino-L-proline methyl ester in step 1 and phenethylamine was substituted with 1,2,3,4-(R)-tetrahydronaphthyl-1-amine in Step 6. MS (m/z) M+1=1045.8.

Compound 35.2HCl

Step 1: Intermediate 27-1

Intermediate 10-1 (3.90 g, 6.68 mmol) was dissolved in THF (100 mL) and treated with piperidine (5.0 mL, 68.2 mmol). The solution was stirred for 16 hrs at room temperature before volatiles were removed under reduced pressure to provide a semi-solid which was suspended in MeOH (5 mL) and filtered. The filtrate was concentrated, suspended in MeOH (5 mL), filtered and the filtrate concentrated to provide intermediate 27-1 as a semi-solid (80% pure).

Step 2: Intermediate 27-2

To a solution of carbobenzyloxyglycine (699 mg, 3.34 mmol) in DMF cooled to 0° C. were sequentially added DIPEA (2.40 mL, 13.9 mmol), HOBt (488 mg, 3.61 mmol) and HBTU (1.37 g, 3.61 mmol). After stirring for 10 minutes intermediate 27-1 (1.00 g, 2.78 mmol) was added and the reaction mixture was stirred overnight at room temperature. Water and ethyl acetate were added, the organic layer was separated, washed with 10% citric acid, aqueous $NaHCO_3$ and brine, dried over anhydrous $MgSO_4$, filtered and concentrated in vacuo. Purification by silica gel chromatography provided intermediate 27-2 as a white solid.

Step 3: Intermediate 27-3.TFA

Intermediate 27-2 (1.42 g, 2.58 mmol) was dissolved in a mixture of $CH_2Cl_2$ (15 mL) and TFA (15 mL). The solution was stirred for 1 hr at room temperature. Volatiles were removed under reduced pressure and the residue was triturated with diethyl ether to provide intermediate 27-3-TFA as a white solid. MS (m/z) M+1=451.4

Step 4: Intermediate 27-4

To a solution of Boc-α-tBuGly-OH (668 mg, 2.89 mmol) in DMF cooled to 0° C. were sequentially added DIPEA (2.1 mL, 12.0 mmol), HOBt (488 mg, 3.61 mmol) and HBTU (1.37 g, 3.61 mmol). After stirring for 10 minutes intermediate 27-3*TFA (1.36 g, 2.41 mmol) was added and the reaction mixture was stirred overnight at room temperature. Water and ethyl acetate were added, the organic layer was separated, washed with 10% citric acid, aqueous $NaHCO_3$ and brine, dried over anhydrous $MgSO_4$, filtered and concentrated in vacuo. Purification by silica gel chromatography provided intermediate 27-4 as a white solid.

Step 5: Intermediate 27-5.TFA

Intermediate 27-4 (1.38 g, 2.08 mmol) was dissolved in a mixture of DCM (10 mL) and TFA (10 mL). The solution was stirred for 4 hrs at room temperature. Volatiles were removed under reduced pressure and the residue was triturated with diethyl ether to provide intermediate 27-5.TFA as a white solid. MS (m/z) M+1=564.4

Step 6: Intermediate 27-6

To a solution of Boc-NMe-Ala-OH (902 mg, 4.44 mmol) in DMF cooled to 0° C. were sequentially added DIPEA (3.50 mL, 20.2 mmol), HOBt (682 mg, 5.05 mmol) and HBTU (1.92 g, 5.05 mmol). After stirring for 10 minutes intermediate 27-5.TFA (1.14 g, 1.68 mmol) was added and the reaction mixture was stirred overnight at room temperature. Water and ethyl acetate were added, the organic layer was separated, washed with 10% citric acid, aqueous NaHCO$_3$ and brine, dried over anhydrous MgSO$_4$, filtered and concentrated in vacuo. Purification by silica gel chromatography provided intermediate 27-6 as a white solid.

Step 7: Intermediate 27-7

To a solution of intermediate 27-6 (925 mg, 1.24 mmol) in anhydrous MeOH (25 mL) and stirred under N$_2$ was added 10% Pd/C (125 mg). The reaction mixture was purged with H$_2$ and stirred for 1 hr. The reaction was then filtered through celite and the filtrate was concentrated in vacuo. Purification by silica gel chromatography provided intermediate 27-7 as a white solid. MS (m/z) M+1=615.4

Step 8: Intermediate 27-8

To a solution of intermediate 27-7 (150 mg, 0.25 mmol) in DCM cooled to 0° C. were sequentially added TEA (100 uL, 0.73 mmol) and terephthaloyl chloride (25.0 mg, 0.12 mmol) and the reaction was stirred overnight at room temperature. Water and ethyl acetate were added, the organic layer was separated, washed with 10% citric acid, aqueous NaHCO$_3$ and brine, dried over anhydrous MgSO$_4$, filtered and concentrated in vacuo. Purification by silica gel chromatography provided intermediate 27-8 as a white solid.

Step 9: Compound 35.2HCl

4N HCl in 1,4-dioxane (2 mL) was added to intermediate 27-8 (166 mg, 0.12 mmol) and the solution was stirred for 1 hr at room temperature. Volatiles were removed under reduced pressure and the residue was triturated with diethyl ether to provide compound 35.2HCl as a white solid. MS (m/z) (M+2)/2=580.6.

Compounds 36, 37, and 38 were prepared from intermediate 27-7, in a similar manner to that described for compound 35, using oxalyl)-chloride, isophthaloyl dichloride and 4,4'-biphenyldicarbonyl chloride, respectively, in place of phthaloyl chloride in Step 8

Compound 36-MS (m/z) (M+2)/2=542.6.
Compound 37-MS (m/z) (M+2)/2=580.6.
Compound 38-MS (m/z) (M+2)/2=618.6.

Compound 44

Step 1: Intermediate 26-1

To a solution of intermediate 10-6 (150 mg, 0.27 mmol) in THF were sequentially added TEA (112 uL, 0.81 mmol) and 1,4-phenylene diisocyanate (43 mg, 0.27 mmol) and the reaction was stirred at room temperature for 4 hrs. Volatiles were removed under reduced pressure and the residue purified by silica gel chromatography to provide intermediate 26-1 as a white solid.

Step 2: Compound 44.2TFA

Intermediate 26-1 (148 mg, 0.12 mmol) was dissolved in a mixture of CH$_2$Cl$_2$ (1.5 mL) and TFA (0.4 mL). The solution was stirred for 1 hr at room temperature. Volatiles were removed under reduced pressure and the residue was triturated with diethyl ether to provide compound 44.2TFA as a white solid. MS (m/z) (M+2)/2=538.4.

Compound 62:

Intermediate 21-9 was treated with 4N HCl in 1,4-dioxane for 2 hrs. Volatiles were removed under reduced pressure and the residue was triturated with diethyl ether to provide compounds 62.-HCl as an off white solid. MS (m/z) M+1=787.6.

Intermediate 28-6

Step 1: Intermediate 28-2

(S)-(+)-2-Phenylglycinol, 28-1 (1.64 g, 12.0 mmol) was dissolved in CH$_2$Cl$_2$ (90 mL). Boc$_2$O (2.84 g, 13.0 mmol) and DMAP (34 mg, 0.02 mmol) were added and stirred for 1 hour at room temperature. The reaction mixture was diluted with diethyl ether (200 mL) and 1N HCl (100 mL). The organic layer was washed with 1M HCl (2×100 mL), dried over anhydrous MgSO$_4$, filtered and volatiles removed under reduced pressure. The resulting residue was purified by silica gel chromatography provided an oil to provide intermediate 28-2 as white solid (2.7 g, 95% yield). MS (m/z) M+1=238.2.

Step 2: Intermediate 28-6

Intermediate 28-2 (420 mg, 1.77 mmol) and iodomethane (330 µL, 5.29 mmol) were dissolved in anhydrous DMF (25 mL). The mixture was cooled to 0° C., and then NaH (60% dispersion in oil, 103 mg, 2.58 mmol) was added. After 2 hours, the reaction mixture was diluted with ethyl acetate (200 mL) and 1M HCl (100 mL). The organic layer was washed with 1M HCl (2×100 mL), dried over anhydrous MgSO$_4$, filtered and volatiles removed under reduced pressure. The residue was purified by silica gel chromatography to provide intermediate 28-3 as an oil. Intermediate 28-3 was then chilled to 0° C. and treated with 4M HCl in 1,4-dioxane (5 mL). After stirring for 90 minutes volatiles were removed under reduced pressure and the resulting solid was washed with diethyl ether, to provide intermediate 28-6.HCl as white solid (237 mg, 69% yield). MS (m/z) M+1=152.2.

A similar procedure was used for the preparation of intermediates 28-7 and 28-8, wherein methyl iodide was replaced with benzyl bromide for intermediate 28-7 and iodoacetamide for intermediate 28-8.

Compound 66

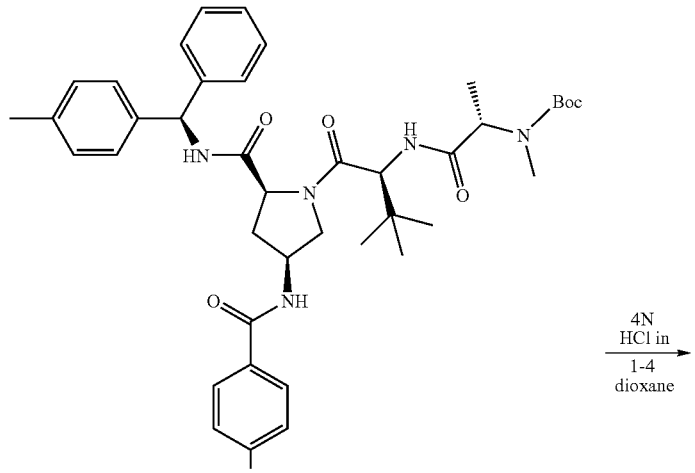

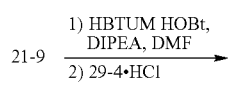

21-9
1) HBTUM HOBt, DIPEA, DMF
2) 29-4•HCl

4N HCl in 1-4 dioxane

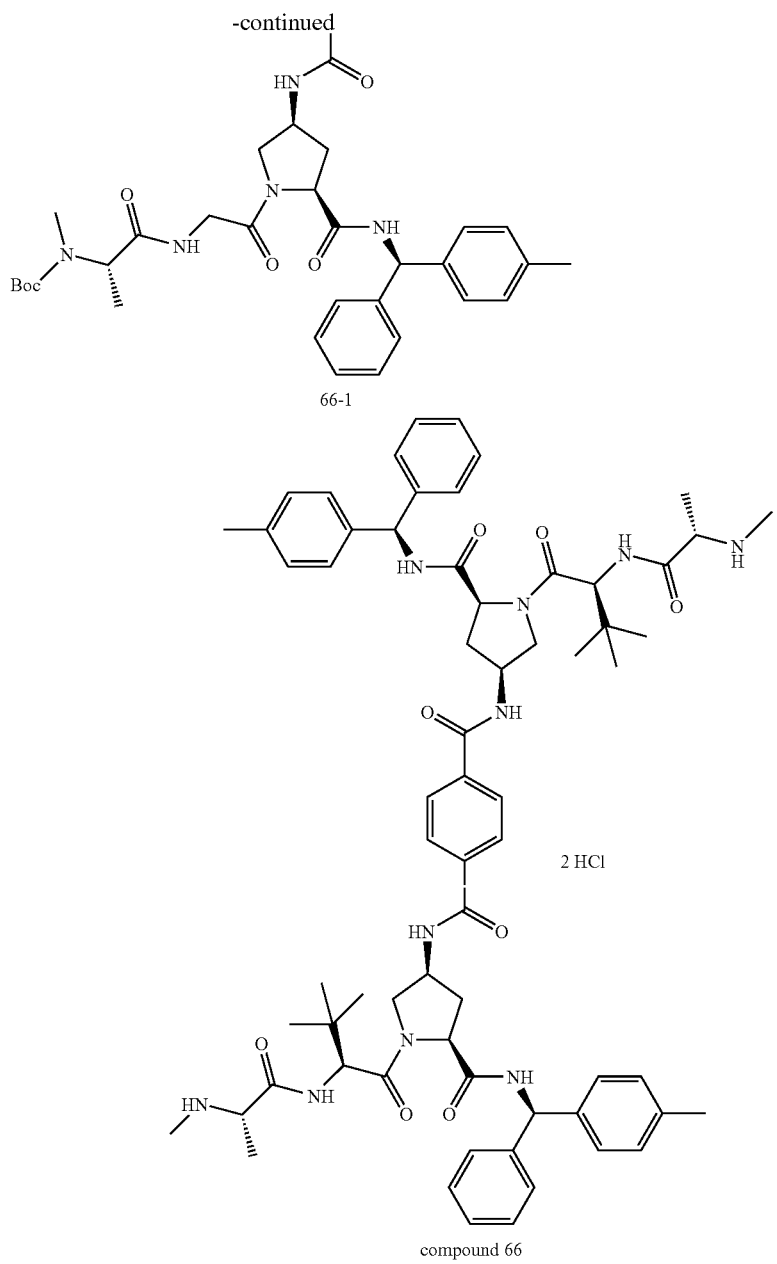

compound 66

Step 1: Intermediate 29-1

To a solution of benzaldehyde (840 μL, 8.25 mmol) in $CH_2Cl_2$ (150 mL) was added (S)-2-methylpropane-2-sulfinamide (1.0 g, 8.25 mmol) and titanium ethoxide (3.5 ml, 16.50 mmol). The reaction mixture was refluxed for 5 hours and cooled to room temperature. Water was added and the mixture was vigorously stirred, then filtered through celite. The aqueous layer was extracted with $CH_2Cl_2$ (3×) and the combined organic extracts were washed with brine, dried over anhydrous $MgSO_4$, filtered and concentrated in vacuo. Purification by silica gel chromatography provided intermediate 29-1 as a yellow oil.

Step 2: Intermediate 29-2

To a suspension of (S,E)-N-benzylidene-2-methylpropane-2-sulfinamide, 29-11, (110 mg, 0.526 mmol), [Rh(cod)(CH₃CN)₂]BF₄ (20.1 mg, 0.053 mmol), para-tolylboronic acid (143 mg, 1.052 mmol) and $Et_3N$ (147 μl, 1.052 mmol) in dioxane (1.2 mL) was added $H_2O$ (2.4 mL). The resulting brown suspension was stirred for 2 days at room temperature. The aqueous layer was extracted with EtOAc (3×) and the combined organic extracts were washed with brine, dried over anhydrous $MgSO_4$, filtered and concentrated in vacuo. Purification by silica gel chromatography provided intermediate 29-2 as a white solid (d.e.=81%).

Step 3: Intermediate 29-4

To a solution of (S)-2-methyl-N—((R)-phenyl(p-tolyl)methyl)propane-2-sulfinamide (82 mg, 0.27 mmol), 29-2, in MeOH (270 μL) was added 4N HCl in 1,4-dioxane 4 (140 μL, 0.54 mmol). The solution was stirred for 1 hr at room temperature, then $Et_2O$ was added and a white precipitate was formed. The precipitate was filtered and washed with $Et_2O$ to provide intermediate 29-4.HCl as white solid.

Step 4: Intermediate 29-5

To a solution of intermediate 21-9 (122 mg, 0.123 mmol) in DMF cooled to 0° C. were sequentially added DIPEA (193 µL, 1.107 mmol), HOBt (42 mg, 0.308 mmol) and HBTU (117 mg, 0.308 mmol). After stirring for 10 minutes intermediate 29-4.HCl (59 mg, 0.253 mmol) was added and the reaction mixture was stirred overnight at room temperature. Water and ethyl acetate were added, the organic layer was separated, washed with 10% citric acid, aqueous NaHCO$_3$ and brine, dried over anhydrous MgSO$_4$, filtered and concentrated in vacuo. Purification by silica gel chromatography provided intermediate 66-1 as a pink solid.

Step 5: Compound 66.2HCl

4N HCl in 1,4-dioxane (1 ml) was added to intermediate 66-1 (135 mg, 0.12 mmol). The solution was stirred for 1 hour at 0° C. Volatiles were removed under reduced pressure and the residue was triturated with diethyl ether to provide compound 6.2HCl as a white solid. MS (m/z) (M+2)/2=573.6.

Representative compounds of the present invention were prepared according to the above procedures and are illustrated in Table 1:

TABLE 1

| COMPOUND | STRUCTURE | MS |
|---|---|---|
| 1 | 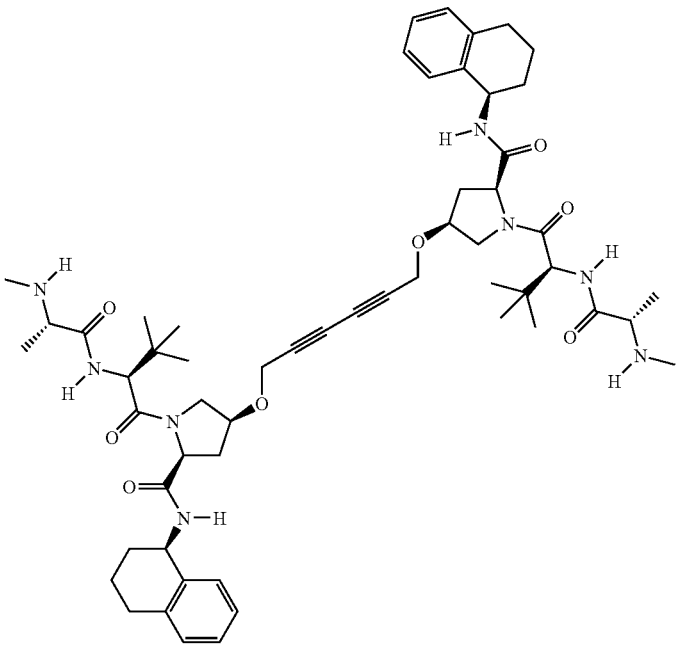 | M + 1 = 991.7<br>[M + 2]/2 = 496.4 |
| 2 | 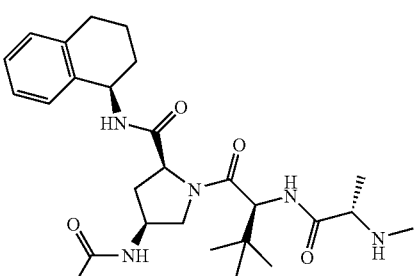 | M + 1 = 1081.8<br>[M + 2]/2 = 541.4 |

TABLE 1-continued
| COMPOUND | STRUCTURE | MS |
|---|---|---|
| 3 | 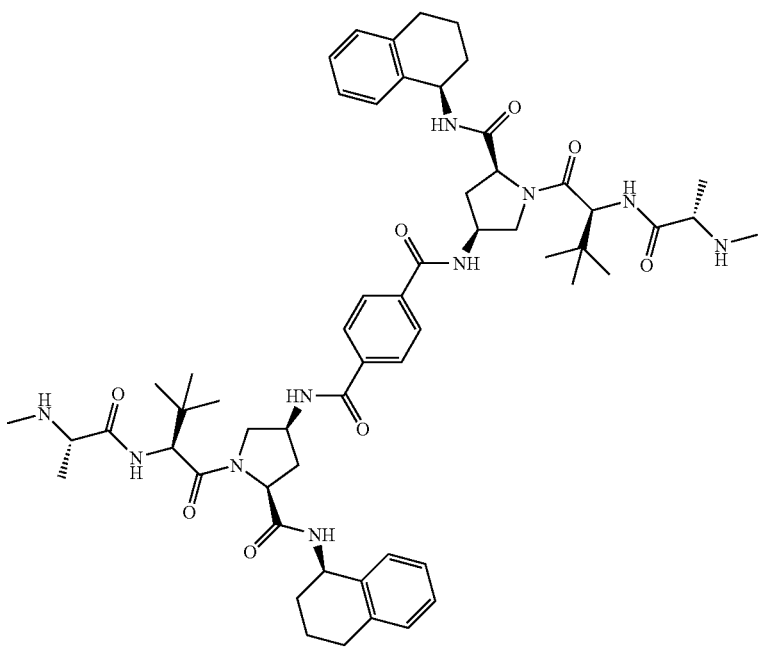 | [M + 2]/2 = 523.4 |
| 4 | 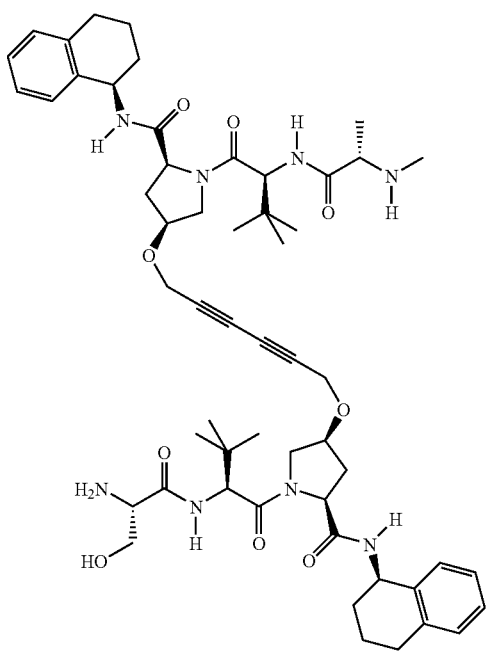 | M + 1 = 993.5. |

TABLE 1-continued
| COMPOUND | STRUCTURE | MS |
|---|---|---|
| 5 | 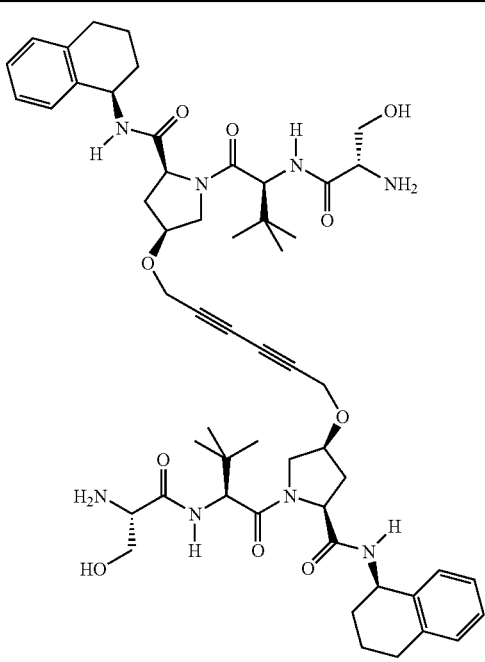 | M + 1 = 995.6<br>(M + 2)/2 = 498.5 |
| 6 | 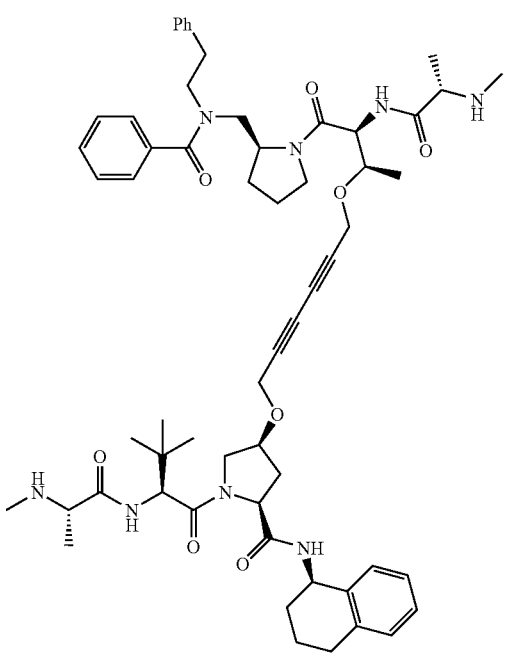 | (M + 2)/2 = 514.4 |

TABLE 1-continued
| COMPOUND | STRUCTURE | MS |
|---|---|---|
| 7 | 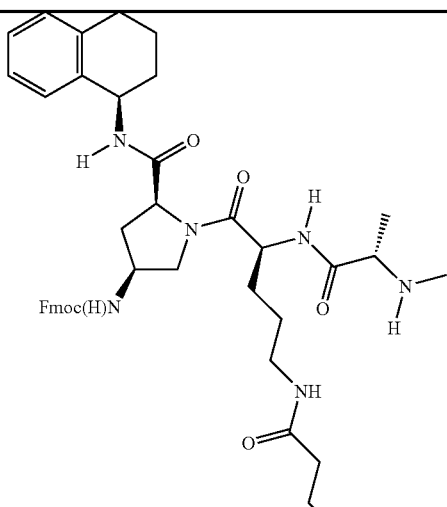 | (M + 2)/2 = 618.0 |
| 8 | 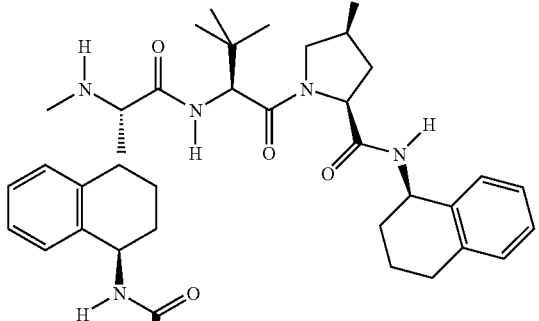 | M + 1 = 1012 |

TABLE 1-continued
| COMPOUND | STRUCTURE | MS |
|---|---|---|
| 9 | 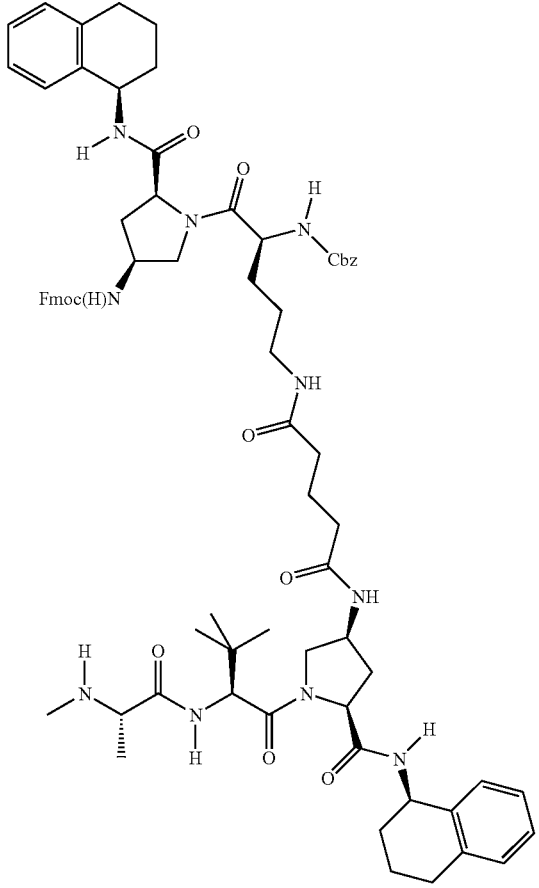 | (M + 2)/2 = 642 |
| 10 | 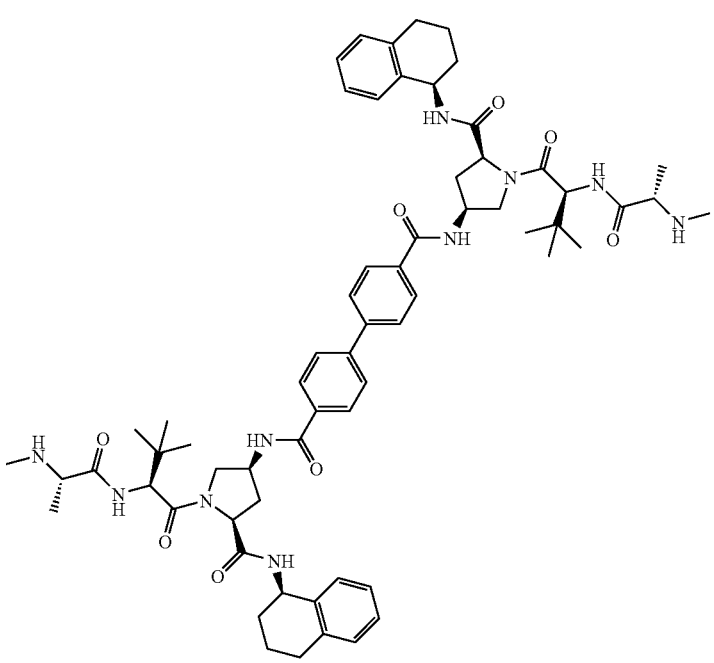 | [M + 2]/2 = 561.6 |

TABLE 1-continued
| COMPOUND | STRUCTURE | MS |
|---|---|---|
| 11 | 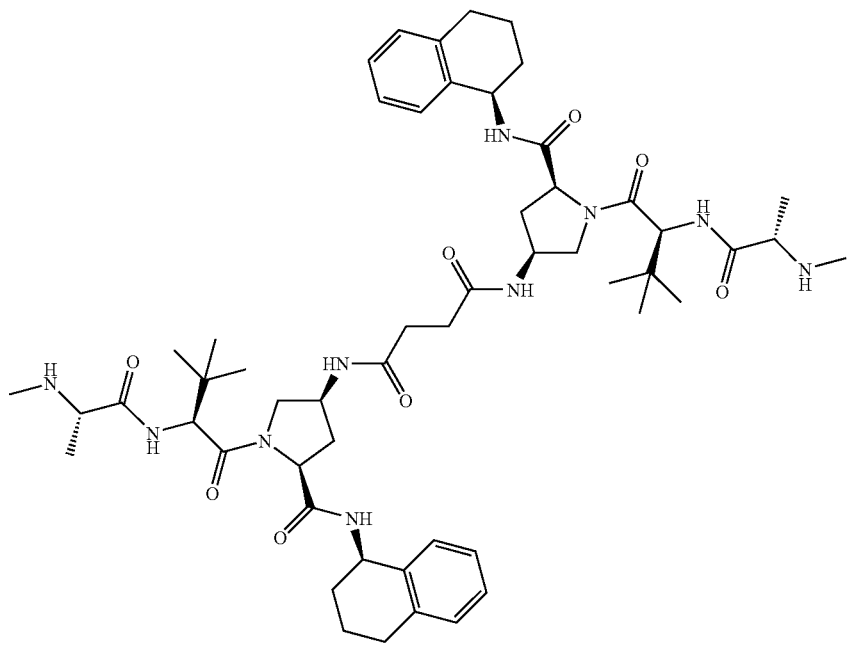 | M + 1 = 997.6<br>[M + 2]/2 = 499.4 |
| 12 | 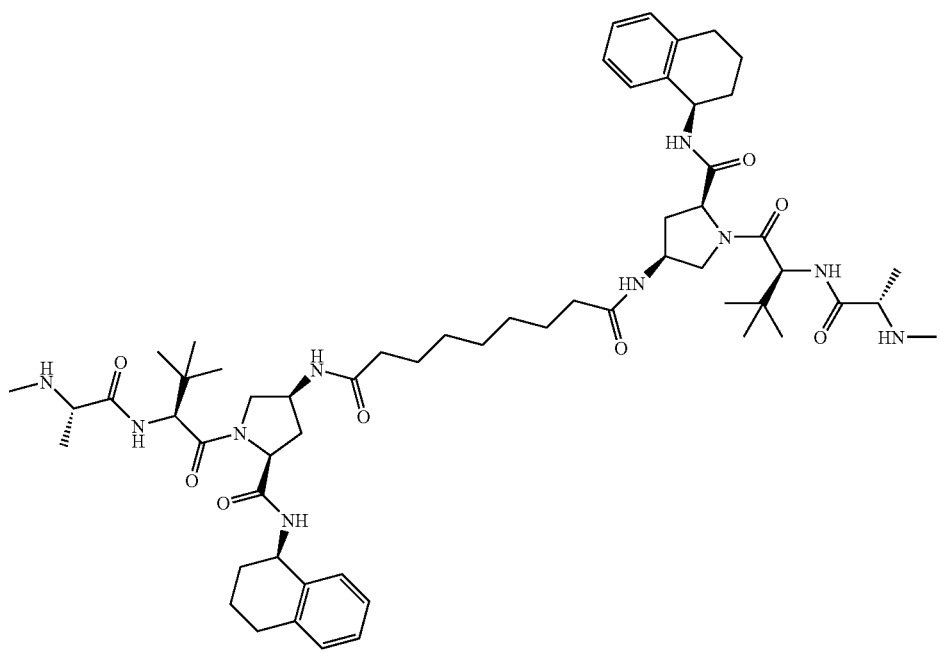 | M + 1 = 1067.6<br>[M + 2]/2 = 534.5 |

TABLE 1-continued
| COMPOUND | STRUCTURE | MS |
|---|---|---|
| 13 | 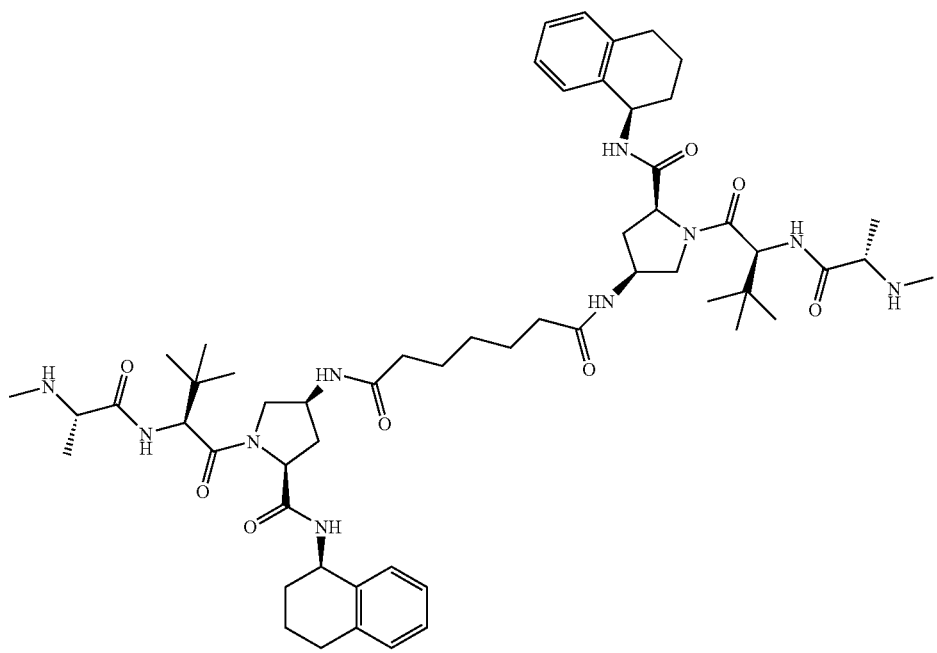 | [M + 2]/2 = 520.4 |
| 14 | 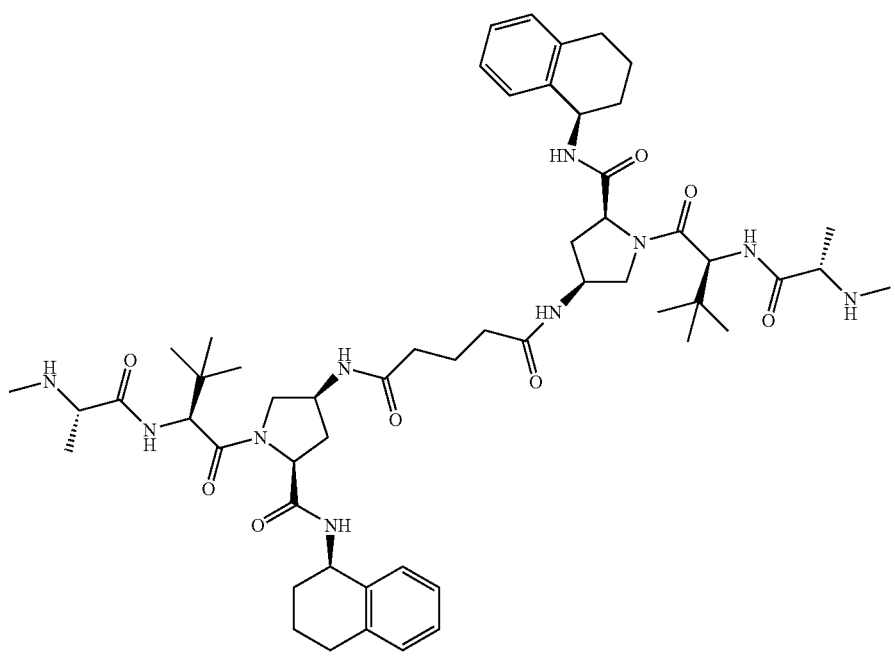 | [M + 2]/2 = 506.4 |

TABLE 1-continued
| COMPOUND | STRUCTURE | MS |
|---|---|---|
| 15 | 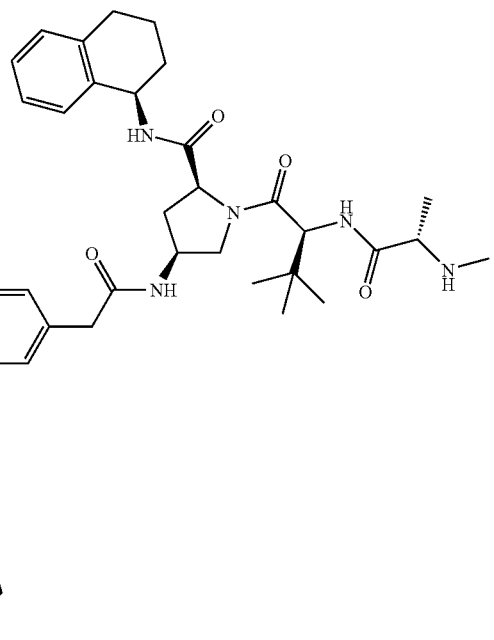 | M + 1 = 1073.6<br>[M + 2]/2 = 537.4 |
| 16 | 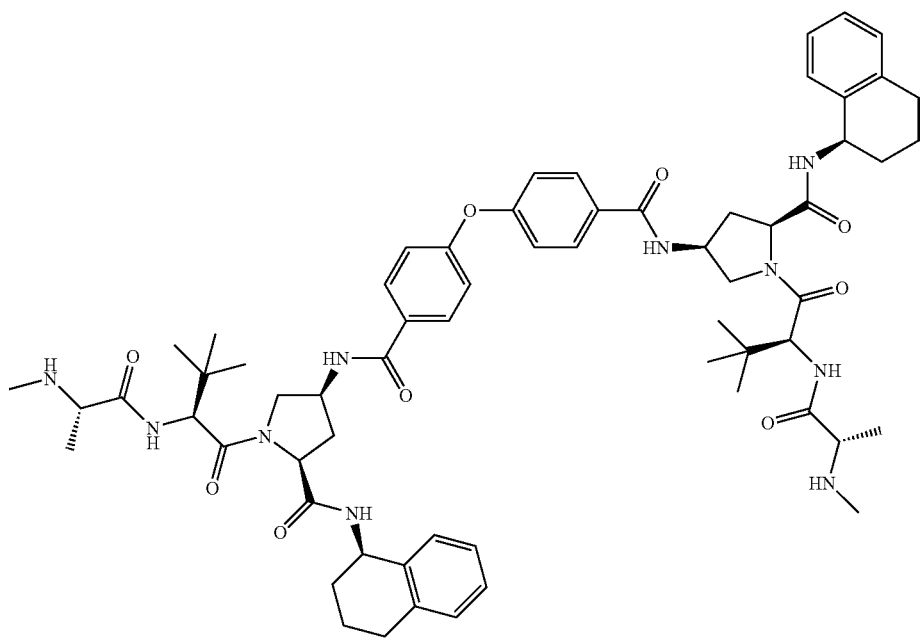 | [M + 2]/2 = 569.4 |

TABLE 1-continued
| COMPOUND | STRUCTURE | MS |
|---|---|---|
| 17 | 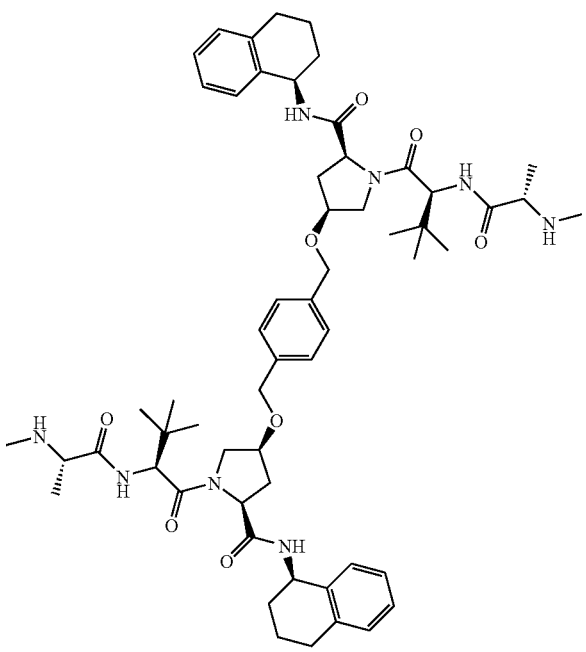 | M + 1 = 1019.6<br>[M + 2]/2 = 510.4 |
| 18 | 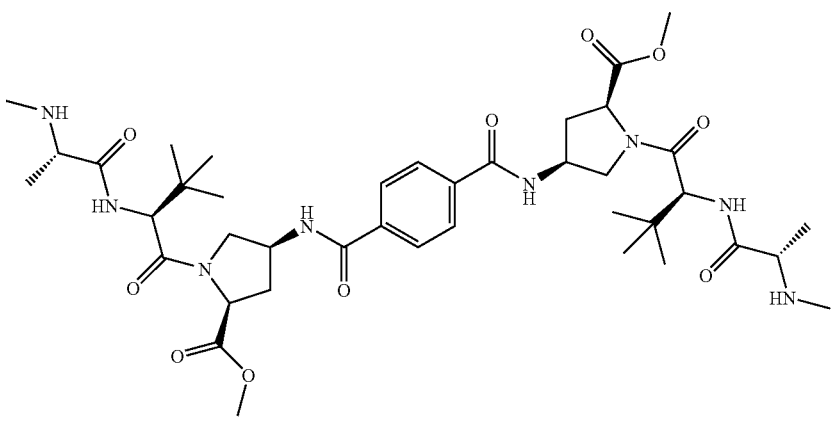 | M + 1 = 815.4<br>[M + 2]/2 = 408.2 |

TABLE 1-continued
| COMPOUND | STRUCTURE | MS |
|---|---|---|
| 19 | 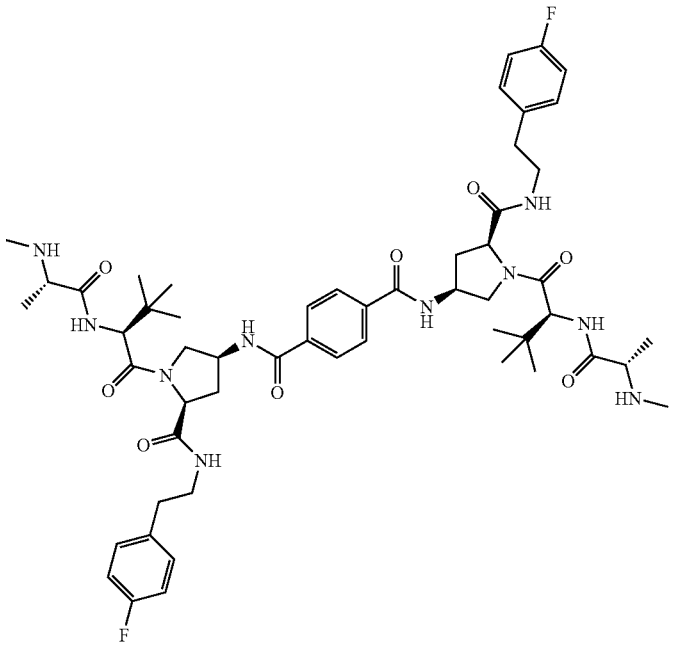 | M + 1 = 1029.6<br>[M + 2]/2 = 515.4 |
| 20 | 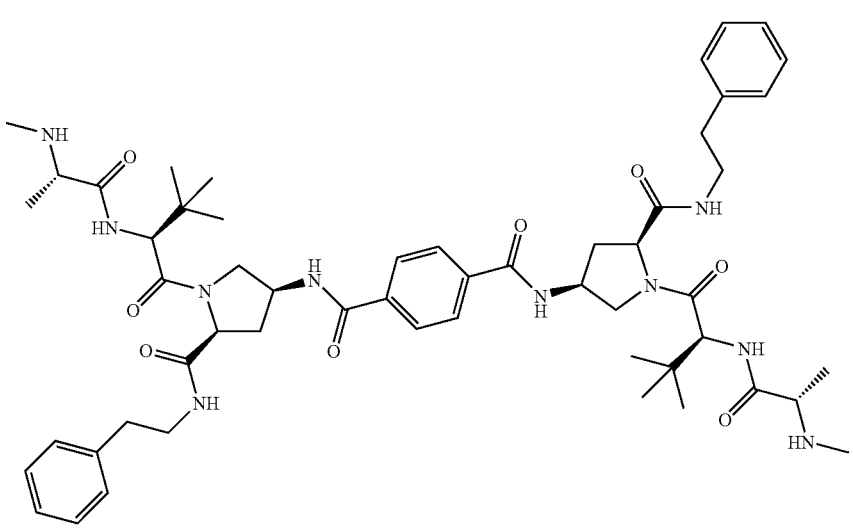 | [M + 2]/2 = 497.6 |

US 7,645,741 B2
193 194
TABLE 1-continued
| COMPOUND | STRUCTURE | MS |
|---|---|---|
| 21 | 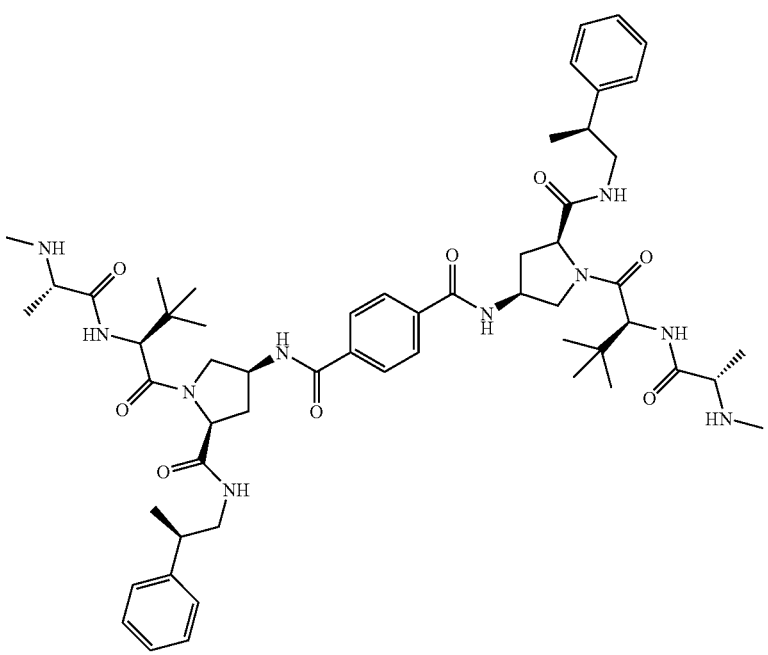 | M + 1 = 1021.6<br>[M + 2]/2 = 511.6 |
| 22 | 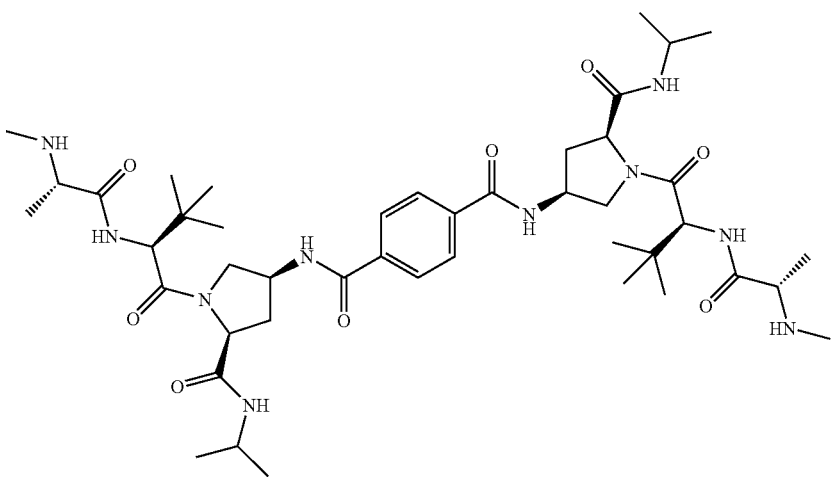 | M + 1 = 869.6<br>[M + 2]/2 = 435.4 |

TABLE 1-continued
| COMPOUND | STRUCTURE | MS |
|---|---|---|
| 23 | 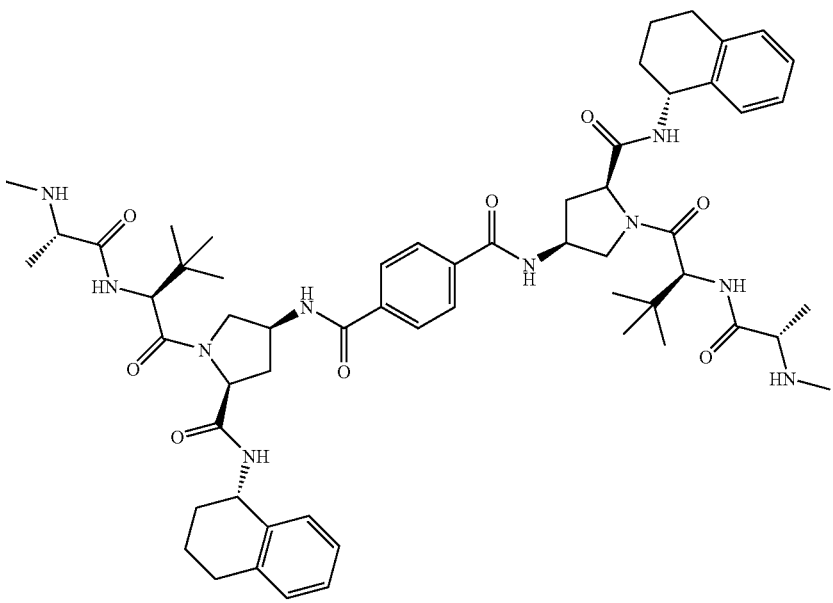 | M + 1 = 1045.8<br>[M + 2]/2 = 523.4 |
| 24 | 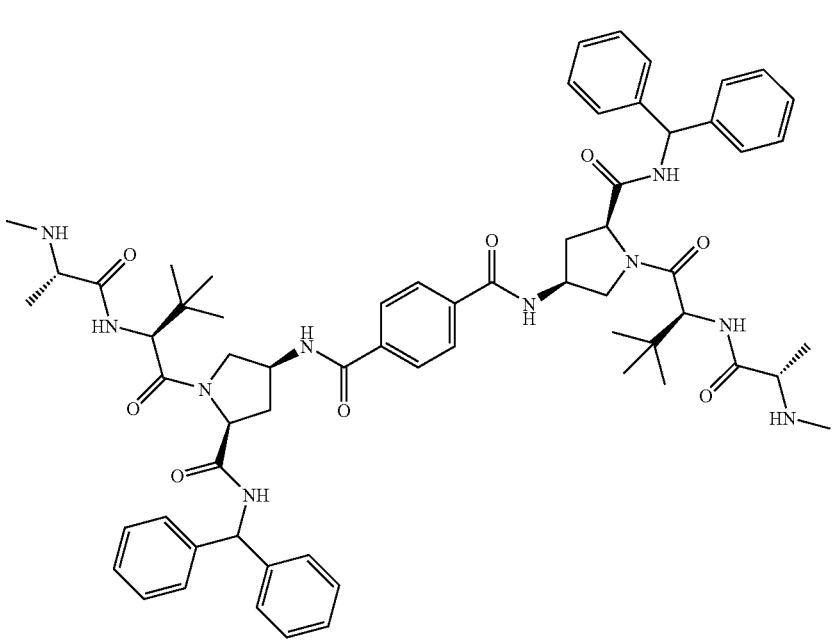 | [M + 2]/2 = 559.4 |

TABLE 1-continued
| COMPOUND | STRUCTURE | MS |
|---|---|---|
| 25 | 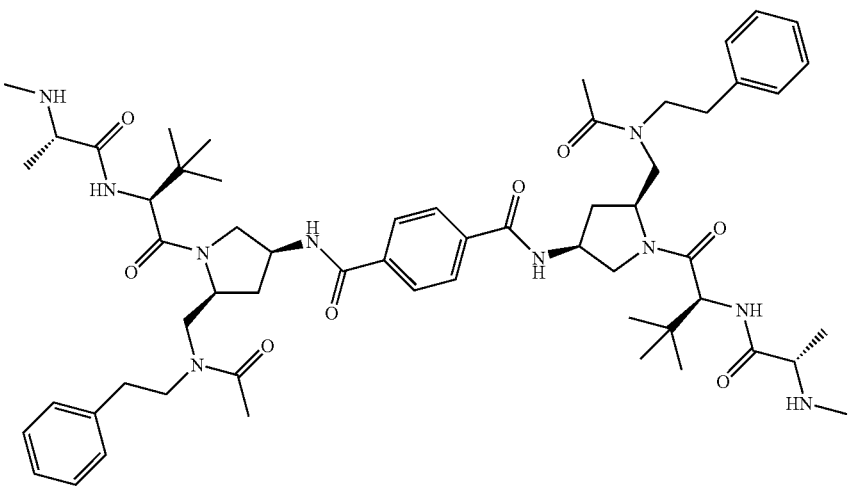 | [M + 2]/2 = 525.6 |
| 26 | 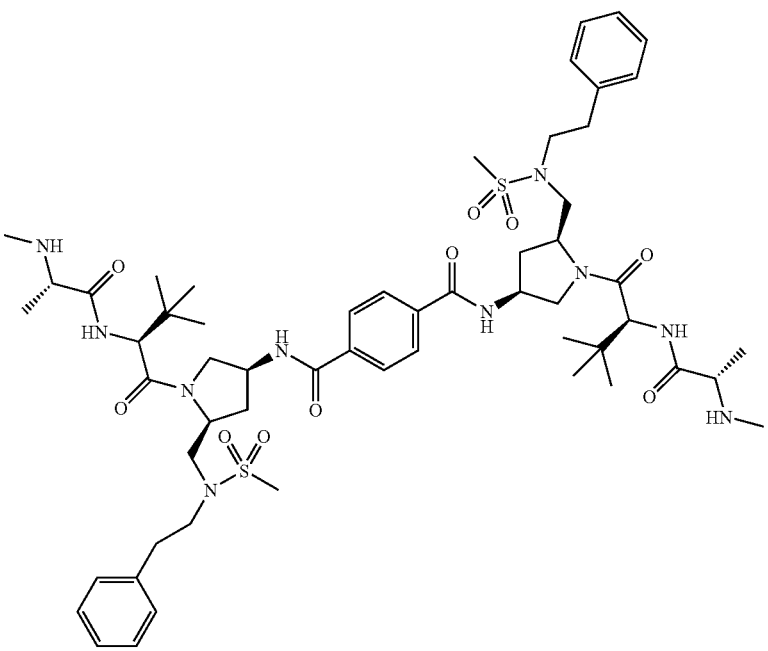 | [M + 2]/2 = 561.4 |

TABLE 1-continued
| COMPOUND | STRUCTURE | MS |
|---|---|---|
| 27 | 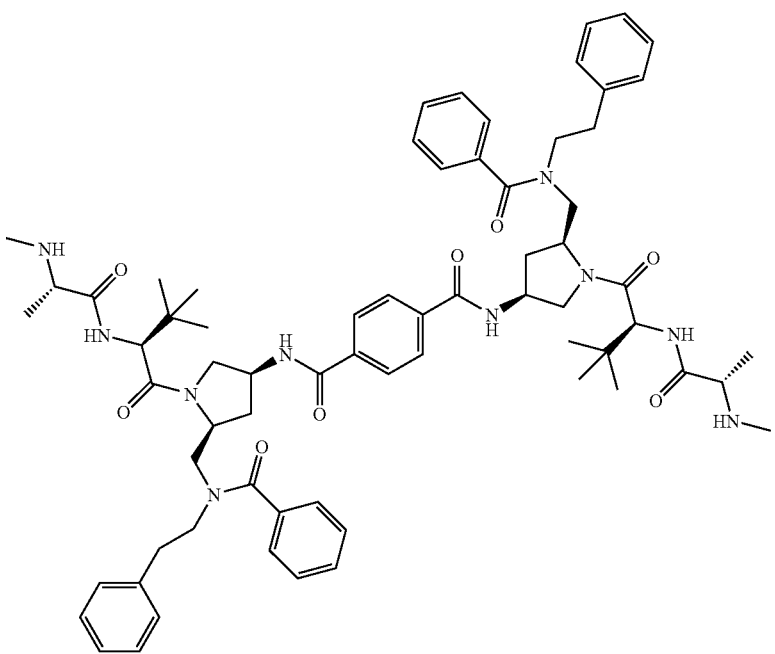 | [M + 2]/2 = 587.6 |
| 28 | 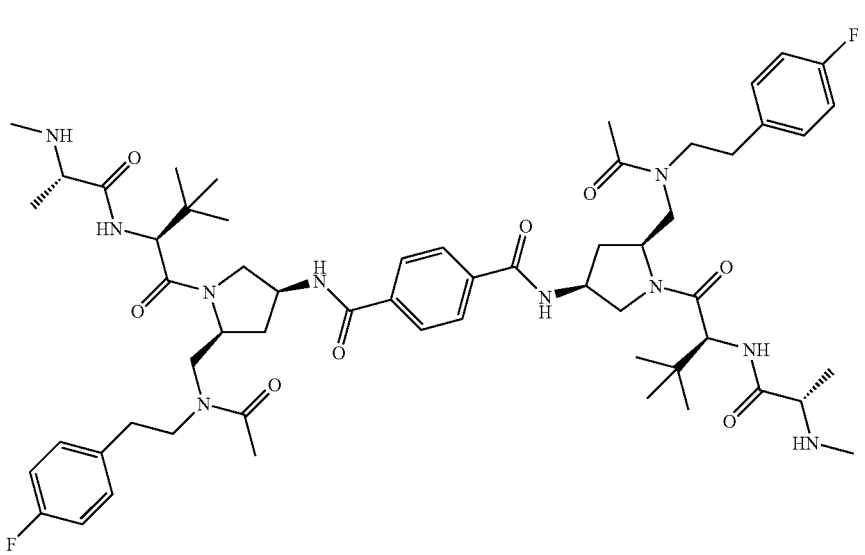 | [M + 2]/2 = 543.6 |

TABLE 1-continued
| COMPOUND | STRUCTURE | MS |
|---|---|---|
| 29 | 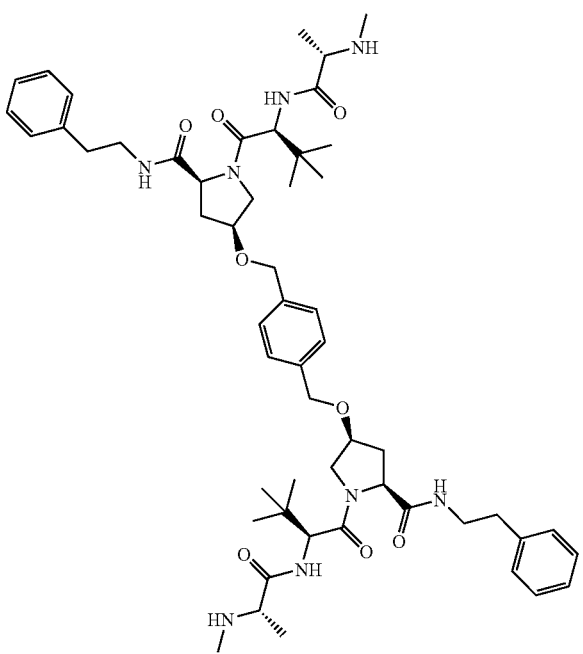 | M + 1 = 967.6<br>[M + 2]/2 = 484.5 |
| 30 | 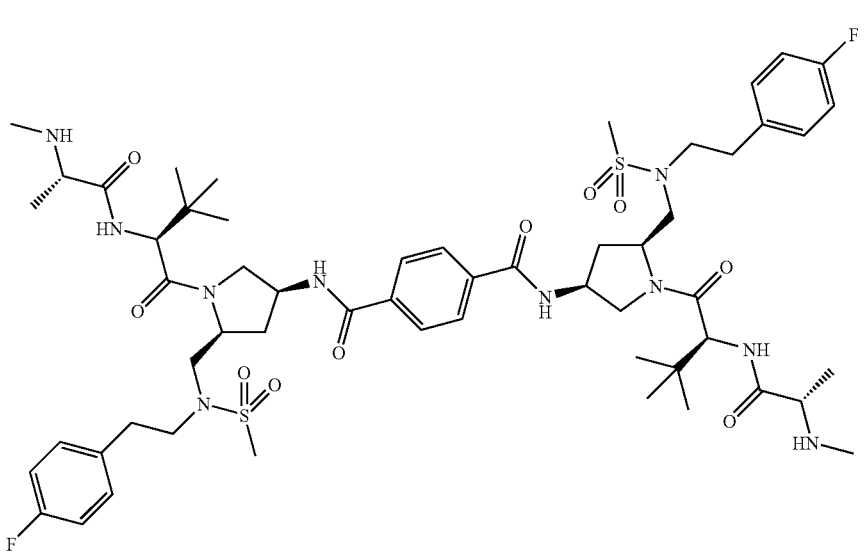 | M + 1 = 1157.6<br>[M + 2]/2 = 579.6 |

TABLE 1-continued

| COM-POUND | STRUCTURE | MS |
|---|---|---|
| 31 | 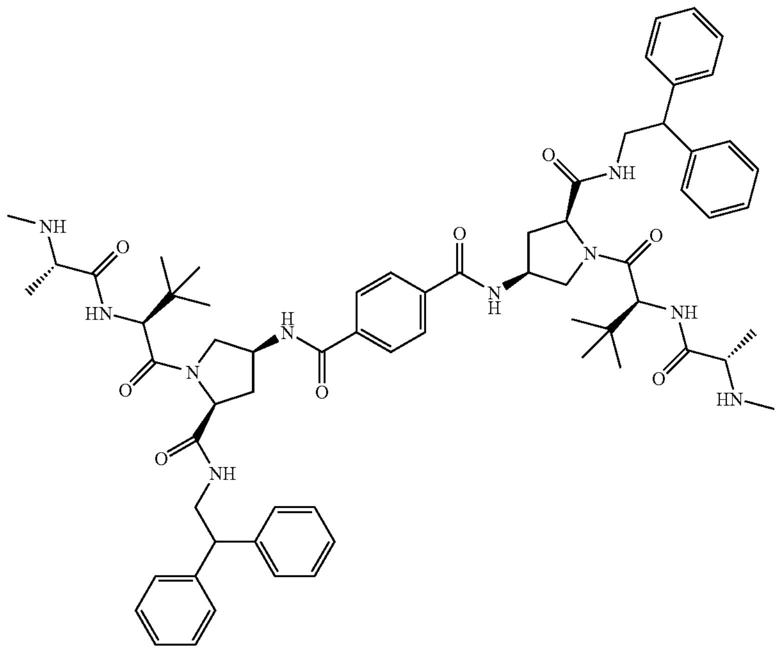 | [M + 2]/2 = 573.6 |
| 32 | 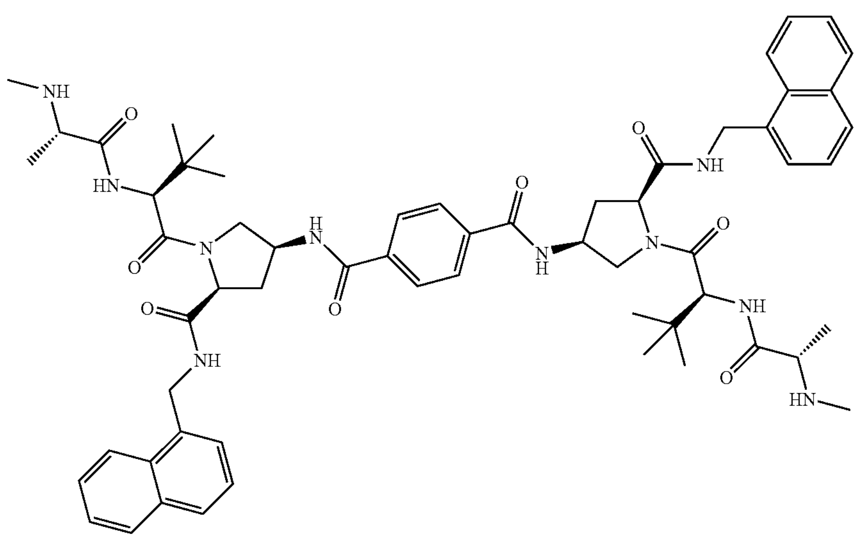 | [M + 2]/2 = 533.6 |

TABLE 1-continued

| COMPOUND | STRUCTURE | MS |
|---|---|---|
| 33 | 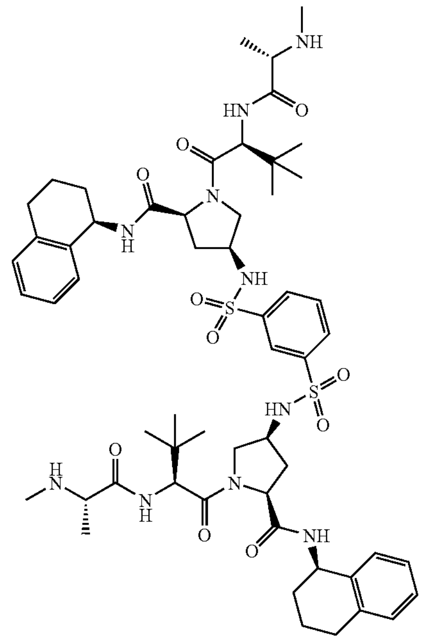 | M + 1 = 1117.6<br>[M + 2]/2 = 559.5 |
| 34 | 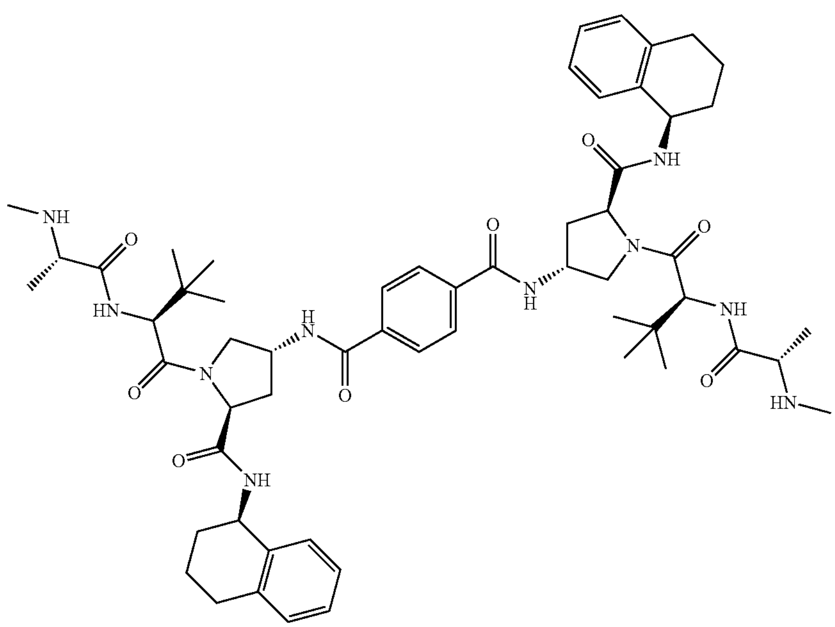 | M + 1 = 1045.8<br>[M + 2]/2 = 523.4 |

TABLE 1-continued

| COMPOUND | STRUCTURE | MS |
|---|---|---|
| 35 | 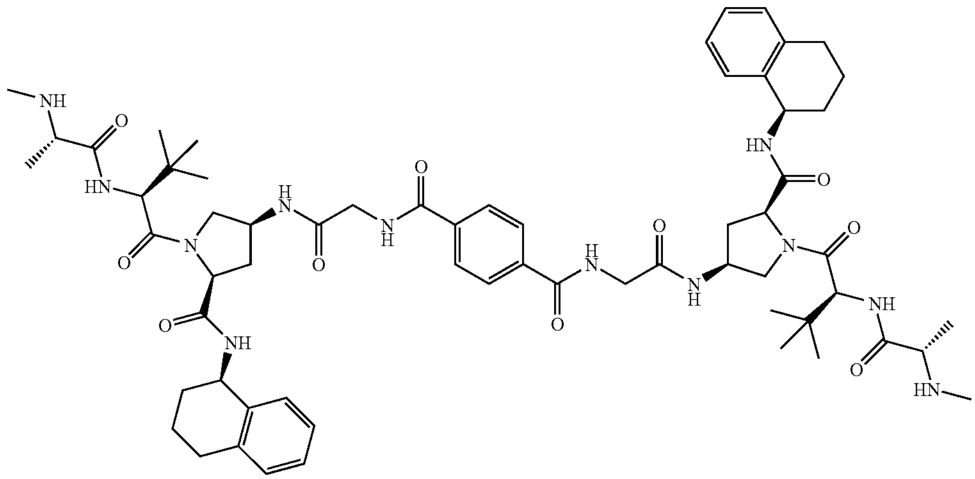 | [M + 2]/2 = 580.6 |
| 36 | 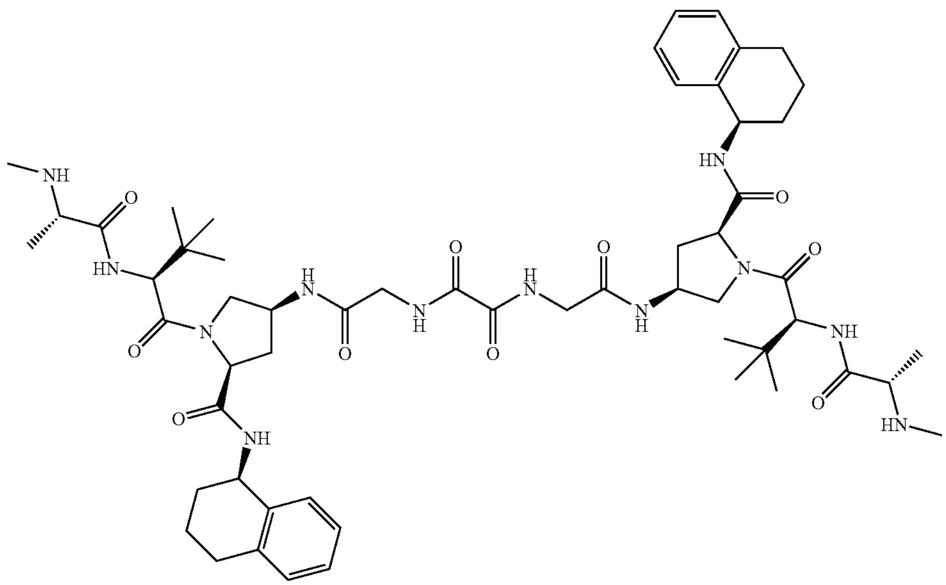 | [M + 2]/2 = 542.6 |
| 37 | 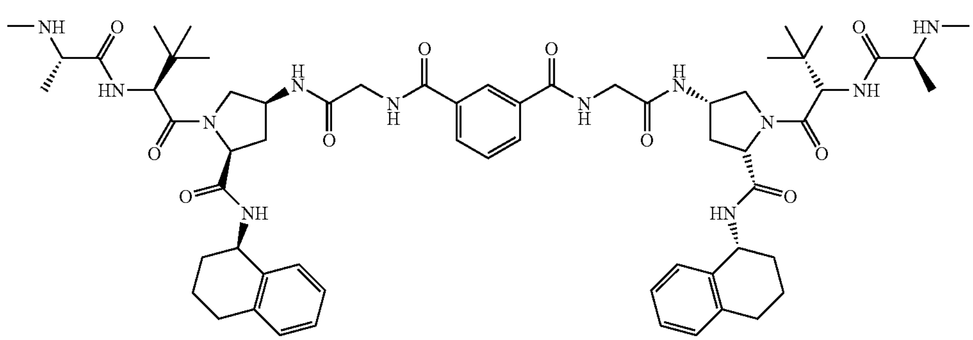 | [M + 2]/2 = 580.6 |

TABLE 1-continued

| COMPOUND | STRUCTURE | MS |
|---|---|---|
| 38 | 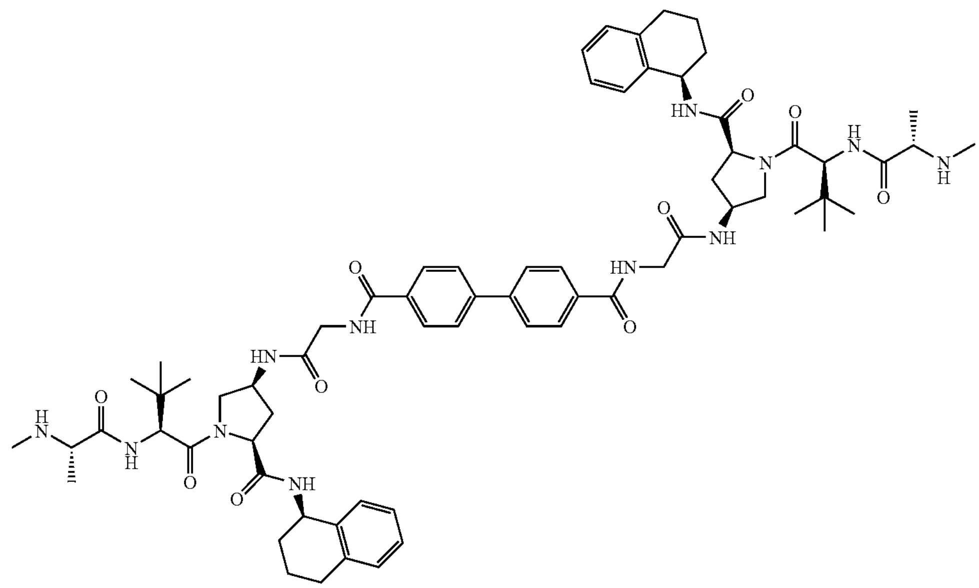 | [M + 2]/2 = 618.6 |
| 39 | 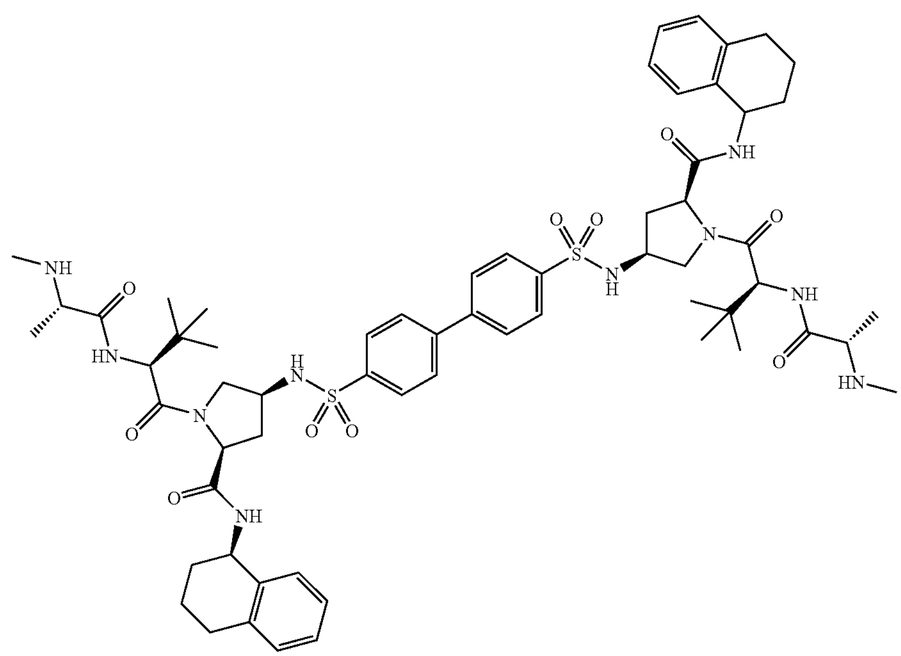 | [M + 2]/2 = 597.4 |

TABLE 1-continued

| COMPOUND | STRUCTURE | MS |
|---|---|---|
| 40 | 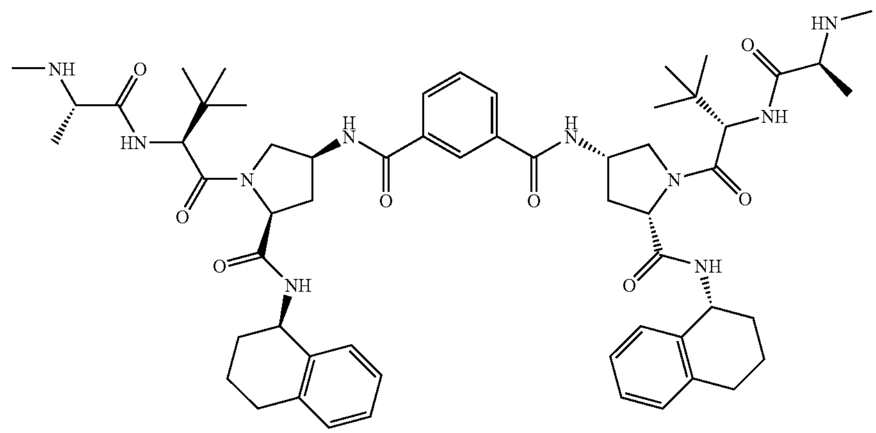 | M + 1 = 1045.6<br>[M + 2]/2 = 523.4 |
| 41 | 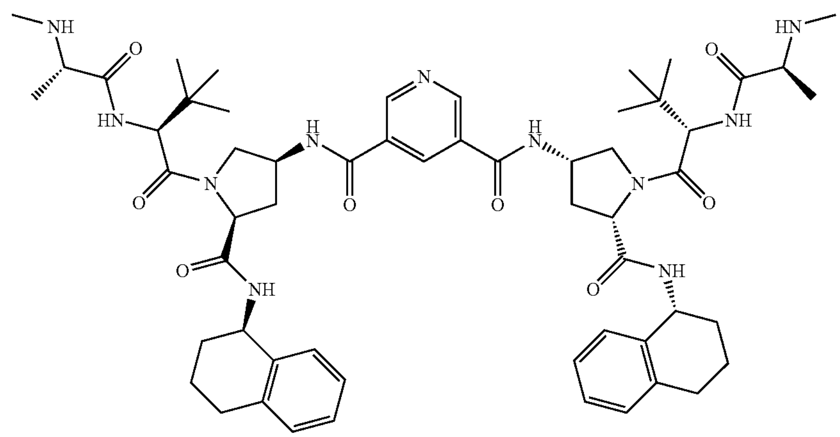 | M + 1 = 1046.6<br>[M + 2]/2 = 523.8 |
| 42 | 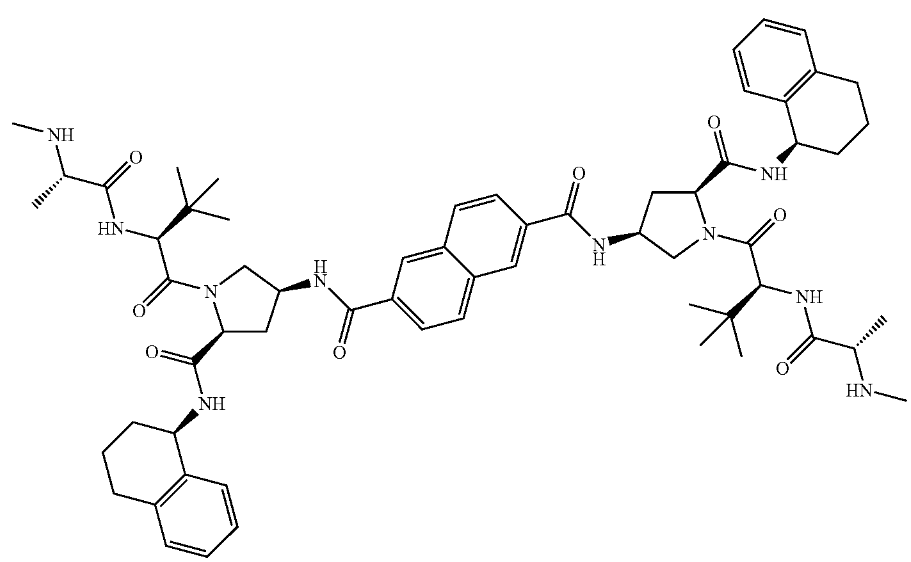 | [M + 2]/2 = 548.4 |

TABLE 1-continued

| COMPOUND | STRUCTURE | MS |
|---|---|---|
| 43 | 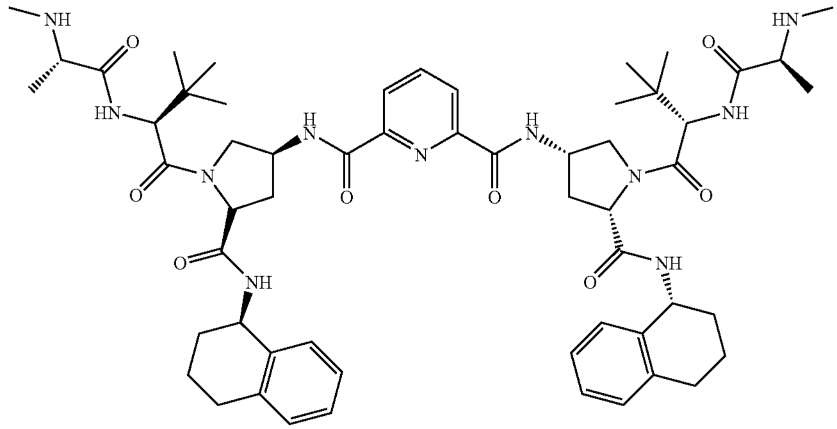 | M + 1 = 1046.6<br>[M + 2]/2 = 523.8 |
| 44 | 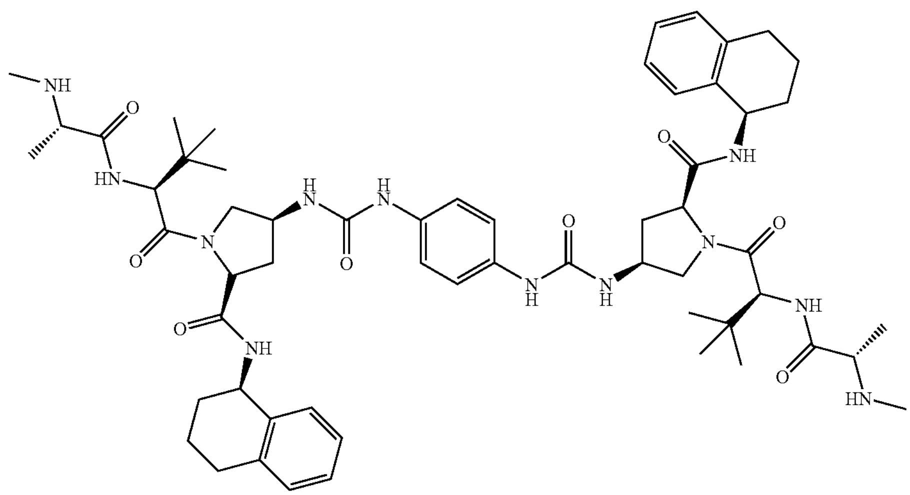 | [M + 2]/2 = 538.4 |
| 45 | 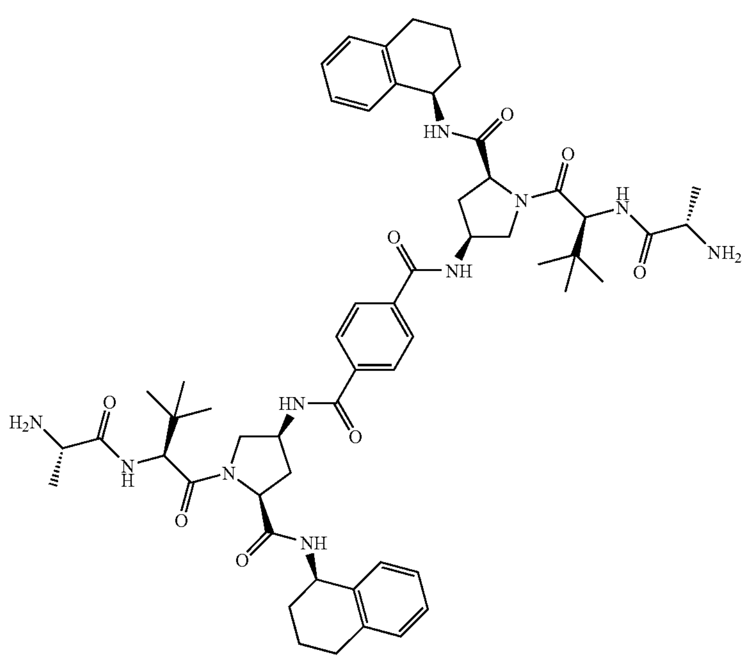 | M + 1 = 1018.8<br>[M + 2]/2 = 509.6 |

TABLE 1-continued
| COM-POUND | STRUCTURE | MS |
|---|---|---|
| 46 | 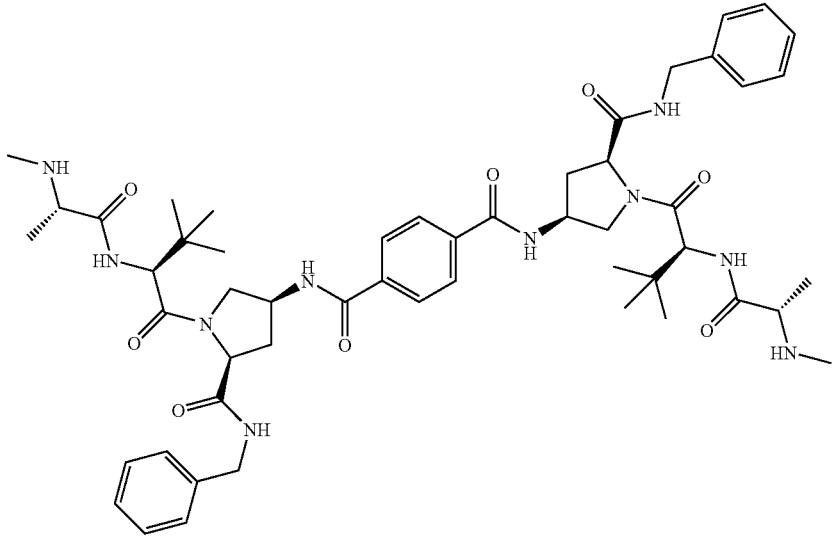 | M + 1 = 965.6<br>[M + 2]/2 = 483.4 |
| 47 | 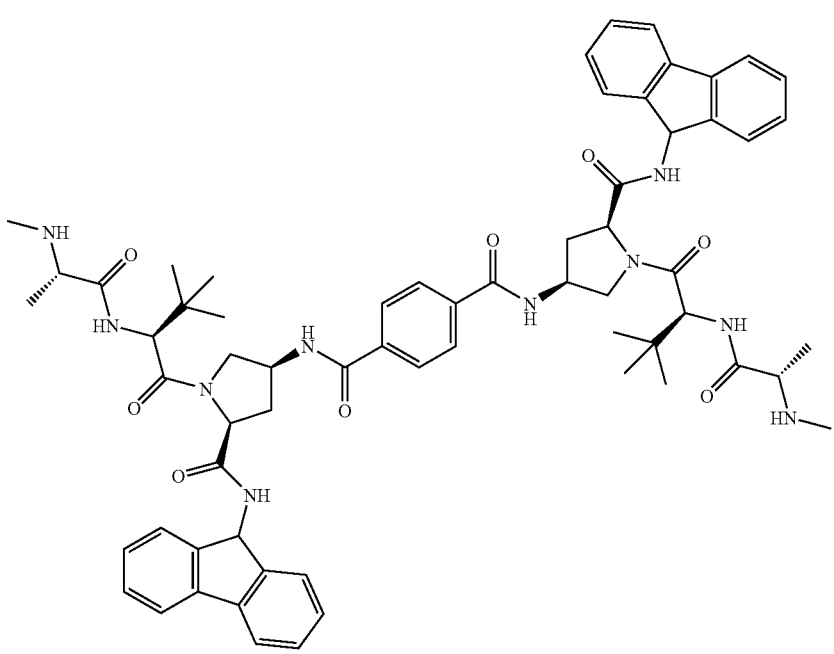 | M + 1 = 1113.8<br>[M + 2]/2 = 557.6 |

TABLE 1-continued

| COMPOUND | STRUCTURE | MS |
|---|---|---|
| 48 | 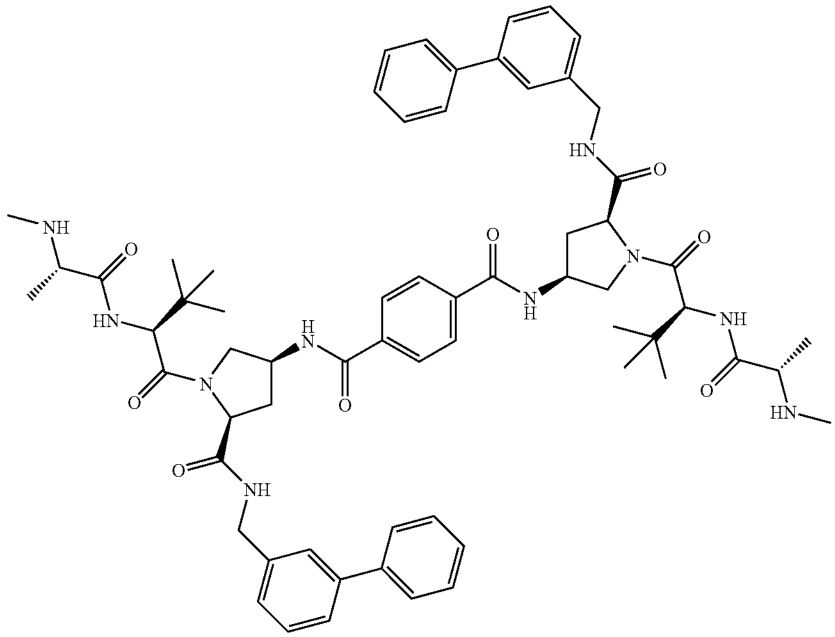 | M + 1 = 1117.8<br>[M + 2]/2 = 559.6 |
| 49 | 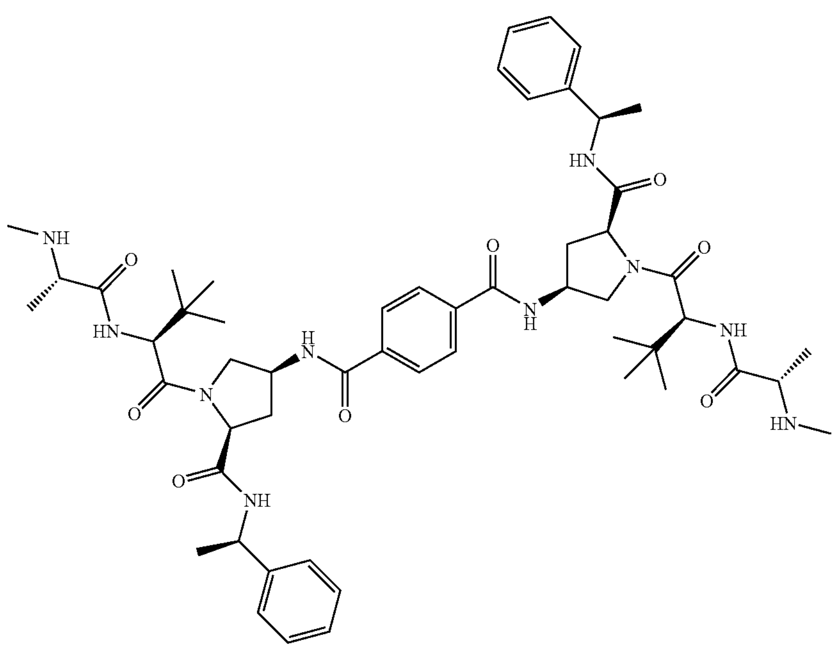 | M + 1 = 993.8<br>[M + 2]/2 = 497.6 |

TABLE 1-continued
| COMPOUND | STRUCTURE | MS |
|---|---|---|
| 50 | 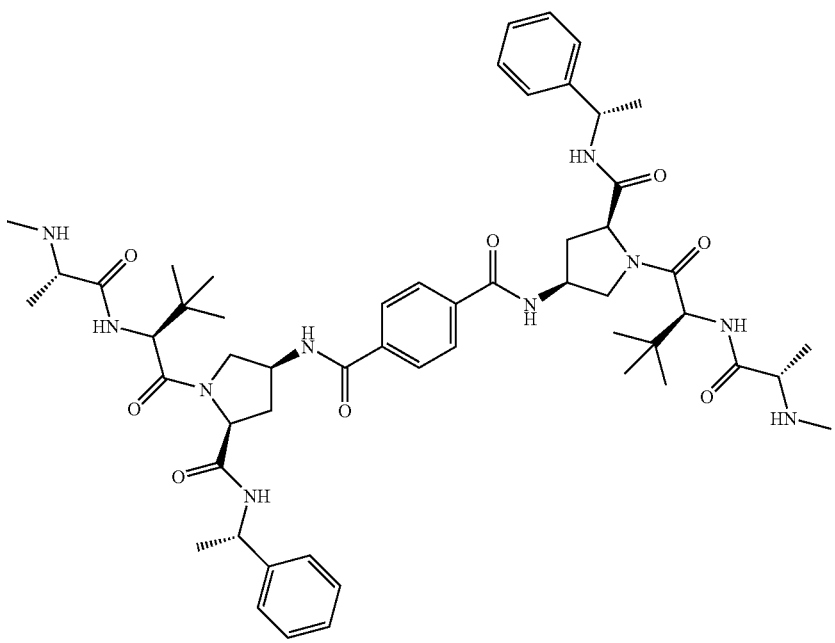 | M + 1 = 993.8<br>[M + 2]/2 = 497.6 |
| 51 | 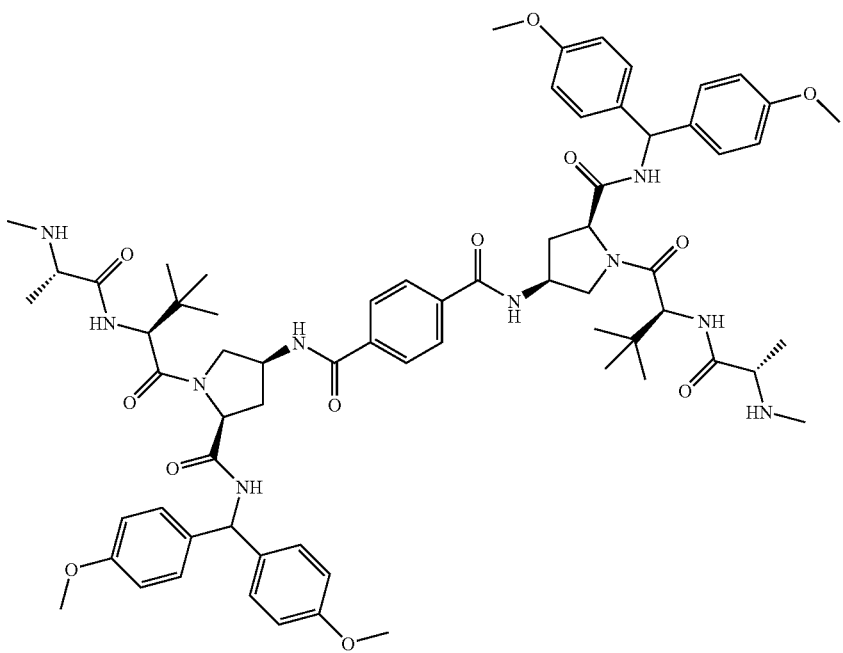 | [M + 2]/2 = 619.9 |

TABLE 1-continued

| COMPOUND | STRUCTURE | MS |
|---|---|---|
| 52 | 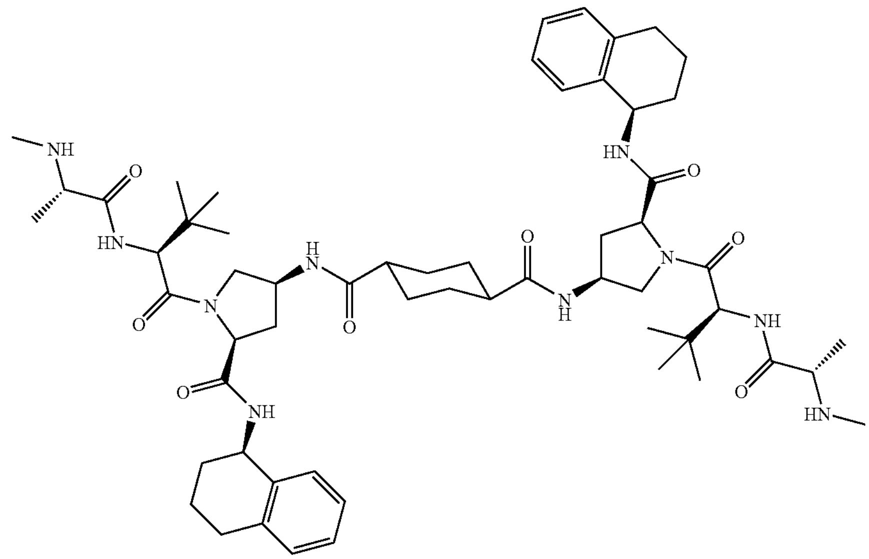 | M + 1 = 1051.8<br>[M + 2]/2 = 526.6 |
| 53 | 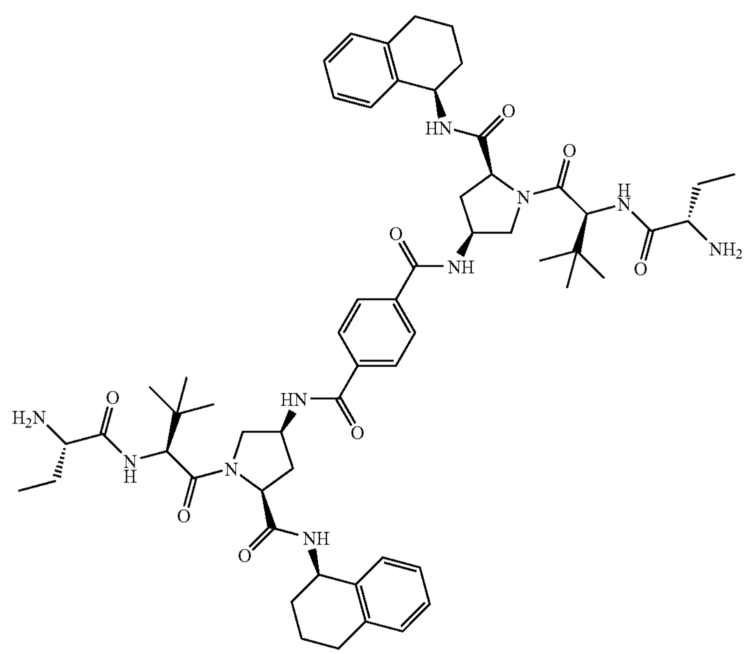 | M + 1 = 1046.8<br>[M + 2]/2 = 523.4 |

TABLE 1-continued

| COMPOUND | STRUCTURE | MS |
|---|---|---|
| 54 | 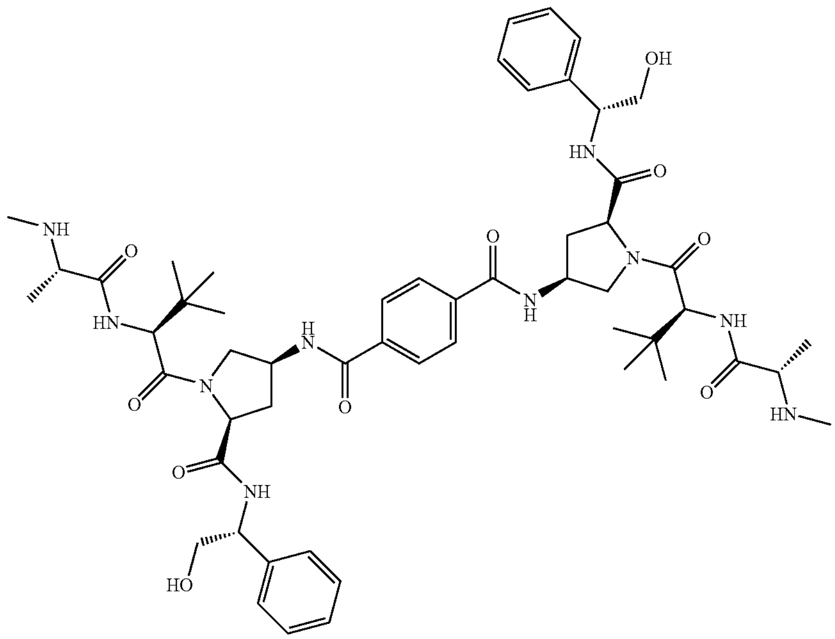 | M + 1 = 1025.8<br>[M + 2]/2 = 513.5 |
| 55 | 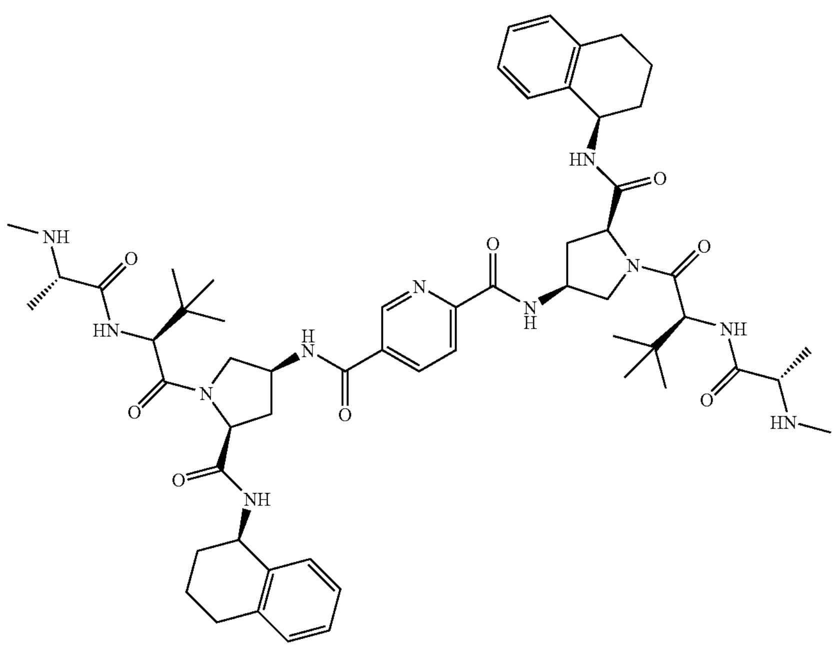 | M + 1 = 1046.8<br>[M + 2]/2 = 524.2 |

| COMPOUND | STRUCTURE | MS |
|---|---|---|
| 56 | 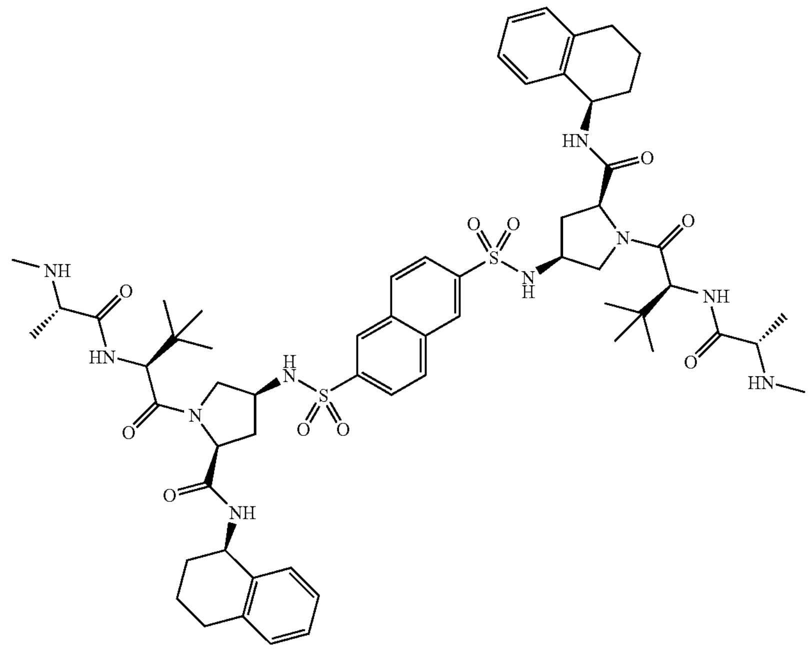 | [M + 2]/2 = 584.6 |
| 57 | 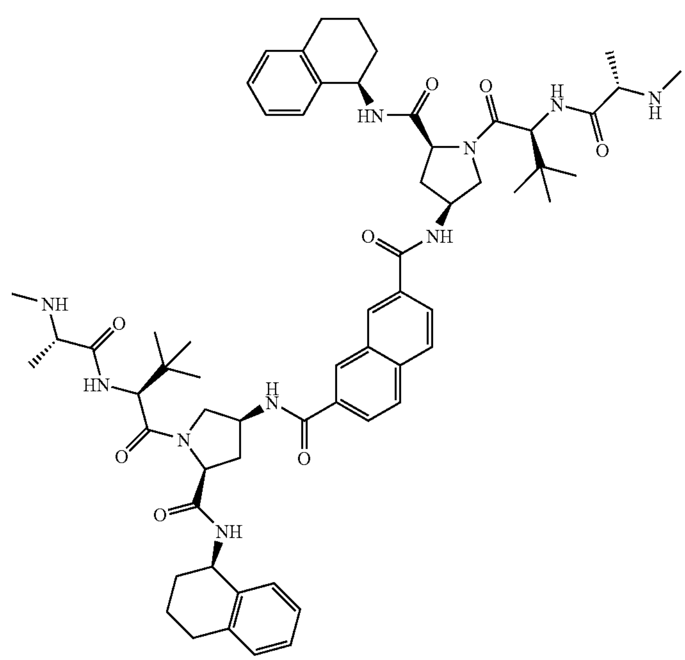 | M + 1 = 1095.8 [M + 2]/2 = 548.6 |

TABLE 1-continued

| COMPOUND | STRUCTURE | MS |
|---|---|---|
| 58 | 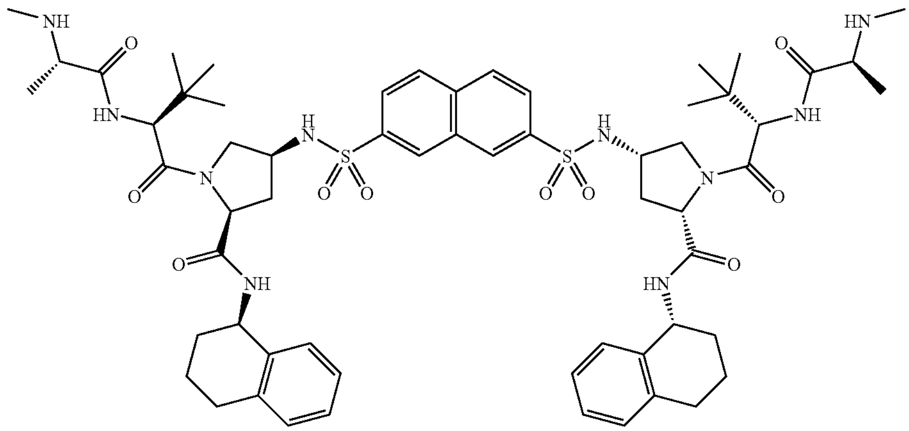 | M + 1 = 1167.8<br>[M + 2]/2 = 584.6 |
| 59 | 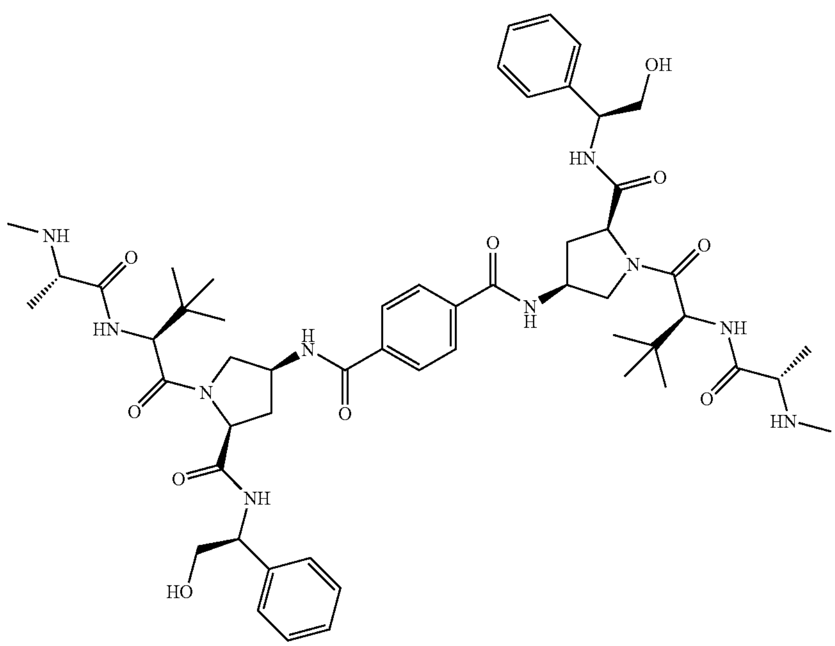 | M + 1 = 1025.8<br>[M + 2]/2 = 513.6 |

| COMPOUND | STRUCTURE | MS |
|---|---|---|
| 60 | 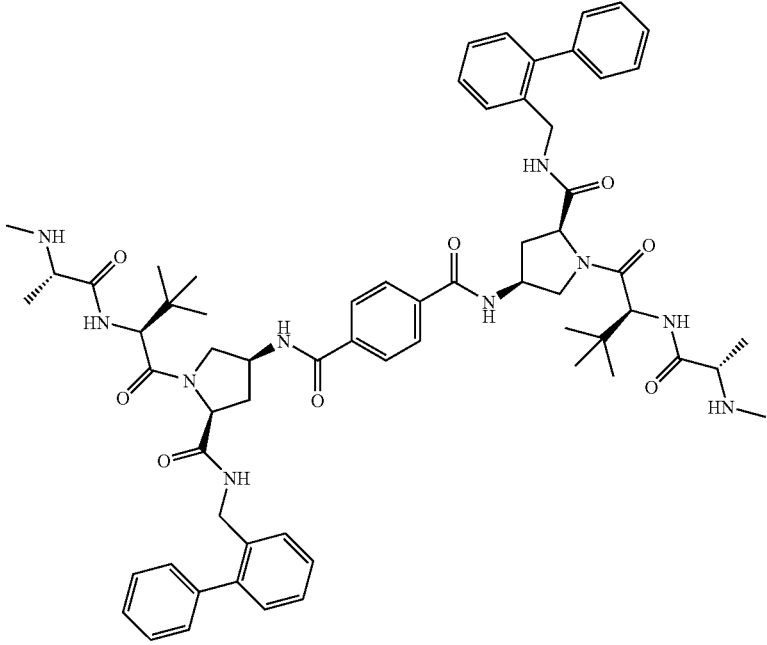 | M + 1 = 1117.8<br>[M + 2]/2 = 559.6 |
| 61 | 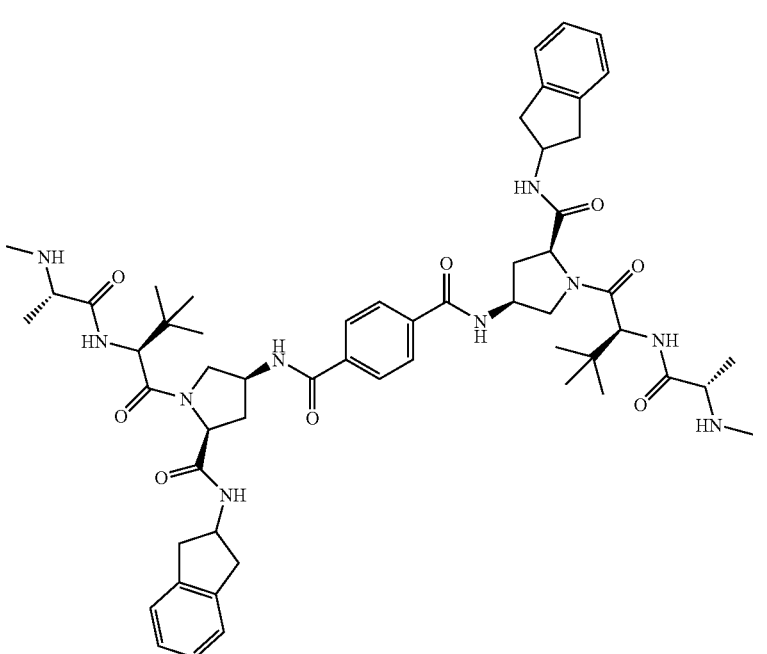 | M + 1 = 1017.8<br>[M + 2]/2 = 509.6 |

TABLE 1-continued
| COMPOUND | STRUCTURE | MS |
|---|---|---|
| 62 | 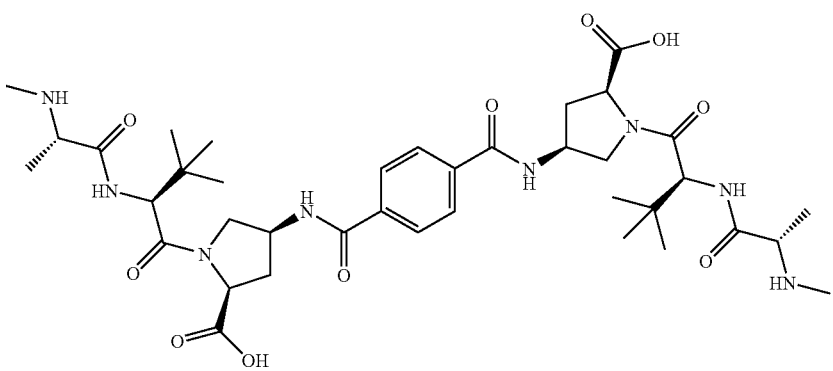 | M + 1 = 787.6<br>[M + 2]/2 = 394.4 |
| 63 | 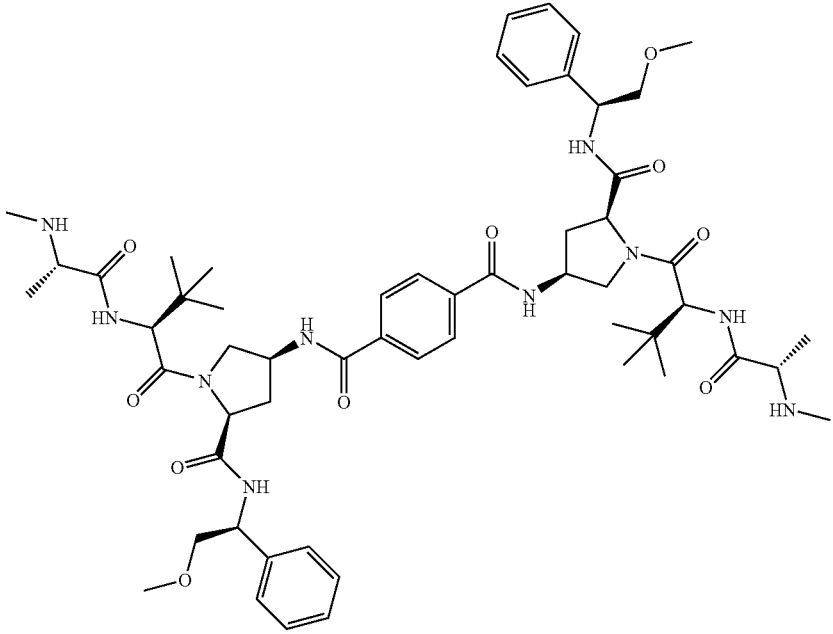 | [M + 1] = 1053.8<br>(M + 2)/2 = 527.8 |

TABLE 1-continued
| COMPOUND | STRUCTURE | MS |
|---|---|---|
| 64 | 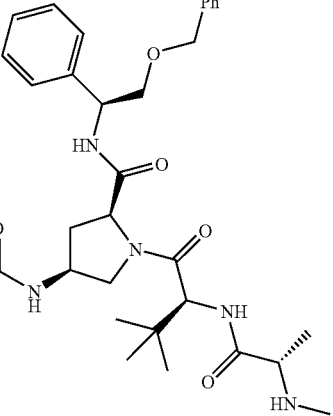 | [M + 1] = 1206.0<br>(M + 2)/2 = 603.6 |
| 65 | 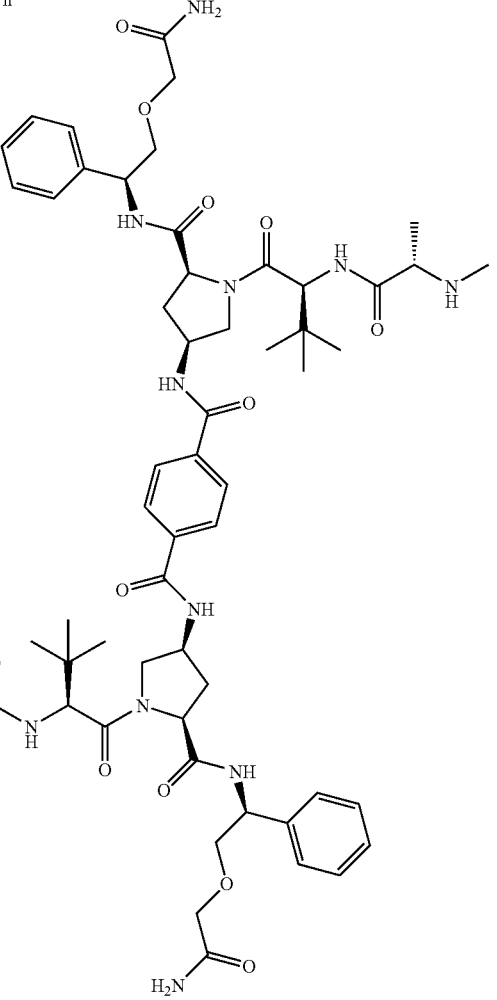 | [M + 1] = 1139.8<br>(M + 2)/2 = 570.6 |

TABLE 1-continued
| COMPOUND | STRUCTURE | MS |
|---|---|---|
| 66 | 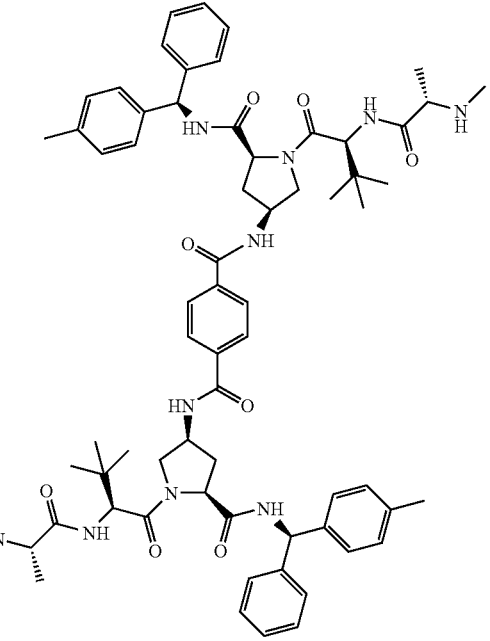 | (M + 2)/2 = 573.6 |
| 67 | 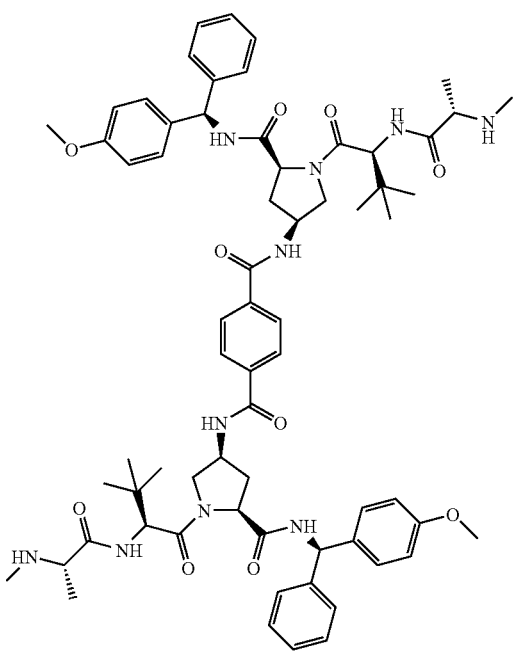 | |
Representative compounds of the present invention which can be prepared by simple modification of the above procedures are illustrated in Tables 2 to 6:

TABLE 2
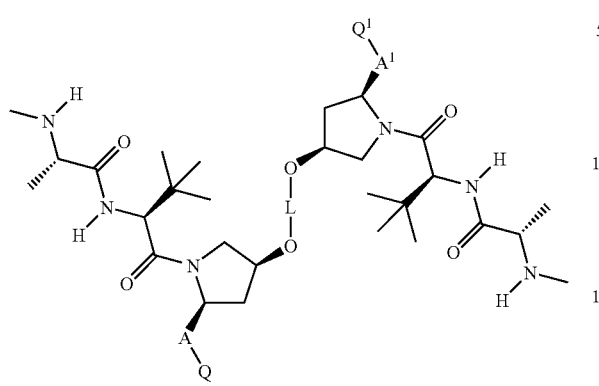
wherein A and A¹ are both CH₂ or both C(O), and
L =
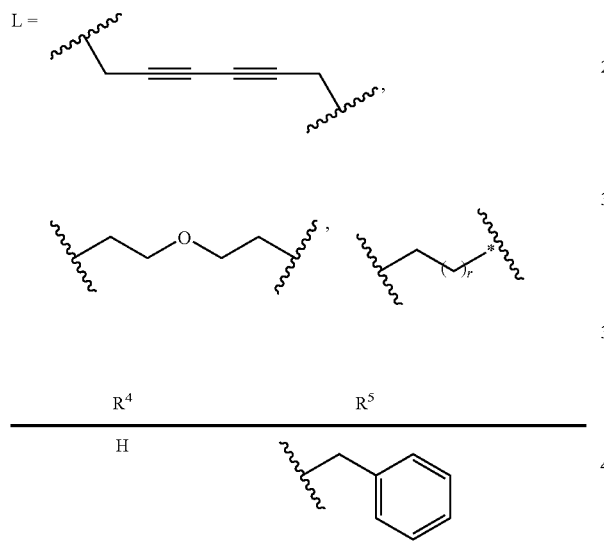
| R⁴ | R⁵ |
|---|---|
| H | 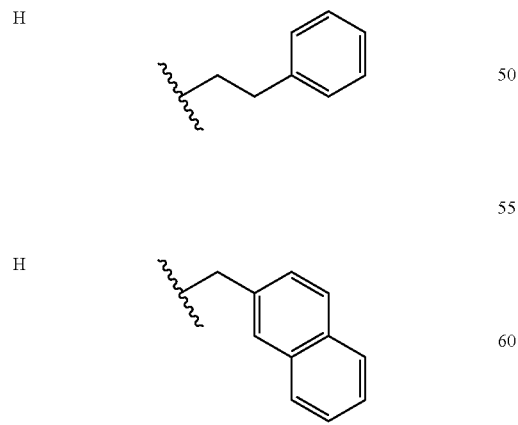 |
| H | |
| H | |
TABLE 2-continued
| | |
|---|---|
| H | —CH₃ |
| H | 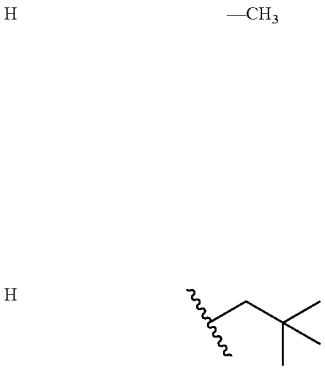 |
| H | |
| H | |
| H | 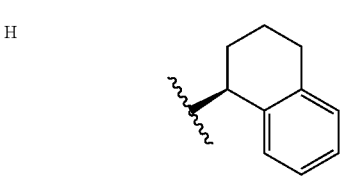 |
| H | 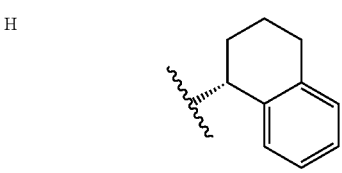 |
| H | 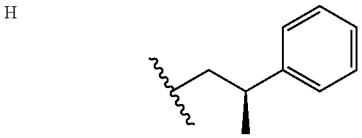 |
| H |  |

TABLE 3
M1-BG-M2
Formula 1A
BG is
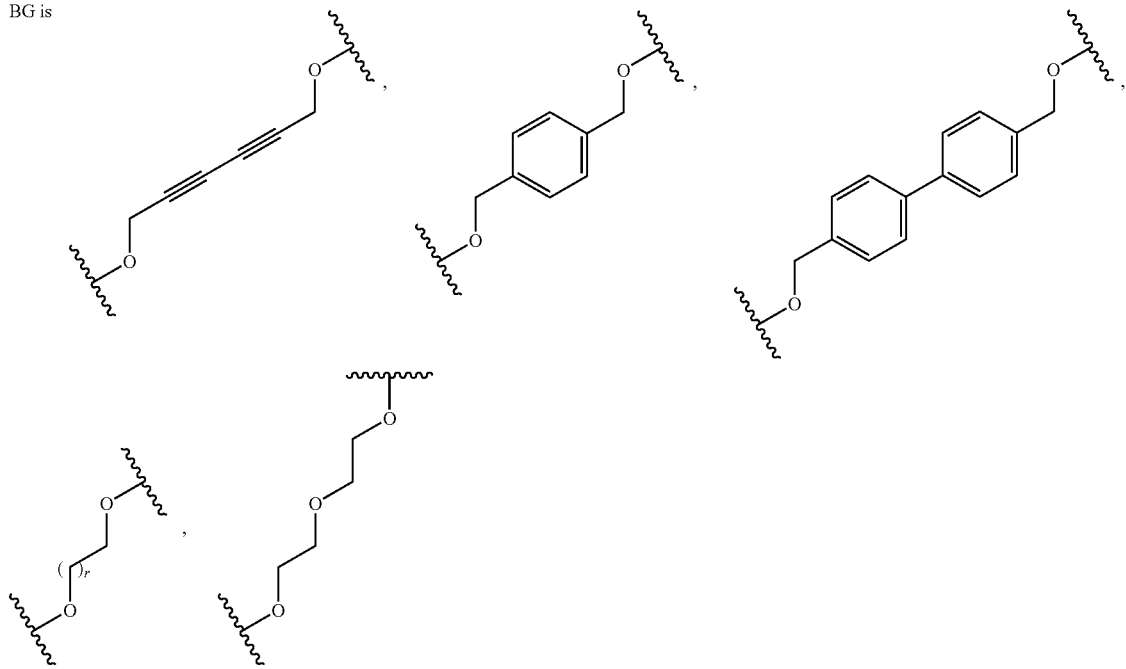
r = 1 to 10
| M1 | M2 |
|---|---|
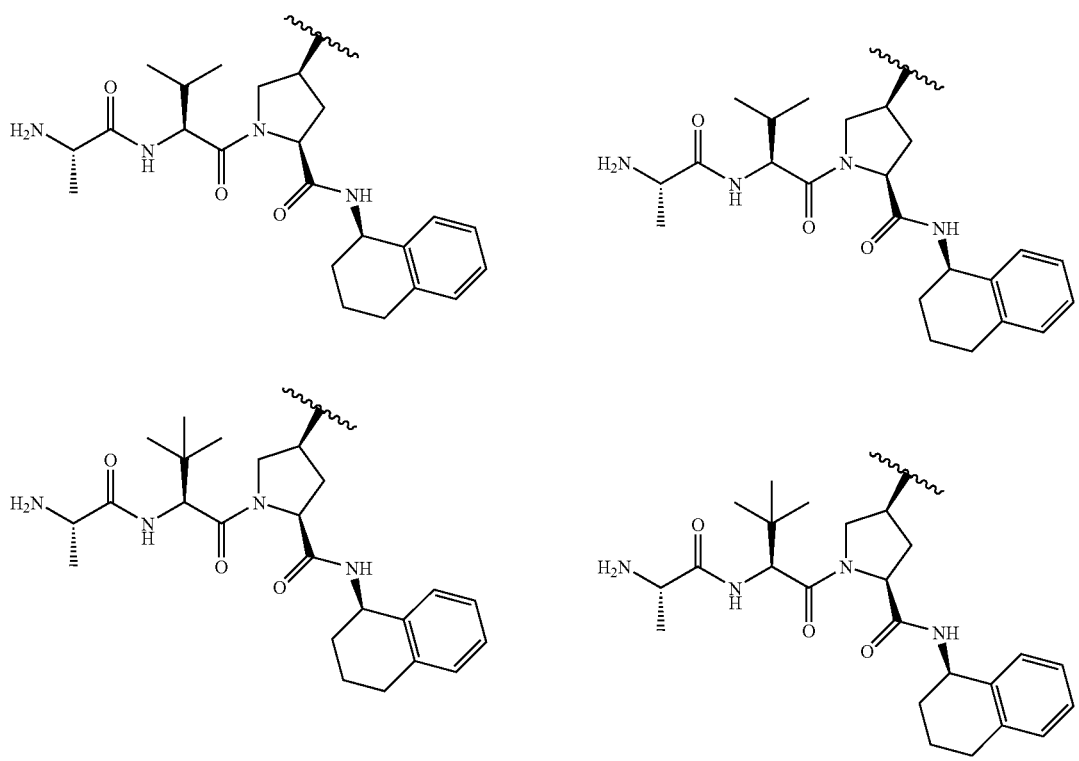

TABLE 3-continued
M1-BG-M2
Formula 1A
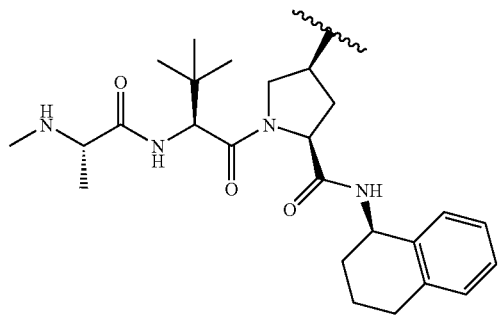
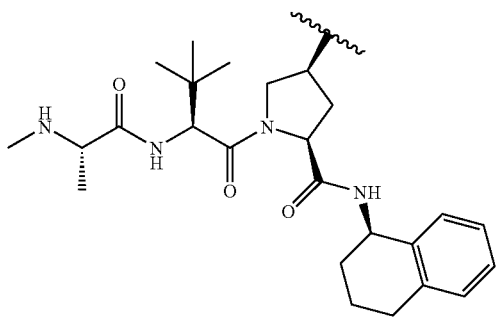
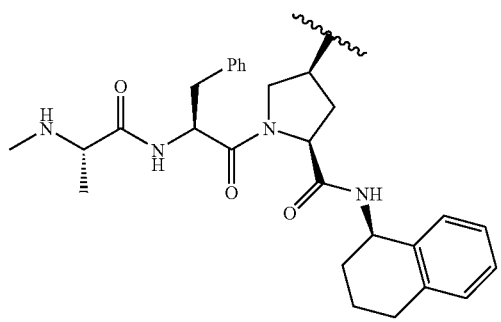
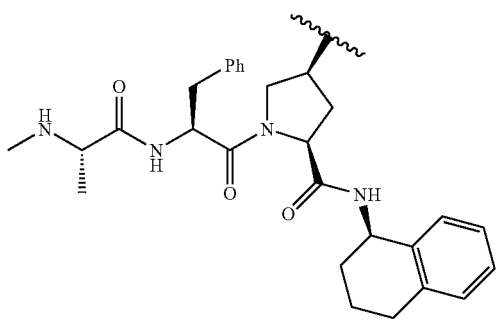
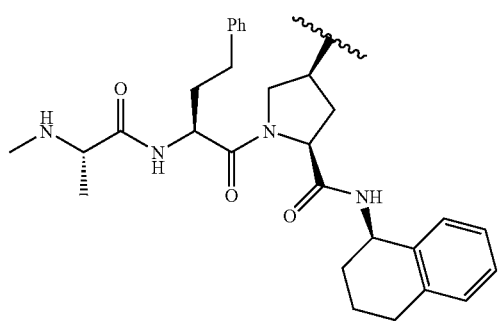
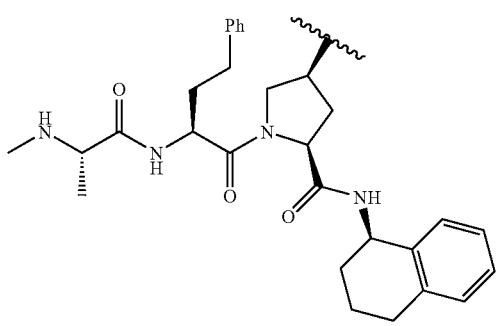
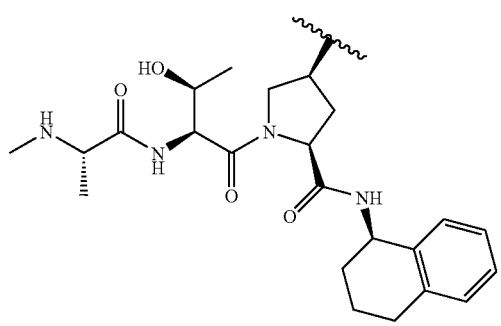
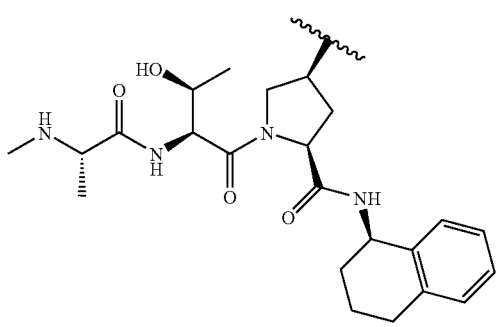

TABLE 3-continued
M1-BG-M2
Formula 1A
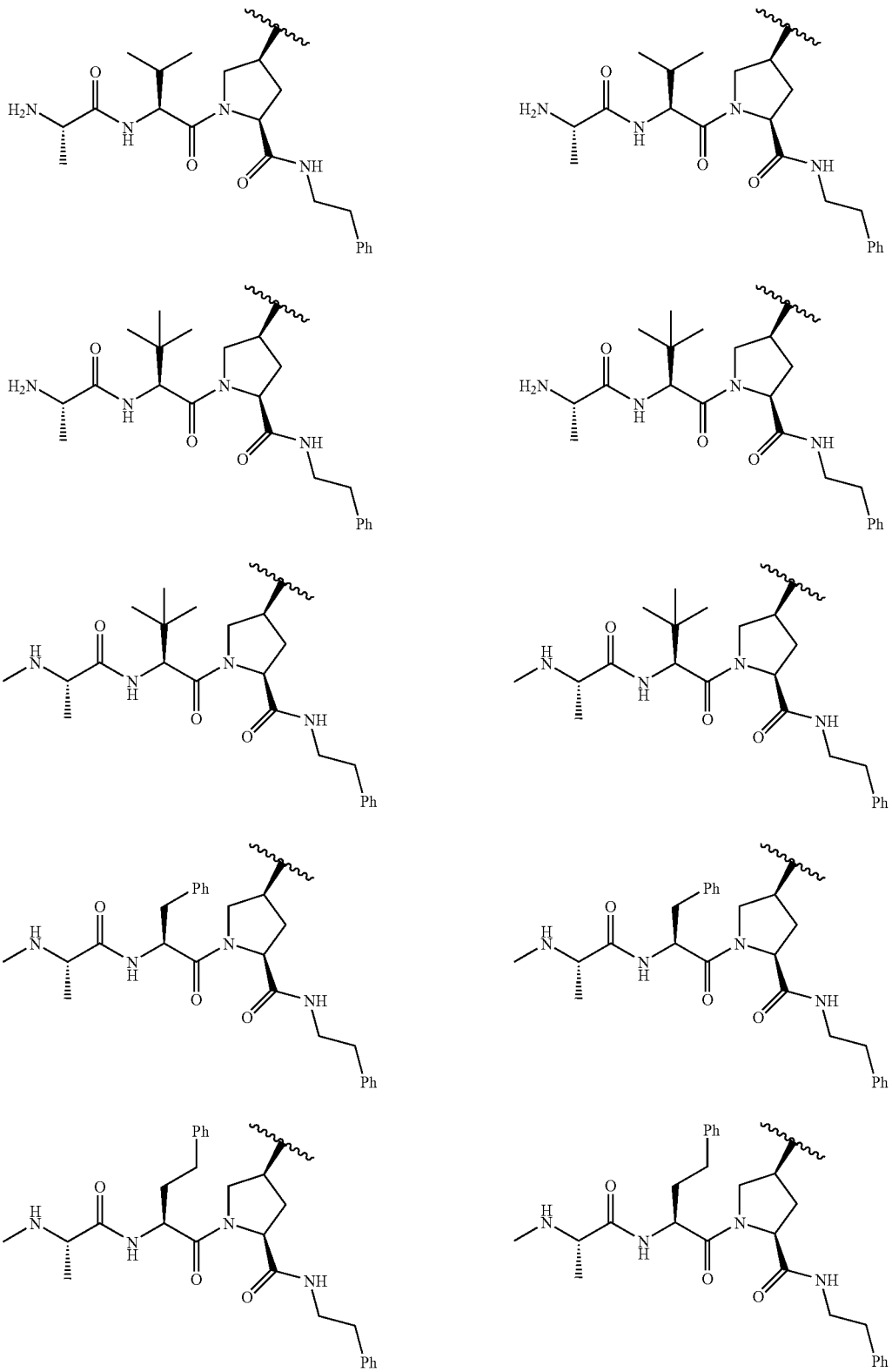

TABLE 3-continued
M1-BG-M2
Formula 1A
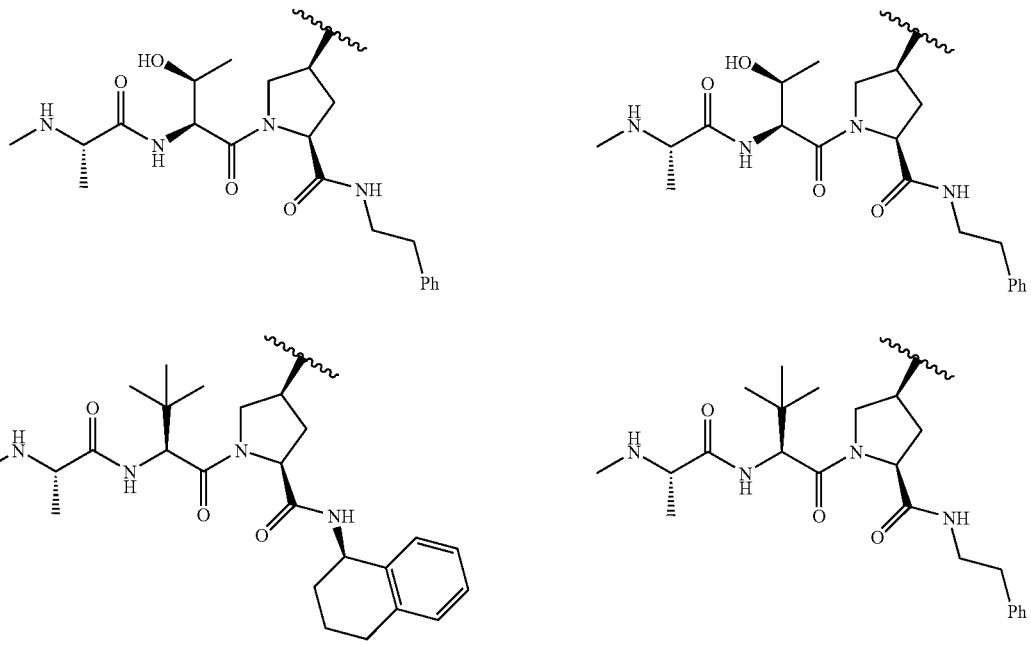
TABLE 4
M1-BG-M2
Formula 1B
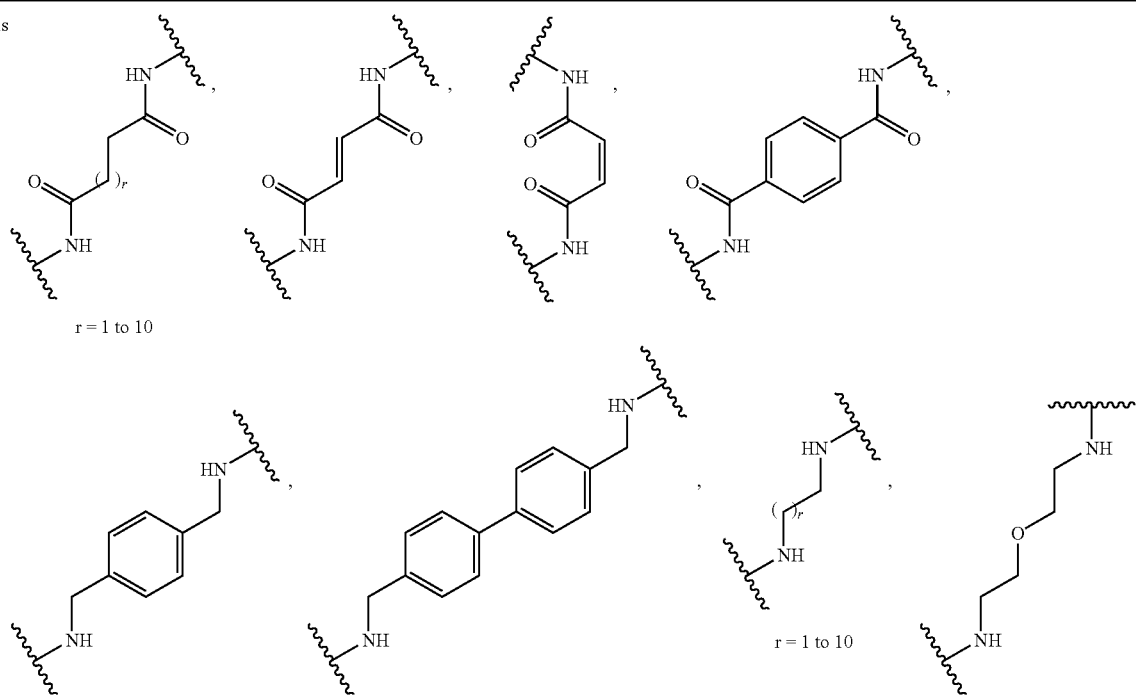

TABLE 4-continued
M1-BG-M2
Formula 1B
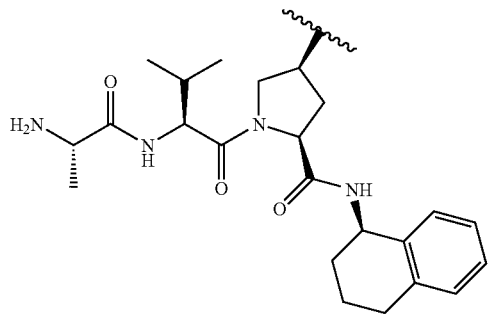
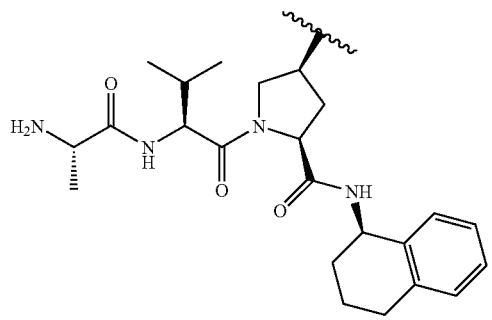
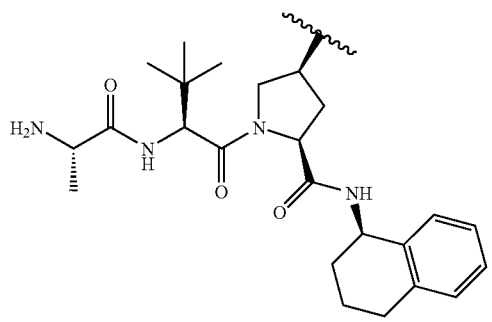
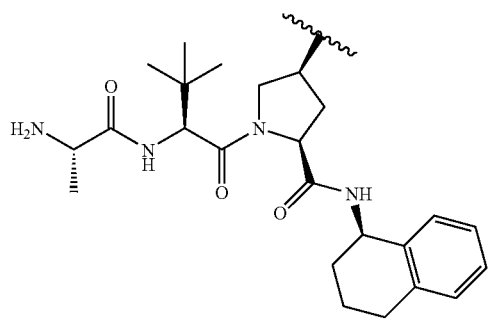
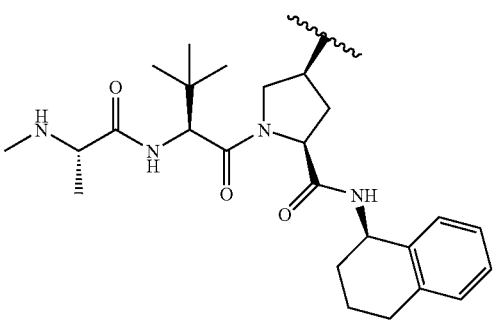
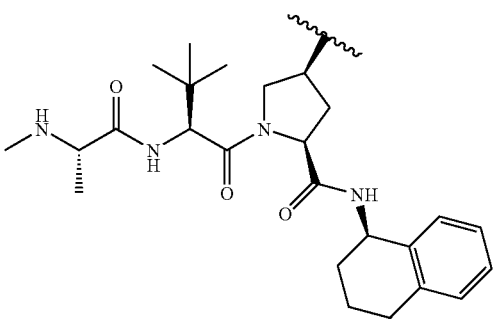
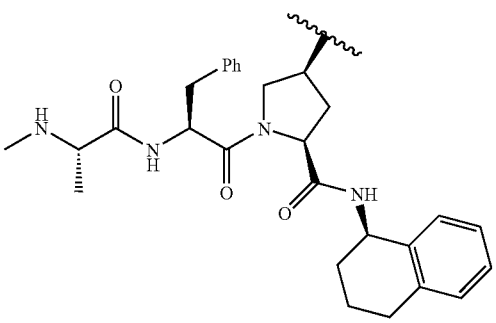
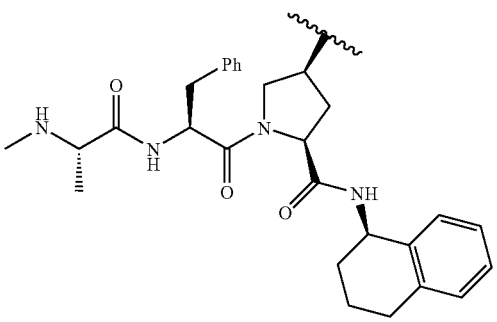

TABLE 4-continued
M1-BG-M2
Formula 1B
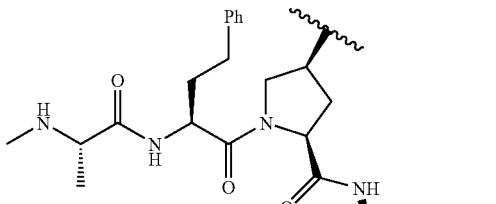
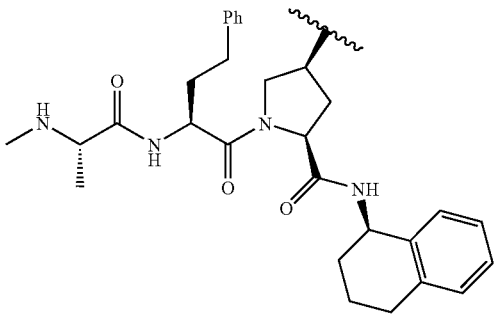
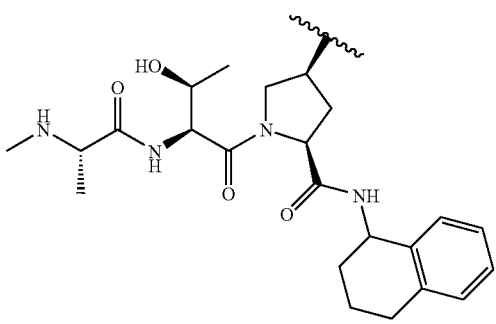
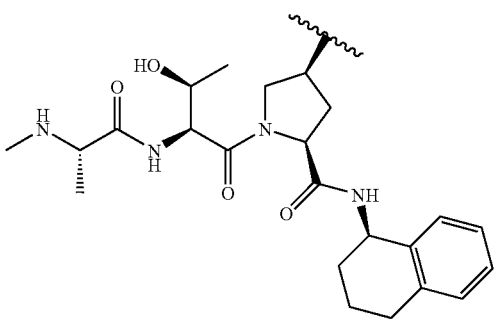
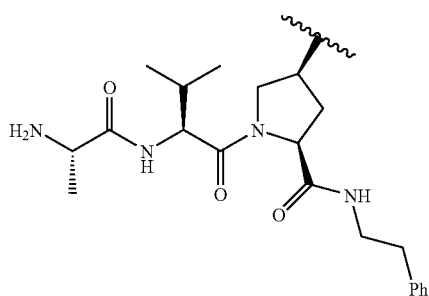
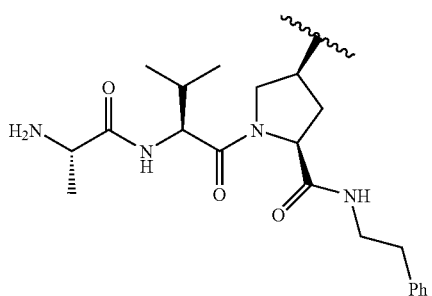
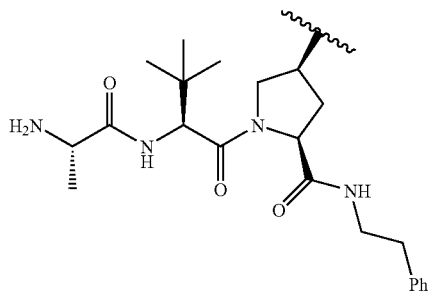
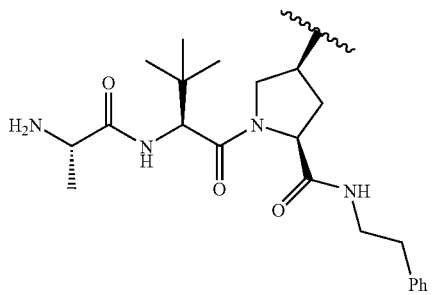
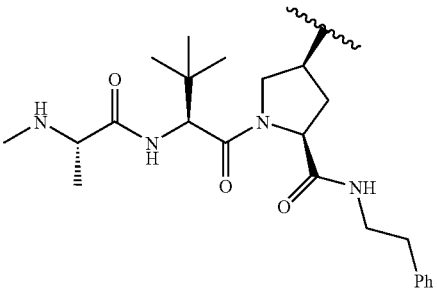
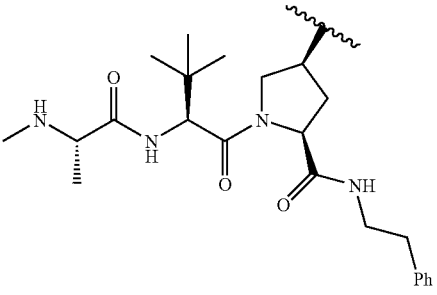

TABLE 4-continued
M1-BG-M2
Formula 1B
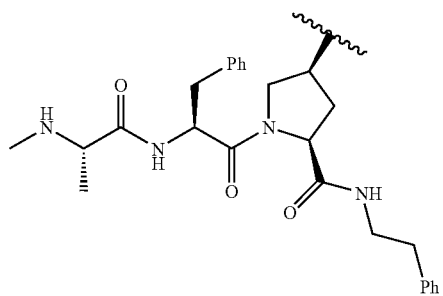 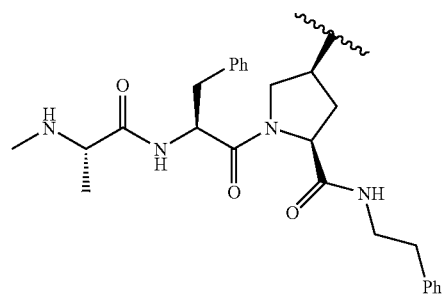
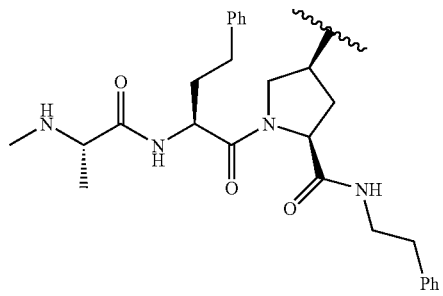 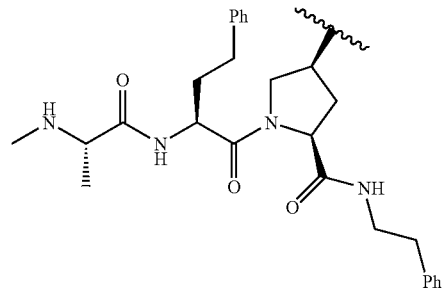
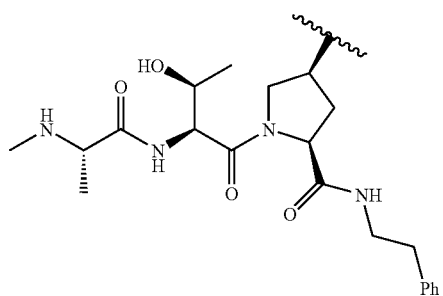 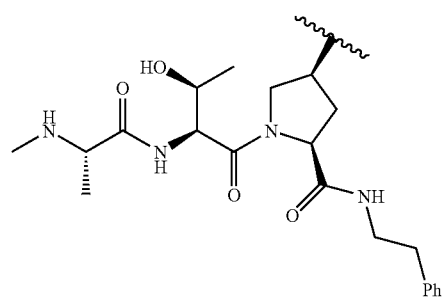
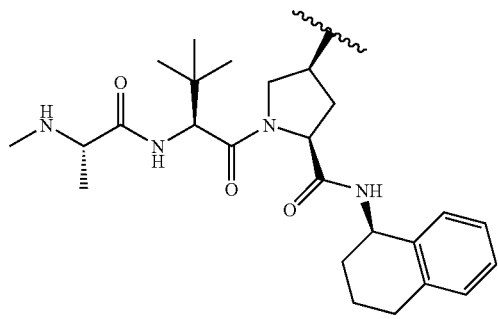 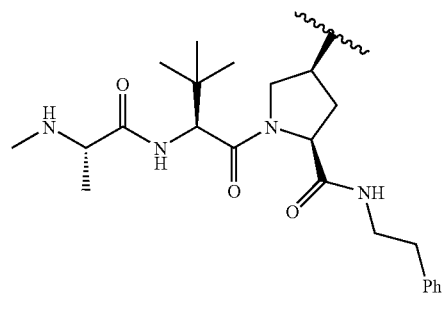

TABLE 5
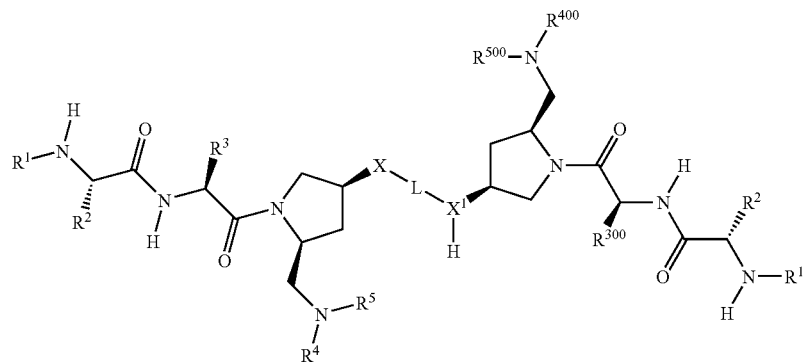
$R^1$, $R^2$, $R^3$, $R^{100}$, $R^{200}$ and $R^{300}$ are defined as hereinabove,
—X—L—X'— is chosen from:
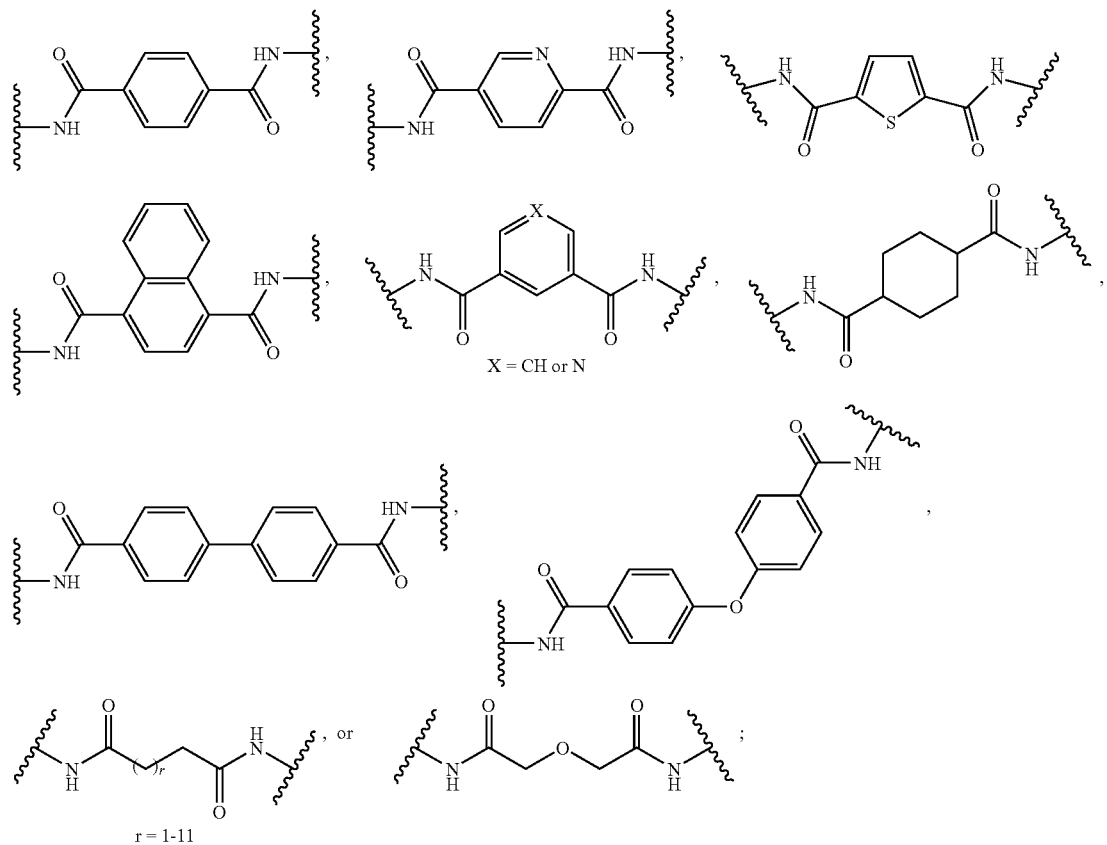
$R^4$ and $R^{400}$ are H;
$R^5$ and $R^{500}$ are chosen from:

TABLE 5-continued
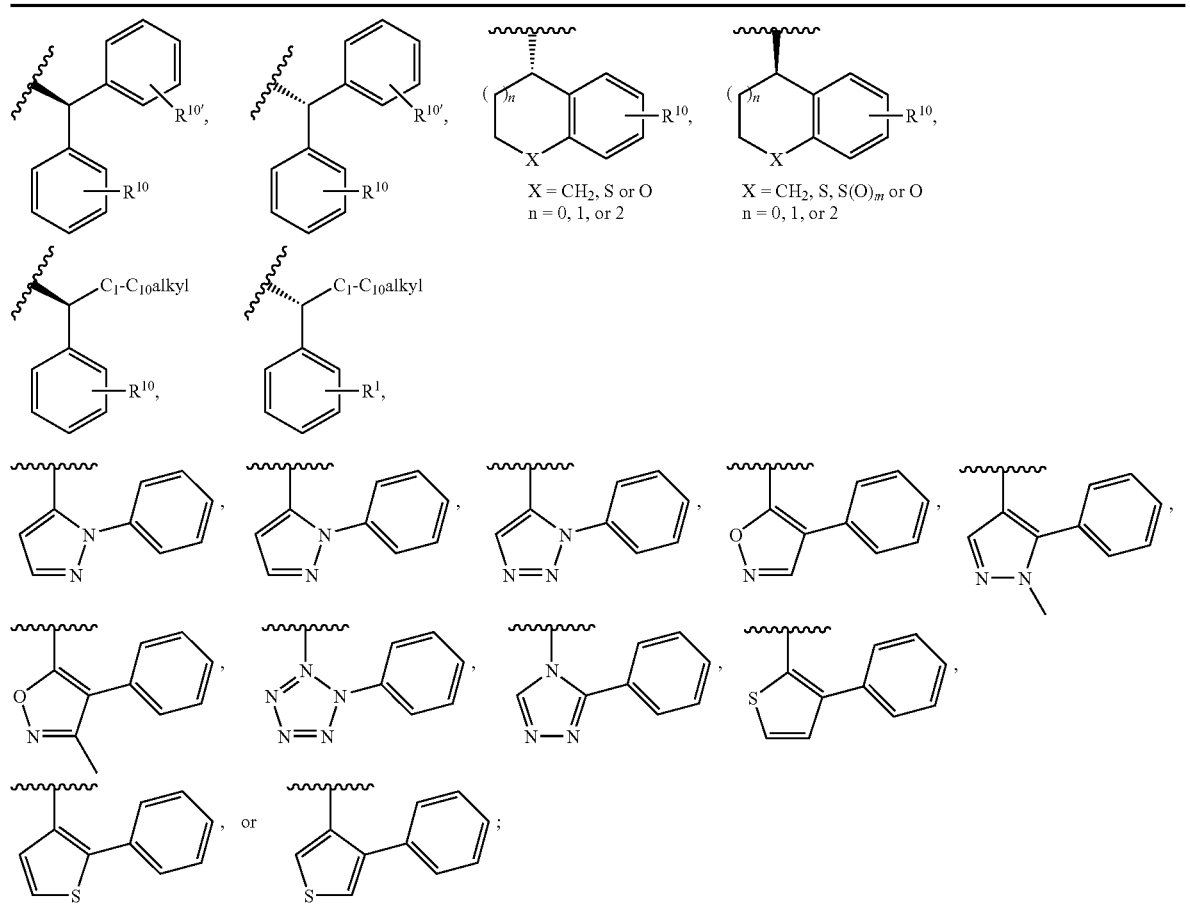
wherein the aryl moieties may be substituted by $R^{10}$ and wherein, $R^{10}$ and $R^{10'}$ are independently defined as $R^{10}$ hereinabove, and wherein the alkyl may be further substituted by $R^6$ as defined hereinabove.
TABLE 6
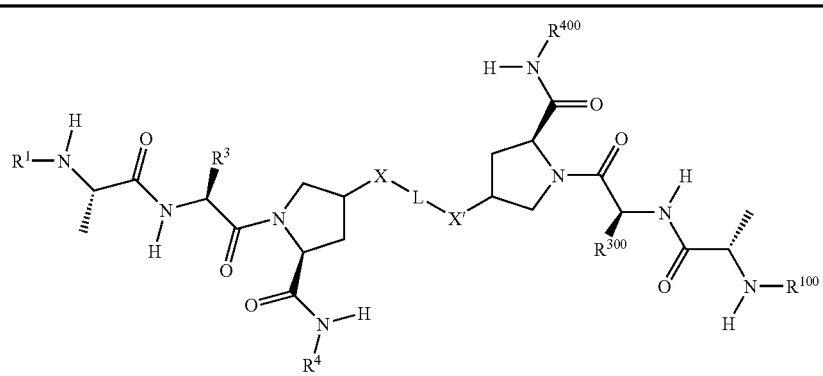
$R^1$, $R^2$, $R^3$, $R^{100}$, $R^{200}$ and $R^{300}$ are defined as hereinabove,
—X—L—X'— is chosen from:

TABLE 6-continued
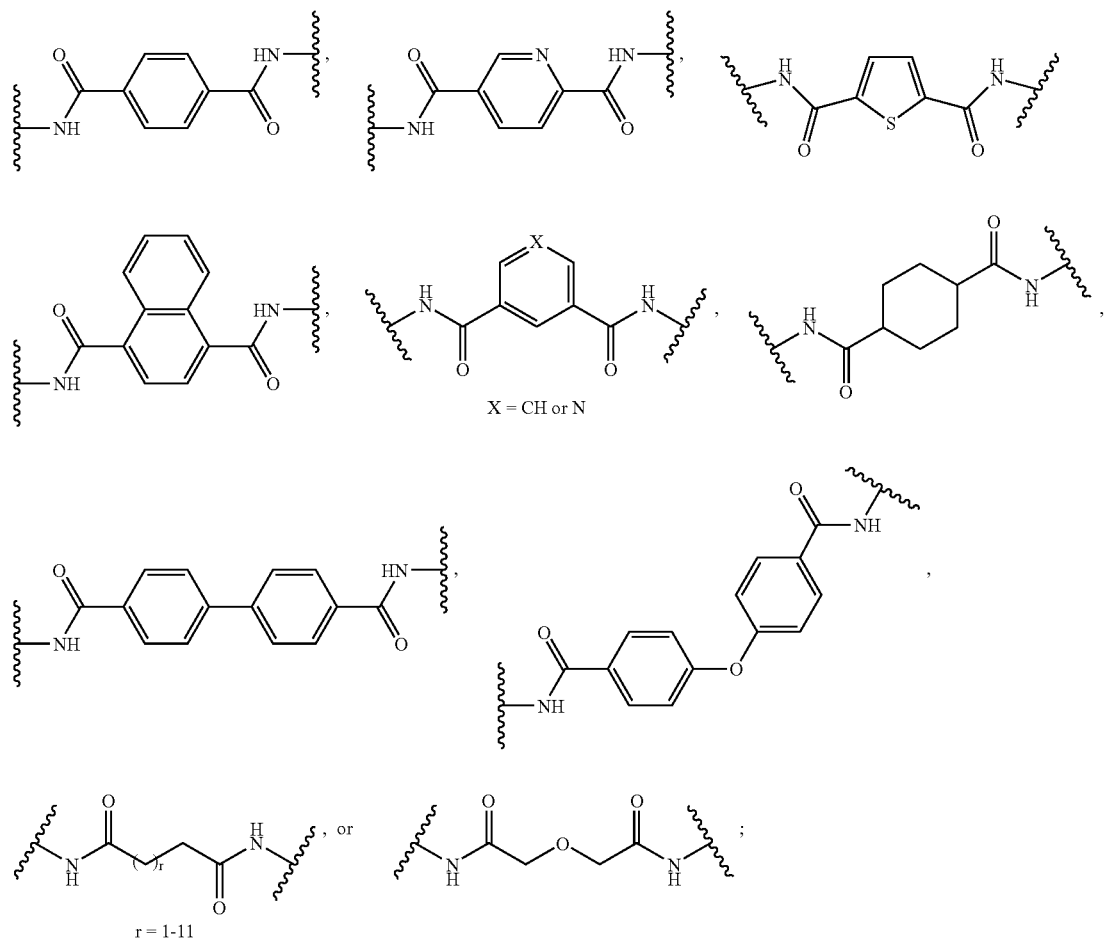
$R^4$ and $R^{400}$ are H;
$R^5$ and $R^{500}$ are chosen from:
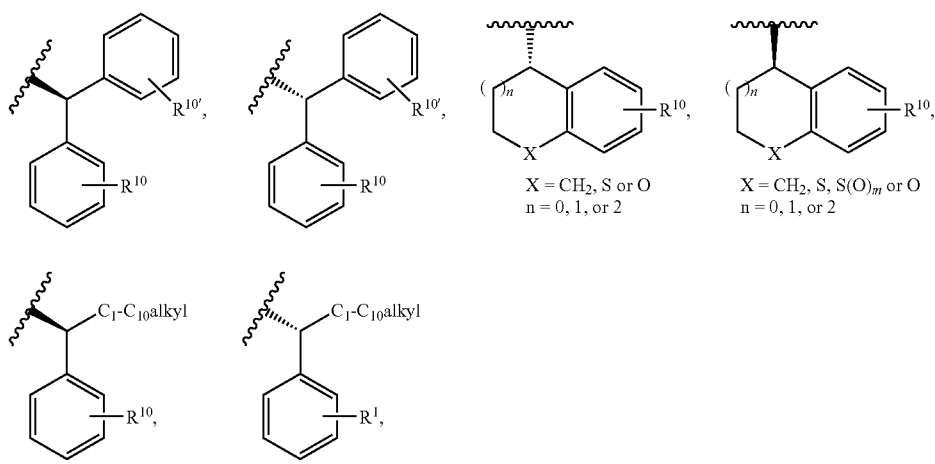

TABLE 6-continued

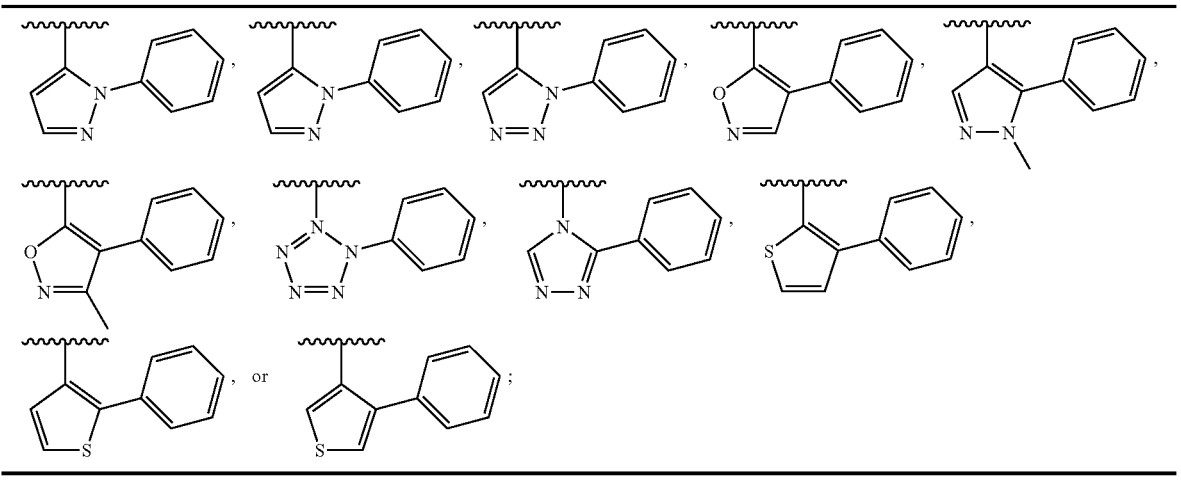

wherein the aryl moieties may be substituted by $R^{10}$ and wherein, $R^{10}$ and $R^{10'}$ are independently defined as $R^{10}$ hereinabove, and wherein the alkyl may be further substituted by $R^6$ as defined hereinabove.

Assays

Molecular Constructs for Expression

GST-XIAP BIR3RING: XIAP coding sequence amino acids 246-497 cloned into PGEX2T1 via BamH1 and AVA I. The plasmid was transformed into E. coli DH5α for use in protein expression and purification.

GST-HIAP2 (cIAP-1) BIR 3: HIAP2 coding sequence from amino acids 251-363 cloned into PGex4T3 via BamH1 and XhoI. The plasmid was transformed into E. coli DH5α for use in protein expression and purification.

GST-HIAP1(cIAP-2) BIR 3: HIAP1 coding sequence from amino acids 236-349, cloned into PGex4T3 via BamH1 and XhoI. The plasmid was transformed into E. coli DH5α for use in protein expression and purification.

GST-linker BIR 2 BIR3Ring: XIAP coding sequence from amino acids 93-497 cloned into PGex4T1 via BamH1 and XhoI. Amino acids 93-497 were amplified from full length XIAP in pGex4t3, using the primers: TTAATAGGATCCAT-CAACGGCTTTTATC and GCTGCATGTGTGTCAGAGG, using standard PCR conditions. The PCR fragment was TA cloned into pCR-2.1 (invitrogen). Linker BIR 2 BIR 3Ring was subcloned into pGex4T1 by BamH1/XhoI digestion. The plasmid was transformed into E. coli DH5α for use in protein expression and purification.

Full-length human XIAP, AEG plasmid number 23. XIAP coding sequence amino acids 1-497 cloned into GST fusion vector, PGEX4T1 via BamH1 and Xho I restriction sites. The plasmid was transformed into E. coli DH5α for use in protein purification.

GST-XIAP linker BIR 2: XIAP linker BIR 2 coding sequence from amino acids 93-497 cloned into pGex4T3 via BamH1 and XhoI. The plasmid was transformed into E. coli DH5α for use in protein expression and purification.

Expression and Purification of Recombinant Proteins

A. Expression of Recombinant Proteins

Glutathione S-transferase (GST) tagged proteins were expressed in *Escherichia coli* strains DH5-alpha. For expression full length XIAP, individual or combinations of XIAP-BIR domains, cIAP-1, cIAP-2 and Livin transformed bacteria were cultured overnight at 37° C. in Luria Broth (LB) medium supplemented with 50 ug/ml of ampicillin. The overnight culture was then diluted 25 fold into fresh LB ampicillin supplemented media and bacteria were grown up to $A_{600}$=0.6 then induced with 1 mM isopropyl-D-1-thiogalactopyranoside for 3 hours. Upon induction, cells were centrifuged at 5000 RPM for 10 minutes and the media was removed. Each pellet obtained from a 1 liter culture received 10 ml of lysis buffer (50 mM Tris-HCl, 200 mM NaCl, 1 mM DTT, 1 mM PMSF, 2 mg/ml of lysosyme, 100 μg/ml)), was incubated at 4° C. with gentle shaking. After 20 minutes of incubation, the cell suspension was placed at −80° C. overnight or until needed.

B. Purification of Recombinant Proteins

For purification of recombinant proteins, the IPTG-induced cell lysate was thawed vortexed and then disrupted by flash freezing in liquid nitrogen two times with vortexing after each thaw. The cells were disrupted further by passing the extract four times through a Bio-Neb Cell disruptor device (Glas-col) set at 100 psi with Nitrogen gas. The extract was clarified by centrifugation at 4° C. at 15000 RPM in a SS-34 Beckman rotor for 30 minutes. The resulting supernatant was then mixed with 2 ml of glutathione-Sepharose beads (Pharmacia) per 500 ml cell culture (per 1000 ml culture for full length XIAP) for 1 hour at 4C. Afterwards, the beads were washed 3 times with 1× Tris-Buffered Saline (TBS) to remove unbound proteins. The retained proteins were eluted with 2 washes of 2 ml of 50 mM TRIS pH 8.0 containing 10 mM reduced glutathione. The eluted proteins were pooled and precipitated with 604 g/liter of ammonium sulfate and the resulting pellet re-suspended into an appropriate buffer. As judged by SDS-PAGE the purified proteins were >90% pure. The protein concentration of purified proteins was determined from the Bradford method.

His-tag proteins were expressed in the E. Coli strain in E. coli AD494 cells using a pet28ACPP32 construct. The soluble protein fraction was prepared as described above. For protein purification, the supernatant was purified by affinity chromatography using chelating-Sepharose (Pharmacia) charged with $NiSO_4$ according to the manufacturer's instructions. Purity of the eluted protein was >90% pure as determined by SDS-PAGE. The protein concentration of purified proteins was determined from the Bradford assay.

Synthesis of Fluorescent Probe P1

A fluorescent peptide probe, Fmoc-Ala-Val-Pro-Phe-Tyr(t-Bu)-Leu-Pro-Gly(t-Bu)-Gly-OH was prepared using standard Fmoc chemistry on 2-chlorotrityl chloride resin (Int. J. Pept. Prot. Res. 38:555-561, 1991). Cleavage from the resin was performed using 20% acetic acid in dichloromehane (DCM), which left the side chain still blocked. The C-terminal protected carboxylic acid was coupled to 4'-(aminomethyl)fluorescein (Molecular Probes, A-1351; Eugene, Oreg.) using excess diisopropylcarbodiimide (DIC) in dimethylformamide (DMF) at room temperature and was purified by silica gel chromatography (10% methanol in DCM). The N-terminal Fmoc protecting group was removed using piperidine (20%) in DMF, and purified by silica gel chromatography (20% methanol in DCM, 0.5% HOAc). Finally, the t-butyl side chain protective groups were removed using 95% trifluoroacetic acid containing 2.5% water and 2.5% triisopropyl silane, to provide probe P1 (>95% pure, HPLC).

Probe P2

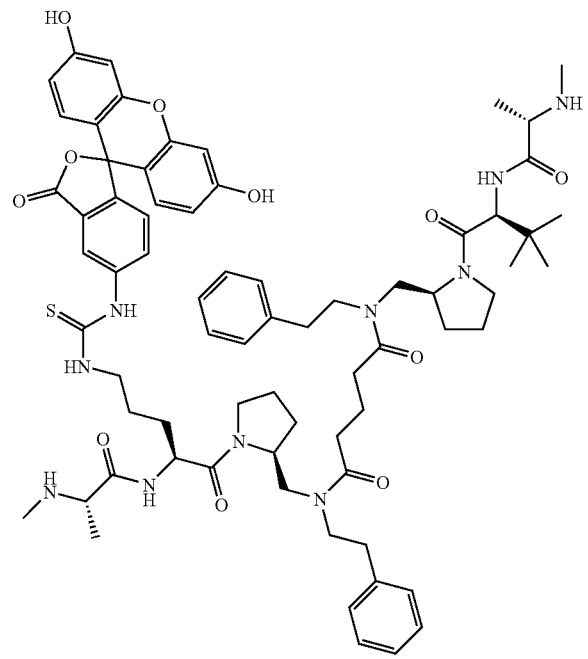

Binding Assay

Fluorescence Polarization-Based Competition Assay

For all assays, the fluorescence and fluorescence-polarization was evaluated using a Tecan Polarion instrument with the excitation filter set at 485 nm and the emission filter set at 535 nm. For each assay, the concentration of the target protein was first established by titration of the selected protein in order to produce a linear dose-response signal when incubated alone in the presence of the fluorescent probe P1 or P2. Upon establishing these conditions, the compounds potency ($IC_{50}$) and selectivity, was assessed in the presence of a fix defined-amount of target protein and fluorescent probe and a 10 point serial dilution of the selected compounds. For each $IC_{50}$ curve, the assays were run as followed: 25 uL/well of diluted compound in 50 mM MES buffer pH 6.5 were added into a black 96 well plate then 25 ul/well of bovine serum albumin (BSA) at 0.5 mg/ml in 50 mM MES pH 6.5. Auto-fluorescence for each compound was first assessed by performing a reading of the compound/BSA solution alone. Then 25 uL of the fluorescein probe diluted into 50 mM MES containing 0.05 mg/ml BSA were added and a reading to detect quenching of fluorescein signal done. Finally 25 uL/well of the target or control protein (GST-BIRs) diluted at the appropriate concentration in 50 mM MES containing 0.05 mg/ml BSA were added and the fluorescence polarization evaluated.

Determination of $IC_{50}$ and Inhibitory Constants

For each assay the relative polarization-fluorescence units were plotted against the final concentrations of compound and the $IC_{50}$ calculated using the Grad pad prism software and/or Cambridge soft. The ki value were derived from the calculated $IC_{50}$ value as described above and according to the equation described in Nikolovska-Coleska, Z. (2004) Anal Biochem 332, 261-273.

Fluorescence Polarization Competition Assay

The $k_i$ of various compounds in the BIR2-BIR3-ring FP assay, using probe P2, was determined as described above. For example, compound 3 displayed a $k_i$ of less than 100 nM.

Caspase-3 Full Length XIAP, Linker BIR2 or Linker-BIR2-BIR3-RING Derepression Assay In order to determine the relative activity of the selected compound against XIAP-Bir2, we setup an in vitro assay where caspase-3 was inhibited by GST fusion proteins of XIAP linker-Bir2, XIAP Linker Bir2-Bir3-RING or full-length XIAP. Caspase 3 (0.125 ul) and 12.25-34.25 nM (final concentration) of GST-XIAP fusion protein (GST-Bir2, GST-Bir2Bir3RING or full-length XIAP) were co-incubated with serial dilutions of compound (200 uM-5 pM). Caspase 3 activity was measured by overlaying 25 uL of a 0.4 mM DEVD-AMC solution. Final reaction volume was 100 uL. All dilutions were performed in caspase buffer (50 mM Hepes pH 7.4, 100 mM NaCl, 10% sucrose, 1 mM EDTA, 10 mM DTT, 0.1% CHAPS (Stennicke, H. R., and Salvesen, G. S. (1997). Biochemical characteristics of caspase-3, -6, -7, and -8. J. Biol. Chem. 272, 25719-25723).

The fluorescent AMC released from the caspase-3 hydrolysis of the substrate was measured in a TECAN spectrophotometer at 360 nm excitation and 444 nm emission, after 15 minutes of incubation at room temperature. $IC_{50}$ values were calculated on a one or two-site competition model using GraphPad v4.0, using the fluorescence values after 15 minutes of incubation plotted against the log 10 concentration of compound.

$IC_{50}$ values of preferred compounds were shown to correlate with $EC_{50}$ values against SKOV3s and were typically less that 1 uM.

Cell-Free Assay

Caspase De-Repression Assay using Cellular Extracts (apoptosome)

100 ug of 293 cell S100 extract and 0.25 uM-2 uM of GST-XIAP fusion protein (XIAP-Bir3RING, XIAP-Bir2Bir3RING, or full-length XIAP) were co-incubated with serial dilutions of compound (40 uM-5 µM). Caspases present in the extracts were activated by adding 1 mM dATP, 0.1 mM ALLN, 133 ug Cytochrome C (final concentrations), and incubating at 37° C. for 25 minutes. All reactions and dilutions used S100 buffer (50 mM Pipes pH 7.0, 50 mM KCl, 0.5 mM EGTA pH 8.0, 2 mM $MgCl_2$ supplemented with 1/1000 dilutions of 2 mg/ml Cytochalisin B, 2 mg/ml Chymotstatin, Leupeptin, Pepstatin, Antipain, 0.1M PMSF, 1M DTT). Final reaction volume was 30 ul. Caspase-3 activity was measured by overlaying 30 ul of a 0.4 mM DEVD-AMC solution. Released AMC cleavage was measured in a TECAN spectrophotometer at 360 nm excitation and 444 nm emission, on a kinetic cycle of 1 hour with readings taken every 5 minutes.

Caspase activity was calculated as $V_o$ of AMC fluorescence/sec. Caspase de-repression by our compounds was compared to fully activated extract and activated extract repressed by the presence of XIAP fusion protein.

$IC_{50}$ values of preferred compounds were shown to correlate with $EC_{50}$ values against SKOV3s and were typically less that 1 uM.

Cell Culture and Cell Death Assays

A. Cell Culture

MDA-MD-231 (breast) and H460 (lung) cancer cells were cultured in RPMI1640 media supplemented with 10% FBS and 100 units/mL of Penicillin and Steptomycin.

B. Assays

Survival assays were performed on various cell lines including MDA-MB-231, SKOV3, H460, PC3, HCT-116, and SW480 cells. Cells were seeded in 96 well plates at a respective density of 5000 and 2000 cells per well and incubated at 37° C. in presence of 5% $CO_2$ for 24 hours. Selected compounds were diluted into the media at various concentration ranging from 0.01 uM up to 100 uM. Diluted compounds were added onto the MDA-MB-231 cells. For the MDA-MB-231 SKOV3, H460, PC3, HCT-116, and SW480 cells, the compounds were added either alone or in presence of 1-3 ng/ml of TRAIL. After 72 hours cellular viability was evaluated by MTS based assays. A solution of [3-(4,5-dimethylthiazol-2-yl)-5-(3-carboxymethoxyphenyl)-2-(4-sulfophenyl)-2H-tetrazolium, inner salt; MTS] was added onto cells for a period of 1 to 4 hours. Upon incubation the amount of converted MTS was evaluated using a Tecan spectrophotometer set at 570 nm.

MDA-MB-231, SKOV3, and PC3 cells were treated with selected compounds of the present invention and found to have $EC_{50}$s of 100 nM or less. When the above cell lines were treated with the compounds of the present invention in the presence of TRAIL, they were shown to have $EC_{50}$s of 50 nM or less.

Survival MTT Assay

One day prior the treatment with compound, 2000 to 4000 cells per well were plated in a tissue culture treated 96 well format dish with 100 ul of media and incubated at 37° C., 5% $CO_2$. On the day of compound treatment, compounds were diluted with cell culture media to a working stock concentration of 2×. 100 uL of diluted compound were then added to each well. The treated plate was incubated for 72 h at 37° C., 5% $CO_2$. Upon incubation, the cell viability was assessed as followed 20 uL of MTT reagent at 5 mg/ml were added per well to cell plate. The plate was incubated for 2 h at 37° C. in presence of 5% $CO_2$. The supernatant was then removed from the plate and 100 uL of isopropanol were added. The absorbance was measured in a TECAN spectrophotometer at 570 nm. The percentage of viability was expressed in percentage of the signal obtained with non treated cells.

As seen in Table 7, compounds represented in Table 1 hereinabove generally displayed $EC_{50}$ values against MDA-MB-231 and SKOV-3 cells of <1 μM. Select compounds had $EC_{50}$ of <50 nM.

TABLE 7

| Compound | MDA-MB231 $EC_{50}$ (nM) | SKOV-3 $EC_{50}$ (nM) |
| --- | --- | --- |
| 1 | A | A |
| 2 | A | A |
| 3 | A | A |
| 5 | C | |

TABLE 7-continued

| Compound | MDA-MB231 $EC_{50}$ (nM) | SKOV-3 $EC_{50}$ (nM) |
| --- | --- | --- |
| 10 | A | A |
| 11 | | A |
| 12 | | A |
| 13 | | A |
| 14 | | A |
| 15 | | A |
| 16 | | A |
| 17 | | A |
| 18 | | D |
| 19 | | A |
| 20 | | A |
| 21 | | A |
| 22 | | B |
| 23 | | A |
| 24 | | A |
| 25 | | A |
| 26 | | B |
| 27 | | B |
| 28 | | A |
| 29 | | B |
| 30 | | C |
| 31 | | B |
| 32 | | B |
| 33 | | A |
| 34 | | B |
| 35 | | B |
| 36 | | C |
| 37 | | C |
| 38 | | B |
| 39 | | A |
| 40 | | A |
| 41 | | A |
| 42 | | A |
| 43 | | B |
| 44 | | A |
| 45 | | D |
| 46 | | B |
| 47 | | A |
| 48 | | B |
| 49 | | A |
| 50 | | B |
| 51 | | B |
| 52 | | A |
| 53 | | D |
| 54 | | D |
| 55 | | A |
| 56 | | A |
| 57 | | A |
| 58 | | B |
| 59 | | B |
| 60 | | A |
| 61 | | A |
| 64 | | A |

A - $EC_{50}$ less than 50 nM
B - $EC_{50}$ less than 250 nM
C - $EC_{50}$ more than 1000 nM
D - $EC_{50}$ more than 1000 nM Apoptosis Assay: Measurement of Caspase-3 Activity from Cultured Cells One day, prior to the treatment, 10,000 cells per well were plated in a white tissue culture treated 96 well plate with 100 uL of media. On the day of compound treatment, compounds were diluted with cell culture media to a working stock concentration of 2× and 100 ul of diluted compound were added to each well and the plate was incubated for 5 h at 37° C. in presence of 5% $CO_2$. Upon incubation, the plate was washed twice with 200 uL of cold TRIS Buffered Saline (TBS) buffer. Cells were lysed with 50 ul of Caspase assay buffer (20 mM Tris-HCl pH 7.4, 0.1% NP-40, 0.1% Chaps, 1 mM DTT, 0.1 mM EDTA, 0.1 mM PMSF, 2 mg/ml Chymostatin, Leupeptin, Pepstatin, Antipapin) then incubated at 4° C. with shaking for 30 minutes. 45 ul of Caspase assay buffer and 5 uL of Ac-DEVD-AMC at 1 mg/ml were added to each well, the plate shaken and incubated for 16 h at 37° C. The amount of release AMC was measured in a TECAN spectrophotometer at with the excitation and emission filter set at 360 nm and 444 nm. The percentage of Caspase-3 activity was expressed in comparison of the signal obtained with the non-treated cells.

$IC_{50}$ values of preferred compounds were shown to correlate with $EC_{50}$ values against SKOV3s and were typically less that 1 uM.

Cellular Biochemistry:

A. Detection of XIAP and PARP/Caspase-3/Caspase-9

Detection of cell expressed XIAP and PARP were done by western blotting. Cells were plated at 300 000 cells/well in a 60 mm wells (6 wells plate dish). The next day the cells were treated with selected compound at the indicated concentration. 24 hours later cells the trypsinized cells, pelleted by centrifugation at 1800 rpm at 4° C. The resulting pellet was rinsed twice with cold TBS. The final washed pellet of cells was the lysed with 250 uL Lysis buffer (NP-40, glycerol, 1% of a protease inhibitor cocktail (Sigma)), placed at 4° C. for 25 min with gentle shaking. The cells extract was centrifuged at 4° C. for 10 min at 10,000 rpm. Both the supernatant and the pellet were kept for western blotting analysis as described below. From the supernatant, the protein content was evaluated and about 50 ug of protein was fractionated onto a 10% SDS-PAGE. Pellets were washed with the lysis buffer and re-suspend into 50 ul of Lamelli buffer 1×, boiled and fractionated on SDS-PAGE. Upon electrophoresis each gel was electro-transferred onto a nitrocellulose membrane at 0.6A for 2 hours. Membrane non-specific sites were blocked for 1 hours with 5% Skim milk in TBST (TBS containing 0.1% (v/v) Tween-20) at RT. For protein immuno-detection, membranes were incubated overnight with primary antibodies raised against XIAP clone 48 obtained from Becton-Dickinson) or PARP: obtained from Cell signal or caspase-3 or caspase-9 primary antibodies were incubated at 4° C. with shaking at dilutions as follows:

| | |
|---|---|
| XIAP clone 80 (Becton-Dickinson) | 1/2500 |
| PARP (Cell Signal) | 1/2500 |
| Caspase 3 (Sigma) | 1/1500 |
| Caspase 9 (Upstate) | 1/1000 |

Upon overnight incubation, the membranes received three washes of 15 min in TBST then were incubated for 1 hour at room temperature in the presence of a secondary antibody coupled with HRP-enzyme (Chemicon) and diluted at 1/5 000. Upon incubation each membrane were washed three times with TBST and the immunoreactive bands were detected by addition of a luminescent substrate (ECL kit Amersham) and capture of signal on a X-RAY film for various time of exposure.

Certain exemplified compounds were shown to induce the cleavage of PARP near concentrations which correlate with $EC_{50}$ values against SKOV3s and were typically less that 1 uM.

Hollow Fiber Model

Hollow fiber in vivo model were used to demonstrate in vivo efficacy of selected compounds against selected cell lines as single agent therapy or in combination with selected cytotoxic agents. At day 1, selected cell lines were cultured and the fiber filled at a cell density of about 40,000 cells/fiber. At the day of operation (day 4), three fibers are implanted sub-cutaneous into 28-35 Nu/Nu CD-1 male mice. On day 5, mice start to receive daily injection via sub-cutaneous route of control vehicle or vehicle containing the selected compound at the appropriate concentration and/or injection of cytotoxic agent via intra-peritoneal route. Upon 3-7 days of consecutive drug treatments, the animals are sacrificed, each fiber is removed and the metabolic viability of the remaining cells determined by MTT assay. Efficacy of the compound is define as the difference between the vehicle-treated animal and the animal treated with the compound alone or the compound given in combination of the cytotoxic agent.

MDA-MB-231 cells were implanted on day 1. Compound 3 was administered for 4 consecutive days via IV bolus (tail vein) injections at 1, 3, and 10 mg/kg (2 mg/mL in 20% aqueous HPCD). Complete suppression of cell growth, as compared to 20% HPCD control, was observed for compound 3 at drug concentrations of 3 mg/kg.

SKOV-3 Human Ovarian Cancer Cell Line Xenograpt Study with Compound 3

Female CD-1 nude mice (approximately 20-25 g) were subcutaneously injected $5 \times 10^6$ SKOV-3 human ovarian tumor cells in 50% matrigel subcutaneously in the right flank. On day 55, when tumors were approximately 100 mm³, treatment was initiated with compound 3 on a 5 on/2 off treatment schedule for the duration of the experiment. Tumor size was measured with digital calipers and calculated as $V=(a \times b^2)/2$, wherein, a is the longest dimension and b is the width.

Tumor regression was observed while dosing compound 3 at 1 mg/kg while tumor stasis was observed while dosing compound 3 at 0.3 mg/kg (see FIG. 1).

MDA-MB-231 Human Mammary Cancer Cell Line Xenograph Study with Compound 3

Female CD-1 nude mice (approximately 20-25 g) were subcutaneously injected $1 \times 10^6$ MDA-MB-231 human mammary tumor cells in the right flank. On day 71, when tumors were approximately 90 mm³, treatment was initiated with compound 3 on a 5 on/2 off treatment schedule for the duration of the experiment. Tumor size was measured with digital calipers and calculated as $V=(a \times b^2)/2$, wherein, a is the longest dimension and b is the width.

Figure 2:
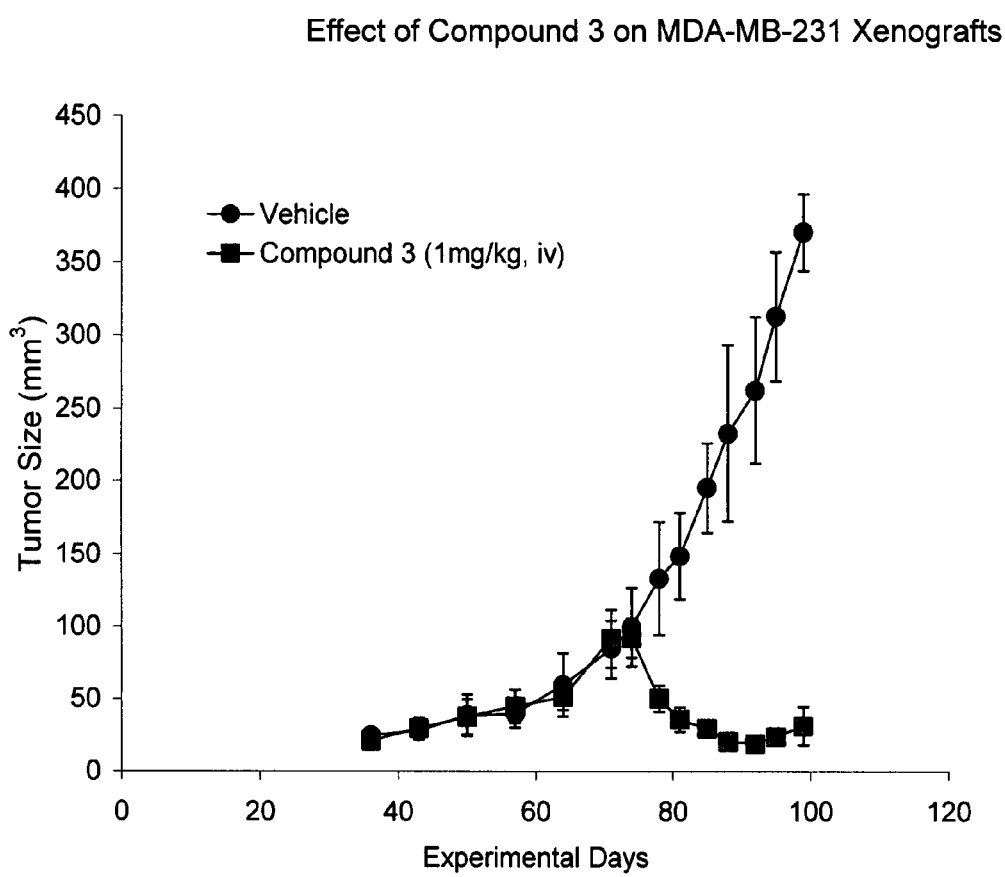
FIG. 2 depicts MDA-MB-231 Human Mammary Cancer Cell Line Xenograph Study with compound 3. Female CD-1 nude mice (approximately 20-25 g) were subcutaneously injected $1\times10^6$ MDA-MB-231 human mammary tumor cells in the right flank. On day 71, when tumors were approximately 90 mm$^3$, treatment was initiated with compound 3 treating with compound for 5 consecutive days followed by 2 days with no drug treatment for the duration of the experiment. Tumor size was measured with digital calipers and calculated as $V=(a\times b^2)/2$, wherein, a is the longest dimension and b is the width. Tumor regression was observed at 1 mg/kg.

Tumor regression was observed while dosing compound 3 at 1 mg/kg (see FIG. 2).

Pharmacokinetic Studies

Selected compounds were dissolved into normal saline and given at various doses using different route of administration, including intravenous bolus, intravenous infusion, oral and subcutaneous injection.

Compound of the present invention demonstrated acceptable pharmacokinetics via various routes of administration.

In vitro Potency

Compounds of the instant invention were shown to kill SKOV3 (ovarian), MDA-MB-231 (breast), BT549 (breast), HL-60 (acute promyelocytic leukemia) and PANC-1 (pancreatic), cell lines in vitro, demonstrating $EC_{50}$s ranging of 0.1 nM to 1000 nM (see Table 7).

The SAR of these compounds was mapped using SKOV3s and several interesting trends emerged. Changing the stereochemistry at the pyrrolidine bridging site effected the potency of the compounds as seen in the $EC_{50}$s of the cis- and trans-proline derivatives 3 and 29 ($EC_{50}$=1 nM, 88 nM, respectively. Amide bridging units provided active compounds, however, a significant range in potency against SKOV3 cells was observed by varying the components of the bridging units. Small, conformationally constrained bridging units including, but not limited to, 1,4-phenyl dicarboxamides (terephthaloylamides), 1,3-phenyl dicarboxamides, 2,6-naphthyl dicarboxamides, 1,4-cyclohexyl dicarboxamides, 3,5-pyridyl dicarboxamides, or $C_2$-$C_{10}$ aliphatic dicarboxamides provide highly active compounds. Bridging units containing bis-glycine amides such as compounds 30 provide less active compounds ($EC_{50}$=188 nM).

Ether, urea and sulfonamide bridging units provide compounds which were active against SKOV3 cells, although the sulfonamide bridged compounds were generally less active.

Significant shifts in potency against SKOV3 cells were observed by varying the P4 substitution, wherein (R)-stereochemistry at the $R^4$/$R^{400}$ amide provides compounds which are 5-10 times more potent than the corresponding (S)-isomer. The introduction of hydrophilic moieties close to the amide provide less active compounds such as compound 49.

Additionally, alkylation of the N-terminal alanine moiety provides compounds which are up to 100 fold more potent than the corresponding unsubstituted N-terminal alanine derivative.

A subet of cancer cell lines, however, were not innately sensitive to compounds of the instant invention, with $EC_{50}$s greater than 1000 nM. We have demonstrated that IAP BIR binding compounds demonstrate synergistic killing of various cancer cell lines with death receptor agonists such of TRAIL, agonist TRAIL receptor anti-bodies, TNF-α, and others. We herein disclose that compound of formula I and II also demonstrate synergistic killing of various cancer cell lines with death receptor agonists such of TRAIL. When these cells were treated with compound and TRAIL, or antagonist TRAIL antibody, these cell lines were highly sensitive to compound with $EC_{50}$s generally less than 100 nM.

These cancer cell lines include HELA (cervical), HCT116 (colon), PC3 (prostate), OVCAR-3 (ovarian), HEY (ovarian), and H460 (lung). In the presence of TRAIL (1-3 ng/mL) and varying concentrations of compound 3 the $EC_{50}$s for the above cell lines were less than 1000 nM.

In vivo Potency

Compound 3 was tested in SKOV3 and MDA-MB-231 xenograph tumour models (see FIGS. 1 and 2). In both cases tumour regression was observed at 1 mg/kg when given 5 days on and 2 days off. Tumour stasis was observed in SKOV3 xenograph at 0.1 mg/kg.

Discussion

The above results suggest that the IAP BIR binding compounds of the instant invention are highly potent agents, both in vitro and in vivo, wherein a mechanistic link between IAP binding and IAP modulations can be correlated to anti-cancer efficacy. We have demonstrated that compounds of the instant invention bind to the BIR domains of the IAPs with high affinity resulting in the release of active caspases 3 and 9. Further, these compounds result in the induction of apoptosis in cancer cells while synergistically sensitizing cancer cell lines to death receptor agonists such as TRAIL. Moreover, when tumour bearing animals were treated with compounds of the instant invention demonstrated tumour stasis and/or tumour regression at pharmaceutically relavent doses.

Compounds of the instant invention demonstrated acceptable pharmacokinetics via several routes of administration.

OTHER EMBODIMENTS

From the foregoing description, it will be apparent to one of ordinary skill in the art that variations and modifications may be made to the invention described herein to adapt it to various usages and conditions. Such embodiments are also within the scope of the present invention.

All publications mentioned in this specification are hereby incorporated by reference.

We claim:
1. A compound represented by Formula I:

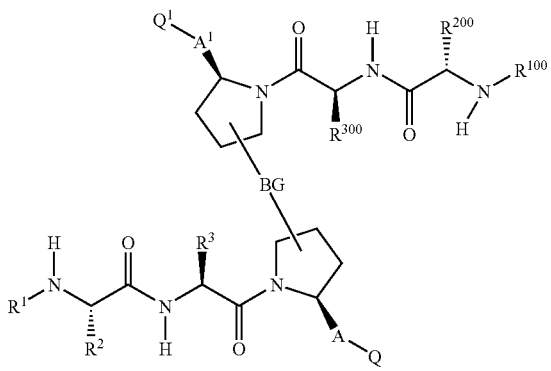

wherein
  m is 0, 1 or 2;
  Y is NH, O or S;
  BG is —X-L-$X^1$—;
  X and $X^1$ are independently
   1) O,
   2) $NR^{13}$,
   3) S,
   4) —$C_1$-$C_6$ alkyl-,
   5) —$C_1$-$C_6$ alkyl-O,
   6) —$C_1$-$C_6$ alkyl-$NR^{13}$—,
   7) —$C_1$-$C_6$ alkyl-S—,
  8) 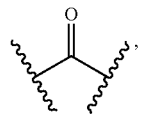
  9) 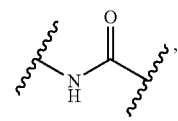
  10) 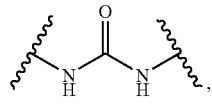
  11) 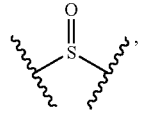
  12) 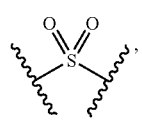
  13) 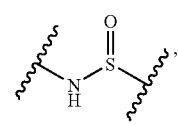

14) 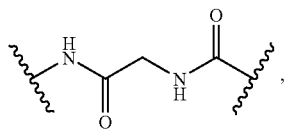, or

15) 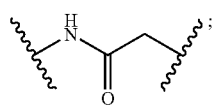;

L is:
1) —$C_1$-$C_{20}$ alkyl-,
2) —$C_2$-$C_6$ alkenyl-,
3) —$C_2$-$C_4$ alkynyl-,
4) —$C_3$-$C_7$ cycloalkyl-,
5) -aryl-,
6) -biphenyl-,
7) -heteroaryl-,
8) -heterocyclyl-,
9) —$C_1$-$C_6$ alkyl-($C_2$-$C_6$ alkenyl)-$C_1$-$C_6$ alkyl-,
10) —$C_1$-$C_6$ alkyl-($C_2$-$C_4$ alkynyl)-$C_1$-$C_6$ alkyl-,
11) —$C_1$-$C_6$ alkyl-($C_3$-$C_7$ cycloalkyl)-$C_1$-$C_6$ alkyl-,
12) —$C_1$-$C_6$alky-aryl-$C_1$-$C_6$ alkyl-,
13) —$C_1$-$C_6$ alkyl-biphenyl-$C_1$-$C_6$ alkyl-,
14) —$C_1$-$C_6$ alkyl-heteroaryl-$C_1$-$C_6$ alkyl-,
15) —$C_1$-$C_6$ alkyl-heterocycyl-$C_1$-$C_6$ alkyl-,
16) —$C_1$-$C_6$ alkyl-Y—$C_1$-$C_6$ alkyl-,
17) -aryl-Y-aryl-,
18) -heteroaryl-Y-heteroaryl-,
19) -heterocyclyl-Y-heterocyclyl-, 20) 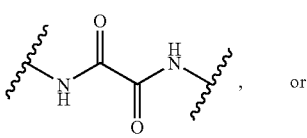, or 21) 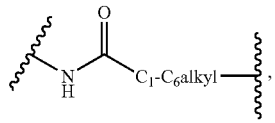, wherein the alkyl, alkenyl, alkynyl and cycloalkyl are optionally substituted with one or more $R^6$ substituents, and the aryl, biphenyl, heteroaryl, and heterocyclyl are optionally substituted with one or more $R^{10}$ substituents;

Q and $Q^1$ are independently
1) $NR^4R^5$,
2) $OR^{11}$, or
3) $S(O)_mR^{11}$; or Q and $Q^1$ are independently
1) aryl, or
2) heteroaryl, the aryl and the heteroaryl being optionally substituted with one or more $R^{10}$ substituents;

A and $A^1$ are independently
1) —$CH_2$—,
2) —$CH_2CH_2$—,
3) —CH($C_1$-$C_6$ alkyl)-,
4) —CH($C_3C_7$ cycloalkyl)-,
5) —$C_3C_7$ cycloalkyl-,
6) —CH($C_1$-$C_6$ alkyl-$C_3$-$C_7$ cycloalkyl)-,
7) —C(O)—, or
8) —C(O)$OR^{13}$;

$R^1$ and $R^{100}$ are independently
1) H, or
2) $C_1$-$C_6$ alkyl optionally substituted with one or more $R^6$ substituents;

$R^2$ and $R^{200}$ are independently
1) H,or
2) $C_1$-$C_6$ alkyl optionally substituted with one or more $R^6$ substituents;

$R^3$ and $R^{300}$ are independently $C_1$-$C_6$ alkyl optionally substituted with one or more $R^6$ substituents;

$R^4$ and $R^5$ are each independently
1) H,
2) haloalkyl,
3) $C_1$-$C_6$ alkyl,
4) $C_2$-$C_6$ alkenyl,
5) $C_2$-$C_4$ alkynyl,
6) $C_3$-$C_7$ cycloalkyl,
7) $C_3$-$C_7$ cycloalkenyl,
8) aryl,
9) heteroaryl,
10) heterocyclyl,
11) heterobicyclyl,
12) C(O)—$R^{11}$,
13) C(O)O—$R^{11}$,
14) C(=Y)$NR^8R^9$, or
15) $S(O)_2$—$R^{11}$, wherein the alkyl, alkenyl, alkynyl, cycloalkyl, and cycloalkenyl are optionally substituted with one or more $R^6$ substituents; and wherein the aryl, heteroaryl, heterocyclyl, and heterobicyclyl are optionally substituted with one or more $R^{10}$ substituents;

$R^6$ is
1) halogen,
2) $NO_2$,
3) CN,
4) haloalkyl,
5) $C_1$-$C_6$ alkyl,
6) $C_2$-$C_6$ alkenyl,
7) $C_2$-$C_4$ alkynyl,
8) $C_3$-$C_7$ cycloalkyl,
9) $C_3$-$C_7$ cycloalkenyl,
10) aryl,
11) heteroaryl,
12) heterocyclyl,
13) heterobicyclyl,
14) $OR^7$,
15) $S(O)_mR^7$,
16) $NR^8R^9$,
17) $NR^8S(O)_2R^{11}$,
18) $COR^7$,
19) $C(O)OR^7$,
20) $CONR^8R^9$,
21) $S(O)_2NR^8R^9$
22) $OC(O)R^7$,
23) $OC(O)Y$—$R^{11}$,
24) $SC(O)R^7$, or
25) $NC(Y)NR^8R^9$, wherein the aryl, heteroaryl, heterocyclyl, and heterobicyclyl are optionally substituted with one or more $R^{10}$ substituents;

$R^7$ is
1) H,
2) haloalkyl,
3) $C_1$-$C_6$ alkyl,

4) $C_2$-$C_6$ alkenyl,
5) $C_2$-$C_4$ alkynyl,
6) $C_3$-$C_7$ cycloalkyl,
7) $C_3$-$C_7$ cycloalkenyl,
8) aryl,
9) hereroaryl,
10) heterocyclyl,
11) heterobicyclyl,
12) $R^8R^9NC(=Y)$, or
13) $C_1$-$C_6$ alkyl-$C_2$-$C_4$ alkenyl, or
14) $C_1$-$C_6$ alkyl-$C_2$-$C_4$ alkynyl,
wherein the alkyl, alkenyl, alkynyl, cycloalkyl, and cycloalkenyl are optionally substituted with one or more $R^6$ substituents; and wherein the aryl, heteroaryl, heterocyclyl, and heterobicyclyl are optionally substituted with one or more $R^{10}$ substituents;

$R^8$ and $R^9$ are independently
1) H,
2) haloalkyl,
3) $C_1$-$C_6$ alkyl,
4) $C_2$-$C_6$ alkenyl,
5) $C_2$-$C_4$ alkynyl,
6) $C_3$-$C_7$ cycloalkyl,
7) $C_3$-$C_7$ cycloalkenyl,
8) aryl,
9) heteroaryl,
10) heterocyclyl,
11) heterobicyclyl,
12) $C(O)R^{11}$,
13) $C(O)Y-R^{11}$, or
14) $S(O)_2-R^{11}$,
wherein the alkyl, alkenyl, alkynyl, cycloalkyl, and cycloalkenyl are optionally substituted with one or more $R^6$ substituents; and wherein the aryl, heteroaryl, heterocyclyl, and heterobicyclyl are optionally substituted with one or more $R^{10}$ substituents;
or $R^8$ and $R^9$ together with the nitrogen atom to which they are bonded form a five, six or seven membered heterocyclic ring optionally substituted with one or more $R^6$ substituents;

$R^{10}$ is
1) halogen,
2) $NO_2$,
3) CN,
4) $B(OR^{13})(OR^{14})$,
5) $C_1$-$C_6$ alkyl,
6) $C_2$-$C_6$ alkenyl,
7) $C_2$-$C_4$ alkynyl,
8) $C_3$-$C_7$ cycloalkyl,
9) $C_3$-$C_7$ cycloalkenyl,
10) haloalkyl,
11) $OR^7$,
12) $NR^8R^9$,
13) $SR^7$,
14) $COR^7$,
15) $C(O)OR^7$,
16) $S(O)_mR^7$,
17) $CONR^8R^9$,
18) $S(O)_2NR^8R^9$,
19) aryl,
20) heteroaryl,
21) heterocyclyl, or
22) heterobicyclyl,
wherein the alkyl, alkenyl, alkynyl, cycloalkyl, and cycloalkenyl are optionally substituted with one or more $R^6$ substituents;

$R^{11}$ is
1) haloalkyl,
2) $C_1$-$C_6$ alkyl,
3) $C_2$-$C_6$ alkenyl,
4) $C_2$-$C_4$ alkynyl,
5) $C_3$-$C_7$ cycloalkyl,
6) $C_3$-$C_7$ cycloalkenyl,
7) aryl,
8) heteroaryl,
9) heterocyclyl, or
10) heterobicyclyl,
wherein the alkyl, alkenyl, alkynyl, cycloalkyl, and cycloalkenyl are optionally substituted with one or more $R^6$ substituents; and wherein the aryl, heteroaryl, heterocyclyl, and heterobicyclyl are optionally substituted with one or more $R^{10}$ substituents;

$R^{13}$ and $R^{14}$ are independently
1) H, or
2) $C_1$-$C_6$ alkyl; or
$R^{13}$ and $R^{14}$ are combined to form a heterocyclic ring or a heterobicyclic ring;
or a salt thereof.

2. The compound, according to claim 1, wherein the compound is a pharmaceutically acceptable salt.

3. A compound, according to claim 1, of any one of Formulas 1a through 1c:

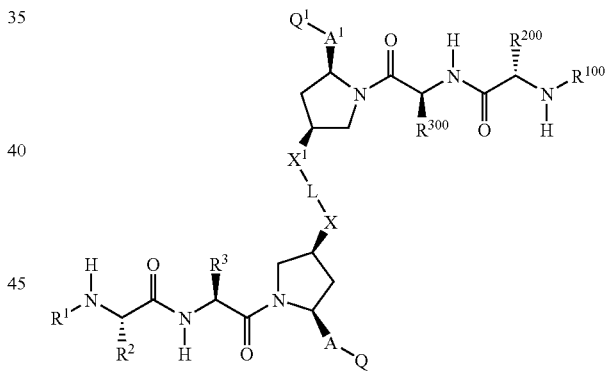

1a

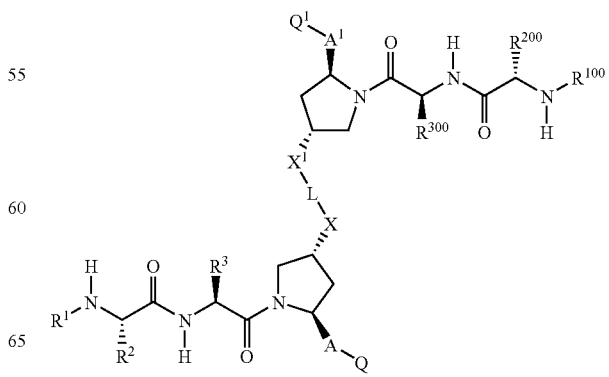

1b

-continued
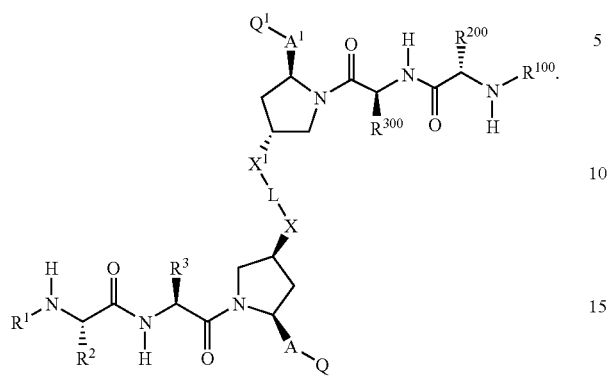
1c
4. A compound, according to claim 1, of any one of Formulas 1.1, 1.2, or 1.4 through 1.18:
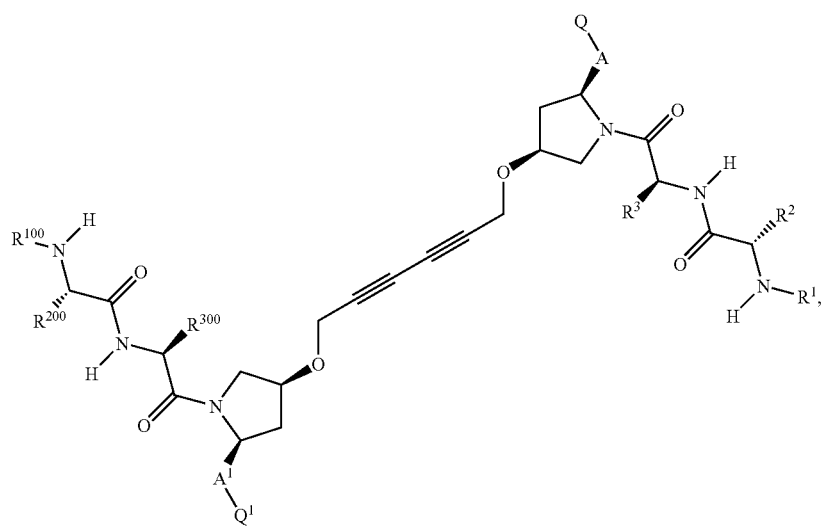
1.1
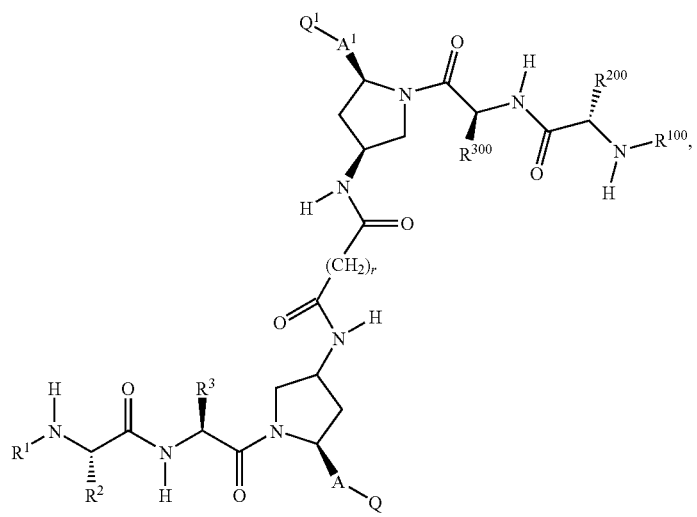
1.2

-continued
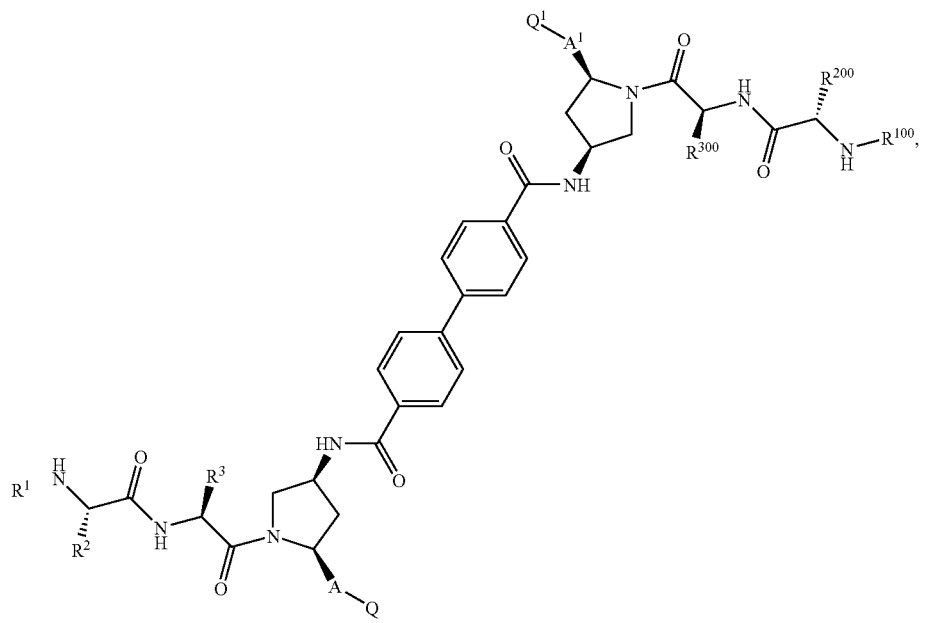
1.4
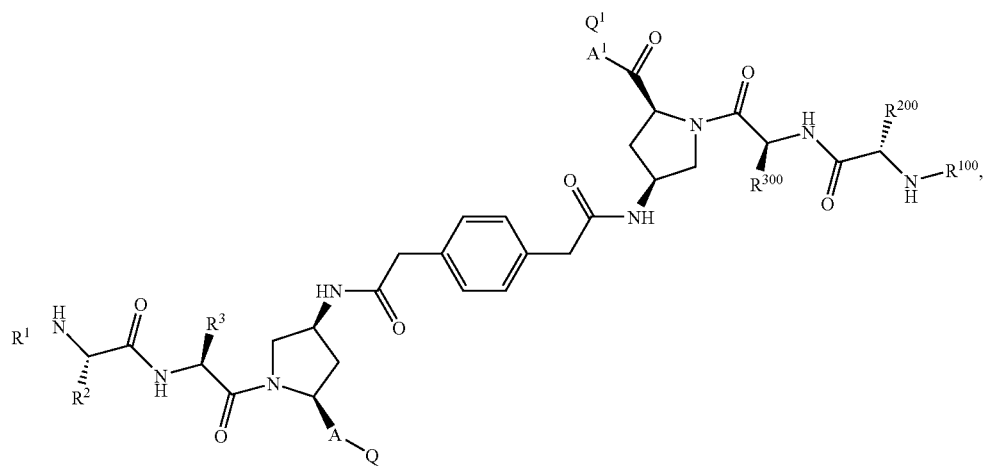
1.5
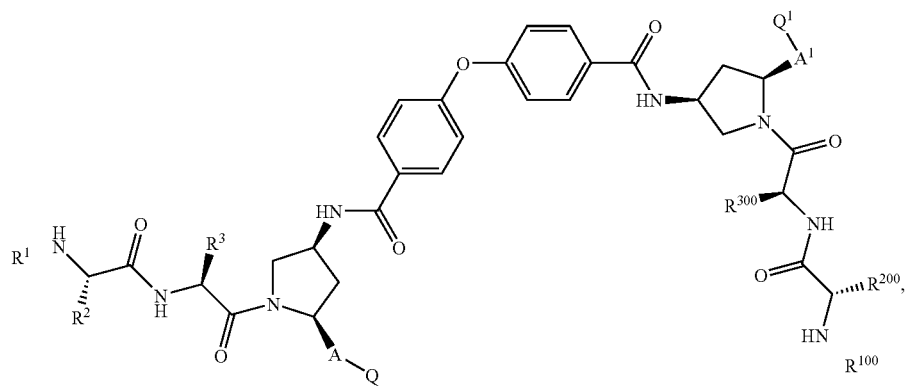
1.6

-continued
1.7
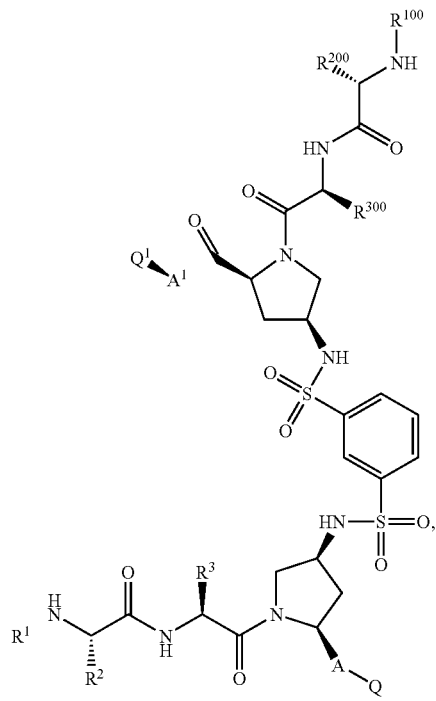
1.8
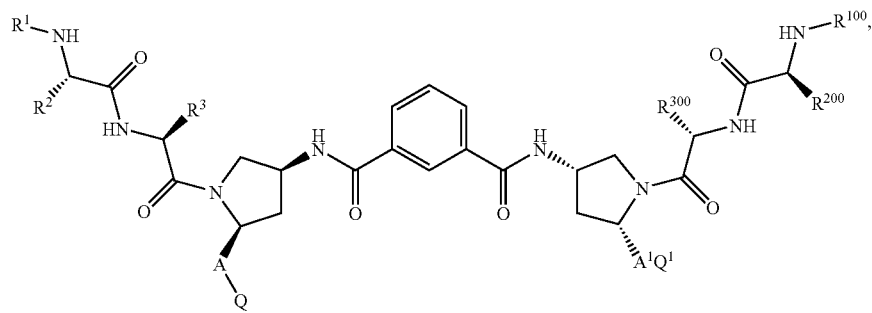
1.9
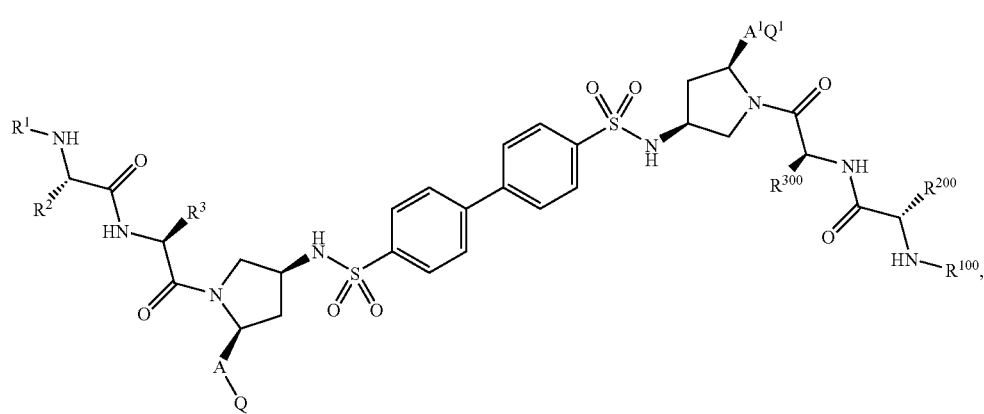

-continued
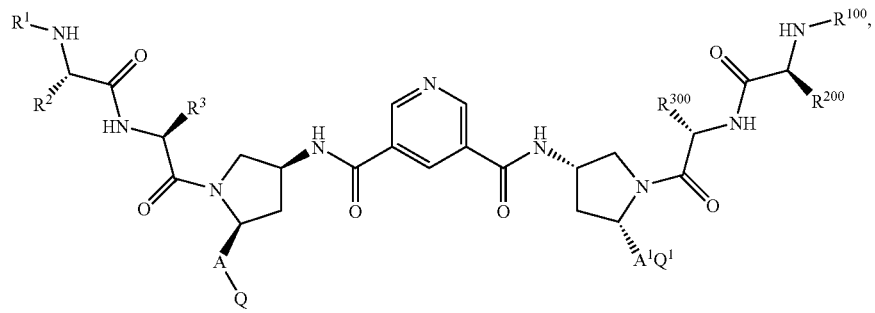
1.10
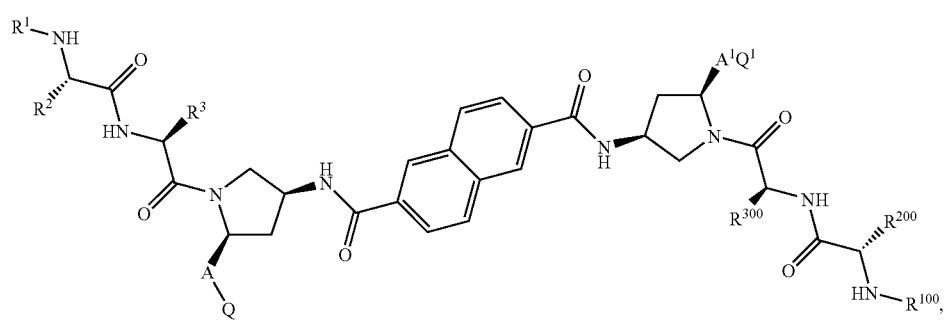
1.11
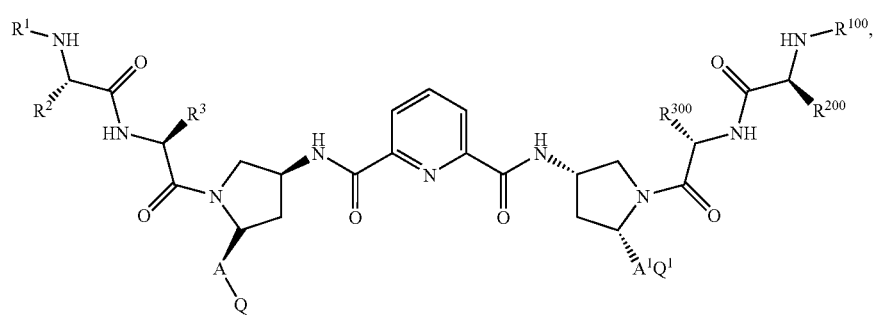
1.12
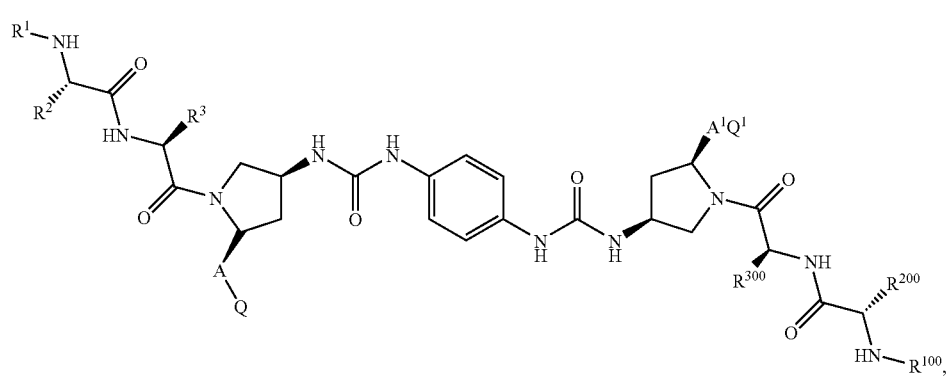
1.13
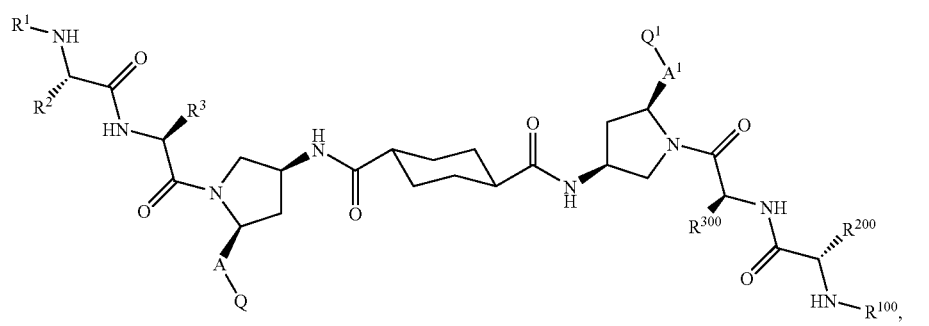
1.14

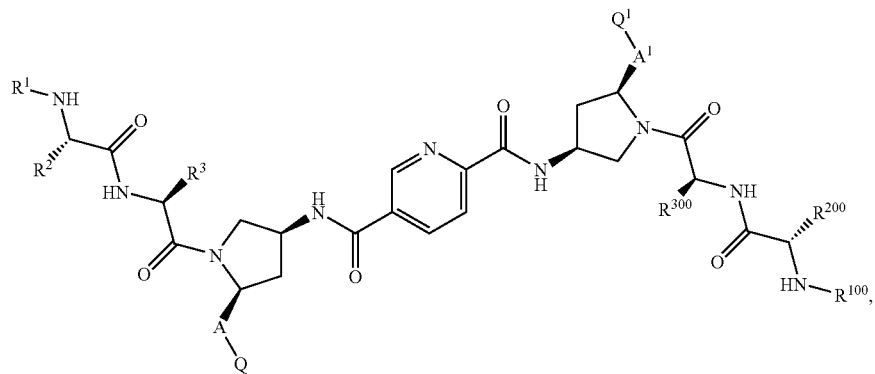
1.15
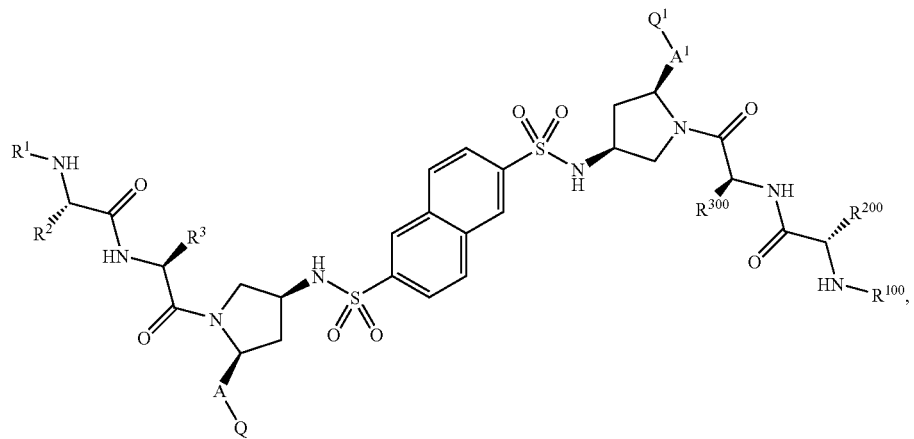
1.16
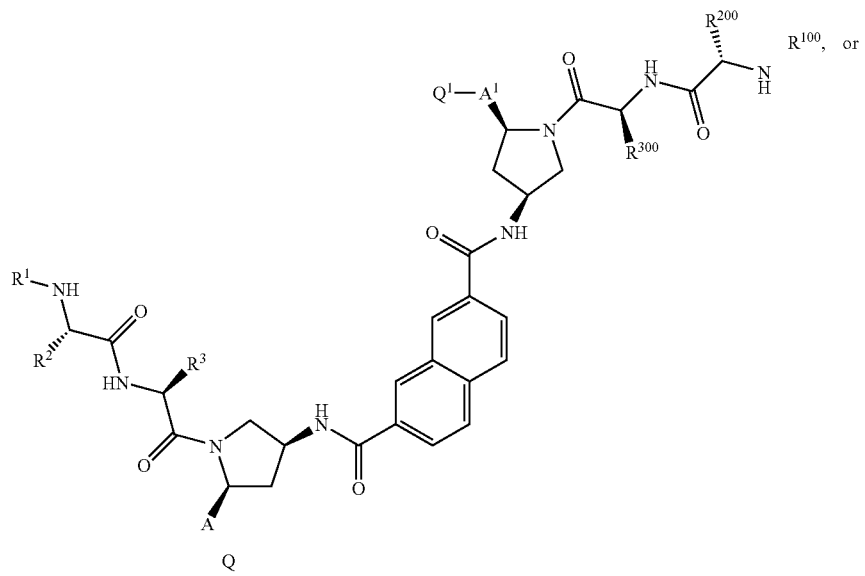
1.17

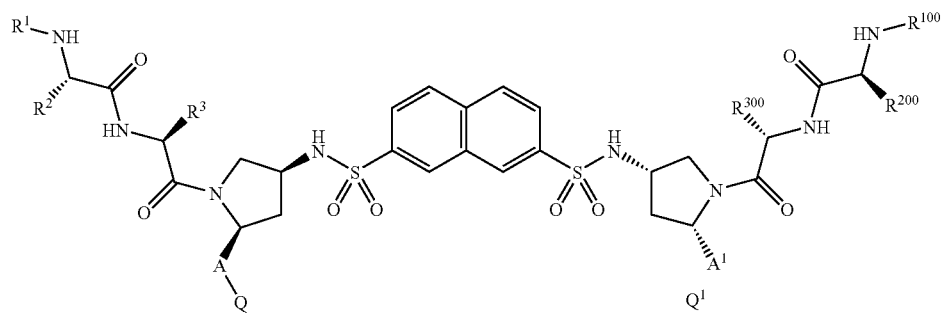
wherein r is an integer of 1, 2, 3, 4, 5, 6, 7, 8, 9 or 10.
5. The compound, according to claim 1, in which $R^1$ and $R^{100}$ are both $CR_3$.
6. The compound, according to claim 1, in which $R^3$ and $R^{300}$ are both $C(CH_3)_3$.
7. The compound, according to claim 1, in which A and $A^1$ are both C=O, and Q and $Q^1$ are:
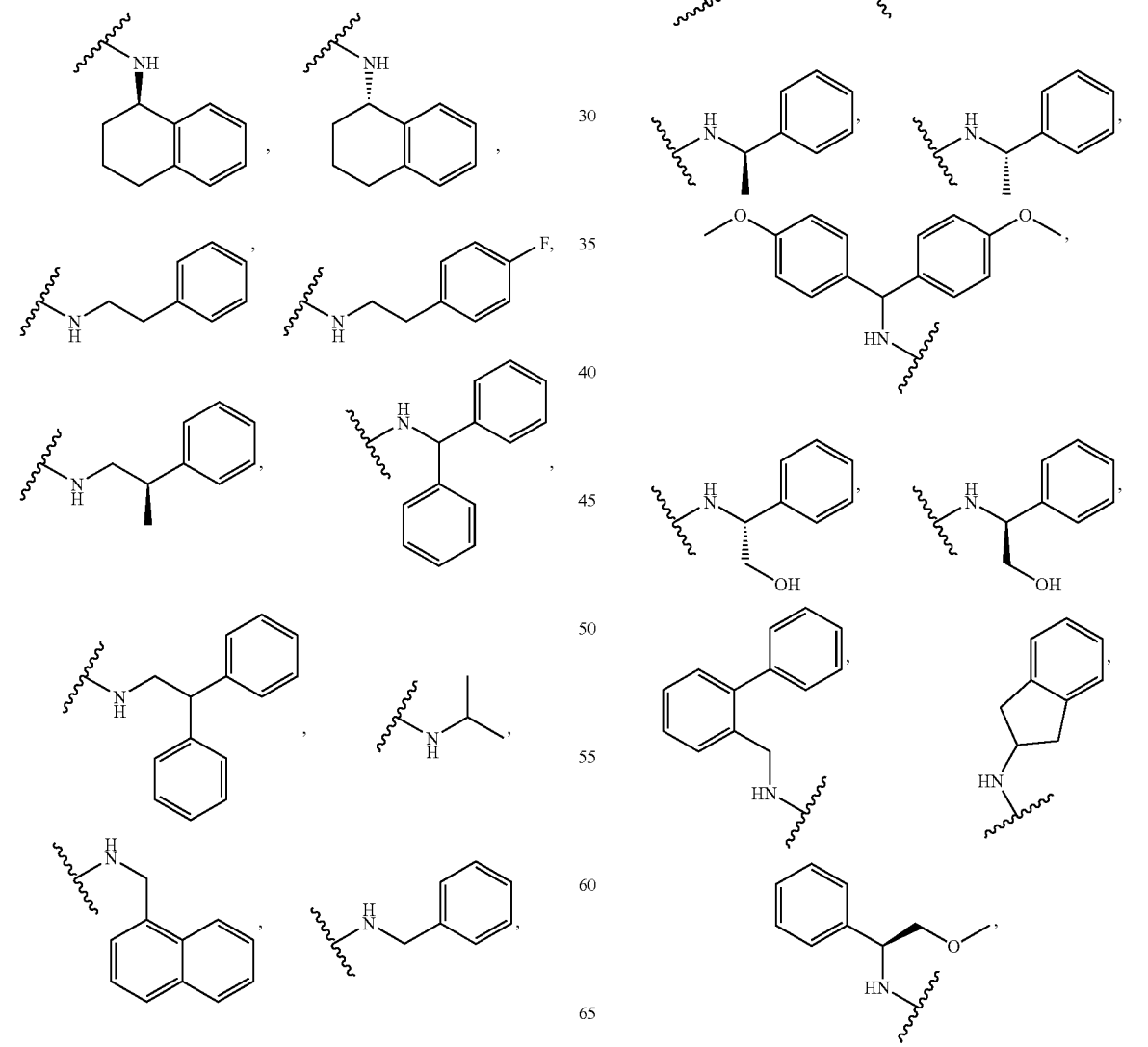

-continued
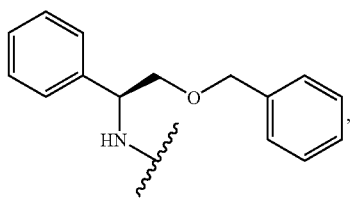
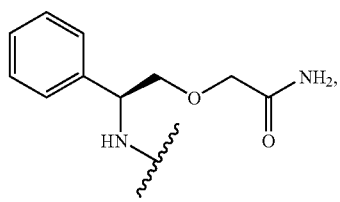
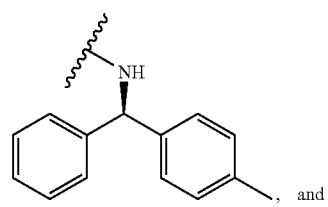, and
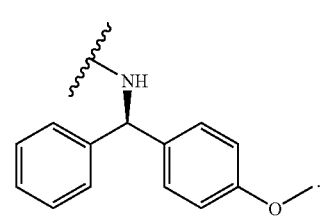.
8. The compound, according to claim 1, in which A and $A^1$ are both $CH_2$ and Q and $Q^1$ are:
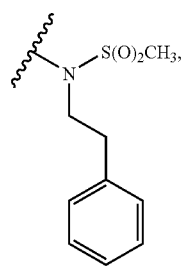 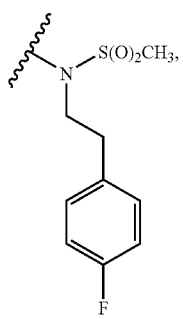
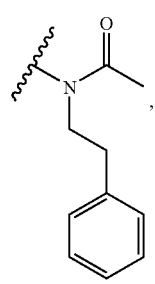, 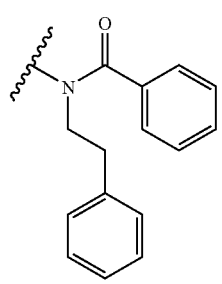 or
-continued
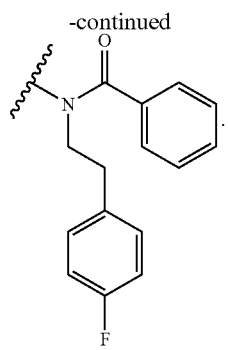.
9. The compound, according to claim 1, wherein X and $X^1$ are independently
1) O,
2) 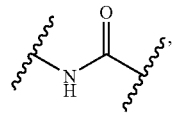
3) 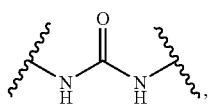,
4) 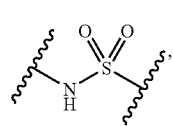,
5) 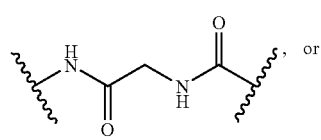 or
6) 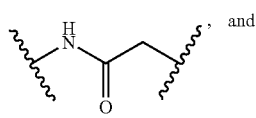, and
10. The compound, according to claim 9, in which L is:
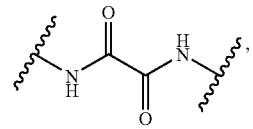,
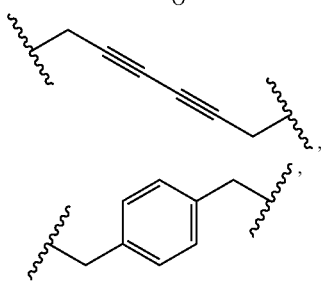, -continued

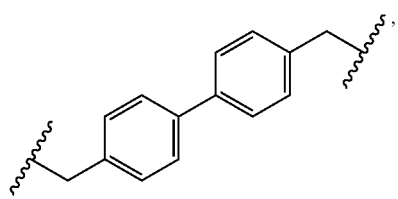

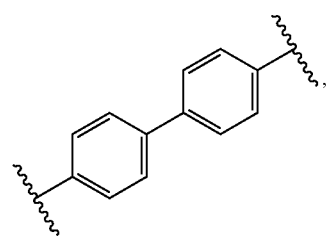

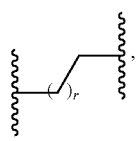

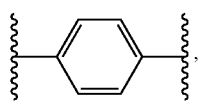

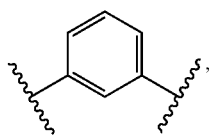, 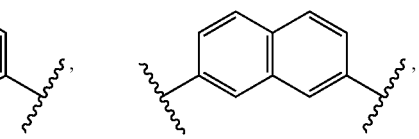

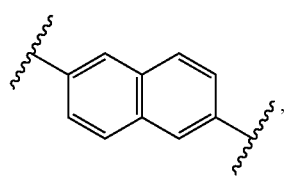

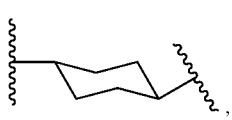

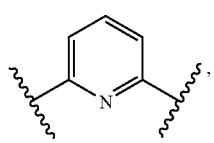

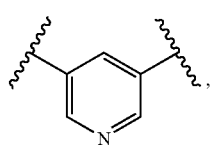

-continued

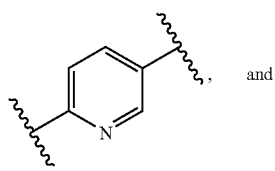, and

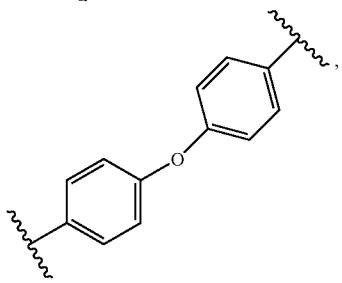

wherein r is an integer of 1, 2, 3, 4, 5, 6, 7, 8, 9 or 10.

11. The compound, according to claim 1, in which Q and $Q^1$ are both $NR^4R^5$.

12. The compound, according to claim 1, in which A and $A^1$ are both $CH_2$.

13. The compound, according to claim 1, in which A and $A^1$ are both C=O.

14. The compound, according to claim 1, in which A and $A^1$ are both C=O, and Q and $Q^1$ are both $NR^4R^5$, wherein $R^4$ is H and
$R^5$ is
1) $C_1$-$C_6$ alkyl,
2) $C_2$-$C_6$ alkenyl,
3) $C_2$-$C_4$ alkynyl,
4) $C_3$-$C_7$ cycloalkyl,
5) $C_3$-$C_7$ cycloalkenyl,
6) aryl,
7) heteroqryl,
8) heterocyclyl, or
9) hererobicyclyl,
wherein the alkyl, alkenyl, alknyl, cycloalkyl, and cycoalkenyl are optionally substituted with one or more $R^6$ substituents; and wherein the aryl, heteroaryl, and heterobicyclyl are optionally substituted with one more $R^{10}$ substituents.

15. The compound, according to claim 1, in which A and $A^1$ are both $CH_2$, and Q and $Q^1$ are both $NR^4R^5$, wherein $R^4$ and $R^5$ are each independently
1) haloalkyl,
2) $C_1$-$C_6$ alkyl,
3) $C_2$-$C_6$ alkenyl,
4) $C_2$-$C_4$ alkynyl,
5) $C_3$-$C_7$ cycloalkyl,
6) $C_3$-$C_7$ cycloalkenyl,
7) aryl,
8) heteroaryl,
9) heterocyclyl,
10) heterobicyclyl,
11) C(O)—$R^{11}$,
12) C(O)O—$R^{11}$,
13) C(=Y)$NR^8R^9$, or
14) S(O)$_2$—$R^{11}$,
wherein the alkyl, alkenyl, alkynyl, cycloalkyl, and cycloalkenyl are optionally substituted with one or more $R^6$ substituents; and wherein the aryl, heteroaryl, heterocyclyl, and heterobicyclyl are optionally substituted with one or more $R^{10}$ substituents.

16. A compound, according to claim 1, wherein the compound is:
| Cpd | STRUCTURE |
|---|---|
| 1 | 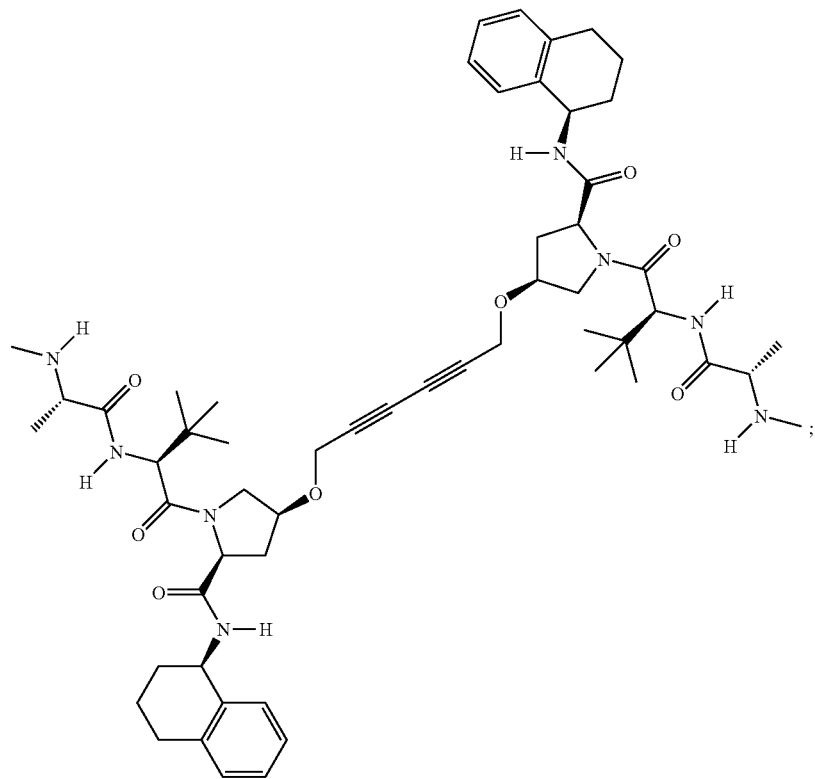 |
| 2 | 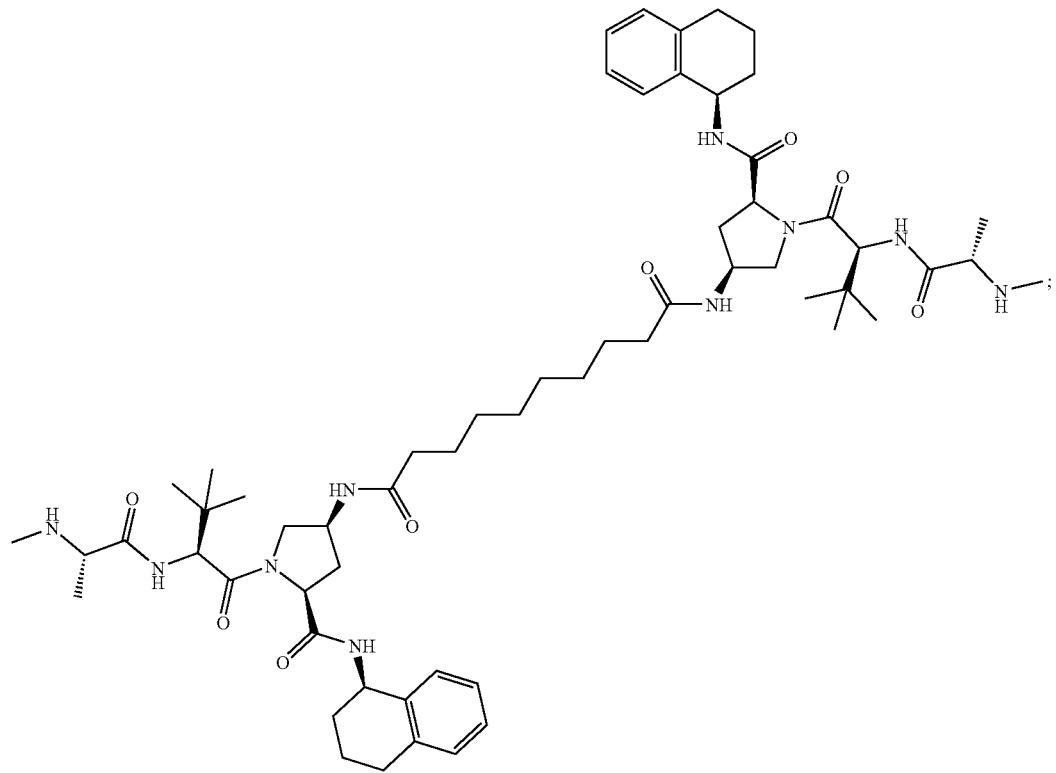 |

-continued
| Cpd | STRUCTURE |
|---|---|
| 4 | 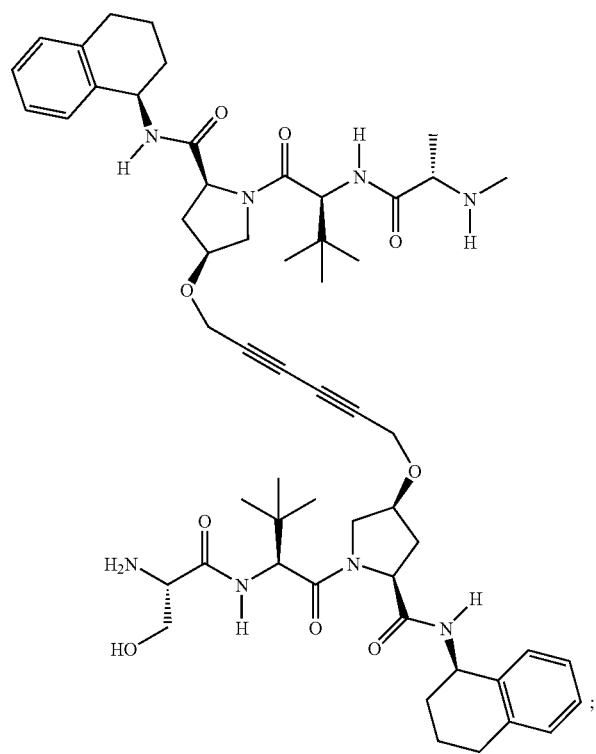 |
| 5 | 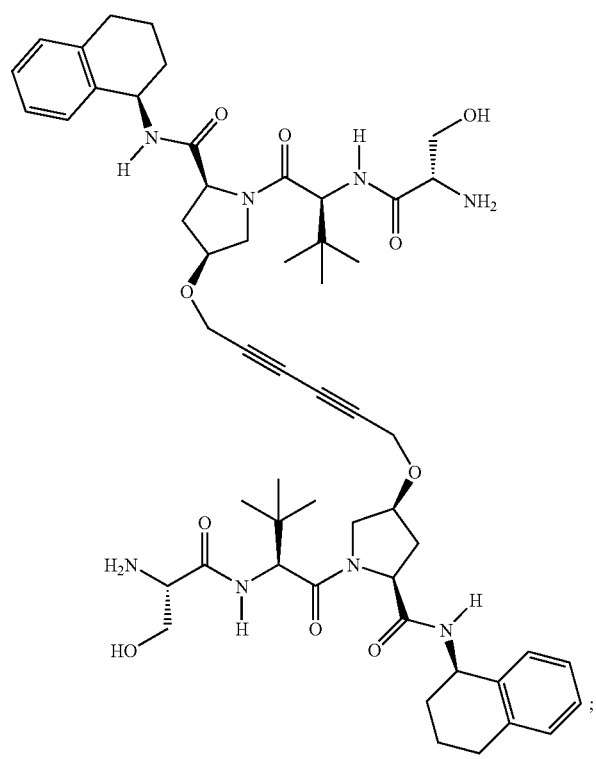 |

-continued
| Cpd | STRUCTURE |
|---|---|
| 10 | 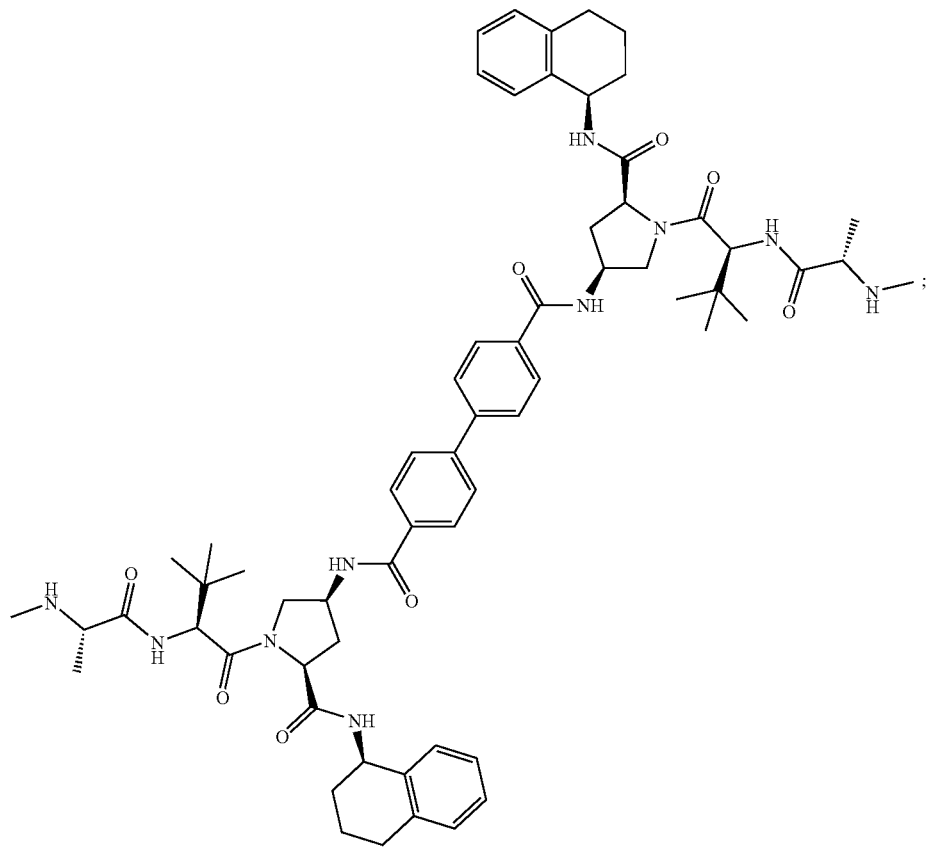 |
| 11 | 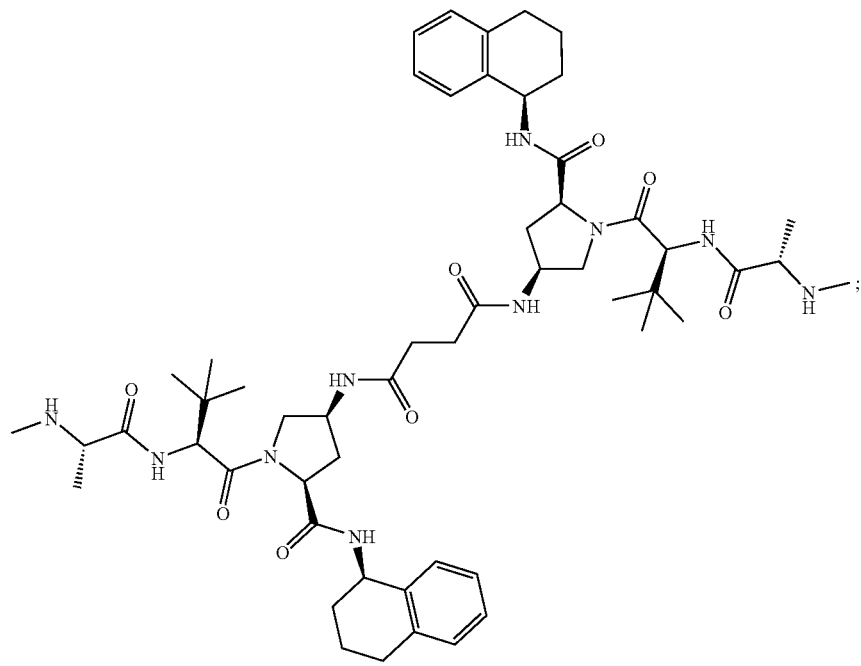 |

-continued
| Cpd | STRUCTURE |
|---|---|
| 12 | 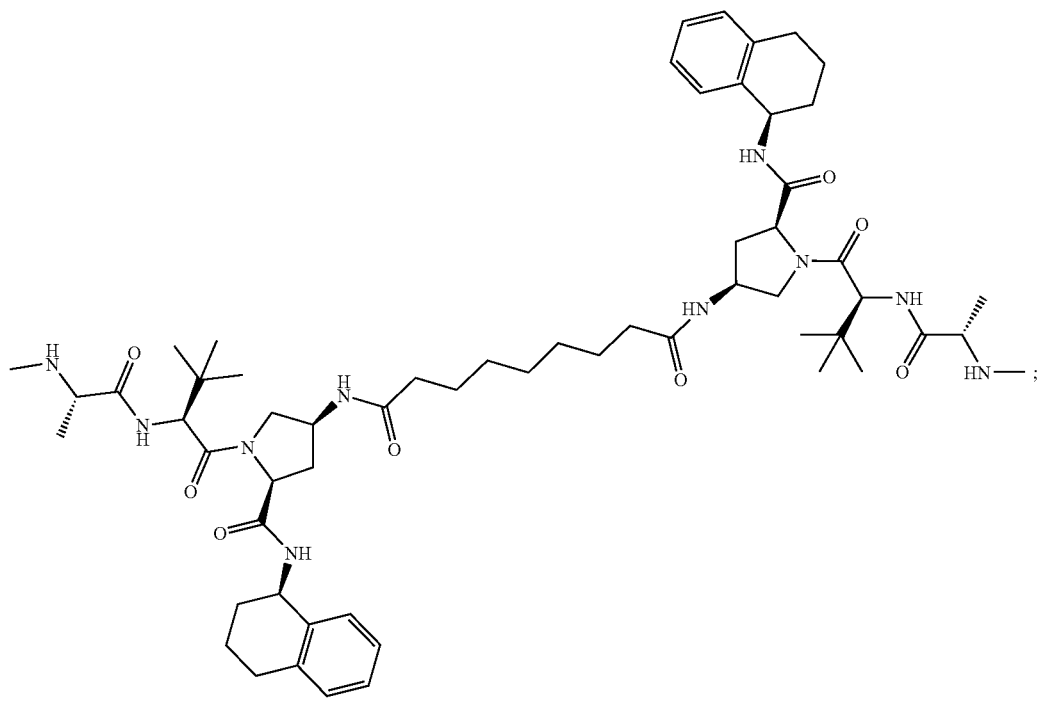 |
| 13 | 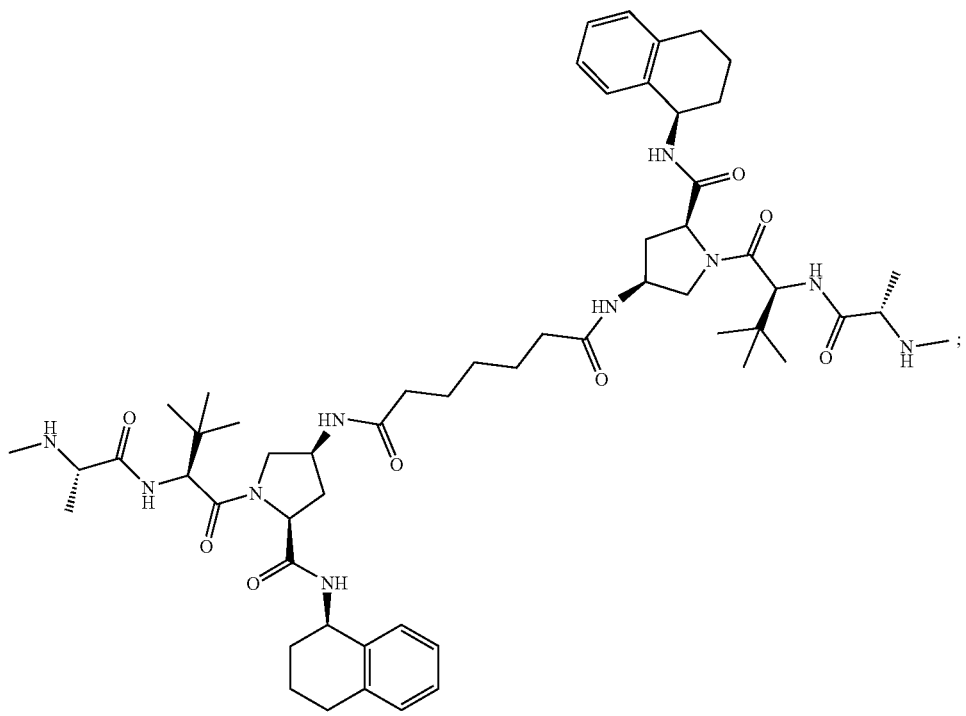 |

| Cpd | STRUCTURE |
|---|---|
| 14 | 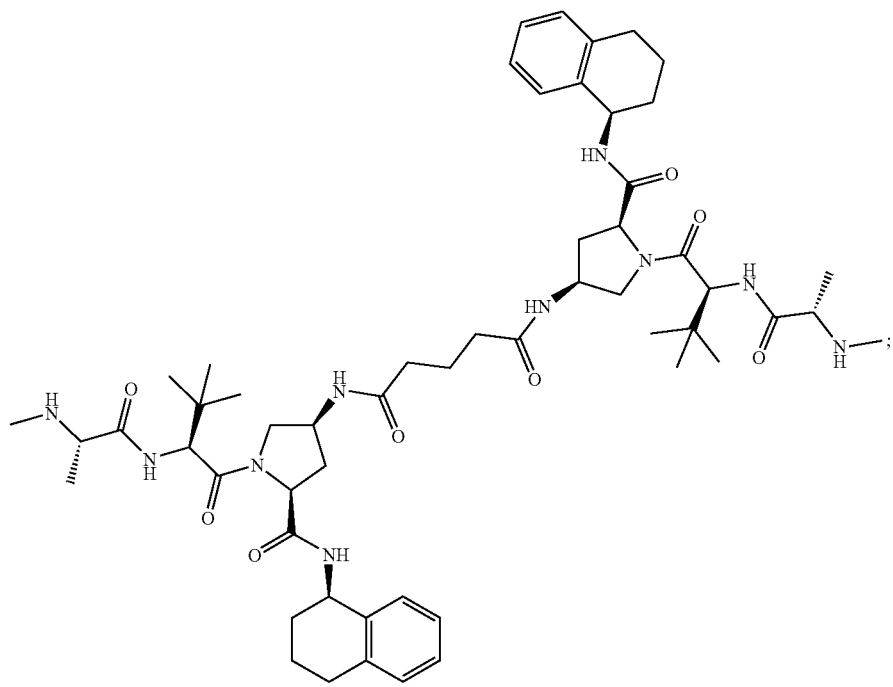 |
| 15 | 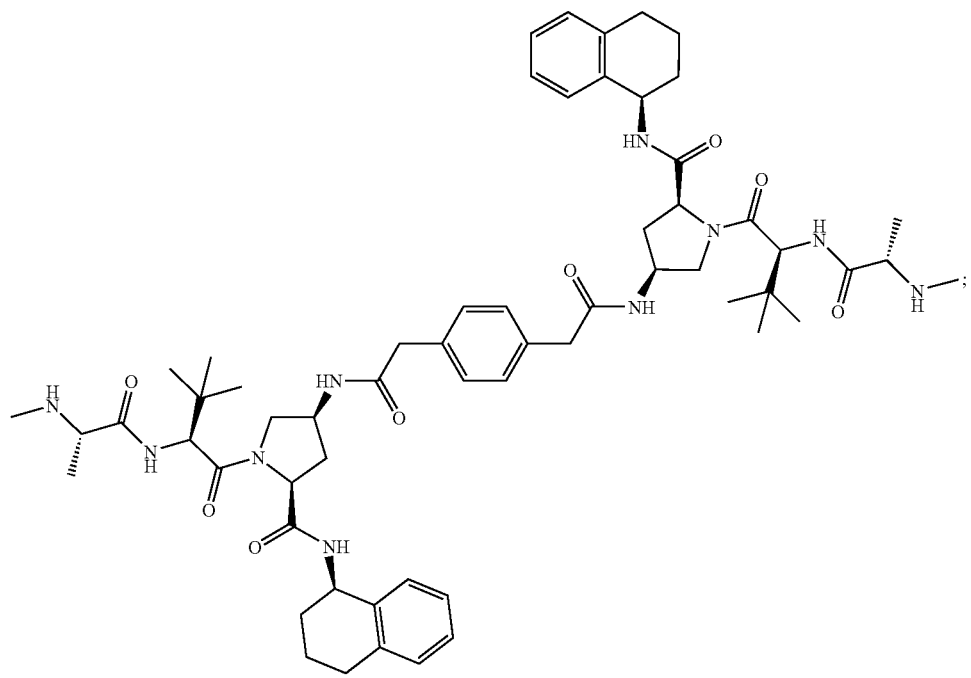 |

-continued
| Cpd | STRUCTURE |
|---|---|
| 16 | 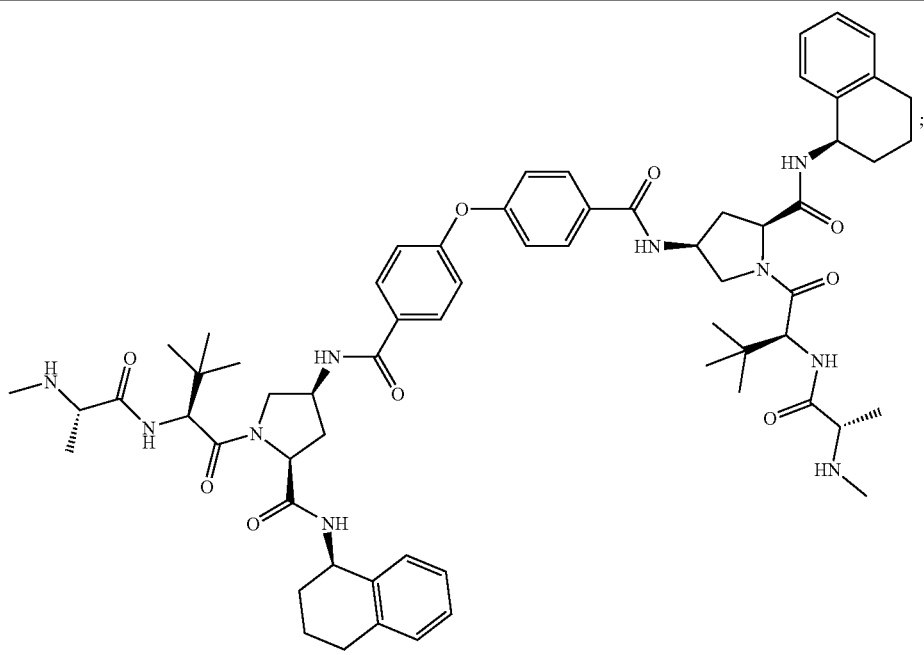 |
| 17 | 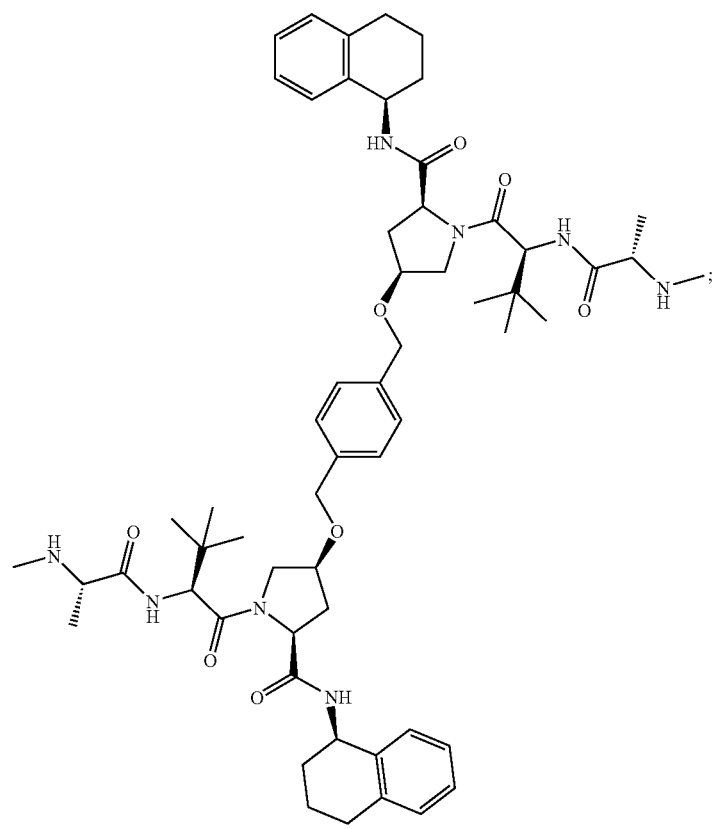 |

| Cpd | STRUCTURE |
|---|---|
| 29 | 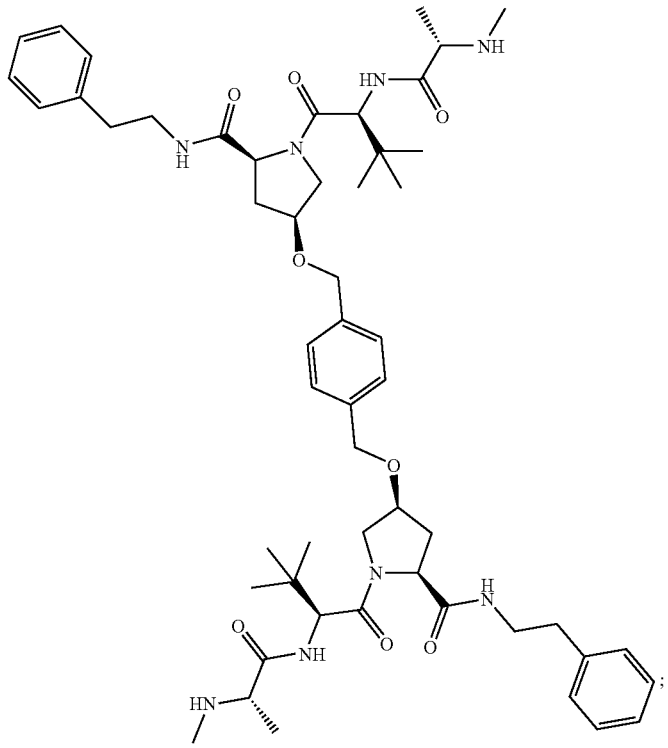 |
| 33 | 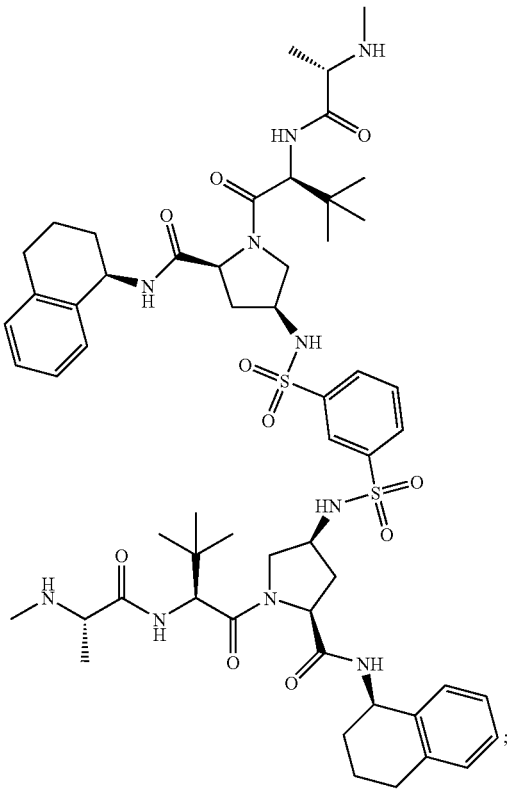 |

-continued
| Cpd | STRUCTURE |
|---|---|
| 35 | 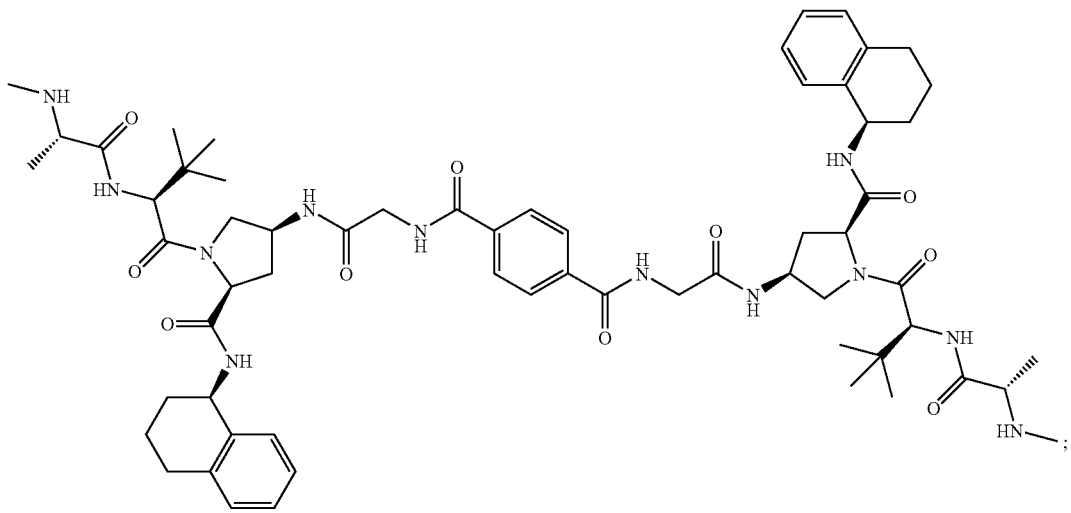 |
| 36 | 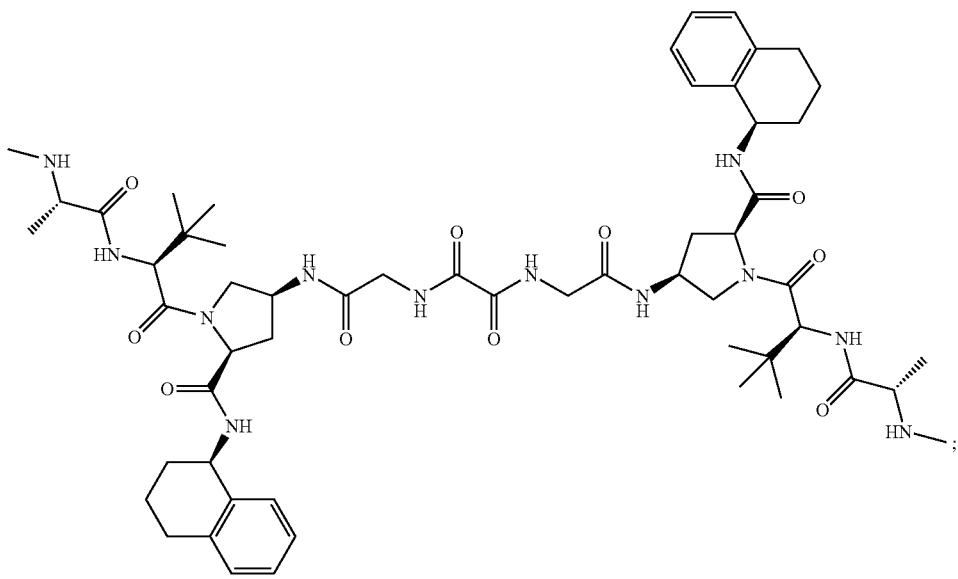 |
| 37 | 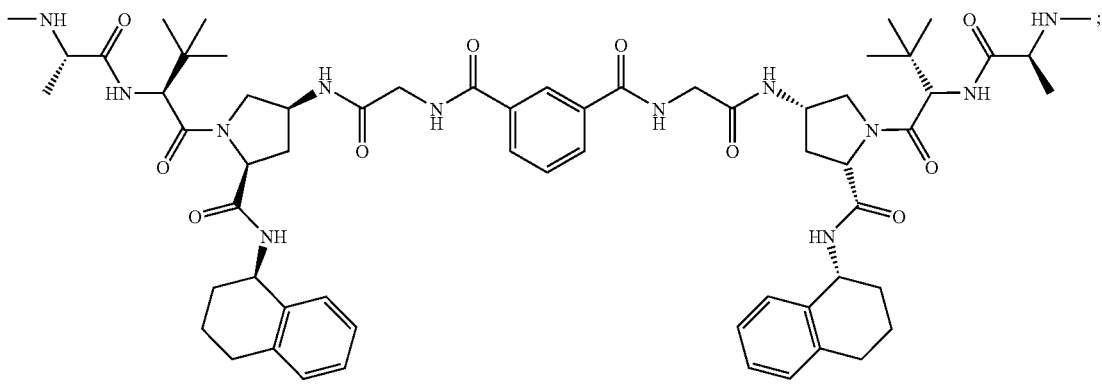 |

-continued
| Cpd | STRUCTURE |
|---|---|
| 38 | 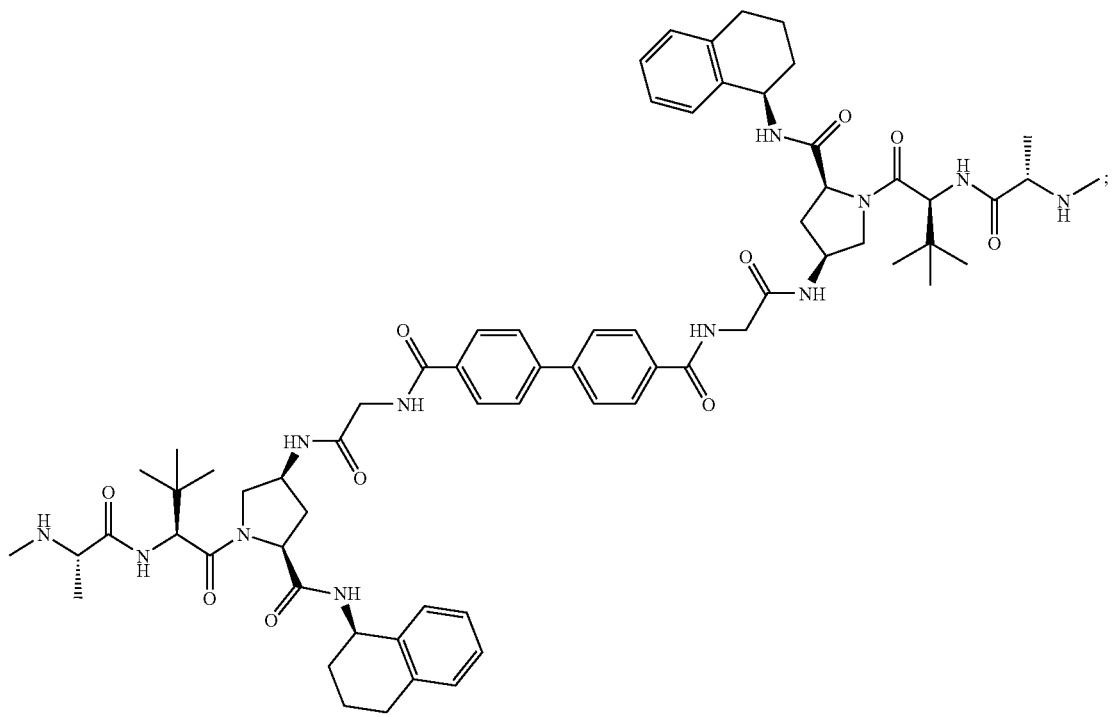 |
| 39 | 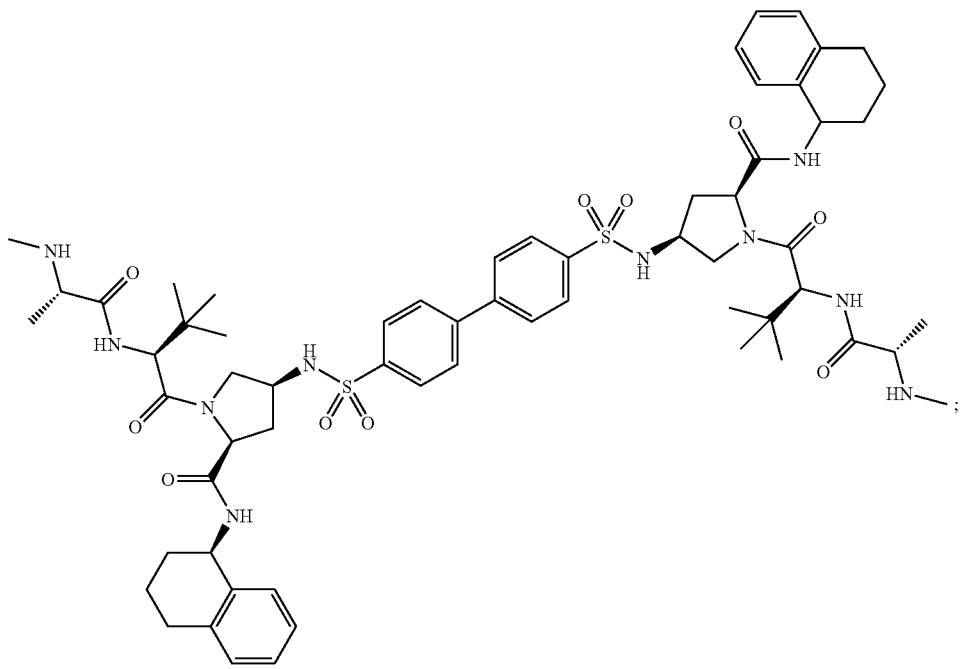 |

-continued
| Cpd | STRUCTURE |
|---|---|
| 40 | 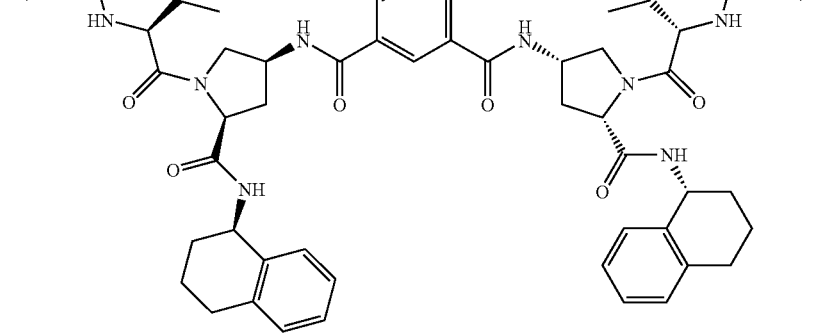 |
| 41 | 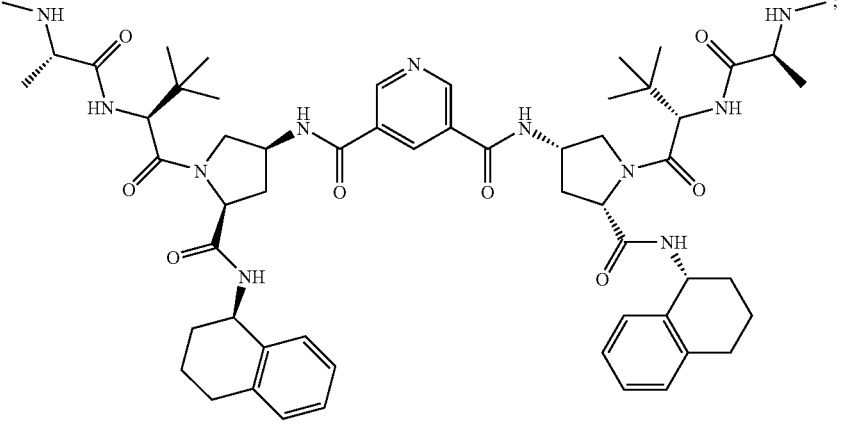 |
| 42 | 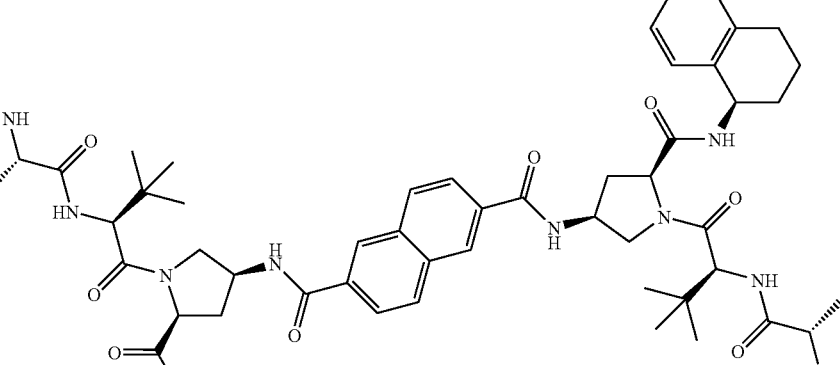 |

-continued
| Cpd | STRUCTURE |
|---|---|
| 43 | 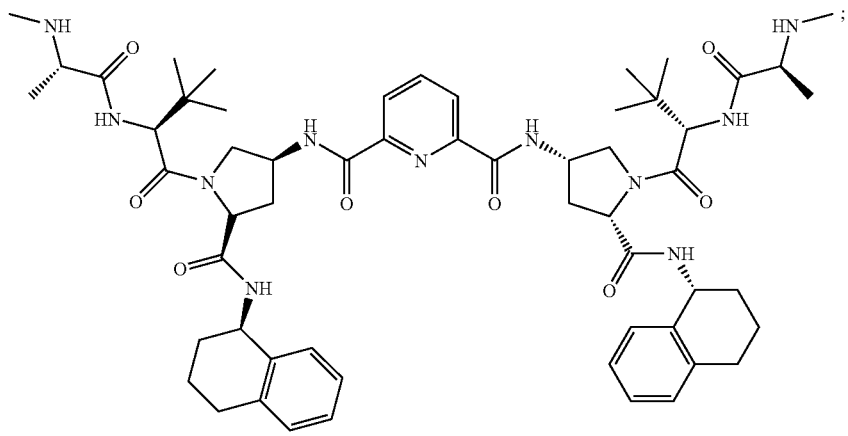 |
| 44 | 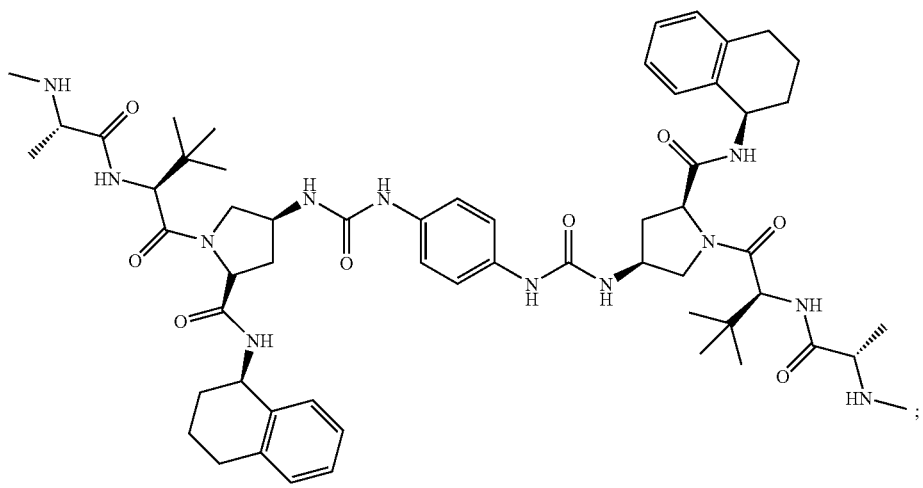 |
| 52 | 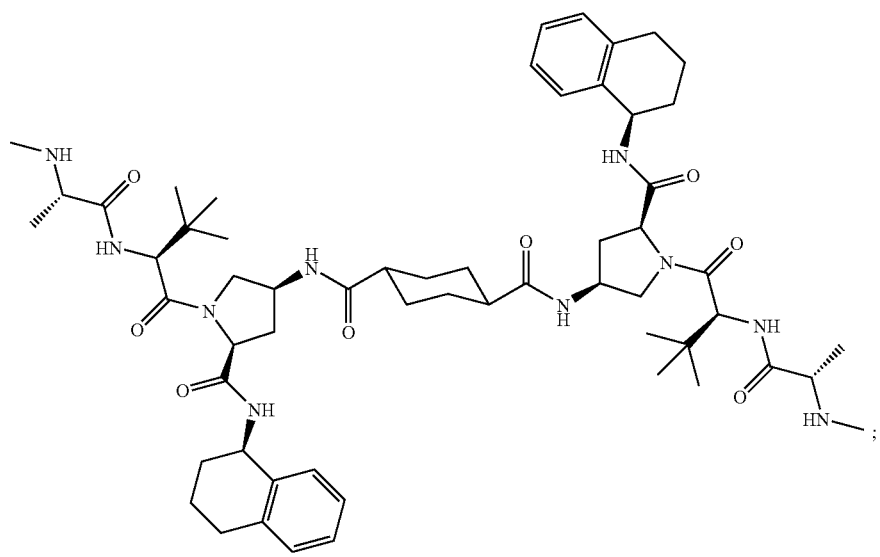 |

-continued
| Cpd | STRUCTURE |
|---|---|
| 55 | 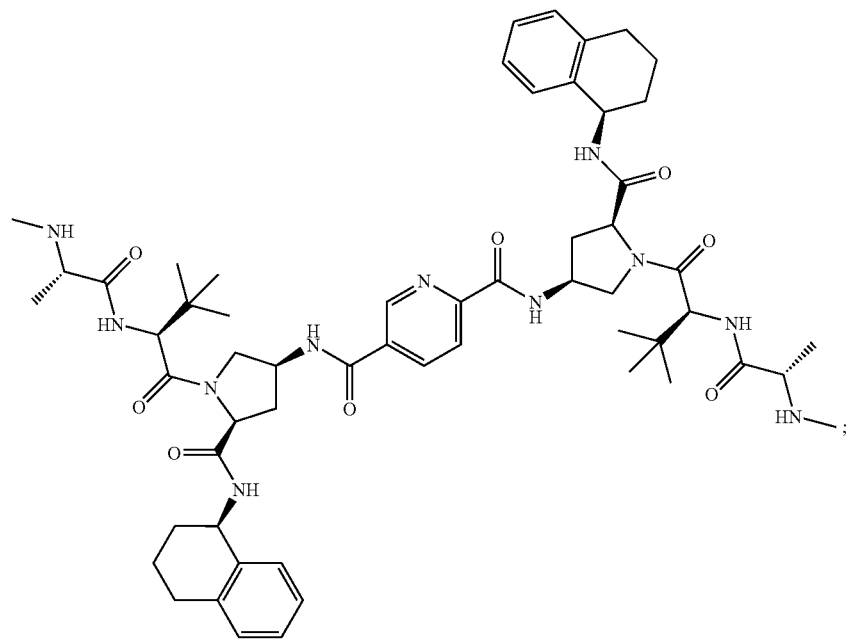 |
| 56 | 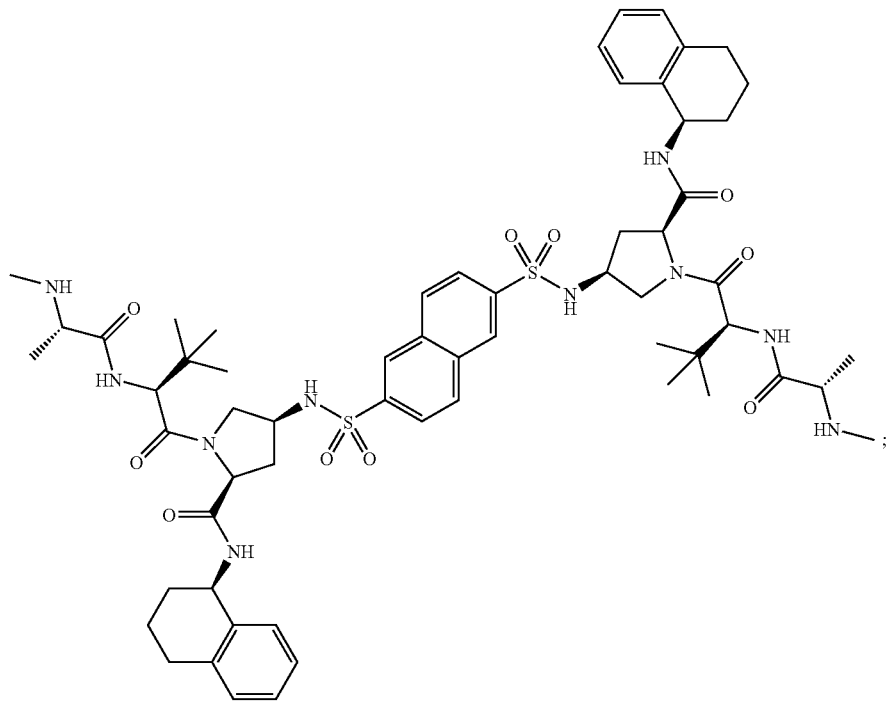 |

-continued

| Cpd | STRUCTURE |
|---|---|
| 57 | 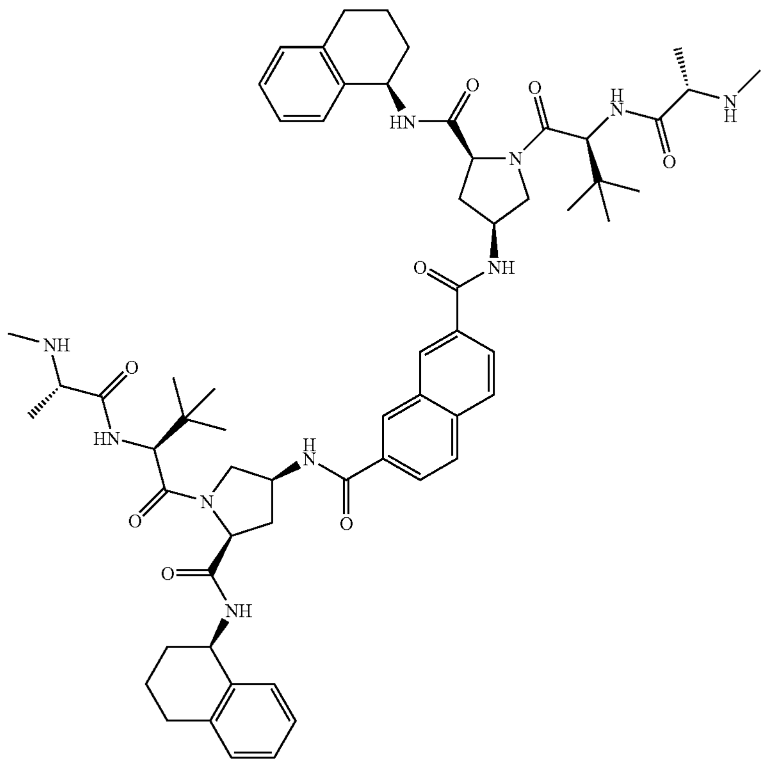 |
| 58 | 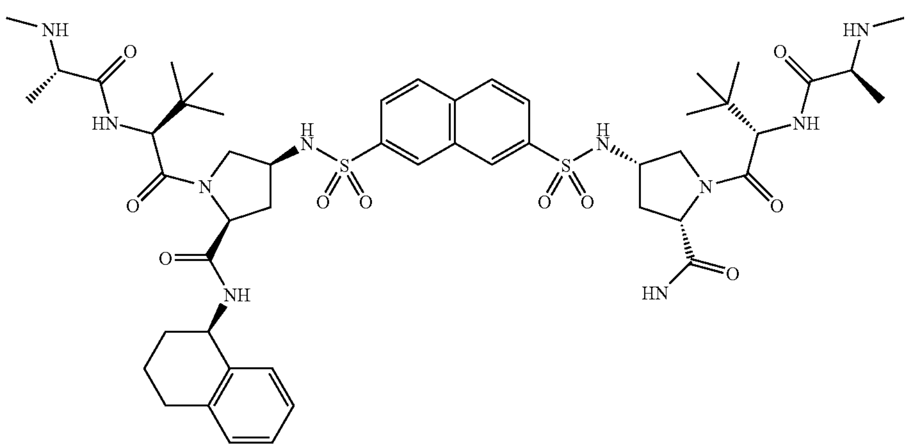 |

17. A pharmaceutical composition comprising a compound of Formula I, according to claim 1, and a pharmaceutically acceptable carrier, diluent or excipient.

18. A pharmaceutical composition comprising a compound of Formula I or salt thereof according to claim 1, in combination with any compound that increases the circulating level of one or more death receptor agonists.

19. A method for the preparation of a pharmaceutically acceptable salt of a compound of Formula I, according to claim 1, by the treatment of a compound of Formula I with 1 to 2 equiv of a pharmaceutically acceptable acid.

20. A method for the treatment of breast or ovarian cancer in a subject, the method comprising administering to the subject a therapeutically effective amount of a compound of Formula I or a salt thereon according to claim 1.

21. The method, according to claim 20, further comprising administering to the subject a therapeutically effective amount of a chemotherapeutic agent prior to, simultaneously with, or after administration of the compound.

22. The method, according to claim 20, further comprising administering to the subject a therapeutically effective amount of a death receptor agonist prior to, simultaneously with, or after administration of the compound.

23. The method, according to claim 22, in which the death receptor agonist is TRAIL.

24. The method, according to claim 22, in which the death receptor agonist is a TRAIL receptor antibody.

25. The method, according to claim 22, in which the death receptor agonist is administered in an amount that produces a synergistic effect.

26. The method, according to claim 22, in which the subject is a human.

27. A method for the treatment of breast or ovarian cancer in a subject, the method comprising administering to the subject a therapeutically effective amount of the pharmaceutical composition according to claim 17 so as to treat the breast or ovarian cancer.

28. The method, according to claim 27, in which the subject is a human.

29. The method, according to claim 20, wherein the salt of the compound is administered intravenously.

30. A process for producing a compound of claim 1, the process comprising:
    a) coupling two intermediates represented by Formula 1(iv):

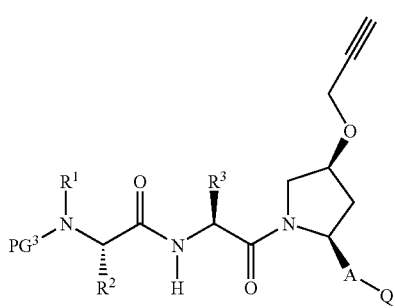

1 (iv)

wherein $PG^3$, $R^1$, $R^2$, $R^3$, A, and Q are as defined in claim 1, in a solvent; and
    b) removing the protecting groups so as to produce a compound of claim 1.

31. A process for producing a compound of claim 1, the process comprising:
    a) coupling two intermediates represented by Formula 3-i:

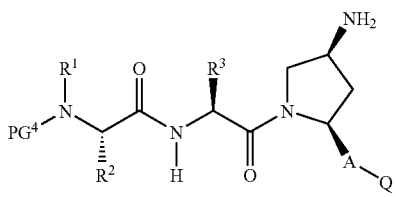

3-i wherein $PG^4$ is a protecting group, and $R^1$, $R^2$, $R^3$, A, and Q are as defined in claim 1 and an activated diacid in a solvent; and
    b) removing the protecting groups so as to produce a compound of claim 1.

32. The compound, according to claim 12, wherein $R^2$ and $R^{200}$ are $C_1$-$C_6$ alkyl optionally substituted with OH.

33. The compound, according to claim 32, wherein Q and $Q^1$ are $NR^4R^5$.

34. The compound, according to claim 33, wherein $R^4$ and $R^5$ are independently
    1) H,
    2) haloalkyl,
    3) $C_1$-$C_6$ alkyl,
    4) $C_2$-$C_6$ alkenyl,
    5) $C_2$-$C_4$ alkynyl,
    6) $C_3$-$C_7$ cycloalkyl,
    7) $C_3$-$C_7$ cycloalkenyl,
    8) aryl,
    9) heteroaryl,
    10) heterocyclyl,
    11) heterobicyclyl,
    12) C(O)—$R^{11}$,
    13) C(O)O—$R^{11}$,
    14) C(=Y)$NR^8R^9$, or
    15) $S(O)_2$—$R^{11}$,
wherein the alkyl, alkenyl, alkynyl, cycloalkyl, and cycloalkenyl is optionally substituted with one or more $R^6$ substituents; and wherein the aryl, heteroaryl, heterocyclyl, and heterobicyclyl is optionally substituted with one or more $R^{10}$ substituents.

35. The compound according to claim 34, wherein $R^4$ and $R^5$ are independently
    1) $C_1$-$C_6$ alkyl,
    2) C(O)—$R^{11}$,
    3) C(O)O—$R^{11}$, or
    5) $S(O)_2$—$R^{11}$,
wherein the alkyl is substituted with one or mote $R^6$ substituents.

36. The compound, according to claim 13, wherein $R^2$ and $R^{200}$ are $C_1$-$C_6$ alkyl optionally substituted with OH.

37. The compound, according to claim 36, wherein Q and $Q^1$ are $NR^4R^5$.

38. The compound, according to claim 37, wherein $R^4$ is H and $R^5$ is
    1) $C_1$-$C_6$ alkyl,
    2) $C_2$-$C_5$ alkenyl,
    3) $C_2$-$C_4$ alkynyl,
    4) $C_3$-$C_7$ cycloalkyl,
    5) $C_3$-$C_7$ cycloalkenyl,
    6) aryl,
    7) heteroaryl,
    8) heterocyclyl, or
    9) heterobicyclyl,
wherein the alkyl, alkenyl, alkynyl, cycloalkyl, and cycloalkenyl is optionally substituted with one or more $R^6$ substituents; and wherein the aryl, heteroaryl, heterocyclyl, and heterobicyclyl is optionally substituted with one or more $R^{10}$ substituents.

39. The compound, according to claim 38, wherein $R^5$ is $C_1C_6$ alkyl optionally substituted with one or more $R^6$ substituents or aryl optionally substituted with one or more $R^{10}$ substituents.

40. The compound of claim 38, wherein $R^5$ is:

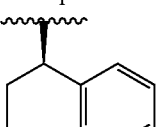 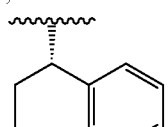

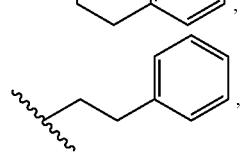 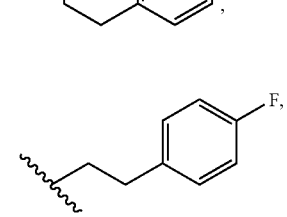

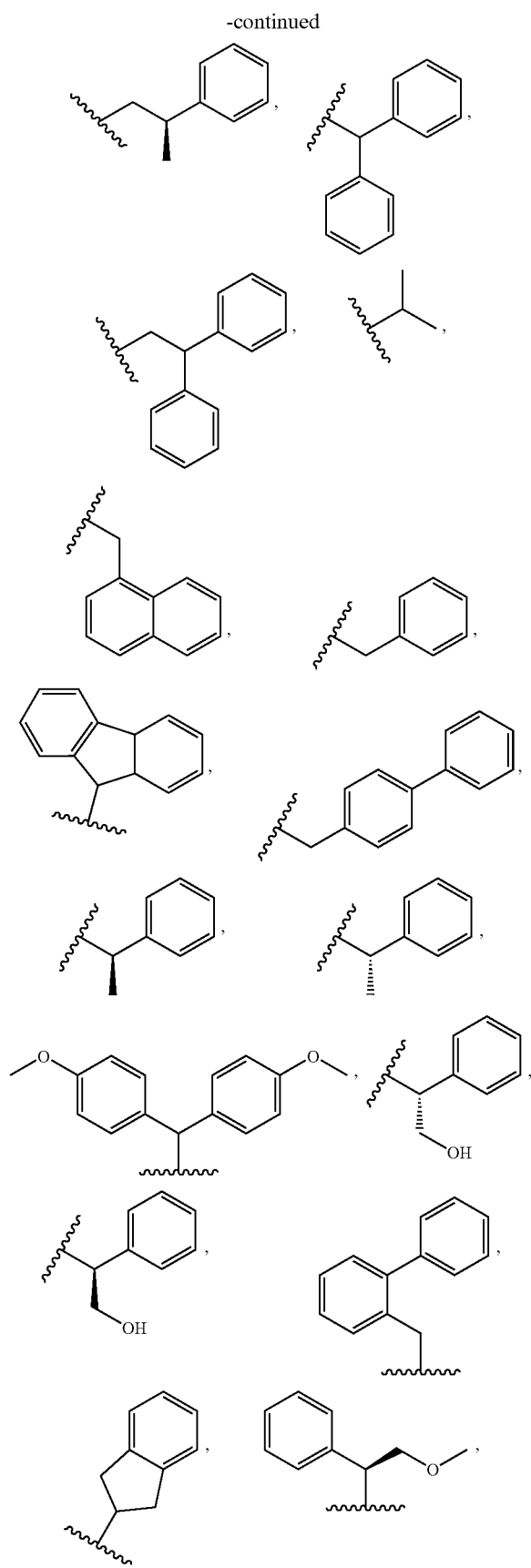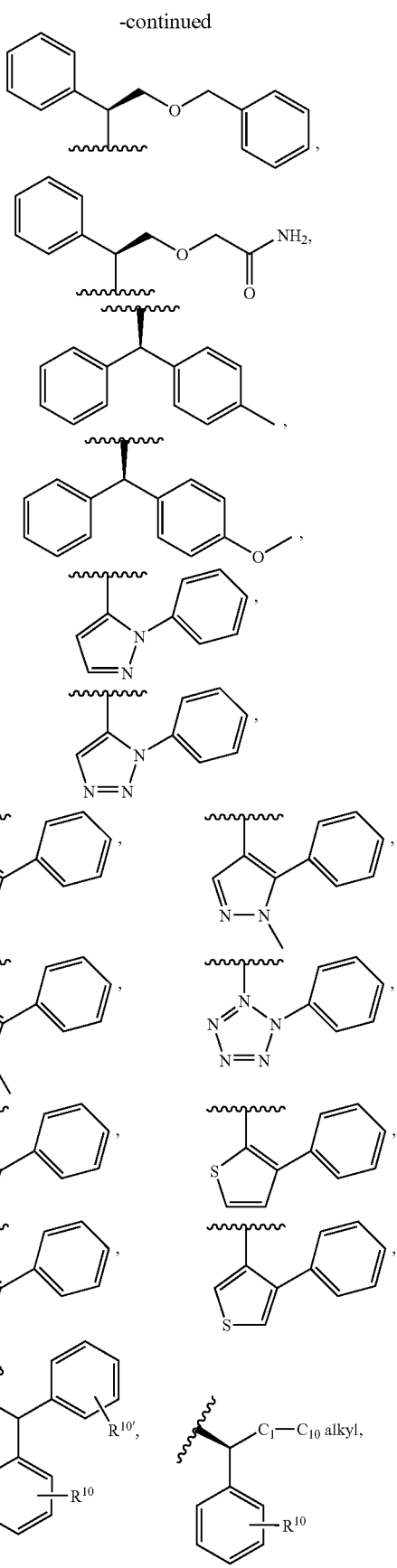

-continued
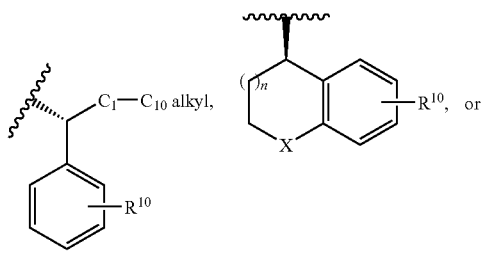
wherein n is 0,1, or 2 and X is O, S or SO₂.
41. The compound, according to claim 37, wherein Q and Q¹ are:
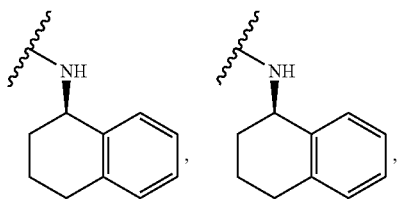
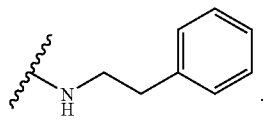
42. The compound, according to claim 1, wherein the compound is
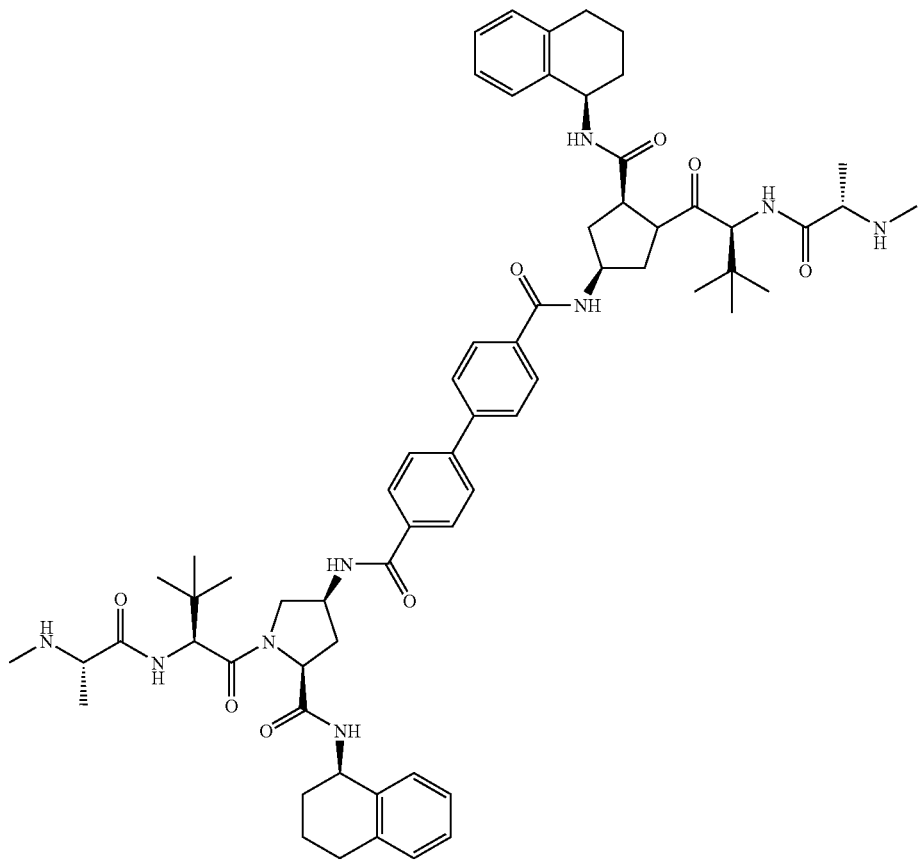

43. The compound, according to claim 1, wherein the compound is
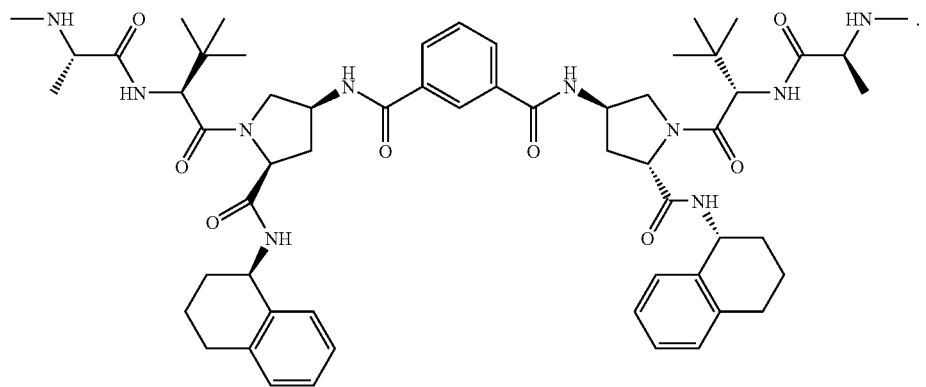
44. The compound, according to claim 1, wherein the compound is
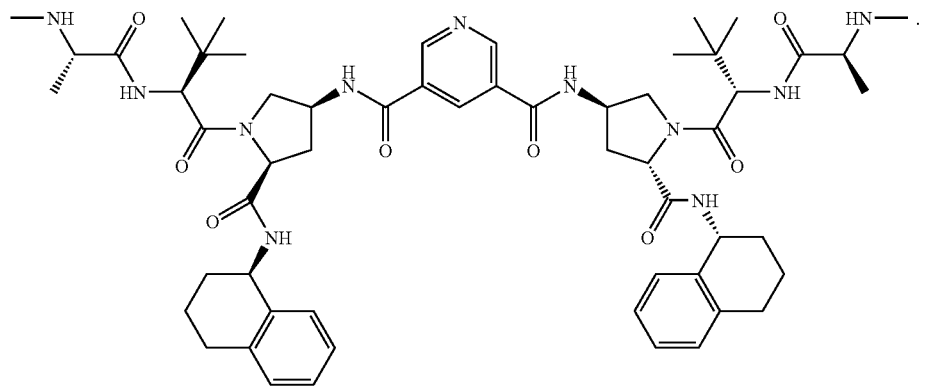
45. The compound, according to claim 1, wherein the compound is
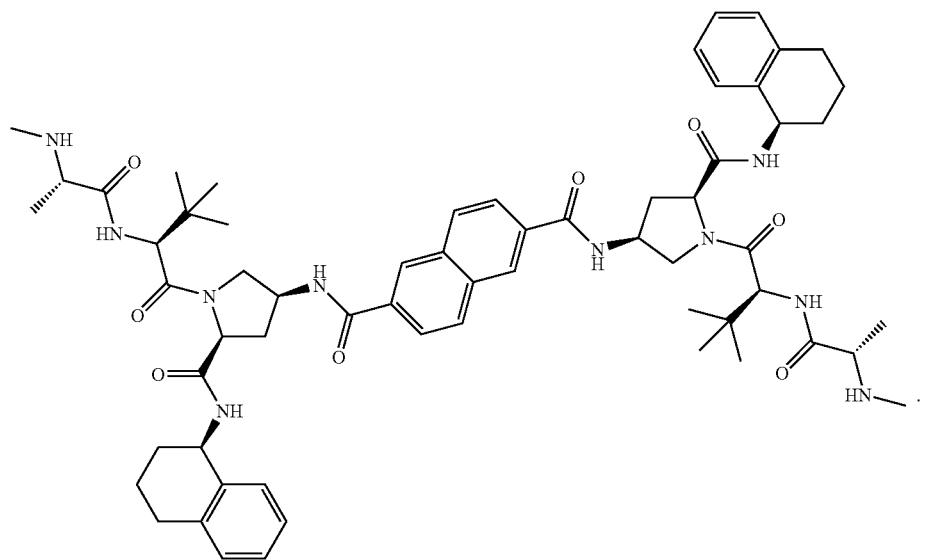

46. A pharmaceutical composition comprising a compound of Formula I or salt thereof, according to claim 1, in combination with a TRAIL receptor antibody.
47. A compound, according to claim 1, of Formula 1.3:
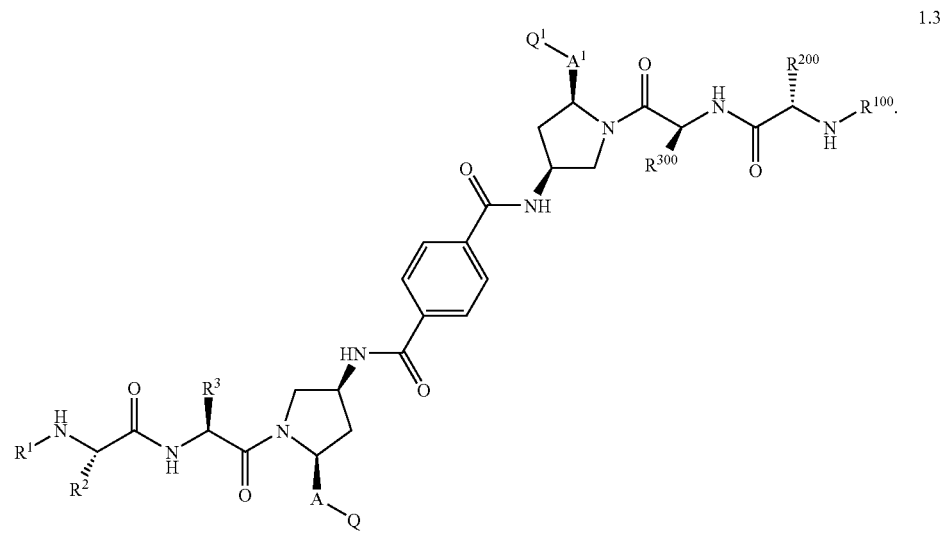
1.3
* * * * *